(12) United States Patent
Banks et al.

(10) Patent No.: US 11,535,868 B2
(45) Date of Patent: Dec. 27, 2022

(54) MINIATURIZED DYSTROPHINS HAVING SPECTRIN FUSION DOMAINS AND USES THEREOF

(71) Applicant: BRISTOL-MYERS SQUIBB COMPANY, Princeton, NJ (US)

(72) Inventors: Glen Banks, Yardley, PA (US); Jonathan Harry Davis, Madison, WI (US); Paul Charles Levesque, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 17/242,357

(22) Filed: Apr. 28, 2021

(65) Prior Publication Data

US 2021/0340195 A1 Nov. 4, 2021

Related U.S. Application Data

(60) Provisional application No. 63/017,148, filed on Apr. 29, 2020.

(51) Int. Cl.
| | |
|---|---|
| *A61K 48/00* | (2006.01) |
| *C12N 15/86* | (2006.01) |
| *A61K 35/76* | (2015.01) |
| *C12N 15/12* | (2006.01) |
| *A61P 21/00* | (2006.01) |
| *A61K 38/00* | (2006.01) |
| *C07K 14/47* | (2006.01) |

(52) U.S. Cl.
CPC .............. *C12N 15/86* (2013.01); *A61P 21/00* (2018.01); *A61K 38/00* (2013.01); *C07K 14/47* (2013.01); *C12N 2750/14143* (2013.01); *C12N 2830/50* (2013.01)

(58) Field of Classification Search
None
See application file for complete search history.

(56) References Cited

U.S. PATENT DOCUMENTS

| | | | |
|---|---|---|---|
| 6,869,777 B2 | 3/2005 | Chamberlain et al. | |
| 7,001,761 B2 | 2/2006 | Xiao | |
| 7,241,447 B1 | 7/2007 | Engelhardt et al. | |
| 7,282,199 B2 | 10/2007 | Gao et al. | |
| 7,510,867 B2 | 3/2009 | Xiao et al. | |
| 7,655,467 B2 | 2/2010 | Chamberlain et al. | |
| 7,790,449 B2 | 9/2010 | Gao et al. | |
| 7,803,622 B2 | 9/2010 | Engelhardt et al. | |
| 7,892,824 B2 | 2/2011 | Duan et al. | |
| 8,236,557 B2 | 8/2012 | Dongsheng et al. | |
| 8,318,480 B2 | 11/2012 | Gao et al. | |
| 8,501,920 B2 | 8/2013 | Chamberlain et al. | |
| 8,846,030 B2 | 9/2014 | Engelhardt et al. | |
| 8,962,330 B2 | 2/2015 | Gao et al. | |
| 9,624,282 B2 | 4/2017 | Lai et al. | |
| 9,862,945 B2 | 1/2018 | Flanigan et al. | |
| 10,166,272 B2 | 1/2019 | Dickson et al. | |
| 10,351,611 B2 | 7/2019 | Lai et al. | |
| 10,479,821 B2 | 11/2019 | Chamberlain et al. | |
| 10,543,260 B2 | 1/2020 | Steinman | |
| 10,590,435 B2 | 3/2020 | Gao et al. | |
| 10,647,751 B2 | 5/2020 | Dickson | |
| 10,786,546 B2 | 9/2020 | Dickson et al. | |
| 11,202,840 B2 | 12/2021 | Duan et al. | |
| 2003/0017131 A1 | 1/2003 | Park et al. | |
| 2013/0091326 A1 | 4/2013 | Choi et al. | |
| 2014/0234255 A1* | 8/2014 | Lai .................... | C07K 14/4708 424/93.2 |
| 2015/0214960 A1 | 6/2015 | Kim et al. | |
| 2015/0196670 A1 | 7/2015 | Popplewell et al. | |
| 2015/0321416 A1 | 11/2015 | Patel et al. | |
| 2016/0207893 A1 | 7/2016 | Kelly et al. | |
| 2016/0214960 A1 | 7/2016 | Kuduk et al. | |
| 2016/0311236 A1 | 10/2016 | Kozuma et al. | |
| 2017/0021000 A1 | 1/2017 | Steinman et al. | |
| 2017/0157213 A1 | 6/2017 | Dickson et al. | |
| 2017/0349640 A1 | 12/2017 | Lai et al. | |
| 2017/0368198 A1* | 12/2017 | Xiao ...................... | A61K 45/06 |
| 2018/0148488 A1* | 5/2018 | Chamberlain ......... | C12N 15/85 |
| 2018/0265859 A1* | 9/2018 | Tremblay ............. | A61K 48/005 |
| 2018/0271069 A1 | 9/2018 | Min et al. | |
| 2018/0346533 A1 | 12/2018 | Dickson | |
| 2019/0184033 A1* | 6/2019 | Duan .................. | C07K 14/4716 |
| 2019/0365926 A1* | 12/2019 | Alexander ............. | C12N 15/86 |
| 2020/0031890 A1 | 1/2020 | Chamberlain et al. | |
| 2020/0078473 A1 | 3/2020 | Lochmuller | |

(Continued)

FOREIGN PATENT DOCUMENTS

| | | |
|---|---|---|
| EP | 3044319 A1 | 7/2016 |
| JP | 14213498 A | 5/1998 |

(Continued)

OTHER PUBLICATIONS

Legrand et al., Computational Study of the Human Dystrophin Repeats: Interaction Properties and Molecular Dynamics, 2011, pp. 1-11pages.*
Sequence listing, from WO 2020193636, downloaded Oct. 29, 2020.*
U.S. Appl. No. 61/797,012, filed Nov. 26, 2012, Lai, et al.
Amit C. Nathwani, "Advances in Gene Therapy for Hemophilia", Human Gene Therapy, 2017, vol. 28, 11—1004-1012.
Andrew K.M. Cheung, et al., "Integration of the Adeno-Associated Virus Genome into Cellular DNA in Latently Infected Human Detroit 6 Cells", Journal of Virology, 1980, 739-748.
Atchison, R.W., et al., "Adenovirus-Associated Defective Virus Particles", Science, 1965, 149(3685), 754-755.

(Continued)

*Primary Examiner* — Maria Marvich
(74) *Attorney, Agent, or Firm* — Melissa Wenk

(57) ABSTRACT

Disclosed herein are nucleic acid molecules, polypeptides, cells, vectors, and pharmaceutical compositions relating to miniaturized dystrophin. Methods of production and methods of therapeutic use of the miniaturized dystrophin are also disclosed.

26 Claims, 26 Drawing Sheets

Specification includes a Sequence Listing.

(56) References Cited

U.S. PATENT DOCUMENTS

| | | |
|---|---|---|
| 2020/0095298 A1 | 3/2020 | Chamberlain et al. |
| 2020/0168938 A1 | 5/2020 | Fleck et al. |
| 2020/0376141 A1 | 12/2020 | Xiao et al. |
| 2020/0405824 A1 | 12/2020 | Odom et al. |

FOREIGN PATENT DOCUMENTS

| | | | |
|---|---|---|---|
| WO | | 198706844 A1 | 11/1987 |
| WO | | 200183695 A2 | 11/2001 |
| WO | | 200229056 A2 | 4/2002 |
| WO | | 2003052051 A2 | 6/2003 |
| WO | | 2005049850 A2 | 6/2005 |
| WO | | 2005099763 A2 | 10/2005 |
| WO | | 2008088895 A2 | 7/2008 |
| WO | | 2014009567 A1 | 1/2014 |
| WO | | 2014172669 A1 | 10/2014 |
| WO | | 2015197232 A1 | 12/2015 |
| WO | | 2015197869 A1 | 12/2015 |
| WO | | 2016109596 A1 | 7/2016 |
| WO | | 2016115543 A2 | 7/2016 |
| WO | | 2016177911 A1 | 11/2016 |
| WO | | 2017181011 A1 | 10/2017 |
| WO | | 2017181014 A1 | 10/2017 |
| WO | | 2017181015 A1 | 10/2017 |
| WO | | 2017221145 A1 | 12/2017 |
| WO | | 2017223128 A1 | 12/2017 |
| WO | | 2018022608 A2 | 2/2018 |
| WO | | 2018170408 A1 | 9/2018 |
| WO | | 2019012336 A2 | 1/2019 |
| WO | | 2019078916 A1 | 4/2019 |
| WO | | 2019118806 A1 | 6/2019 |
| WO | | 2019195362 A1 | 10/2019 |
| WO | | 2019245973 A1 | 12/2019 |
| WO | | 2019246480 A1 | 12/2019 |
| WO | | 2020086844 A1 | 4/2020 |
| WO | WO 2020193636 | * | 10/2020 |
| WO | | 2020261178 A1 | 12/2020 |
| WO | | 2021026075 A1 | 2/2021 |
| WO | | 2021108755 A2 | 6/2021 |
| WO | | 2021142435 A1 | 7/2021 |
| WO | | 2021142447 A1 | 7/2021 |

OTHER PUBLICATIONS

Catherine A. Laughlin, et al., "Cloning of infectious adeno-associated virus genomes in bacterial plasmids", Gene., 1983, 65-73.

Christopher D. Saudek, et al., "A Preliminary Trial of the Programmable Implantable Medication System For Insulin Delivery", The New England Journal of Medicine, 1989, 321, 574-579.

Dan Wang, et al., "Adeno-associated virus vector as a platform for gene therapy delivery", Nature, 2019, vol. 18, 358-378.

Elizabeth M. McNally, et al., "Contemporary Cardiac Issues in Duchenne Muscular Dystrophy", HHS Public Access, 2015, 131(18), 1590-1598.

Faber, R.M., et al., "Myofiber branching rather than myofiber hyperplasia contributes to muscle hypertrophy in mdx mice", Skeletal Muscle, 2014, vol. 4:10, 1-11.

Glen B. Banks, et al., "Muscle Structure Influences Utrophin Expression in mdx Mice", PLOS Genetics, 2014, 10(6), e1004431.

Glen B. Banks, et al., The Polyproline Site in Hinge 2 Influences the Functional Capacity of Truncated Dystrophins, Open Acess, 2010, 6(5), e1000958.

Gottlieb, John, "In Vitro Excision of Adeno-Associated Virus DNA from Recombinant Plasmids: Isolation of an Enzyme Fraction from HeLa Cells That Cleaves DNA at Poly(G) Sequences, Molecular and Cellular Biology", 1988, 6(8), 2513-2522.

Henry Buchwald, M.D., et al., "Long-term, continuous intravenous heparin administration by an implantable infusion pump in ambulatory patients with recurrent venous thrombosis", Surgery, 1980, 88(4), 507-16.

J. Sambrook, et al., "Molecular Cloning", a Laboratory Manual, Second Edition, Synthetic Oligonucleotide Probes, 1989, 11.1-11. 61.

James A. Rose, "Evidence for a single-stranded adenovirus-associated virus genome: Formation of a DNA Density Hybrid on Release of Viral DNA", Natl Institute of Allergy and Infectious Diseases, National Institute of Health, 1969, 863-869.

Jerry R. Mendell, et al., "Gene Therapy for Muscular Dystrophy: Lessons Learned and Path Forward", NIH Public Access; 2012, 527(2), 90-99.

Jerry R. Mendell, MD, et al., "Molecular Therapeutic Strategies Targeting Duchenne Muscular Dystrophy", 2010, 25(9), 1145-1148.

Jorge L. Santiego-Ortiz, et al.,, "Adeno-Associated Virus (AAV) Vectors in Cancer Gene Therapy", HHS Public Access, Author Manuscript, J Control Release, 2016, 240, 287-301.

Keeler, AM, et al., "Gene Therapy 2017:Progress and Future Directions", Clinical Transl Sci, 2017, 10, 242-248.

Kutmeier G., et al., "Assembly of Humanized Antibody Genes from Synthetic Oligonucleotides Using a Single-Round PCR", Biotechniques. 1994, 17:242-6.

Louis R. Rodino-Klapac, et al., "Update on the Treatment of Duchenne Muscular Dystrophy", HHS Public Access, 2013, 13(3),332, 1-11.

Manuel AFV Goncalves, "Adeno-associated virus: from defective virus to effective vector", Virology Journal, 2005, 2:(43), 1-17.

Matthew J. During, MD, et al., "Controlled Release of Dopamine from a Polymeric Brain Implant: In Vivo Characterization", Ann. Neurol., 1989-25:351-356.

Michael V. Sefton, "Implantable Pumps—Characteristics of the Ideal Implantable Pump", CRC Critical Reviews in Biomedical Engineering, 1987, vol. 14, Issue 3, 201-240.

Paul L. Hermonat, et al, "Use of adeno-associated virus as a mammalian DNA cloning vector: Transduction of neomycin resistance into mammalian tissue culture cells", Proc. Natl. Acad. Sci.,81(20), pp. 6466-6470, 1984.

Paul N. Valdmanis, et al., "Future of rAAV Gene Therapy: Platform for RNAi, Gene Editing, and Beyond", Human Gene Therapy, 2017, vol. 28, 4, 361-374.

Periannan Senapathy, et al., "Replication of Adeno-associated Virus DNA", J. Mol. Biol., 1984, 178, 179, 1-20.

Ramzi J. Khairallah, et al., "Microtubules Underlie Dysfunction in Duchenne Muscular Dystrophy", Physiology, 2012, 5(236), 1-12.

Richard J. Samulski, et al., Rescue of Adeno-Associated Virus from Recombinant Plasmids: Gene Correction within the Terminal Repeats of AAV, Cell, 1983, vol. 33, 135-143.

Richard Jude Samulski, et al., "A Recombinant Plasmid from Which an Infectious Adeno-Associated Virus Genome Can be Excised In Vitro and Its Use to Study Viral Replication", Journal of Virology, 61(10), 1987, 3096-3101.

Robert J. Levy, "Ocelli: A Celestial Compass in the Desert Ant Cataglyphis", 1985, Science, 190-192.

Robert Langer, "New Methods of Drug Delivery", Science, 1990, 249, 1527-33.

Scott Q. Harper, "Molecular dissection of dystrophin identifies the docking site for nNOS", PNAS, 2013, 110, 2, 387-388.

Scott Q. Harper, et al., Modular flexibility of dystrophin: Implications for gene therapy of Duchenne muscular dystrophy, Nature Medicine, 2002, 8, 3, 253-261.

Xiao Xiao, et al., "Production of High-titer Recombinant Adeno-Associated Virus Vectors in the Absence of Helper Adenovirus", Journal of Virology, 1998, vol. 72, 3, 2224-2232.

Yi Lai, et al., Edited by Louis M. Kunkel, "Dystrophins carrying spectrin-like repeats 16 and 17 anchor nNOS to the sarcolemma and enhance exercise performance in a mouse model of muscular dystrophy", J. Clin Invest., 2009, 119(3), 624-635.

Yutaka Takebe, et al., "SR Alpha Promoter: an Efficient and Versatile Mammalian cDNA Expression System Composed of the Simian Virus 40 Early Promoter and the R-U5 Segment of Human T-Cell Leukemia Virus Type 1 Long Terminal Repeat", Molecular and Cellular Biology, Jan. 1988, p. 466-472.

LeRumeur, et al., Dystrophin: More than just the sum of its parts, Biochimica ET Biophysica Acta (BBA), Proteins and Proteomics, ElSevier, Netherlands, 1804(9), 2010, 1713-1722.

(56) References Cited

OTHER PUBLICATIONS

Lai, et al., Edited by Louis M. Kunkel, "Alpha 2 and Alpha3 helices of dystrophin R16 and R17 frame a microdomain in the Alpha1 helix of dystrophin R17 for neuronal NOS binding", PNAS, 2013, 110, 2, 525-530.

McRae W. Williams, et al., Extensive but Coordinated Reorganization of the Membrane Skeleton in Myofibers of Dystrophic (mdx) Mice, The Journal of Cell Biology, 1999, vol. 144, 6, 1259-1270.

Nathalie Vincent, et al., Long-term correction of mouse dystrophic degeneration by adenovirus-mediated transfer of a minidystrophin gene, Nature Genetics, 1993, 5, 130-134.

T. Matsushita, et al., "Adeno-associated virus vectors can be efficiently produced without helper virus", Gene Therapy, 1998, 5, 938-945.

Earley, et al., "Human Gene Therapy" AAV ITR Promoter, vol. 31, 3, 4, p. 151-163.

Khairallah, et al., "Microtubules Underlie Dysfunction in Duchenne Muscular Dystrophy", Physiology, 2012, vol. 5, 236, p. 1-11.

Lai, Yi, et al., "Alpha 2 and Alpha 3 helices of dystrophin R16 and R17" PNAS 2012, 525-530.

* cited by examiner

SEQUENCE LISTING

<160> NUMBER OF SEQ ID NOS: 122

<210> SEQ ID NO 1
<211> LENGTH: 3685
<212> TYPE: PRT
<213> ORGANISM: Homo sapiens

<400> SEQUENCE: 1

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140
```

-continued

```
Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
            165                 170                 175

Arg Pro Asp Leu Phe Asp Trp Asn Ser Val Val Cys Gln Gln Ser Ala
                180                 185                 190

Thr Gln Arg Leu Glu His Ala Phe Asn Ile Ala Arg Tyr Gln Leu Gly
            195                 200                 205

Ile Glu Lys Leu Leu Asp Pro Glu Asp Val Asp Thr Thr Tyr Pro Asp
210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Asp Glu Ser Ser Gly Asp His Ala Thr Ala Ala
        515                 520                 525

Leu Glu Glu Gln Leu Lys Val Leu Gly Asp Arg Trp Ala Asn Ile Cys
    530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
```

-continued

```
                565                 570                 575
Glu Lys Glu Asp Ala Val Asn Lys Ile His Thr Thr Gly Phe Lys Asp
            580                 585                 590
Gln Asn Glu Met Leu Ser Ser Leu Gln Lys Leu Ala Val Leu Lys Ala
            595                 600                 605
Asp Leu Glu Lys Lys Lys Gln Ser Met Gly Lys Leu Tyr Ser Leu Lys
            610                 615                 620
Gln Asp Leu Leu Ser Thr Leu Lys Asn Lys Ser Val Thr Gln Lys Thr
625                 630                 635                 640
Glu Ala Trp Leu Asp Asn Phe Ala Arg Cys Trp Asp Asn Leu Val Gln
            645                 650                 655
Lys Leu Glu Lys Ser Thr Ala Gln Ile Ser Gln Ala Val Thr Thr Thr
            660                 665                 670
Gln Pro Ser Leu Thr Gln Thr Thr Val Met Glu Thr Val Thr Thr Val
            675                 680                 685
Thr Thr Arg Glu Gln Ile Leu Val Lys His Ala Gln Glu Glu Leu Pro
            690                 695                 700
Pro Pro Pro Pro Gln Lys Lys Arg Gln Ile Thr Val Asp Ser Glu Ile
705                 710                 715                 720
Arg Lys Arg Leu Asp Val Asp Ile Thr Glu Leu His Ser Trp Ile Thr
            725                 730                 735
Arg Ser Glu Ala Val Leu Gln Ser Pro Glu Phe Ala Ile Phe Arg Lys
            740                 745                 750
Glu Gly Asn Phe Ser Asp Leu Lys Glu Lys Val Asn Ala Ile Glu Arg
            755                 760                 765
Glu Lys Ala Glu Lys Phe Arg Lys Leu Gln Asp Ala Ser Arg Ser Ala
            770                 775                 780
Gln Ala Leu Val Glu Gln Met Val Asn Glu Gly Val Asn Ala Asp Ser
785                 790                 795                 800
Ile Lys Gln Ala Ser Glu Gln Leu Asn Ser Arg Trp Ile Glu Phe Cys
            805                 810                 815
Gln Leu Leu Ser Glu Arg Leu Asn Trp Leu Glu Tyr Gln Asn Asn Ile
            820                 825                 830
Ile Ala Phe Tyr Asn Gln Leu Gln Gln Leu Glu Gln Met Thr Thr Thr
            835                 840                 845
Ala Glu Asn Trp Leu Lys Ile Gln Pro Thr Thr Pro Ser Glu Pro Thr
            850                 855                 860
Ala Ile Lys Ser Gln Leu Lys Ile Cys Lys Asp Glu Val Asn Arg Leu
865                 870                 875                 880
Ser Gly Leu Gln Pro Gln Ile Glu Arg Leu Lys Ile Gln Ser Ile Ala
            885                 890                 895
Leu Lys Glu Lys Gly Gln Gly Pro Met Phe Leu Asp Ala Asp Phe Val
            900                 905                 910
Ala Phe Thr Asn His Phe Lys Gln Val Phe Ser Asp Val Gln Ala Arg
            915                 920                 925
Glu Lys Glu Leu Gln Thr Ile Phe Asp Thr Leu Pro Pro Met Arg Tyr
            930                 935                 940
Gln Glu Thr Met Ser Ala Ile Arg Thr Trp Val Gln Gln Ser Glu Thr
945                 950                 955                 960
Lys Leu Ser Ile Pro Gln Leu Ser Val Thr Asp Tyr Glu Ile Met Glu
            965                 970                 975
Gln Arg Leu Gly Glu Leu Gln Ala Leu Gln Ser Ser Leu Gln Glu Gln
            980                 985                 990
```

-continued

```
Gln Ser Gly Leu Tyr Tyr Leu Ser Thr Thr Val Lys Glu Met Ser Lys
        995                 1000                1005

Lys Ala Pro Ser Glu Ile Ser Arg Lys Tyr Gln Ser Glu Phe Glu
    1010                1015                1020

Glu Ile Glu Gly Arg Trp Lys Lys Leu Ser Ser Gln Leu Val Glu
    1025                1030                1035

His Cys Gln Lys Leu Glu Glu Gln Met Asn Lys Leu Arg Lys Ile
    1040                1045                1050

Gln Asn His Ile Gln Thr Leu Lys Lys Trp Met Ala Glu Val Asp
    1055                1060                1065

Val Phe Leu Lys Glu Glu Trp Pro Ala Leu Gly Asp Ser Glu Ile
    1070                1075                1080

Leu Lys Lys Gln Leu Lys Gln Cys Arg Leu Leu Val Ser Asp Ile
    1085                1090                1095

Gln Thr Ile Gln Pro Ser Leu Asn Ser Val Asn Glu Gly Gly Gln
    1100                1105                1110

Lys Ile Lys Asn Glu Ala Glu Pro Glu Phe Ala Ser Arg Leu Glu
    1115                1120                1125

Thr Glu Leu Lys Glu Leu Asn Thr Gln Trp Asp His Met Cys Gln
    1130                1135                1140

Gln Val Tyr Ala Arg Lys Glu Ala Leu Lys Gly Gly Leu Glu Lys
    1145                1150                1155

Thr Val Ser Leu Gln Lys Asp Leu Ser Glu Met His Glu Trp Met
    1160                1165                1170

Thr Gln Ala Glu Glu Glu Tyr Leu Glu Arg Asp Phe Glu Tyr Lys
    1175                1180                1185

Thr Pro Asp Glu Leu Gln Lys Ala Val Glu Glu Met Lys Arg Ala
    1190                1195                1200

Lys Glu Glu Ala Gln Gln Lys Glu Ala Lys Val Lys Leu Leu Thr
    1205                1210                1215

Glu Ser Val Asn Ser Val Ile Ala Gln Ala Pro Pro Val Ala Gln
    1220                1225                1230

Glu Ala Leu Lys Lys Glu Leu Glu Thr Leu Thr Thr Asn Tyr Gln
    1235                1240                1245

Trp Leu Cys Thr Arg Leu Asn Gly Lys Cys Lys Thr Leu Glu Glu
    1250                1255                1260

Val Trp Ala Cys Trp His Glu Leu Leu Ser Tyr Leu Glu Lys Ala
    1265                1270                1275

Asn Lys Trp Leu Asn Glu Val Glu Phe Lys Leu Lys Thr Thr Glu
    1280                1285                1290

Asn Ile Pro Gly Gly Ala Glu Glu Ile Ser Glu Val Leu Asp Ser
    1295                1300                1305

Leu Glu Asn Leu Met Arg His Ser Glu Asp Asn Pro Asn Gln Ile
    1310                1315                1320

Arg Ile Leu Ala Gln Thr Leu Thr Asp Gly Gly Val Met Asp Glu
    1325                1330                1335

Leu Ile Asn Glu Glu Leu Glu Thr Phe Asn Ser Arg Trp Arg Glu
    1340                1345                1350

Leu His Glu Glu Ala Val Arg Arg Gln Lys Leu Leu Glu Gln Ser
    1355                1360                1365

Ile Gln Ser Ala Gln Glu Thr Glu Lys Ser Leu His Leu Ile Gln
    1370                1375                1380
```

| | | | | | | | | | | |
|---|---|---|---|---|---|---|---|---|---|---|
|Glu|Ser|Leu|Thr|Phe|Ile|Asp|Lys|Gln|Leu|Ala|Ala|Tyr|Ile|Ala|
| |1385| | | |1390| | | |1395| |

Asp Lys Val Asp Ala Ala Gln Met Pro Gln Glu Ala Gln Lys Ile
    1400            1405            1410

Gln Ser Asp Leu Thr Ser His Glu Ile Ser Leu Glu Glu Met Lys
    1415            1420            1425

Lys His Asn Gln Gly Lys Glu Ala Ala Gln Arg Val Leu Ser Gln
    1430            1435            1440

Ile Asp Val Ala Gln Lys Lys Leu Gln Asp Val Ser Met Lys Phe
    1445            1450            1455

Arg Leu Phe Gln Lys Pro Ala Asn Phe Glu Gln Arg Leu Gln Glu
    1460            1465            1470

Ser Lys Met Ile Leu Asp Glu Val Lys Met His Leu Pro Ala Leu
    1475            1480            1485

Glu Thr Lys Ser Val Glu Gln Glu Val Val Gln Ser Gln Leu Asn
    1490            1495            1500

His Cys Val Asn Leu Tyr Lys Ser Leu Ser Glu Val Lys Ser Glu
    1505            1510            1515

Val Glu Met Val Ile Lys Thr Gly Arg Gln Ile Val Gln Lys Lys
    1520            1525            1530

Gln Thr Glu Asn Pro Lys Glu Leu Asp Glu Arg Val Thr Ala Leu
    1535            1540            1545

Lys Leu His Tyr Asn Glu Leu Gly Ala Lys Val Thr Glu Arg Lys
    1550            1555            1560

Gln Gln Leu Glu Lys Cys Leu Lys Leu Ser Arg Lys Met Arg Lys
    1565            1570            1575

Glu Met Asn Val Leu Thr Glu Trp Leu Ala Ala Thr Asp Met Glu
    1580            1585            1590

Leu Thr Lys Arg Ser Ala Val Glu Gly Met Pro Ser Asn Leu Asp
    1595            1600            1605

Ser Glu Val Ala Trp Gly Lys Ala Thr Gln Lys Glu Ile Glu Lys
    1610            1615            1620

Gln Lys Val His Leu Lys Ser Ile Thr Glu Val Gly Glu Ala Leu
    1625            1630            1635

Lys Thr Val Leu Gly Lys Lys Glu Thr Leu Val Glu Asp Lys Leu
    1640            1645            1650

Ser Leu Leu Asn Ser Asn Trp Ile Ala Val Thr Ser Arg Ala Glu
    1655            1660            1665

Glu Trp Leu Asn Leu Leu Glu Tyr Gln Lys His Met Glu Thr
    1670            1675            1680

Phe Asp Gln Asn Val Asp His Ile Thr Lys Trp Ile Ile Gln Ala
    1685            1690            1695

Asp Thr Leu Leu Asp Glu Ser Glu Lys Lys Lys Pro Gln Gln Lys
    1700            1705            1710

Glu Asp Val Leu Lys Arg Leu Lys Ala Glu Leu Asn Asp Ile Arg
    1715            1720            1725

Pro Lys Val Asp Ser Thr Arg Asp Gln Ala Ala Asn Leu Met Ala
    1730            1735            1740

Asn Arg Gly Asp His Cys Arg Lys Leu Val Glu Pro Gln Ile Ser
    1745            1750            1755

Glu Leu Asn His Arg Phe Ala Ala Ile Ser His Arg Ile Lys Thr
    1760            1765            1770

Gly Lys Ala Ser Ile Pro Leu Lys Glu Leu Glu Gln Phe Asn Ser

```
            1775                1780                1785

Asp Ile Gln Lys Leu Leu Glu Pro Leu Glu Ala Glu Ile Gln Gln
        1790                1795                1800

Gly Val Asn Leu Lys Glu Glu Asp Phe Asn Lys Asp Met Asn Glu
        1805                1810                1815

Asp Asn Glu Gly Thr Val Lys Glu Leu Leu Gln Arg Gly Asp Asn
        1820                1825                1830

Leu Gln Gln Arg Ile Thr Asp Glu Arg Lys Arg Glu Glu Ile Lys
        1835                1840                1845

Ile Lys Gln Gln Leu Leu Gln Thr Lys His Asn Ala Leu Lys Asp
        1850                1855                1860

Leu Arg Ser Gln Arg Arg Lys Lys Ala Leu Glu Ile Ser His Gln
        1865                1870                1875

Trp Tyr Gln Tyr Lys Arg Gln Ala Asp Asp Leu Leu Lys Cys Leu
        1880                1885                1890

Asp Asp Ile Glu Lys Lys Leu Ala Ser Leu Pro Glu Pro Arg Asp
        1895                1900                1905

Glu Arg Lys Ile Lys Glu Ile Asp Arg Glu Leu Gln Lys Lys Lys
        1910                1915                1920

Glu Glu Leu Asn Ala Val Arg Arg Gln Ala Glu Gly Leu Ser Glu
        1925                1930                1935

Asp Gly Ala Ala Met Ala Val Glu Pro Thr Gln Ile Gln Leu Ser
        1940                1945                1950

Lys Arg Trp Arg Glu Ile Glu Ser Lys Phe Ala Gln Phe Arg Arg
        1955                1960                1965

Leu Asn Phe Ala Gln Ile His Thr Val Arg Glu Glu Thr Met Met
        1970                1975                1980

Val Met Thr Glu Asp Met Pro Leu Glu Ile Ser Tyr Val Pro Ser
        1985                1990                1995

Thr Tyr Leu Thr Glu Ile Thr His Val Ser Gln Ala Leu Leu Glu
        2000                2005                2010

Val Glu Gln Leu Leu Asn Ala Pro Asp Leu Cys Ala Lys Asp Phe
        2015                2020                2025

Glu Asp Leu Phe Lys Gln Glu Glu Ser Leu Lys Asn Ile Lys Asp
        2030                2035                2040

Ser Leu Gln Gln Ser Ser Gly Arg Ile Asp Ile Ile His Ser Lys
        2045                2050                2055

Lys Thr Ala Ala Leu Gln Ser Ala Thr Pro Val Glu Arg Val Lys
        2060                2065                2070

Leu Gln Glu Ala Leu Ser Gln Leu Asp Phe Gln Trp Glu Lys Val
        2075                2080                2085

Asn Lys Met Tyr Lys Asp Arg Gln Gly Arg Phe Asp Arg Ser Val
        2090                2095                2100

Glu Lys Trp Arg Arg Phe His Tyr Asp Ile Lys Ile Phe Asn Gln
        2105                2110                2115

Trp Leu Thr Glu Ala Glu Gln Phe Leu Arg Lys Thr Gln Ile Pro
        2120                2125                2130

Glu Asn Trp Glu His Ala Lys Tyr Lys Trp Tyr Leu Lys Glu Leu
        2135                2140                2145

Gln Asp Gly Ile Gly Gln Arg Gln Thr Val Val Arg Thr Leu Asn
        2150                2155                2160

Ala Thr Gly Glu Glu Ile Ile Gln Gln Ser Ser Lys Thr Asp Ala
        2165                2170                2175
```

-continued

Ser Ile Leu Gln Glu Lys Leu Gly Ser Leu Asn Leu Arg Trp Gln
2180                2185                2190

Glu Val Cys Lys Gln Leu Ser Asp Arg Lys Lys Arg Leu Glu Glu
2195                2200                2205

Gln Lys Asn Ile Leu Ser Glu Phe Gln Arg Asp Leu Asn Glu Phe
2210                2215                2220

Val Leu Trp Leu Glu Glu Ala Asp Asn Ile Ala Ser Ile Pro Leu
2225                2230                2235

Glu Pro Gly Lys Glu Gln Gln Leu Lys Glu Lys Leu Glu Gln Val
2240                2245                2250

Lys Leu Leu Val Glu Glu Leu Pro Leu Arg Gln Gly Ile Leu Lys
2255                2260                2265

Gln Leu Asn Glu Thr Gly Gly Pro Val Leu Val Ser Ala Pro Ile
2270                2275                2280

Ser Pro Glu Glu Gln Asp Lys Leu Glu Asn Lys Leu Lys Gln Thr
2285                2290                2295

Asn Leu Gln Trp Ile Lys Val Ser Arg Ala Leu Pro Glu Lys Gln
2300                2305                2310

Gly Glu Ile Glu Ala Gln Ile Lys Asp Leu Gly Gln Leu Glu Lys
2315                2320                2325

Lys Leu Glu Asp Leu Glu Glu Gln Leu Asn His Leu Leu Leu Trp
2330                2335                2340

Leu Ser Pro Ile Arg Asn Gln Leu Glu Ile Tyr Asn Gln Pro Asn
2345                2350                2355

Gln Glu Gly Pro Phe Asp Val Gln Glu Thr Glu Ile Ala Val Gln
2360                2365                2370

Ala Lys Gln Pro Asp Val Glu Glu Ile Leu Ser Lys Gly Gln His
2375                2380                2385

Leu Tyr Lys Glu Lys Pro Ala Thr Gln Pro Val Lys Arg Lys Leu
2390                2395                2400

Glu Asp Leu Ser Ser Glu Trp Lys Ala Val Asn Arg Leu Leu Gln
2405                2410                2415

Glu Leu Arg Ala Lys Gln Pro Asp Leu Ala Pro Gly Leu Thr Thr
2420                2425                2430

Ile Gly Ala Ser Pro Thr Gln Thr Val Thr Leu Val Thr Gln Pro
2435                2440                2445

Val Val Thr Lys Glu Thr Ala Ile Ser Lys Leu Glu Met Pro Ser
2450                2455                2460

Ser Leu Met Leu Glu Val Pro Ala Leu Ala Asp Phe Asn Arg Ala
2465                2470                2475

Trp Thr Glu Leu Thr Asp Trp Leu Ser Leu Leu Asp Gln Val Ile
2480                2485                2490

Lys Ser Gln Arg Val Met Val Gly Asp Leu Glu Asp Ile Asn Glu
2495                2500                2505

Met Ile Ile Lys Gln Lys Ala Thr Met Gln Asp Leu Glu Gln Arg
2510                2515                2520

Arg Pro Gln Leu Glu Glu Leu Ile Thr Ala Ala Gln Asn Leu Lys
2525                2530                2535

Asn Lys Thr Ser Asn Gln Glu Ala Arg Thr Ile Ile Thr Asp Arg
2540                2545                2550

Ile Glu Arg Ile Gln Asn Gln Trp Asp Glu Val Gln Glu His Leu
2555                2560                2565

```
Gln Asn Arg Arg Gln Gln Leu Asn Glu Met Leu Lys Asp Ser Thr
2570                2575                2580

Gln Trp Leu Glu Ala Lys Glu Glu Ala Glu Gln Val Leu Gly Gln
2585                2590                2595

Ala Arg Ala Lys Leu Glu Ser Trp Lys Glu Gly Pro Tyr Thr Val
2600                2605                2610

Asp Ala Ile Gln Lys Lys Ile Thr Glu Thr Lys Gln Leu Ala Lys
2615                2620                2625

Asp Leu Arg Gln Trp Gln Thr Asn Val Asp Val Ala Asn Asp Leu
2630                2635                2640

Ala Leu Lys Leu Leu Arg Asp Tyr Ser Ala Asp Asp Thr Arg Lys
2645                2650                2655

Val His Met Ile Thr Glu Asn Ile Asn Ala Ser Trp Arg Ser Ile
2660                2665                2670

His Lys Arg Val Ser Glu Arg Glu Ala Ala Leu Glu Glu Thr His
2675                2680                2685

Arg Leu Leu Gln Gln Phe Pro Leu Asp Leu Glu Lys Phe Leu Ala
2690                2695                2700

Trp Leu Thr Glu Ala Glu Thr Thr Ala Asn Val Leu Gln Asp Ala
2705                2710                2715

Thr Arg Lys Glu Arg Leu Leu Glu Asp Ser Lys Gly Val Lys Glu
2720                2725                2730

Leu Met Lys Gln Trp Gln Asp Leu Gln Gly Glu Ile Glu Ala His
2735                2740                2745

Thr Asp Val Tyr His Asn Leu Asp Glu Asn Ser Gln Lys Ile Leu
2750                2755                2760

Arg Ser Leu Glu Gly Ser Asp Asp Ala Val Leu Leu Gln Arg Arg
2765                2770                2775

Leu Asp Asn Met Asn Phe Lys Trp Ser Glu Leu Arg Lys Lys Ser
2780                2785                2790

Leu Asn Ile Arg Ser His Leu Glu Ala Ser Ser Asp Gln Trp Lys
2795                2800                2805

Arg Leu His Leu Ser Leu Gln Glu Leu Leu Val Trp Leu Gln Leu
2810                2815                2820

Lys Asp Asp Glu Leu Ser Arg Gln Ala Pro Ile Gly Gly Asp Phe
2825                2830                2835

Pro Ala Val Gln Lys Gln Asn Asp Val His Arg Ala Phe Lys Arg
2840                2845                2850

Glu Leu Lys Thr Lys Glu Pro Val Ile Met Ser Thr Leu Glu Thr
2855                2860                2865

Val Arg Ile Phe Leu Thr Glu Gln Pro Leu Glu Gly Leu Glu Lys
2870                2875                2880

Leu Tyr Gln Glu Pro Arg Glu Leu Pro Pro Glu Glu Arg Ala Gln
2885                2890                2895

Asn Val Thr Arg Leu Leu Arg Lys Gln Ala Glu Glu Val Asn Thr
2900                2905                2910

Glu Trp Glu Lys Leu Asn Leu His Ser Ala Asp Trp Gln Arg Lys
2915                2920                2925

Ile Asp Glu Thr Leu Glu Arg Leu Gln Glu Leu Gln Glu Ala Thr
2930                2935                2940

Asp Glu Leu Asp Leu Lys Leu Arg Gln Ala Glu Val Ile Lys Gly
2945                2950                2955

Ser Trp Gln Pro Val Gly Asp Leu Leu Ile Asp Ser Leu Gln Asp
```

-continued

```
                  2960                2965                2970
His Leu Glu Lys Val Lys Ala Leu Arg Gly Glu Ile Ala Pro Leu
    2975                2980                2985
Lys Glu Asn Val Ser His Val Asn Asp Leu Ala Arg Gln Leu Thr
    2990                2995                3000
Thr Leu Gly Ile Gln Leu Ser Pro Tyr Asn Leu Ser Thr Leu Glu
    3005                3010                3015
Asp Leu Asn Thr Arg Trp Lys Leu Leu Gln Val Ala Val Glu Asp
    3020                3025                3030
Arg Val Arg Gln Leu His Glu Ala His Arg Asp Phe Gly Pro Ala
    3035                3040                3045
Ser Gln His Phe Leu Ser Thr Ser Val Gln Gly Pro Trp Glu Arg
    3050                3055                3060
Ala Ile Ser Pro Asn Lys Val Pro Tyr Tyr Ile Asn His Glu Thr
    3065                3070                3075
Gln Thr Thr Cys Trp Asp His Pro Lys Met Thr Glu Leu Tyr Gln
    3080                3085                3090
Ser Leu Ala Asp Leu Asn Asn Val Arg Phe Ser Ala Tyr Arg Thr
    3095                3100                3105
Ala Met Lys Leu Arg Arg Leu Gln Lys Ala Leu Cys Leu Asp Leu
    3110                3115                3120
Leu Ser Leu Ser Ala Ala Cys Asp Ala Leu Asp Gln His Asn Leu
    3125                3130                3135
Lys Gln Asn Asp Gln Pro Met Asp Ile Leu Gln Ile Ile Asn Cys
    3140                3145                3150
Leu Thr Thr Ile Tyr Asp Arg Leu Glu Gln Glu His Asn Asn Leu
    3155                3160                3165
Val Asn Val Pro Leu Cys Val Asp Met Cys Leu Asn Trp Leu Leu
    3170                3175                3180
Asn Val Tyr Asp Thr Gly Arg Thr Gly Arg Ile Arg Val Leu Ser
    3185                3190                3195
Phe Lys Thr Gly Ile Ile Ser Leu Cys Lys Ala His Leu Glu Asp
    3200                3205                3210
Lys Tyr Arg Tyr Leu Phe Lys Gln Val Ala Ser Ser Thr Gly Phe
    3215                3220                3225
Cys Asp Gln Arg Arg Leu Gly Leu Leu Leu His Asp Ser Ile Gln
    3230                3235                3240
Ile Pro Arg Gln Leu Gly Glu Val Ala Ser Phe Gly Gly Ser Asn
    3245                3250                3255
Ile Glu Pro Ser Val Arg Ser Cys Phe Gln Phe Ala Asn Asn Lys
    3260                3265                3270
Pro Glu Ile Glu Ala Ala Leu Phe Leu Asp Trp Met Arg Leu Glu
    3275                3280                3285
Pro Gln Ser Met Val Trp Leu Pro Val Leu His Arg Val Ala Ala
    3290                3295                3300
Ala Glu Thr Ala Lys His Gln Ala Lys Cys Asn Ile Cys Lys Glu
    3305                3310                3315
Cys Pro Ile Ile Gly Phe Arg Tyr Arg Ser Leu Lys His Phe Asn
    3320                3325                3330
Tyr Asp Ile Cys Gln Ser Cys Phe Phe Ser Gly Arg Val Ala Lys
    3335                3340                3345
Gly His Lys Met His Tyr Pro Met Val Glu Tyr Cys Thr Pro Thr
    3350                3355                3360
```

| | | | | | | | | | |
|---|---|---|---|---|---|---|---|---|---|
| Thr | Ser | Gly | Glu | Asp | Val | Arg | Asp | Phe | Ala | Lys | Val | Leu | Lys | Asn |
| | 3365 | | | | 3370 | | | | 3375 | | | |

Thr Ser Gly Glu Asp Val Arg Asp Phe Ala Lys Val Leu Lys Asn
    3365               3370               3375

Lys Phe Arg Thr Lys Arg Tyr Phe Ala Lys His Pro Arg Met Gly
    3380               3385               3390

Tyr Leu Pro Val Gln Thr Val Leu Glu Gly Asp Asn Met Glu Thr
    3395               3400               3405

Pro Val Thr Leu Ile Asn Phe Trp Pro Val Asp Ser Ala Pro Ala
    3410               3415               3420

Ser Ser Pro Gln Leu Ser His Asp Asp Thr His Ser Arg Ile Glu
    3425               3430               3435

His Tyr Ala Ser Arg Leu Ala Glu Met Glu Asn Ser Asn Gly Ser
    3440               3445               3450

Tyr Leu Asn Asp Ser Ile Ser Pro Asn Glu Ser Ile Asp Asp Glu
    3455               3460               3465

His Leu Leu Ile Gln His Tyr Cys Gln Ser Leu Asn Gln Asp Ser
    3470               3475               3480

Pro Leu Ser Gln Pro Arg Ser Pro Ala Gln Ile Leu Ile Ser Leu
    3485               3490               3495

Glu Ser Glu Glu Arg Gly Glu Leu Glu Arg Ile Leu Ala Asp Leu
    3500               3505               3510

Glu Glu Glu Asn Arg Asn Leu Gln Ala Glu Tyr Asp Arg Leu Lys
    3515               3520               3525

Gln Gln His Glu His Lys Gly Leu Ser Pro Leu Pro Ser Pro Pro
    3530               3535               3540

Glu Met Met Pro Thr Ser Pro Gln Ser Pro Arg Asp Ala Glu Leu
    3545               3550               3555

Ile Ala Glu Ala Lys Leu Leu Arg Gln His Lys Gly Arg Leu Glu
    3560               3565               3570

Ala Arg Met Gln Ile Leu Glu Asp His Asn Lys Gln Leu Glu Ser
    3575               3580               3585

Gln Leu His Arg Leu Arg Gln Leu Leu Glu Gln Pro Gln Ala Glu
    3590               3595               3600

Ala Lys Val Asn Gly Thr Thr Val Ser Ser Pro Ser Thr Ser Leu
    3605               3610               3615

Gln Arg Ser Asp Ser Ser Gln Pro Met Leu Leu Arg Val Val Gly
    3620               3625               3630

Ser Gln Thr Ser Asp Ser Met Gly Glu Glu Asp Leu Leu Ser Pro
    3635               3640               3645

Pro Gln Asp Thr Ser Thr Gly Leu Glu Glu Val Met Glu Gln Leu
    3650               3655               3660

Asn Asn Ser Phe Pro Ser Ser Arg Gly Arg Asn Thr Pro Gly Lys
    3665               3670               3675

Pro Met Arg Glu Asp Thr Met
    3680               3685

<210> SEQ ID NO 2
<211> LENGTH: 13957
<212> TYPE: DNA
<213> ORGANISM: Homo sapiens

<400> SEQUENCE: 2
gggattccct cactttcccc ctacaggact cagatctggg aggcaattac cttcggagaa    60
aaacgaatag gaaaaactga agtgttactt tttttaaagc tgctgaagtt tgttggtttc   120

-continued

```
tcattgtttt taagcctact ggagcaataa agtttgaaga acttttacca ggttttttt      180
atcgctgcct tgatatacac ttttcaaaat gctttggtgg gaagaagtag aggactgtta     240
tgaaagagaa gatgttcaaa agaaaacatt cacaaaatgg gtaaatgcac aattttctaa    300
gtttgggaag cagcatattg agaacctctt cagtgaccta caggatggga ggcgcctcct    360
agacctcctc gaaggcctga cagggcaaaa actgccaaaa gaaaaaggat ccacaagagt    420
tcatgccctg aacaatgtca acaaggcact gcgggttttg cagaacaata atgttgattt    480
agtgaatatt ggaagtactg acatcgtaga tggaaatcat aaactgactc ttggtttgat    540
ttggaatata atcctccact ggcaggtcaa aaatgtaatg aaaaatatca tggctggatt    600
gcaacaaacc aacagtgaaa agattctcct gagctgggtc cgacaatcaa ctcgtaatta    660
tccacaggtt aatgtaatca acttcaccac cagctggtct gatggcctgg ctttgaatgc    720
tctcatccat agtcataggc cagacctatt tgactggaat agtgtggttt gccagcagtc    780
agccacacaa cgactggaac atgcattcaa catcgccaga tatcaattag catagagaa     840
actactcgat cctgaagatg ttgataccac ctatccagat aagaagtcca tcttaatgta    900
catcacatca ctcttccaag ttttgcctca acaagtgagc attgaagcca tccaggaagt    960
ggaaatgttg ccaaggccac ctaaagtgac taaagaagaa catttcagt tacatcatca     1020
aatgcactat tctcaacaga tcacggtcag tctagcacag ggatatgaga gaacttcttc    1080
ccctaagcct cgattcaaga gctatgccta cacacaggct gcttatgtca ccacctctga    1140
ccctacacgg agcccatttc cttcacagca tttggaagct cctgaagaca agtcatttgg    1200
cagttcattg atggagagtg aagtaaacct ggaccgttat caaacagctt tagaagaagt    1260
attatcgtgg cttctttctg ctgaggacac attgcaagca caggagaga tttctaatga     1320
tgtggaagtg gtgaaagacc agtttcatac tcatgagggg tacatgatgg atttgacagc    1380
ccatcagggc cgggttggta atattctaca attgggaagt aagctgattg aacaggaaa     1440
attatcagaa gatgaagaaa ctgaagtaca agagcagatg aatctcctaa attcaagatg    1500
ggaatgcctc agggtagcta gcatggaaaa acaaagcaat ttacatagag ttttaatgga    1560
tctccagaat cagaaactga agagttgaa tgactggcta acaaaaacag aagaaagaac     1620
aaggaaaatg gaggaagagc ctcttggacc tgatcttgaa gacctaaaac gccaagtaca    1680
acaacataag gtgcttcaag aagatctaga acaagaacaa gtcagggtca attctctcac    1740
tcacatggtg gtggtagttg atgaatctag tggagatcac gcaactgctg ctttggaaga    1800
acaacttaag gtattgggag atcgatgggc aaacatctgt agatggacag aagaccgctg    1860
ggttctttta caagacatcc ttctcaaatg gcaacgtctt actgaagaac agtgcctttt    1920
tagtgcatgg ctttcagaaa aagaagatgc agtgaacaag attcacacaa ctggctttaa    1980
agatcaaaat gaaatgttat caagtcttca aaaactggcc gttttaaaag cggatctaga    2040
aaagaaaaag caatccatgg gcaaactgta ttcactcaaa caagatcttc tttcaacact    2100
gaagaataag tcagtgaccc agaagacgga agcatggctg gataactttg cccggtgttg    2160
ggataatttta gtccaaaaac ttgaaaagag tacagcacag atttcacagg ctgtcaccac    2220
cactcagcca tcactaacac agacaactgt aatggaaaca gtaactacgg tgaccacaag    2280
ggaacagatc ctggtaaagc atgctcaaga ggaacttcca ccaccacctc cccaaaagaa    2340
gaggcagatt actgtggatt ctgaaattag gaaaaggttg gatgttgata taactgaact    2400
tcacagctgg attactcgct cagaagctgt gttgcagagt cctgaatttg caatctttcg    2460
gaaggaaggc aacttctcag acttaaaaga aaaagtcaat gccatagagc gagaaaaagc    2520
```

```
tgagaagttc agaaaactgc aagatgccag cagatcagct caggccctgg tggaacagat    2580
ggtgaatgag ggtgttaatg cagatagcat caaacaagcc tcagaacaac tgaacagccg    2640
gtggatcgaa ttctgccagt tgctaagtga gagacttaac tggctggagt atcagaacaa    2700
catcatcgct ttctataatc agctacaaca attggagcag atgacaacta ctgctgaaaa    2760
ctggttgaaa atccaaccca ccaccccatc agagccaaca gcaattaaaa gtcagttaaa    2820
aatttgtaag gatgaagtca accggctatc aggtcttcaa cctcaaattg aacgattaaa    2880
aattcaaagc atagccctga agagaaagg acaaggaccc atgttcctgg atgcagactt    2940
tgtggccttt acaaatcatt ttaagcaagt cttttctgat gtgcaggcca gagagaaga    3000 gctacagaca attttgaca ctttgccacc aatgcgctat caggagacca tgagtgccat    3060
caggacatgg gtccagcagt cagaaaccaa actctccata cctcaactta gtgtcaccga    3120
ctatgaaatc atggagcaga gactcgggga attgcaggct ttacaaagtt ctctgcaaga    3180
gcaacaaagt ggcctatact atctcagcac cactgtgaaa gagatgtcga agaaagcgcc    3240
ctctgaaatt agccggaaat atcaatcaga atttgaagaa attgagggac gctggaagaa    3300
gctctcctcc cagctggttg agcattgtca aaagctagag gagcaaatga ataaactccg    3360
aaaaattcag aatcacatac aaaccctgaa gaaatggatg gctgaagttg atgtttttct    3420
gaaggaggaa tggcctgccc ttggggattc agaaattcta aaaaagcagc tgaaacagtg    3480
cagactttta gtcagtgata ttcagacaat tcagcccagt ctaaacagtg tcaatgaagg    3540
tgggcagaag ataaagaatg aagcagagcc agagtttgct tcgagacttg agacagaact    3600
caaagaactt aacactcagt gggatcacat gtgccaacag gtctatgcca gaaaggaggc    3660
cttgaaggga ggtttggaga aaactgtaag cctccagaaa gatctatcag agatgcacga    3720
atggatgaca caagctgaag aagagtatct tgagagagat tttgaatata aaactccaga    3780
tgaattacag aaaagcagttg aagagatgaa gagagctaaa gaagaggccc aacaaaaaga    3840
agcgaaagtg aaactcctta ctgagtctgt aaatagtgtc atagctcaag ctccacctgt    3900
agcacaagag gccttaaaaa aggaacttga aactctaacc accaactacc agtggctctg    3960
cactaggctg aatgggaaat gcaagacttt ggaagaagtt tgggcatgtt ggcatgagtt    4020
attgtcatac ttggagaaag caaacaagtg gctaaatgaa gtagaattta aacttaaaac    4080
cactgaaaac attcctggcg gagctgagga atctctgag gtgctagatt cacttgaaaa    4140
tttgatgcga cattcagagg ataacccaaa tcagattcgc atattggcac agaccctaac    4200
agatggcgga gtcatggatg agctaatcaa tgaggaactt gagacattta attctcgttg    4260
gagggaacta catgaagagg ctgtaaggag gcaaaagttg cttgaacaga gcatccagtc    4320
tgcccaggag actgaaaaat ccttacactt aatccaggag tccctcacat tcattgacaa    4380
gcagttggca gcttatattg cagacaaggt ggacgcagct caaatgcctc aggaagccca    4440
gaaaatccaa tctgatttga caagtcatga gatcagttta aagaaatga agaaacataa    4500 tcaggggaag gaggctgccc aaagagtcct gtctcagatt gatgttgcac agaaaaaatt    4560
acaagatgtc tccatgaagt ttcgattatt ccagaaacca gccaattttg agcagcgtct    4620
acaagaaagt aagatgattt tagatgaagt gaagatgcac ttgcctgcat ggaaacaaa    4680 gagtgtggaa caggaagtag tacagtcaca gctaaatcat tgtgtgaact tgtataaaag    4740
tctgagtgaa gtgaagtctg aagtggaaat ggtgataaag actggacgtc agattgtaca    4800
gaaaaagcag acggaaaatc ccaaagaact tgatgaaaga gtaacagctt tgaaattgca    4860
```

```
ttataatgag ctgggagcaa aggtaacaga aagaaagcaa cagttggaga aatgcttgaa    4920
attgtcccgt aagatgcgaa aggaaatgaa tgtcttgaca gaatggctgg cagctacaga    4980
tatggaattg acaaagagat cagcagttga aggaatgcct agtaatttgg attctgaagt    5040
tgcctgggga aaggctactc aaaaagagat tgagaaacag aaggtgcacc tgaagagtat    5100
cacagaggta ggagaggcct tgaaaacagt tttgggcaag aaggagacgt tggtggaaga    5160
taaactcagt cttctgaata gtaactggat agctgtcacc tcccgagcag aagagtggtt    5220
aaatcttttg ttggaatacc agaaacacat ggaaactttt gaccagaatg tggaccacat    5280
cacaaagtgg atcattcagg ctgacacact tttggatgaa tcagagaaaa agaaacccca    5340
gcaaaaagaa gacgtgctta agcgtttaaa ggcagaactg aatgacatac gcccaaaggt    5400
ggactctaca cgtgaccaag cagcaaactt gatggcaaac cgcggtgacc actgcaggaa    5460
attagtagag ccccaaatct cagagctcaa ccatcgattt gcagccattt cacacagaat    5520
taagactgga aaggcctcca ttcctttgaa ggaattggag cagtttaact cagatataca    5580
aaaattgctt gaaccactgg aggctgaaat tcagcagggg gtgaatctga agaggaaga    5640
cttcaataaa gatatgaatg aagacaatga gggtactgta aaagaattgt tgcaaagagg    5700
agacaactta caacaaagaa tcacagatga gagaaagaga gaggaaataa agataaaaca    5760
gcagctgtta cagacaaaac ataatgctct caaggatttg aggtctcaaa gaagaaaaa    5820
ggctctagaa atttctcatc agtggtatca gtacaagagg caggctgatg atctcctgaa    5880
atgcttggat gacattgaaa aaaaattagc cagcctacct gagcccagag atgaaaggaa    5940
aataaaggaa attgatcggg aattgcagaa gaagaaagag gagctgaatg cagtgcgtag    6000
gcaagctgag ggcttgtctg aggatggggc cgcaatggca gtggagccaa ctcagatcca    6060
gctcagcaag cgctggcggg aaattgagag caaatttgct cagtttcgaa gactcaactt    6120
tgcacaaatt cacactgtcc gtgaagaaac gatgatggtg atgactgaag acatgccttt    6180
ggaaatttct tatgtgcctt ctacttattt gactgaaatc actcatgtct cacaagccct    6240
attagaagtg gaacaacttc tcaatgctcc tgacctctgt gctaaggact tgaagatct    6300
ctttaagcaa gaggagtctc tgaagaatat aaaagatagt ctacaacaaa gctcaggtcg    6360
gattgacatt attcatagca agaagacagc agcattgcaa agtgcaacgc ctgtggaaag    6420
ggtgaagcta caggaagctc tctcccagct tgatttccaa tgggaaaaag ttaacaaaat    6480
gtacaaggac cgacaagggc gatttgacag atctgttgag aaatggcggc gttttcatta    6540
tgatataaag atatttaatc agtggctaac agaagctgaa cagtttctca gaaagacaca    6600
aattcctgag aattgggaac atgctaaata caaatggtat cttaaggaac tccaggatgg    6660
cattgggcag cggcaaactg ttgtcagaac attgaatgca actggggaag aaataattca    6720
gcaatcctca aaaacagatg ccagtattct acaggaaaaa ttgggaagcc tgaatctgcg    6780
gtggcaggag gtctgcaaac agctgtcaga cagaaaaaag aggctagaag aacaaaagaa    6840
tatcttgtca gaatttcaaa gagatttaaa tgaatttgtt ttatggttgg aggaagcaga    6900
taacattgct agtatcccac ttgaacctgg aaaagagcag caactaaaag aaaagcttga    6960
gcaagtcaag ttactggtgg aagagttgcc cctgcgccag ggaattctca acaattaaa    7020
tgaaactgga ggacccgtgc ttgtaagtgc tcccataagc ccagaagagc aagataaact    7080
tgaaaataag ctcaagcaga caaatctcca gtggataaag gtttccagag ctttacctga    7140
gaaacaagga gaaattgaag ctcaaataaa agaccttggg cagcttgaaa aaagcttga    7200
agaccttgaa gagcagttaa atcatctgct gctgtggtta tctcctatta ggaatcagtt    7260
```

```
ggaaatttat aaccaaccaa accaagaagg accatttgac gttcaggaaa ctgaaatagc   7320
agttcaagct aaacaaccgg atgtggaaga gattttgtct aaagggcagc atttgtacaa   7380
ggaaaaacca gccactcagc cagtgaagag gaagttagaa gatctgagct ctgagtggaa   7440
ggcggtaaac cgtttacttc aagagctgag ggcaaagcag cctgacctag ctcctggact   7500
gaccactatt ggagcctctc ctactcagac tgttactctg gtgacacaac ctgtggttac   7560
taaggaaact gccatctcca aactagaaat gccatcttcc ttgatgttgg aggtacctgc   7620
tctggcagat ttcaaccggg cttggacaga acttaccgac tggctttctc tgcttgatca   7680
agttataaaa tcacagaggg tgatggtggg tgaccttgag gatatcaacg agatgatcat   7740
caagcagaag gcaacaatgc aggatttgga acagaggcgt ccccagttgg aagaactcat   7800
taccgctgcc caaaatttga aaacaagac cagcaatcaa gaggctagaa caatcattac   7860
ggatcgaatt gaaagaattc agaatcagtg ggatgaagta caagaacacc ttcagaaccg   7920
gaggcaacag ttgaatgaaa tgttaaagga ttcaacacaa tggctggaag ctaaggaaga   7980
agctgagcag gtcttaggac aggccagagc caagcttgag tcatggaagg agggtcccta   8040
tacagtagat gcaatccaaa agaaaatcac agaaaccaag cagttggcca agacctccg   8100 ccagtggcag acaaatgtag atgtggcaaa tgacttggcc ctgaaacttc tccgggatta   8160
ttctgcagat gataccagaa aagtccacat gataacagag aatatcaatg cctcttggag   8220
aagcattcat aaaagggtga gtgagcgaga ggctgctttg gaagaaactc atagattact   8280
gcaacagttc cccctggacc tggaaaagtt tcttgcctgg cttacagaag ctgaaacaac   8340
tgccaatgtc ctacaggatg ctacccgtaa ggaaaggctc tagaagact ccaagggagt   8400 aaaagagctg atgaaacaat ggcaagacct ccaaggtgaa attgaagctc acacagatgt   8460
ttatcacaac ctggatgaaa acagccaaaa aatcctgaga tccctggaag gttccgatga   8520
tgcagtcctg ttacaaagac gtttggataa catgaacttc aagtggagtg aacttcggaa   8580
aaagtctctc aacattaggt cccatttgga agccagttct gaccagtgga agcgtctgca   8640
cctttctctg caggaacttc tggtgtggct acagctgaaa gatgatgaat taagccggca   8700
ggcacctatt ggaggcgact tccagcagt tcagaagcag aacgatgtac ataggggcctt   8760 caagagggaa ttgaaaacta agaacctgt aatcatgagt actcttgaga ctgtacgaat   8820
atttctgaca gagcagcctt tggaaggact agagaaactc taccaggagc ccagagagct   8880
gcctcctgag gagagagccc agaatgtcac tcggcttcta cgaaagcagg ctgaggaggt   8940
caatactgag tgggaaaaat tgaacctgca ctccgctgac tggcagagaa aaatagatga   9000
gacccttgaa agactccagg aacttcaaga ggccacggat gagctggacc tcaagctgcg   9060
ccaagctgag gtgatcaagg atcctggca gcccgtgggc gatctcctca ttgactctct   9120
ccaagatcac ctcgagaaag tcaaggcact tcgaggagaa attgcgcctc tgaaagagaa   9180
cgtgagccac gtcaatgacc ttgctcgcca gcttaccact ttgggcattc agctctcacc   9240
gtataacctc agcactctgg aagacctgaa caccagatgg aagcttctgc aggtggccgt   9300
cgaggaccga gtcaggcagc tgcatgaagc ccacagggac tttggtccag catctcagca   9360 cttctttcc acgtctgtcc agggtccctg ggagagagcc atctcgccaa acaaagtgcc   9420
ctactatatc aaccacgaga ctcaaacaac ttgctgggac catcccaaaa tgacagagct   9480
ctaccagtct ttagctgacc tgaataatgt cagattctca gcttatagga ctgccatgaa   9540
actccgaaga ctgcagaagg cccttttgctt ggatctcttg agcctgtcag ctgcatgtga   9600
```

```
tgccttggac cagcacaacc tcaagcaaaa tgaccagccc atggatatcc tgcagattat    9660
taattgtttg accactattt atgaccgcct ggagcaagag cacaacaatt tggtcaacgt    9720
ccctctctgc gtggatatgt gtctgaactg gctgctgaat gtttatgata cgggacgaac    9780
agggaggatc cgtgtcctgt cttttaaaac tggcatcatt tccctgtgta aagcacattt    9840
ggaagacaag tacagatacc ttttcaagca agtggcaagt tcaacaggat tttgtgacca    9900
gcgcaggctg ggcctccttc tgcatgattc tatccaaatt ccaagacagt tgggtgaagt    9960
tgcatccttt gggggcagta acattgagcc aagtgtccgg agctgcttcc aatttgctaa   10020
taataagcca gagatcgaag cggccctctt cctagactgg atgagactgg aacccccagtc  10080 catggtgtgg ctgcccgtcc tgcacagagt ggctgctgca gaaactgcca agcatcaggc   10140
caaatgtaac atctgcaaag agtgtccaat cattggattc aggtacagga gtctaaagca   10200
ctttaattat gacatctgcc aaagctgctt tttttctggt cgagttgcaa aaggccataa   10260
aatgcactat cccatggtgg aatattgcac tccgactaca tcaggagaag atgttcgaga   10320
ctttgccaag gtactaaaaa acaaatttcg aaccaaaagg tattttgcga agcatccccg   10380
aatgggctac ctgccagtgc agactgtctt agaggggac aacatggaaa ctcccgttac    10440
tctgatcaac ttctggccag tagattctgc gcctgcctcg tccctcagc tttcacacga     10500 tgatactcat tcacgcattg aacattatgc tagcaggcta gcagaaatgg aaaacagcaa   10560
tggatcttat ctaaatgata gcatctctcc taatgagagc atagatgatg aacatttgtt   10620
aatccagcat tactgccaaa gtttgaacca ggactccccc ctgagccagc ctcgtagtcc   10680
tgcccagatc ttgatttcct tagagagtga ggaaagaggg gagctagaga gaatcctagc   10740
agatcttgag gaagaaaaca ggaatctgca agcagaatat gaccgtctaa gcagcagca   10800 cgaacataaa ggcctgtccc cactgccgtc ccctcctgaa atgatgccca cctctcccca   10860
gagtccccgg gatgctgagc tcattgctga ggccaagcta ctgcgtcaac acaaaggccg   10920
cctggaagcc aggatgcaaa tcctggaaga ccacaataaa cagctggagt cacagttaca   10980
caggctaagg cagctgctgg agcaaccccca ggcagaggcc aaagtgaatg cacaacggt   11040 gtcctctcct tctacctctc tacagaggtc cgacagcagt cagcctatgc tgctccgagt   11100
ggttggcagt caaacttcgg actccatggg tgaggaagat cttctcagtc ctccccagga   11160
cacaagcaca gggttagagg aggtgatgga gcaactcaac aactccttcc ctagttcaag   11220
aggaagaaat acccctggaa agccaatgag agaggacaca atgtaggaag tcttttccac   11280
atggcagatg atttgggcag agcgatggag tccttagtat cagtcatgac agatgaagaa   11340
ggagcagaat aaatgtttta caactcctga ttcccgcatg gttttataa tattcataca    11400 acaaagagga ttagacagta agagtttaca agaaataaat ctatattttt gtgaagggta   11460
gtggtattat actgtagatt tcagtagttt ctaagtctgt tattgttttg ttaacaatgg   11520
caggttttac acgtctatgc aattgtacaa aaaagttata agaaaactac atgtaaaatc   11580
ttgatagcta ataacttgc catttcttta tatggaacgc attttgggtt gtttaaaaat    11640
ttataacagt tataagaaa gattgtaaac taagtgtgc tttataaaaa aaagttgttt     11700 ataaaaccc ctaaaacaa acaaacaca cacacacaca catacacaca cacacacaaa      11760
actttgaggc agcgcattgt tttgcatcct tttggcgtga tatccatatg aaattcatgg   11820 ctttttctttt ttttgcatat taaagataag acttcctcta ccaccacacc aaatgactac  11880
tacacactgc tcatttgaga actgtcagct gagtggggca ggcttgagtt ttcatttcat   11940
atatctatat gtctataagt atataaatac tatagttata tagataaaga gatacgaatt   12000
```

```
tctatagact gacttttcc attttttaaa tgttcatgtc acatcctaat agaaagaaat    12060
tacttctagt cagtcatcca ggcttacctg cttggtctag aatggatttt tcccggagcc    12120
ggaagccagg aggaaactac accacactaa acattgtct acagctccag atgtttctca     12180
ttttaaacaa ctttccactg acaacgaaag taaagtaaag tattggatt ttttaaaggg     12240
aacatgtgaa tgaatacaca ggacttatta tatcagagtg agtaatcggt tggttggttg    12300
attgattgat tgattgatac attcagcttc ctgctgctag caatgccacg atttagattt    12360
aatgatgctt cagtggaaat caatcagaag gtattctgac cttgtgaaca tcagaaggta    12420
ttttttaact cccaagcagt agcaggacga tgatagggct ggagggctat ggattcccag    12480
cccatccctg tgaaggagta ggccactctt aagtgaagg attggatgat tgttcataat     12540
acataaagtt ctctgtaatt acaactaaat tattatgccc tcttctcaca gtcaaaagga    12600
actgggtggt ttggtttttg ttgctttttt agatttattg tcccatgtgg gatgagtttt    12660
taaatgccac aagacataat ttaaaataaa taaactttgg gaaaaggtgt aagacagtag    12720
ccccatcaca tttgtgatac tgacaggtat caacccagaa gcccatgaac tgtgtttcca    12780
tcctttgcat ttctctgcga gtagttccac acaggtttgt aagtaagtaa gaaagaaggc    12840
aaattgattc aaatgttaca aaaaaccct tcttggtgga ttagacaggt taaatatata    12900
aacaaacaaa caaaaattgc tcaaaaaaga ggagaaaagc tcaagaggaa aagctaagga    12960
ctggtaggaa aaagctttac tctttcatgc cattttattt cttttgatt tttaaatcat     13020
tcattcaata gataccaccg tgtgacctat aattttgcaa atctgttacc tctgacatca    13080
agtgtaatta gcttttggag agtgggctga catcaagtgt aattagcttt tggagagtgg    13140
gttttgtcca ttattaataa ttaattaatt aacatcaaac acggcttctc atgctatttc    13200
tacctcactt tggttttggg gtgttcctga taattgtgca cacctgagtt cacagcttca    13260
ccacttgtcc attgcgttat tttcttttc ctttataatt cttctttttt ccttcataat    13320
tttcaaaaga aaccccaaag ctctaaggta acaaattacc aaattacatg aagatttggt    13380
ttttgtcttg cattttttc ctttatgtga cgctggacct tttctttacc caaggatttt    13440
taaaactcag atttaaaaca aggggttact ttacatccta ctaagaagtt taagtaagta    13500
agtttcattc taaaatcaga ggtaaataga gtgcataaat aatttgttt taatcttttt    13560
gttttctttt tagacacatt agctctggag tgagtctgtc ataatatttg aacaaaaatt    13620
gagagcttta ttgctgcatt taagcataa ttaatttgga cattatttcg tgttgtgttc     13680
tttataacca ccgagtatta aactgtaaat cataatgtaa ctgaagcata aacatcacat    13740
ggcatgtttt gtcattgttt tcaggtactg agttcttact tgagtatcat aatatattgt    13800
gttttaacac caacactgta acatttacga attattttt taaacttcag ttttactgca    13860
ttttcacaac atatcagact tcaccaaata tatgccttac tattgtatta tagtactgct    13920
ttactgtgta tctcaataaa gcacgcagtt atgttac                            13957
```

<210> SEQ ID NO 3
<211> LENGTH: 252
<212> TYPE: PRT
<213> ORGANISM: Homo sapiens

<400> SEQUENCE: 3

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
```

```
                20                  25                  30
Gly Lys Gln His Ile Glu Asn Leu Phe Ser Asp Leu Gln Asp Gly Arg
            35                  40                  45

Arg Leu Leu Asp Leu Leu Glu Gly Leu Thr Gly Gln Lys Leu Pro Lys
        50                  55                  60

Glu Lys Gly Ser Thr Arg Val His Ala Leu Asn Asn Val Asn Lys Ala
65                  70                  75                  80

Leu Arg Val Leu Gln Asn Asn Val Asp Leu Val Asn Ile Gly Ser
                85                  90                  95

Thr Asp Ile Val Asp Gly Asn His Lys Leu Thr Leu Gly Leu Ile Trp
                100                 105                 110

Asn Ile Ile Leu His Trp Gln Val Lys Asn Val Met Lys Asn Ile Met
            115                 120                 125

Ala Gly Leu Gln Gln Thr Asn Ser Glu Lys Ile Leu Leu Ser Trp Val
        130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
                180                 185                 190

Thr Gln Arg Leu Glu His Ala Phe Asn Ile Ala Arg Tyr Gln Leu Gly
            195                 200                 205

Ile Glu Lys Leu Leu Asp Pro Glu Asp Val Asp Thr Thr Tyr Pro Asp
        210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu
                245                 250

<210> SEQ ID NO 4
<211> LENGTH: 85
<212> TYPE: PRT
<213> ORGANISM: Homo sapiens

<400> SEQUENCE: 4

Met Leu Pro Arg Pro Pro Lys Val Thr Lys Glu Glu His Phe Gln Leu
1               5                   10                  15

His His Gln Met His Tyr Ser Gln Gln Ile Thr Val Ser Leu Ala Gln
                20                  25                  30

Gly Tyr Glu Arg Thr Ser Ser Pro Lys Pro Arg Phe Lys Ser Tyr Ala
            35                  40                  45

Tyr Thr Gln Ala Ala Tyr Val Thr Thr Ser Asp Pro Thr Arg Ser Pro
        50                  55                  60

Phe Pro Ser Gln His Leu Glu Ala Pro Glu Asp Lys Ser Phe Gly Ser
65                  70                  75                  80

Ser Leu Met Glu Ser
                85

<210> SEQ ID NO 5
<211> LENGTH: 109
<212> TYPE: PRT
<213> ORGANISM: Homo sapiens

<400> SEQUENCE: 5

Glu Val Asn Leu Asp Arg Tyr Gln Thr Ala Leu Glu Glu Val Leu Ser
```

-continued

```
                1               5                    10                   15
           Trp Leu Leu Ser Ala Glu Asp Thr Leu Gln Ala Gln Gly Glu Ile Ser
                            20                   25                   30

Asn Asp Val Glu Val Val Lys Asp Gln Phe His Thr His Glu Gly Tyr
                            35                   40                   45

Met Met Asp Leu Thr Ala His Gln Gly Arg Val Gly Asn Ile Leu Gln
                            50                   55                   60

Leu Gly Ser Lys Leu Ile Gly Thr Gly Lys Leu Ser Glu Asp Glu Glu
            65                   70                   75                   80

Thr Glu Val Gln Glu Gln Met Asn Leu Leu Asn Ser Arg Trp Glu Cys
                            85                   90                   95

Leu Arg Val Ala Ser Met Glu Lys Gln Ser Asn Leu His
                            100                  105
```

<210> SEQ ID NO 6
<211> LENGTH: 111
<212> TYPE: PRT
<213> ORGANISM: Homo sapiens

<400> SEQUENCE: 6

```
           Arg Val Leu Met Asp Leu Gln Asn Gln Lys Leu Lys Glu Leu Asn Asp
            1               5                    10                   15

Trp Leu Thr Lys Thr Glu Glu Arg Thr Arg Lys Met Glu Glu Glu Pro
                            20                   25                   30

Leu Gly Pro Asp Leu Glu Asp Leu Lys Arg Gln Val Gln Gln His Lys
                            35                   40                   45

Val Leu Gln Glu Asp Leu Glu Gln Glu Gln Val Arg Val Asn Ser Leu
                            50                   55                   60

Thr His Met Val Val Val Asp Glu Ser Ser Gly Asp His Ala Thr
            65                   70                   75                   80

Ala Ala Leu Glu Glu Gln Leu Lys Val Leu Gly Asp Arg Trp Ala Asn
                            85                   90                   95

Ile Cys Arg Trp Thr Glu Asp Arg Trp Val Leu Leu Gln Asp Ile
                            100                  105                  110
```

<210> SEQ ID NO 7
<211> LENGTH: 111
<212> TYPE: PRT
<213> ORGANISM: Homo sapiens

<400> SEQUENCE: 7

```
           Leu Leu Lys Trp Gln Arg Leu Thr Glu Glu Cys Leu Phe Ser Ala
            1               5                    10                   15

Trp Leu Ser Glu Lys Glu Asp Ala Val Asn Lys Ile His Thr Thr Gly
                            20                   25                   30

Phe Lys Asp Gln Asn Glu Met Leu Ser Ser Leu Gln Lys Leu Ala Val
                            35                   40                   45

Leu Lys Ala Asp Leu Glu Lys Lys Gln Ser Met Gly Lys Leu Tyr
                            50                   55                   60

Ser Leu Lys Gln Asp Leu Leu Ser Thr Leu Lys Asn Lys Ser Val Thr
            65                   70                   75                   80

Gln Lys Thr Glu Ala Trp Leu Asp Asn Phe Ala Arg Cys Trp Asp Asn
                            85                   90                   95

Leu Val Gln Lys Leu Glu Lys Ser Thr Ala Gln Ile Ser Gln Ala
                            100                  105                  110
```

<210> SEQ ID NO 8
<211> LENGTH: 49
<212> TYPE: PRT
<213> ORGANISM: Homo sapiens

<400> SEQUENCE: 8

Val Thr Thr Thr Gln Pro Ser Leu Thr Gln Thr Thr Val Met Glu Thr
1               5                   10                  15

Val Thr Thr Val Thr Thr Arg Glu Gln Ile Leu Val Lys His Ala Gln
            20                  25                  30

Glu Glu Leu Pro Pro Pro Pro Gln Lys Lys Arg Gln Ile Thr Val
        35                  40                  45

Asp

<210> SEQ ID NO 9
<211> LENGTH: 111
<212> TYPE: PRT
<213> ORGANISM: Homo sapiens

<400> SEQUENCE: 9

Ser Glu Ile Arg Lys Arg Leu Asp Val Asp Ile Thr Glu Leu His Ser
1               5                   10                  15

Trp Ile Thr Arg Ser Glu Ala Val Leu Gln Ser Pro Glu Phe Ala Ile
            20                  25                  30

Phe Arg Lys Glu Gly Asn Phe Ser Asp Leu Lys Glu Lys Val Asn Ala
        35                  40                  45

Ile Glu Arg Glu Lys Ala Glu Lys Phe Arg Lys Leu Gln Asp Ala Ser
    50                  55                  60

Arg Ser Ala Gln Ala Leu Val Glu Gln Met Val Asn Glu Gly Val Asn
65                  70                  75                  80

Ala Asp Ser Ile Lys Gln Ala Ser Glu Gln Leu Asn Ser Arg Trp Ile
                85                  90                  95

Glu Phe Cys Gln Leu Leu Ser Glu Arg Leu Asn Trp Leu Glu Tyr
            100                 105                 110

<210> SEQ ID NO 10
<211> LENGTH: 109
<212> TYPE: PRT
<213> ORGANISM: Homo sapiens

<400> SEQUENCE: 10

Gln Asn Asn Ile Ile Ala Phe Tyr Asn Gln Leu Gln Gln Leu Glu Gln
1               5                   10                  15

Met Thr Thr Thr Ala Glu Asn Trp Leu Lys Ile Gln Pro Thr Thr Pro
            20                  25                  30

Ser Glu Pro Thr Ala Ile Lys Ser Gln Leu Lys Ile Cys Lys Asp Glu
        35                  40                  45

Val Asn Arg Leu Ser Gly Leu Gln Pro Gln Ile Glu Arg Leu Lys Ile
    50                  55                  60

Gln Ser Ile Ala Leu Lys Glu Lys Gly Gln Gly Pro Met Phe Leu Asp
65                  70                  75                  80

Ala Asp Phe Val Ala Phe Thr Asn His Phe Lys Gln Val Phe Ser Asp
                85                  90                  95

Val Gln Ala Arg Glu Lys Glu Leu Gln Thr Ile Phe Asp
            100                 105

<210> SEQ ID NO 11
<211> LENGTH: 109

<212> TYPE: PRT
<213> ORGANISM: Homo sapiens

<400> SEQUENCE: 11

```
Thr Leu Pro Pro Met Arg Tyr Gln Glu Thr Met Ser Ala Ile Arg Thr
1               5                   10                  15

Trp Val Gln Gln Ser Glu Thr Lys Leu Ser Ile Pro Gln Leu Ser Val
            20                  25                  30

Thr Asp Tyr Glu Ile Met Glu Gln Arg Leu Gly Glu Leu Gln Ala Leu
        35                  40                  45

Gln Ser Ser Leu Gln Glu Gln Ser Gly Leu Tyr Tyr Leu Ser Thr
    50                  55                  60

Thr Val Lys Glu Met Ser Lys Lys Ala Pro Ser Glu Ile Ser Arg Lys
65                  70                  75                  80

Tyr Gln Ser Glu Phe Glu Glu Ile Glu Gly Arg Trp Lys Lys Leu Ser
                85                  90                  95

Ser Gln Leu Val Glu His Cys Gln Lys Leu Glu Glu Gln
            100                 105
```

<210> SEQ ID NO 12
<211> LENGTH: 109
<212> TYPE: PRT
<213> ORGANISM: Homo sapiens

<400> SEQUENCE: 12

```
Met Asn Lys Leu Arg Lys Ile Gln Asn His Ile Gln Thr Leu Lys Lys
1               5                   10                  15

Trp Met Ala Glu Val Asp Val Phe Leu Lys Glu Trp Pro Ala Leu
            20                  25                  30

Gly Asp Ser Glu Ile Leu Lys Lys Gln Leu Lys Gln Cys Arg Leu Leu
        35                  40                  45

Val Ser Asp Ile Gln Thr Ile Gln Pro Ser Leu Asn Ser Val Asn Glu
    50                  55                  60

Gly Gly Gln Lys Ile Lys Asn Glu Ala Glu Pro Glu Phe Ala Ser Arg
65                  70                  75                  80

Leu Glu Thr Glu Leu Lys Glu Leu Asn Thr Gln Trp Asp His Met Cys
                85                  90                  95

Gln Gln Val Tyr Ala Arg Lys Glu Ala Leu Lys Gly Gly
            100                 105
```

<210> SEQ ID NO 13
<211> LENGTH: 109
<212> TYPE: PRT
<213> ORGANISM: Homo sapiens

<400> SEQUENCE: 13

```
Leu Glu Lys Thr Val Ser Leu Gln Lys Asp Leu Ser Glu Met His Glu
1               5                   10                  15

Trp Met Thr Gln Ala Glu Glu Glu Tyr Leu Glu Arg Asp Phe Glu Tyr
            20                  25                  30

Lys Thr Pro Asp Glu Leu Gln Lys Ala Val Glu Glu Met Lys Arg Ala
        35                  40                  45

Lys Glu Glu Ala Gln Gln Lys Glu Ala Lys Val Lys Leu Leu Thr Glu
    50                  55                  60

Ser Val Asn Ser Val Ile Ala Gln Ala Pro Pro Val Ala Gln Glu Ala
65                  70                  75                  80

Leu Lys Lys Glu Leu Glu Thr Leu Thr Thr Asn Tyr Gln Trp Leu Cys
```

-continued

```
                85                  90                  95
Thr Arg Leu Asn Gly Lys Cys Lys Thr Leu Glu Glu Val
            100                 105

<210> SEQ ID NO 14
<211> LENGTH: 104
<212> TYPE: PRT
<213> ORGANISM: Homo sapiens

<400> SEQUENCE: 14

Trp Ala Cys Trp His Glu Leu Ser Tyr Leu Glu Lys Ala Asn Lys
1               5                   10                  15

Trp Leu Asn Glu Val Glu Phe Lys Leu Lys Thr Thr Glu Asn Ile Pro
            20                  25                  30

Gly Gly Ala Glu Glu Ile Ser Glu Val Leu Asp Ser Leu Glu Asn Leu
        35                  40                  45

Met Arg His Ser Glu Asp Asn Pro Asn Gln Ile Arg Ile Leu Ala Gln
    50                  55                  60

Thr Leu Thr Asp Gly Gly Val Met Asp Glu Leu Ile Asn Glu Glu Leu
65                  70                  75                  80

Glu Thr Phe Asn Ser Arg Trp Arg Glu Leu His Glu Glu Ala Val Arg
                85                  90                  95

Arg Gln Lys Leu Leu Glu Gln Ser
            100

<210> SEQ ID NO 15
<211> LENGTH: 92
<212> TYPE: PRT
<213> ORGANISM: Homo sapiens

<400> SEQUENCE: 15

Ile Gln Ser Ala Gln Glu Thr Glu Lys Ser Leu His Leu Ile Gln Glu
1               5                   10                  15

Ser Leu Thr Phe Ile Asp Lys Gln Leu Ala Ala Tyr Ile Ala Asp Lys
            20                  25                  30

Val Asp Ala Ala Gln Met Pro Gln Glu Ala Gln Lys Ile Gln Ser Asp
        35                  40                  45

Leu Thr Ser His Glu Ile Ser Leu Glu Glu Met Lys Lys His Asn Gln
    50                  55                  60

Gly Lys Glu Ala Ala Gln Arg Val Leu Ser Gln Ile Asp Val Ala Gln
65                  70                  75                  80

Lys Lys Leu Gln Asp Val Ser Met Lys Phe Arg Leu
                85                  90

<210> SEQ ID NO 16
<211> LENGTH: 109
<212> TYPE: PRT
<213> ORGANISM: Homo sapiens

<400> SEQUENCE: 16

Phe Gln Lys Pro Ala Asn Phe Glu Gln Arg Leu Gln Glu Ser Lys Met
1               5                   10                  15

Ile Leu Asp Glu Val Lys Met His Leu Pro Ala Leu Glu Thr Lys Ser
            20                  25                  30

Val Glu Gln Glu Val Val Gln Ser Gln Leu Asn His Cys Val Asn Leu
        35                  40                  45

Tyr Lys Ser Leu Ser Glu Val Lys Ser Glu Val Glu Met Val Ile Lys
    50                  55                  60
```

```
Thr Gly Arg Gln Ile Val Gln Lys Lys Gln Thr Glu Asn Pro Lys Glu
 65                  70                  75                  80

Leu Asp Glu Arg Val Thr Ala Leu Lys Leu His Tyr Asn Glu Leu Gly
             85                  90                  95

Ala Lys Val Thr Glu Arg Lys Gln Gln Leu Glu Lys Cys
            100                 105

<210> SEQ ID NO 17
<211> LENGTH: 108
<212> TYPE: PRT
<213> ORGANISM: Homo sapiens

<400> SEQUENCE: 17

Leu Lys Leu Ser Arg Lys Met Arg Lys Glu Met Asn Val Leu Thr Glu
 1               5                   10                  15

Trp Leu Ala Ala Thr Asp Met Glu Leu Thr Lys Arg Ser Ala Val Glu
             20                  25                  30

Gly Met Pro Ser Asn Leu Asp Ser Glu Val Ala Trp Gly Lys Ala Thr
         35                  40                  45

Gln Lys Glu Ile Glu Lys Gln Lys Val His Leu Lys Ser Ile Thr Glu
 50                  55                  60

Val Gly Glu Ala Leu Lys Thr Val Leu Gly Lys Lys Glu Thr Leu Val
 65                  70                  75                  80

Glu Asp Lys Leu Ser Leu Leu Asn Ser Asn Trp Ile Ala Val Thr Ser
             85                  90                  95

Arg Ala Glu Glu Trp Leu Asn Leu Leu Leu Glu Tyr
            100                 105

<210> SEQ ID NO 18
<211> LENGTH: 104
<212> TYPE: PRT
<213> ORGANISM: Homo sapiens

<400> SEQUENCE: 18

Gln Lys His Met Glu Thr Phe Asp Gln Asn Val Asp His Ile Thr Lys
 1               5                   10                  15

Trp Ile Ile Gln Ala Asp Thr Leu Leu Asp Glu Ser Glu Lys Lys Lys
             20                  25                  30

Pro Gln Gln Lys Glu Asp Val Leu Lys Arg Leu Lys Ala Glu Leu Asn
         35                  40                  45

Asp Ile Arg Pro Lys Val Asp Ser Thr Arg Asp Gln Ala Ala Asn Leu
 50                  55                  60

Met Ala Asn Arg Gly Asp His Cys Arg Lys Leu Val Glu Pro Gln Ile
 65                  70                  75                  80

Ser Glu Leu Asn His Arg Phe Ala Ala Ile Ser His Arg Ile Lys Thr
             85                  90                  95

Gly Lys Ala Ser Ile Pro Leu Lys
            100

<210> SEQ ID NO 19
<211> LENGTH: 94
<212> TYPE: PRT
<213> ORGANISM: Homo sapiens

<400> SEQUENCE: 19

Glu Leu Glu Gln Phe Asn Ser Asp Ile Gln Lys Leu Leu Glu Pro Leu
 1               5                   10                  15
```

Glu Ala Glu Ile Gln Gln Gly Val Asn Leu Lys Glu Asp Phe Asn
            20                  25                  30

Lys Asp Met Asn Glu Asp Asn Glu Gly Thr Val Lys Glu Leu Leu Gln
                35                  40                  45

Arg Gly Asp Asn Leu Gln Gln Arg Ile Thr Asp Glu Arg Lys Arg Glu
    50                  55                  60

Glu Ile Lys Ile Lys Gln Gln Leu Leu Gln Thr Lys His Asn Ala Leu
65                  70                  75                  80

Lys Asp Leu Arg Ser Gln Arg Lys Lys Ala Leu Glu Ile
                85                  90

<210> SEQ ID NO 20
<211> LENGTH: 98
<212> TYPE: PRT
<213> ORGANISM: Homo sapiens

<400> SEQUENCE: 20

Ser His Gln Trp Tyr Gln Tyr Lys Arg Gln Ala Asp Asp Leu Leu Lys
1               5                   10                  15

Cys Leu Asp Asp Ile Glu Lys Lys Leu Ala Ser Leu Pro Glu Pro Arg
                20                  25                  30

Asp Glu Arg Lys Ile Lys Glu Ile Asp Arg Glu Leu Gln Leu Lys Lys
            35                  40                  45

Glu Glu Leu Asn Ala Val Arg Arg Gln Ala Glu Gly Leu Ser Glu Asp
    50                  55                  60

Gly Ala Ala Met Ala Val Glu Pro Thr Gln Ile Gln Leu Ser Lys Arg
65                  70                  75                  80

Trp Arg Glu Ile Glu Ser Lys Phe Ala Gln Phe Arg Arg Leu Asn Phe
                85                  90                  95

Ala Gln

<210> SEQ ID NO 21
<211> LENGTH: 20
<212> TYPE: PRT
<213> ORGANISM: Homo sapiens

<400> SEQUENCE: 21

Ile His Thr Val Arg Glu Glu Thr Met Met Val Met Thr Glu Asp Met
1               5                   10                  15

Pro Leu Glu Ile
            20

<210> SEQ ID NO 22
<211> LENGTH: 109
<212> TYPE: PRT
<213> ORGANISM: Homo sapiens

<400> SEQUENCE: 22

Ser Tyr Val Pro Ser Thr Tyr Leu Thr Glu Ile Thr His Val Ser Gln
1               5                   10                  15

Ala Leu Leu Glu Val Glu Gln Leu Leu Asn Ala Pro Asp Leu Cys Ala
                20                  25                  30

Lys Asp Phe Glu Asp Leu Phe Lys Gln Glu Gly Ser Leu Lys Asn Ile
            35                  40                  45

Lys Asp Ser Leu Gln Gln Ser Ser Gly Arg Ile Asp Ile Ile His Ser
    50                  55                  60

Lys Lys Thr Ala Ala Leu Gln Ser Ala Thr Pro Val Glu Arg Val Lys
65                  70                  75                  80

```
Leu Gln Glu Ala Leu Ser Gln Leu Asp Phe Gln Trp Glu Lys Val Asn
                85                  90                  95

Lys Met Tyr Lys Asp Arg Gln Gly Arg Phe Asp Arg Ser
            100                 105
```

<210> SEQ ID NO 23
<211> LENGTH: 107
<212> TYPE: PRT
<213> ORGANISM: Homo sapiens

<400> SEQUENCE: 23

```
Val Glu Lys Trp Arg Arg Phe His Tyr Asp Ile Lys Ile Phe Asn Gln
1               5                   10                  15

Trp Leu Thr Glu Ala Glu Gln Phe Leu Arg Lys Thr Gln Ile Pro Glu
            20                  25                  30

Asn Trp Glu His Ala Lys Tyr Lys Trp Tyr Leu Lys Glu Leu Gln Asp
        35                  40                  45

Gly Ile Gly Gln Arg Gln Thr Val Val Arg Thr Leu Asn Ala Thr Gly
    50                  55                  60

Glu Glu Ile Ile Gln Gln Ser Ser Lys Thr Asp Ala Ser Ile Leu Gln
65                  70                  75                  80

Glu Lys Leu Gly Ser Leu Asn Leu Arg Trp Gln Glu Val Cys Lys Gln
                85                  90                  95

Leu Ser Asp Arg Lys Lys Arg Leu Glu Glu Gln
            100                 105
```

<210> SEQ ID NO 24
<211> LENGTH: 117
<212> TYPE: PRT
<213> ORGANISM: Homo sapiens

<400> SEQUENCE: 24

```
Lys Asn Ile Leu Ser Glu Phe Gln Arg Asp Leu Asn Glu Phe Val Leu
1               5                   10                  15

Trp Leu Glu Glu Ala Asp Asn Ile Ala Ser Ile Pro Leu Glu Pro Gly
            20                  25                  30

Lys Glu Gln Gln Leu Lys Glu Lys Leu Glu Gln Val Lys Leu Leu Val
        35                  40                  45

Glu Glu Leu Pro Leu Arg Gln Gly Ile Leu Lys Gln Leu Asn Glu Thr
    50                  55                  60

Gly Gly Pro Val Leu Val Ser Ala Pro Ile Ser Pro Glu Glu Gln Asp
65                  70                  75                  80

Lys Leu Glu Asn Lys Leu Lys Gln Thr Asn Leu Gln Trp Ile Lys Val
                85                  90                  95

Ser Arg Ala Leu Pro Glu Lys Gln Gly Glu Ile Glu Ala Gln Ile Lys
            100                 105                 110

Asp Leu Gly Gln Leu
        115
```

<210> SEQ ID NO 25
<211> LENGTH: 101
<212> TYPE: PRT
<213> ORGANISM: Homo sapiens

<400> SEQUENCE: 25

```
Glu Lys Lys Leu Glu Asp Leu Glu Glu Gln Leu Asn His Leu Leu Leu
1               5                   10                  15
```

Trp Leu Ser Pro Ile Arg Asn Gln Leu Glu Ile Tyr Asn Gln Pro Asn
            20                  25                  30

Gln Glu Gly Pro Phe Asp Val Gln Glu Thr Glu Ile Ala Val Gln Ala
        35                  40                  45

Lys Gln Pro Asp Val Glu Glu Ile Leu Ser Lys Gly Gln His Leu Tyr
50                  55                  60

Lys Glu Lys Pro Ala Thr Gln Pro Val Lys Arg Lys Leu Glu Asp Leu
65                  70                  75                  80

Ser Ser Glu Trp Lys Ala Val Asn Arg Leu Leu Gln Glu Leu Arg Ala
                85                  90                  95

Lys Gln Pro Asp Leu
            100

<210> SEQ ID NO 26
<211> LENGTH: 41
<212> TYPE: PRT
<213> ORGANISM: Homo sapiens

<400> SEQUENCE: 26

Ala Pro Gly Leu Thr Thr Ile Gly Ala Ser Pro Thr Gln Thr Val Thr
1               5                   10                  15

Leu Val Thr Gln Pro Val Val Thr Lys Glu Thr Ala Ile Ser Lys Leu
            20                  25                  30

Glu Met Pro Ser Ser Leu Met Leu Glu
        35                  40

<210> SEQ ID NO 27
<211> LENGTH: 110
<212> TYPE: PRT
<213> ORGANISM: Homo sapiens

<400> SEQUENCE: 27

Val Pro Ala Leu Ala Asp Phe Asn Arg Ala Trp Thr Glu Leu Thr Asp
1               5                   10                  15

Trp Leu Ser Leu Leu Asp Gln Val Ile Lys Ser Gln Arg Val Met Val
            20                  25                  30

Gly Asp Leu Glu Asp Ile Asn Glu Met Ile Ile Lys Gln Lys Ala Thr
        35                  40                  45

Met Gln Asp Leu Glu Gln Arg Arg Pro Gln Leu Glu Glu Leu Ile Thr
50                  55                  60

Ala Ala Gln Asn Leu Lys Asn Lys Thr Ser Asn Gln Glu Ala Arg Thr
65                  70                  75                  80

Ile Ile Thr Asp Arg Ile Glu Arg Ile Gln Asn Gln Trp Asp Glu Val
                85                  90                  95

Gln Glu His Leu Gln Asn Arg Arg Gln Gln Leu Asn Glu Met
            100                 105                 110

<210> SEQ ID NO 28
<211> LENGTH: 109
<212> TYPE: PRT
<213> ORGANISM: Homo sapiens

<400> SEQUENCE: 28

Leu Lys Asp Ser Thr Gln Trp Leu Glu Ala Lys Glu Glu Ala Glu Gln
1               5                   10                  15

Val Leu Gly Gln Ala Arg Ala Lys Leu Glu Ser Trp Lys Glu Gly Pro
            20                  25                  30

Tyr Thr Val Asp Ala Ile Gln Lys Lys Ile Thr Glu Thr Lys Gln Leu

```
            35                  40                  45
Ala Lys Asp Leu Arg Gln Trp Gln Thr Asn Val Asp Val Ala Asn Asp
 50                  55                  60

Leu Ala Leu Lys Leu Leu Arg Asp Tyr Ser Ala Asp Thr Arg Lys
 65                  70                  75                  80

Val His Met Ile Thr Glu Asn Ile Asn Ala Ser Trp Arg Ser Ile His
                     85                  90                  95

Lys Arg Val Ser Glu Arg Glu Ala Ala Leu Glu Glu Thr
                100                 105
```

<210> SEQ ID NO 29
<211> LENGTH: 116
<212> TYPE: PRT
<213> ORGANISM: Homo sapiens

<400> SEQUENCE: 29

```
His Arg Leu Leu Gln Gln Phe Pro Leu Asp Leu Glu Lys Phe Leu Ala
 1               5                  10                  15

Trp Leu Thr Glu Ala Glu Thr Thr Ala Asn Val Leu Gln Asp Ala Thr
                20                  25                  30

Arg Lys Glu Arg Leu Leu Glu Asp Ser Lys Gly Val Lys Glu Leu Met
             35                  40                  45

Lys Gln Trp Gln Asp Leu Gln Gly Glu Ile Glu Ala His Thr Asp Val
 50                  55                  60

Tyr His Asn Leu Asp Glu Asn Ser Gln Lys Ile Leu Arg Ser Leu Glu
 65                  70                  75                  80

Gly Ser Asp Asp Ala Val Leu Leu Gln Arg Arg Leu Asp Asn Met Asn
                85                  90                  95

Phe Lys Trp Ser Glu Leu Arg Lys Lys Ser Leu Asn Ile Arg Ser His
                100                 105                 110

Leu Glu Ala Ser
        115
```

<210> SEQ ID NO 30
<211> LENGTH: 129
<212> TYPE: PRT
<213> ORGANISM: Homo sapiens

<400> SEQUENCE: 30

```
Ser Asp Gln Trp Lys Arg Leu His Leu Ser Leu Gln Glu Leu Leu Val
 1               5                  10                  15

Trp Leu Gln Leu Lys Asp Asp Glu Leu Ser Arg Gln Ala Pro Ile Gly
                20                  25                  30

Gly Asp Phe Pro Ala Val Gln Lys Gln Asn Asp Val His Arg Ala Phe
             35                  40                  45

Lys Arg Glu Leu Lys Thr Lys Glu Pro Val Ile Met Ser Thr Leu Glu
 50                  55                  60

Thr Val Arg Ile Phe Leu Thr Glu Gln Pro Leu Glu Gly Leu Glu Lys
 65                  70                  75                  80

Leu Tyr Gln Glu Pro Arg Glu Leu Pro Pro Glu Glu Arg Ala Gln Asn
                85                  90                  95

Val Thr Arg Leu Leu Arg Lys Gln Ala Glu Glu Val Asn Thr Glu Trp
                100                 105                 110

Glu Lys Leu Asn Leu His Ser Ala Asp Trp Gln Arg Lys Ile Asp Glu
        115                 120                 125

Thr
```

```
<210> SEQ ID NO 31
<211> LENGTH: 108
<212> TYPE: PRT
<213> ORGANISM: Homo sapiens

<400> SEQUENCE: 31

Leu Glu Arg Leu Gln Glu Leu Gln Glu Ala Thr Asp Glu Leu Asp Leu
1               5                   10                  15

Lys Leu Arg Gln Ala Glu Val Ile Lys Gly Ser Trp Gln Pro Val Gly
                20                  25                  30

Asp Leu Leu Ile Asp Ser Leu Gln Asp His Leu Glu Lys Val Lys Ala
            35                  40                  45

Leu Arg Gly Glu Ile Ala Pro Leu Lys Glu Asn Val Ser His Val Asn
        50                  55                  60

Asp Leu Ala Arg Gln Leu Thr Thr Leu Gly Ile Gln Leu Ser Pro Tyr
65                  70                  75                  80

Asn Leu Ser Thr Leu Glu Asp Leu Asn Thr Arg Trp Lys Leu Leu Gln
                85                  90                  95

Val Ala Val Glu Asp Arg Val Arg Gln Leu His Glu
                100                 105

<210> SEQ ID NO 32
<211> LENGTH: 72
<212> TYPE: PRT
<213> ORGANISM: Homo sapiens

<400> SEQUENCE: 32

Ala His Arg Asp Phe Gly Pro Ala Ser Gln His Phe Leu Ser Thr Ser
1               5                   10                  15

Val Gln Gly Pro Trp Glu Arg Ala Ile Ser Pro Asn Lys Val Pro Tyr
                20                  25                  30

Tyr Ile Asn His Glu Thr Gln Thr Thr Cys Trp Asp His Pro Lys Met
            35                  40                  45

Thr Glu Leu Tyr Gln Ser Leu Ala Asp Leu Asn Asn Val Arg Phe Ser
        50                  55                  60

Ala Tyr Arg Thr Ala Met Lys Leu
65                  70

<210> SEQ ID NO 33
<211> LENGTH: 296
<212> TYPE: PRT
<213> ORGANISM: Homo sapiens

<400> SEQUENCE: 33

Arg Arg Leu Gln Lys Ala Leu Cys Leu Asp Leu Leu Ser Leu Ser Ala
1               5                   10                  15

Ala Cys Asp Ala Leu Asp Gln His Asn Leu Lys Gln Asn Asp Gln Pro
                20                  25                  30

Met Asp Ile Leu Gln Ile Ile Asn Cys Leu Thr Thr Ile Tyr Asp Arg
            35                  40                  45

Leu Glu Gln Glu His Asn Asn Leu Val Asn Val Pro Leu Cys Val Asp
        50                  55                  60

Met Cys Leu Asn Trp Leu Leu Asn Val Tyr Asp Thr Gly Arg Thr Gly
65                  70                  75                  80

Arg Ile Arg Val Leu Ser Phe Lys Thr Gly Ile Ile Ser Leu Cys Lys
                85                  90                  95
```

```
Ala His Leu Glu Asp Lys Tyr Arg Tyr Leu Phe Lys Gln Val Ala Ser
            100                 105                 110

Ser Thr Gly Phe Cys Asp Gln Arg Arg Leu Gly Leu Leu Leu His Asp
        115                 120                 125

Ser Ile Gln Ile Pro Arg Gln Leu Gly Glu Val Ala Ser Phe Gly Gly
    130                 135                 140

Ser Asn Ile Glu Pro Ser Val Arg Ser Cys Phe Gln Phe Ala Asn Asn
145                 150                 155                 160

Lys Pro Glu Ile Glu Ala Ala Leu Phe Leu Asp Trp Met Arg Leu Glu
                165                 170                 175

Pro Gln Ser Met Val Trp Leu Pro Val Leu His Arg Val Ala Ala Ala
            180                 185                 190

Glu Thr Ala Lys His Gln Ala Lys Cys Asn Ile Cys Lys Glu Cys Pro
        195                 200                 205

Ile Ile Gly Phe Arg Tyr Arg Ser Leu Lys His Phe Asn Tyr Asp Ile
    210                 215                 220

Cys Gln Ser Cys Phe Phe Ser Gly Arg Val Ala Lys Gly His Lys Met
225                 230                 235                 240

His Tyr Pro Met Val Glu Tyr Cys Thr Pro Thr Thr Ser Gly Glu Asp
                245                 250                 255

Val Arg Asp Phe Ala Lys Val Leu Lys Asn Lys Phe Arg Thr Lys Arg
            260                 265                 270

Tyr Phe Ala Lys His Pro Arg Met Gly Tyr Leu Pro Val Gln Thr Val
        275                 280                 285

Leu Glu Gly Asp Asn Met Glu Thr
    290                 295

<210> SEQ ID NO 34
<211> LENGTH: 277
<212> TYPE: PRT
<213> ORGANISM: Homo sapiens

<400> SEQUENCE: 34

Pro Val Thr Leu Ile Asn Phe Trp Pro Val Asp Ser Ala Pro Ala Ser
1               5                   10                  15

Ser Pro Gln Leu Ser His Asp Asp Thr His Ser Arg Ile Glu His Tyr
            20                  25                  30

Ala Ser Arg Leu Ala Glu Met Glu Asn Ser Asn Gly Ser Tyr Leu Asn
        35                  40                  45

Asp Ser Ile Ser Pro Asn Glu Ser Ile Asp Glu His Leu Leu Ile
50                  55                  60

Gln His Tyr Cys Gln Ser Leu Asn Gln Asp Ser Pro Leu Ser Gln Pro
65                  70                  75                  80

Arg Ser Pro Ala Gln Ile Leu Ile Ser Leu Glu Ser Glu Glu Arg Gly
                85                  90                  95

Glu Leu Glu Arg Ile Leu Ala Asp Leu Glu Glu Asn Arg Asn Leu
            100                 105                 110

Gln Ala Glu Tyr Asp Arg Leu Lys Gln Gln His Glu His Lys Gly Leu
        115                 120                 125

Ser Pro Leu Pro Ser Pro Glu Met Met Pro Thr Ser Pro Gln Ser
    130                 135                 140

Pro Arg Asp Ala Glu Leu Ile Ala Glu Ala Lys Leu Leu Arg Gln His
145                 150                 155                 160

Lys Gly Arg Leu Glu Ala Arg Met Gln Ile Leu Glu Asp His Asn Lys
                165                 170                 175
```

```
Gln Leu Glu Ser Gln Leu His Arg Leu Arg Gln Leu Leu Glu Gln Pro
            180                 185                 190

Gln Ala Glu Ala Lys Val Asn Gly Thr Thr Val Ser Ser Pro Ser Thr
        195                 200                 205

Ser Leu Gln Arg Ser Asp Ser Ser Gln Pro Met Leu Leu Arg Val Val
    210                 215                 220

Gly Ser Gln Thr Ser Asp Ser Met Gly Glu Glu Asp Leu Leu Ser Pro
225                 230                 235                 240

Pro Gln Asp Thr Ser Thr Gly Leu Glu Glu Val Met Glu Gln Leu Asn
                245                 250                 255

Asn Ser Phe Pro Ser Ser Arg Gly Arg Asn Thr Pro Gly Lys Pro Met
            260                 265                 270

Arg Glu Asp Thr Met
        275

<210> SEQ ID NO 35
<211> LENGTH: 208
<212> TYPE: DNA
<213> ORGANISM: Homo sapiens

<400> SEQUENCE: 35
gggattccct cactttcccc ctacaggact cagatctggg aggcaattac cttcggagaa     60
aaacgaatag gaaaaactga agtgttactt tttttaaagc tgctgaagtt tgttggtttc    120
tcattgtttt taagcctact ggagcaataa agtttgaaga acttttacca ggttttttt    180 atcgctgcct tgatatacac ttttcaaa                                       208

<210> SEQ ID NO 36
<211> LENGTH: 756
<212> TYPE: DNA
<213> ORGANISM: Homo sapiens

<400> SEQUENCE: 36
atgctttggt gggaagaagt agaggactgt tatgaaagag aagatgttca aagaaaaaca     60
ttcacaaaat gggtaaatgc acaattttct aagtttggga agcagcatat tgagaacctc    120
ttcagtgacc tacaggatgg gaggcgcctc ctagacctcc tcgaaggcct gacagggcaa    180
aaactgccaa agaaaaagg atccacaaga gttcatgccc tgaacaatgt caacaaggca    240
ctgcgggttt tgcagaacaa taatgttgat ttagtgaata ttggaagtac tgacatcgta    300 gatgaaatc ataaactgac tcttggtttg atttggaata taatcctcca ctggcaggtc    360
aaaaatgtaa tgaaaatat catggctgga ttgcaacaaa ccaacagtga aaagattctc    420
ctgagctggg tccgacaatc aactcgtaat tatccacagg ttaatgtaat caacttcacc    480
accagctggt ctgatggcct ggctttgaat gctctcatcc atagtcatag gccagaccta    540
tttgactgga atagtgtggt ttgccagcag tcagccacac aacgactgga acatgcattc    600
aacatcgcca gatatcaatt aggcatagag aaactactcg atcctgaaga tgttgatacc    660
acctatccag ataagaagtc catcttaatg tacatcacat cactcttcca agttttgcct    720
caacaagtga gcattgaagc catccaggaa gtggaa                              756

<210> SEQ ID NO 37
<211> LENGTH: 255
<212> TYPE: DNA
<213> ORGANISM: Homo sapiens

<400> SEQUENCE: 37
```

```
atgttgccaa ggccacctaa agtgactaaa gaagaacatt ttcagttaca tcatcaaatg    60
cactattctc aacagatcac ggtcagtcta gcacagggat atgagagaac ttcttcccct   120
aagcctcgat tcaagagcta tgcctacaca caggctgctt atgtcaccac ctctgaccct   180
acacggagcc catttccttc acagcatttg gaagctcctg aagacaagtc atttggcagt   240
tcattgatgg agagt                                                    255
```

<210> SEQ ID NO 38
<211> LENGTH: 327
<212> TYPE: DNA
<213> ORGANISM: Homo sapiens

<400> SEQUENCE: 38

```
gaagtaaacc tggaccgtta tcaaacagct ttagaagaag tattatcgtg gcttctttct    60
gctgaggaca cattgcaagc acaaggagag atttctaatg atgtggaagt ggtgaaagac   120
cagtttcata ctcatgaggg gtacatgatg gatttgacag cccatcaggg ccgggttggt   180
aatattctac aattgggaag taagctgatt ggaacaggaa aattatcaga agatgaagaa   240
actgaagtac aagagcagat gaatctccta aattcaagat gggaatgcct cagggtagct   300
agcatggaaa acaaagcaa tttacat                                        327
```

<210> SEQ ID NO 39
<211> LENGTH: 333
<212> TYPE: DNA
<213> ORGANISM: Homo sapiens

<400> SEQUENCE: 39

```
agagttttaa tggatctcca gaatcagaaa ctgaaagagt tgaatgactg gctaacaaaa    60
acagaagaaa gaacaaggaa aatggaggaa gagcctcttg gacctgatct tgaagaccta   120
aaacgccaag tacaacaaca taaggtgctt caagaagatc tagaacaaga acaagtcagg   180
gtcaattctc tcactcacat ggtggtggta gttgatgaat ctagtggaga tcacgcaact   240
gctgctttgg aagaacaact taaggtattg ggagatcgat gggcaaacat ctgtagatgg   300
acagaagacc gctgggttct tttacaagac atc                                333
```

<210> SEQ ID NO 40
<211> LENGTH: 333
<212> TYPE: DNA
<213> ORGANISM: Homo sapiens

<400> SEQUENCE: 40

```
cttctcaaat ggcaacgtct tactgaagaa cagtgccttt ttagtgcatg gctttcagaa    60
aaagaagatg cagtgaacaa gattcacaca actggcttta agatcaaaa tgaaatgtta   120 tcaagtcttc aaaaactggc cgttttaaaa gcggatctag aaaagaaaaa gcaatccatg   180
ggcaaactgt attcactcaa acaagatctt ctttcaacac tgaagaataa gtcagtgacc   240
cagaagacgg aagcatggct ggataacttt gcccggtgtt gggataattt agtccaaaaa   300
cttgaaaaga gtacagcaca gatttcacag gct                                333
```

<210> SEQ ID NO 41
<211> LENGTH: 147
<212> TYPE: DNA
<213> ORGANISM: Homo sapiens

<400> SEQUENCE: 41

```
gtcaccacca ctcagccatc actaacacag acaactgtaa tggaaacagt aactacggtg    60
accacaaggg aacagatcct ggtaaagcat gctcaagagg aacttccacc accacctccc   120
caaaagaaga ggcagattac tgtggat                                       147
```

<210> SEQ ID NO 42
<211> LENGTH: 333
<212> TYPE: DNA
<213> ORGANISM: Homo sapiens

<400> SEQUENCE: 42

```
tctgaaatta ggaaaaggtt ggatgttgat ataactgaac ttcacagctg gattactcgc    60
tcagaagctg tgttgcagag tcctgaattt gcaatctttc ggaaggaagg caacttctca   120
gacttaaaag aaaaagtcaa tgccatagag cgagaaaaag ctgagaagtt cagaaaactg   180
caagatgcca gcagatcagc tcaggccctg gtggaacaga tggtgaatga gggtgttaat   240
gcagatagca tcaaacaagc ctcagaacaa ctgaacagcc ggtggatcga attctgccag   300
ttgctaagtg agagacttaa ctggctggag tat                                333
```

<210> SEQ ID NO 43
<211> LENGTH: 327
<212> TYPE: DNA
<213> ORGANISM: Homo sapiens

<400> SEQUENCE: 43

```
cagaacaaca tcatcgcttt ctataatcag ctacaacaat tggagcagat gacaactact    60
gctgaaaact ggttgaaaat ccaacccacc accccatcag agccaacagc aattaaaagt   120
cagttaaaaa tttgtaagga tgaagtcaac cggctatcag gtcttcaacc tcaaattgaa   180
cgattaaaaa ttcaaagcat agccctgaaa gagaaaggac aaggacccat gttcctggat   240
gcagactttg tggcctttac aaatcatttt aagcaagtct tttctgatgt gcaggccaga   300
gagaaagagc tacagacaat ttttgac                                       327
```

<210> SEQ ID NO 44
<211> LENGTH: 327
<212> TYPE: DNA
<213> ORGANISM: Homo sapiens

<400> SEQUENCE: 44

```
actttgccac caatgcgcta tcaggagacc atgagtgcca tcaggacatg ggtccagcag    60
tcagaaacca aactctccat acctcaactt agtgtcaccg actatgaaat catggagcag   120
agactcgggg aattgcaggc tttacaaagt tctctgcaag agcaacaaag tggcctatac   180
tatctcagca ccactgtgaa agagatgtcg aagaaagcgc cctctgaaat tagccggaaa   240
tatcaatcag aatttgaaga aattgaggga cgctggaaga agctctcctc ccagctggtt   300
gagcattgtc aaaagctaga ggagcaa                                       327
```

<210> SEQ ID NO 45
<211> LENGTH: 327
<212> TYPE: DNA
<213> ORGANISM: Homo sapiens

<400> SEQUENCE: 45

```
atgaataaac tccgaaaaat tcagaatcac atacaaaccc tgaagaaatg gatggctgaa    60
gttgatgttt ttctgaagga ggaatggcct gcccttgggg attcagaaat tctaaaaaag   120
cagctgaaac agtgcagact tttagtcagt gatattcaga caattcagcc cagtctaaac   180
```

```
agtgtcaatg aaggtgggca gaagataaag aatgaagcag agccagagtt tgcttcgaga      240
cttgagacag aactcaaaga acttaacact cagtgggatc acatgtgcca acaggtctat      300
gccagaaagg aggccttgaa gggaggt                                          327
```

<210> SEQ ID NO 46
<211> LENGTH: 327
<212> TYPE: DNA
<213> ORGANISM: Homo sapiens

<400> SEQUENCE: 46

```
ttggagaaaa ctgtaagcct ccagaaagat ctatcagaga tgcacgaatg gatgacacaa       60
gctgaagaag agtatcttga gagagatttt gaatataaaa ctccagatga attacagaaa      120
gcagttgaag agatgaagag agctaaagaa gaggcccaac aaaaagaagc gaaagtgaaa      180
ctccttactg agtctgtaaa tagtgtcata gctcaagctc cacctgtagc acaagaggcc      240
ttaaaaaagg aacttgaaac tctaaccacc aactaccagt ggctctgcac taggctgaat      300
gggaaatgca agactttgga agaagtt                                          327
```

<210> SEQ ID NO 47
<211> LENGTH: 312
<212> TYPE: DNA
<213> ORGANISM: Homo sapiens

<400> SEQUENCE: 47

```
tgggcatgtt ggcatgagtt attgtcatac ttggagaaag caaacaagtg gctaaatgaa       60
gtagaattta aacttaaaac cactgaaaac attcctggcg gagctgagga aatctctgag      120
gtgctagatt cacttgaaaa tttgatgcga cattcagagg ataacccaaa tcagattcgc      180
atattggcac agaccctaac agatggcgga gtcatggatg agctaatcaa tgaggaactt      240
gagacattta attctcgttg gagggaacta catgaagagg ctgtaaggag gcaaagttg       300 cttgaacaga gc                                                          312
```

<210> SEQ ID NO 48
<211> LENGTH: 276
<212> TYPE: DNA
<213> ORGANISM: Homo sapiens

<400> SEQUENCE: 48

```
atccagtctg cccaggagac tgaaaaatcc ttacacttaa tccaggagtc cctcacattc       60
attgacaagc agttggcagc ttatattgca gacaaggtgg acgcagctca aatgcctcag      120
gaagcccaga aaatccaatc tgatttgaca agtcatgaga tcagtttaga agaaatgaag      180
aaacataatc aggggaagga ggctgcccaa agagtcctgt ctcagattga tgttgcacag      240
aaaaaattac aagatgtctc catgaagttt cgatta                                276
```

<210> SEQ ID NO 49
<211> LENGTH: 327
<212> TYPE: DNA
<213> ORGANISM: Homo sapiens

<400> SEQUENCE: 49

```
ttccagaaac cagccaattt tgagcagcgt ctacaagaaa gtaagatgat tttagatgaa       60
gtgaagatgc acttgcctgc attggaaaca aagagtgtgg aacaggaagt agtacagtca      120
cagctaaatc attgtgtgaa cttgtataaa agtctgagtg aagtgaagtc tgaagtggaa      180
```

```
atggtgataa agactggacg tcagattgta cagaaaaagc agacggaaaa tcccaaagaa      240
cttgatgaaa gagtaacagc tttgaaattg cattataatg agctgggagc aaaggtaaca      300
gaaagaaagc aacagttgga gaaatgc                                          327

<210> SEQ ID NO 50
<211> LENGTH: 324
<212> TYPE: DNA
<213> ORGANISM: Homo sapiens

<400> SEQUENCE: 50
ttgaaattgt cccgtaagat gcgaaaggaa atgaatgtct tgacagaatg gctggcagct       60
acagatatgg aattgacaaa gagatcagca gttgaaggaa tgcctagtaa tttggattct      120
gaagttgcct ggggaaaggc tactcaaaaa gagattgaga acagaaaggt gcacctgaag      180
agtatcacag aggtaggaga ggccttgaaa acagttttgg gcaagaagga gacgttggtg      240
gaagataaac tcagtcttct gaatagtaac tggatagctg tcacctcccg agcagaagag      300
tggttaaatc ttttgttgga atac                                             324

<210> SEQ ID NO 51
<211> LENGTH: 312
<212> TYPE: DNA
<213> ORGANISM: Homo sapiens

<400> SEQUENCE: 51
cagaaacaca tggaaacttt tgaccagaat gtggaccaca tcacaaagtg gatcattcag       60
gctgacacac ttttggatga atcagagaaa aagaaacccc agcaaaaaga agacgtgctt      120
aagcgtttaa aggcagaact gaatgacata cgcccaaagg tggactctac acgtgaccaa      180
gcagcaaact tgatggcaaa ccgcggtgac cactgcagga aattagtaga gccccaaatc      240
tcagagctca accatcgatt tgcagccatt tcacacagaa ttaagactgg aaaggcctcc      300
attcctttga ag                                                          312

<210> SEQ ID NO 52
<211> LENGTH: 282
<212> TYPE: DNA
<213> ORGANISM: Homo sapiens

<400> SEQUENCE: 52
gaattggagc agtttaactc agatatacaa aaattgcttg aaccactgga ggctgaaatt       60
cagcaggggg tgaatctgaa agaggaagac ttcaataaag atatgaatga agacaatgag      120
ggtactgtaa agaattgtt gcaaagagga gacaacttac aacaaagaat cacagatgag      180
agaaagagag aggaaataaa gataaaacag cagctgttac agacaaaaca taatgctctc      240
aaggatttga ggtctcaaag aagaaaaaag gctctagaaa tt                         282

<210> SEQ ID NO 53
<211> LENGTH: 294
<212> TYPE: DNA
<213> ORGANISM: Homo sapiens

<400> SEQUENCE: 53
tctcatcagt ggtatcagta caagaggcag gctgatgatc tcctgaaatg cttggatgac       60
attgaaaaaa aattagccag cctacctgag cccagagatg aaaggaaaat aaaggaaatt      120
gatcgggaat tgcagaagaa gaaagaggag ctgaatgcag tgcgtaggca agctgagggc      180
ttgtctgagg atggggccgc aatggcagtg gagccaactc agatccagct cagcaagcgc      240
```
tggcgggaaa ttgagagcaa atttgctcag tttcgaagac tcaactttgc acaa 294

```
<210> SEQ ID NO 54
<211> LENGTH: 60
<212> TYPE: DNA
<213> ORGANISM: Homo sapiens

<400> SEQUENCE: 54
```
attcacactg tccgtgaaga aacgatgatg gtgatgactg agacatgcc tttggaaatt 60

```
<210> SEQ ID NO 55
<211> LENGTH: 327
<212> TYPE: DNA
<213> ORGANISM: Homo sapiens

<400> SEQUENCE: 55
```
tcttatgtgc cttctactta tttgactgaa atcactcatg tctcacaagc cctattagaa 60
gtggaacaac ttctcaatgc tcctgacctc tgtgctaagg actttgaaga tctctttaag 120
caagaggagt ctctgaagaa tataaaagat agtctacaac aaagctcagg tcggattgac 180
attattcata gcaagaagac agcagcattg caaagtgcaa cgcctgtgga aagggtgaag 240
ctacaggaag ctctctccca gcttgatttc caatgggaaa agttaacaa aatgtacaag 300 gaccgacaag ggcgatttga cagatct 327

```
<210> SEQ ID NO 56
<211> LENGTH: 321
<212> TYPE: DNA
<213> ORGANISM: Homo sapiens

<400> SEQUENCE: 56
```
gttgagaaat ggcggcgttt tcattatgat ataaagatat ttaatcagtg gctaacagaa 60
gctgaacagt ttctcagaaa gacacaaatt cctgagaatt gggaacatgc taaatacaaa 120
tggtatctta aggaactcca ggatggcatt gggcagcggc aaactgttgt cagaacattg 180
aatgcaactg gggaagaaat aattcagcaa tcctcaaaaa cagatgccag tattctacag 240
gaaaaattgg gaagcctgaa tctgcggtgg caggaggtct gcaaacagct gtcagacaga 300
aaaaagaggc tagaagaaca a 321

```
<210> SEQ ID NO 57
<211> LENGTH: 351
<212> TYPE: DNA
<213> ORGANISM: Homo sapiens

<400> SEQUENCE: 57
```
aagaatatct tgtcagaatt tcaaagagat ttaaatgaat ttgttttatg gttggaggaa 60
gcagataaca ttgctagtat cccacttgaa cctggaaaag agcagcaact aaaagaaaag 120
cttgagcaag tcaagttact ggtggaagag ttgccctgc gccagggaat tctcaaacaa 180
ttaaatgaaa ctggaggacc cgtgcttgta agtgctccca taagcccaga agagcaagat 240
aaacttgaaa ataagctcaa gcagacaaat ctccagtgga taaaggtttc cagagcttta 300
cctgagaaac aaggagaaat tgaagctcaa ataaagacc ttgggcagct t 351

```
<210> SEQ ID NO 58
<211> LENGTH: 303
<212> TYPE: DNA
<213> ORGANISM: Homo sapiens
```

<400> SEQUENCE: 58

```
gaaaaaaagc ttgaagacct tgaagagcag ttaaatcatc tgctgctgtg gttatctcct      60
attaggaatc agttggaaat ttataaccaa ccaaaccaag aaggaccatt tgacgttcag     120
gaaactgaaa tagcagttca agctaaacaa ccggatgtgg aagagatttt gtctaaaggg     180
cagcatttgt acaaggaaaa accagccact cagccagtga agaggaagtt agaagatctg     240
agctctgagt ggaaggcggt aaaccgttta cttcaagagc tgagggcaaa gcagcctgac     300
cta                                                                   303
```

<210> SEQ ID NO 59
<211> LENGTH: 123
<212> TYPE: DNA
<213> ORGANISM: Homo sapiens

<400> SEQUENCE: 59

```
gctcctggac tgaccactat tggagcctct cctactcaga ctgttactct ggtgacacaa      60
cctgtggtta ctaaggaaac tgccatctcc aaactagaaa tgccatcttc cttgatgttg     120
gag                                                                   123
```

<210> SEQ ID NO 60
<211> LENGTH: 330
<212> TYPE: DNA
<213> ORGANISM: Homo sapiens

<400> SEQUENCE: 60

```
gtacctgctc tggcagattt caaccgggct tggacagaac ttaccgactg gctttctctg      60
cttgatcaag ttataaaatc acagagggtg atggtgggtg accttgagga tatcaacgag     120
atgatcatca gcagaaggc aacaatgcag gatttggaac agaggcgtcc ccagttggaa     180
gaactcatta ccgctgccca aaatttgaaa aacaagacca gcaatcaaga ggctagaaca     240
atcattacgg atcgaattga agaattcag aatcagtggg atgaagtaca agaacacctt     300
cagaaccgga ggcaacagtt gaatgaaatg                                      330
```

<210> SEQ ID NO 61
<211> LENGTH: 327
<212> TYPE: DNA
<213> ORGANISM: Homo sapiens

<400> SEQUENCE: 61

```
ttaaaggatt caacacaatg gctggaagct aaggaagaag ctgagcaggt cttaggacag      60
gccagagcca agcttgagtc atggaaggag ggtccctata cagtagatgc aatccaaaag     120
aaaatcacag aaaccaagca gttggccaaa gacctccgcc agtggcagac aaatgtagat     180
gtggcaaatg acttggccct gaaacttctc cgggattatt ctgcagatga taccagaaaa     240
gtccacatga taacagagaa tatcaatgcc tcttggagaa gcattcataa aagggtgagt     300
gagcgagagg ctgctttgga agaaact                                         327
```

<210> SEQ ID NO 62
<211> LENGTH: 348
<212> TYPE: DNA
<213> ORGANISM: Homo sapiens

<400> SEQUENCE: 62

```
catagattac tgcaacagtt cccctggac ctggaaaagt ttcttgcctg gcttacagaa       60
gctgaaacaa ctgccaatgt cctacaggat gctacccgta aggaaaggct cctagaagac     120
```

```
tccaagggag taaaagagct gatgaaacaa tggcaagacc tccaaggtga aattgaagct      180
cacacagatg tttatcacaa cctggatgaa acagccaaa  aaatcctgag atccctggaa      240
ggttccgatg atgcagtcct gttacaaaga cgtttggata acatgaactt caagtggagt      300
gaacttcgga aaaagtctct caacattagg tcccatttgg aagccagt                   348

<210> SEQ ID NO 63
<211> LENGTH: 387
<212> TYPE: DNA
<213> ORGANISM: Homo sapiens

<400> SEQUENCE: 63
tctgaccagt ggaagcgtct gcacctttct ctgcaggaac ttctggtgtg gctacagctg       60
aaagatgatg aattaagccg gcaggcacct attggaggcg actttccagc agttcagaag      120
cagaacgatg tacatagggc cttcaagagg gaattgaaaa ctaaagaacc tgtaatcatg      180
agtactcttg agactgtacg aatatttctg acagagcagc ctttggaagg actagagaaa      240
ctctaccagg agcccagaga gctgcctcct gaggagagag cccagaatgt cactcggctt      300
ctacgaaagc aggctgagga ggtcaatact gagtgggaaa aattgaacct gcactccgct      360
gactggcaga gaaaaataga tgagacc                                          387

<210> SEQ ID NO 64
<211> LENGTH: 324
<212> TYPE: DNA
<213> ORGANISM: Homo sapiens

<400> SEQUENCE: 64
cttgaaagac tccaggaact tcaagaggcc acggatgagc tggacctcaa gctgcgccaa       60
gctgaggtga tcaagggatc ctggcagccc gtgggcgatc tcctcattga ctctctccaa      120
gatcacctcg agaaagtcaa ggcacttcga ggagaaattg cgcctctgaa agagaacgtg      180
agccacgtca atgaccttgc tcgccagctt accactttgg gcattcagct ctcaccgtat      240
aacctcagca ctctggaaga cctgaacacc agatggaagc ttctgcaggt ggccgtcgag      300
gaccgagtca ggcagctgca tgaa                                             324

<210> SEQ ID NO 65
<211> LENGTH: 216
<212> TYPE: DNA
<213> ORGANISM: Homo sapiens

<400> SEQUENCE: 65
gcccacaggg actttggtcc agcatctcag cactttcttt ccacgtctgt ccagggtccc       60
tgggagagag ccatctcgcc aaacaaagtg ccctactata tcaaccacga gactcaaaca      120
acttgctggg accatcccaa aatgacagag ctctaccagt ctttagctga cctgaataat      180
gtcagattct cagcttatag gactgccatg aaactc                                216

<210> SEQ ID NO 66
<211> LENGTH: 888
<212> TYPE: DNA
<213> ORGANISM: Homo sapiens

<400> SEQUENCE: 66
cgaagactgc agaaggccct ttgcttggat ctcttgagcc tgtcagctgc atgtgatgcc       60
ttggaccagc acaacctcaa gcaaaatgac cagcccatgg atatcctgca gattattaat      120
```

```
tgtttgacca ctatttatga ccgcctggag caagagcaca acaatttggt caacgtccct      180
ctctgcgtgg atatgtgtct gaactggctg ctgaatgttt atgatacggg acgaacaggg      240
aggatccgtg tcctgtcttt taaaactggc atcatttccc tgtgtaaagc acatttggaa      300
gacaagtaca gataccttt caagcaagtg gcaagttcaa caggattttg tgaccagcgc       360
aggctgggcc tccttctgca tgattctatc caaattccaa gacagttggg tgaagttgca      420
tcctttgggg gcagtaacat tgagccaagt gtccggagct gcttccaatt tgctaataat      480
aagccagaga tcgaagcggc cctcttccta gactggatga gactggaacc ccagtccatg      540
gtgtggctgc ccgtcctgca cagagtggct gctgcagaaa ctgccaagca tcaggccaaa      600
tgtaacatct gcaaagagtg tccaatcatt ggattcaggt acaggagtct aaagcacttt      660
aattatgaca tctgccaaag ctgctttttt tctggtcgag ttgcaaaagg ccataaaatg      720
cactatccca tggtggaata ttgcactccg actacatcag agaagatgt tcgagacttt       780 gccaaggtac taaaaaacaa atttcgaacc aaaaggtatt ttgcgaagca tccccgaatg      840
ggctacctgc cagtgcagac tgtcttagag ggggacaaca tggaaact                   888

<210> SEQ ID NO 67
<211> LENGTH: 834
<212> TYPE: DNA
<213> ORGANISM: Homo sapiens

<400> SEQUENCE: 67
cccgttactc tgatcaactt ctggccagta gattctgcgc ctgcctcgtc ccctcagctt       60
tcacacgatg atactcattc acgcattgaa cattatgcta gcaggctagc agaaatggaa      120
aacagcaatg gatcttatct aaatgatagc atctctccta atgagagcat agatgatgaa      180
catttgttaa tccagcatta ctgccaaagt ttgaaccagg actcccccct gagccagcct      240
cgtagtcctg cccagatctt gatttcctta gagagtgagg aaagagggga gctagagaga      300
atcctagcag atcttgagga agaaaacagg aatctgcaag cagaatatga ccgtctaaag      360
cagcagcacg aacataaagg cctgtcccca ctgccgtccc ctcctgaaat gatgcccacc      420
tctccccaga gtccccggga tgctgagctc attgctgagg ccaagctact gcgtcaacac      480
aaaggccgcc tggaagccag gatgcaaatc ctggaagacc acaataaaca gctggagtca      540
cagttacaca ggctaaggca gctgctggag caacccccagg cagaggccaa agtgaatggc      600
acaacggtgt cctctccttc tacctctcta cagaggtccg acagcagtca gcctatgctg      660
ctccgagtgg ttggcagtca aacttcggac tccatgggtg aggaagatct tctcagtcct      720
ccccaggaca caagcacagg gttagaggag gtgatggagc aactcaacaa ctccttccct      780
agttcaagag gaagaaatac ccctggaaag ccaatgagag aggacacaat gtag            834

<210> SEQ ID NO 68
<211> LENGTH: 16
<212> TYPE: PRT
<213> ORGANISM: Artificial Sequence
<220> FEATURE:
<223> OTHER INFORMATION: Modified Spectrin-16 (junction J4V13)

<400> SEQUENCE: 68

Met Asp Leu Gln Asn Gln Lys Leu Thr Glu Ile Thr His Val Ser Gln
1               5                   10                  15

<210> SEQ ID NO 69
<211> LENGTH: 16
<212> TYPE: PRT
```

-continued

```
<213> ORGANISM: Artificial Sequence
<220> FEATURE:
<223> OTHER INFORMATION: Modified Spectrin-16 (junction J4V12)

<400> SEQUENCE: 69

Leu Met Asp Leu Gln Asn Gln Lys Thr Glu Ile Thr His Val Ser Gln
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: Modified Spectrin-16 (junction J4V11)

<400> SEQUENCE: 70

Leu Met Asp Leu Gln Asn Gln Lys Glu Ile Thr His Val Ser Gln Ala
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Modified Spectrin-16 (junction J4V4)

<400> SEQUENCE: 71

Leu His Arg Val Leu Met Asp Leu Thr Tyr Leu Thr Glu Ile Thr His
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: Modified Spectrin-16 (junction J4)

<400> SEQUENCE: 72

Met Glu Lys Gln Ser Asn Leu His Ser Tyr Val Pro Ser Thr Tyr Leu
1               5                   10                  15

<210> SEQ ID NO 73
<211> LENGTH: 252
<212> TYPE: PRT
<213> ORGANISM: Homo sapiens

<400> SEQUENCE: 73

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
                20                  25                  30

Gly Lys Gln His Ile Glu Asn Leu Phe Ser Asp Leu Gln Asp Gly Arg
            35                  40                  45

Arg Leu Leu Asp Leu Leu Glu Gly Leu Thr Gly Gln Lys Leu Pro Lys
        50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125
```

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
                180                 185                 190

Thr Gln Arg Leu Glu His Ala Phe Asn Ile Ala Arg Tyr Gln Leu Gly
            195                 200                 205

Ile Glu Lys Leu Leu Asp Pro Glu Asp Val Asp Thr Thr Tyr Pro Asp
210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu
                245                 250

<210> SEQ ID NO 74
<211> LENGTH: 85
<212> TYPE: PRT
<213> ORGANISM: Homo sapiens

<400> SEQUENCE: 74

Met Leu Pro Arg Pro Pro Lys Val Thr Lys Glu His Phe Gln Leu
1               5                   10                  15

His His Gln Met His Tyr Ser Gln Gln Ile Thr Val Ser Leu Ala Gln
                20                  25                  30

Gly Tyr Glu Arg Thr Ser Ser Pro Lys Pro Arg Phe Lys Ser Tyr Ala
            35                  40                  45

Tyr Thr Gln Ala Ala Tyr Val Thr Thr Ser Asp Pro Thr Arg Ser Pro
    50                  55                  60

Phe Pro Ser Gln His Leu Glu Ala Pro Glu Asp Lys Ser Phe Gly Ser
65                  70                  75                  80

Ser Leu Met Glu Ser
                85

<210> SEQ ID NO 75
<211> LENGTH: 109
<212> TYPE: PRT
<213> ORGANISM: Homo sapiens

<400> SEQUENCE: 75

Glu Val Asn Leu Asp Arg Tyr Gln Thr Ala Leu Glu Glu Val Leu Ser
1               5                   10                  15

Trp Leu Leu Ser Ala Glu Asp Thr Leu Gln Ala Gln Gly Glu Ile Ser
                20                  25                  30

Asn Asp Val Glu Val Val Lys Asp Gln Phe His Thr His Glu Gly Tyr
            35                  40                  45

Met Met Asp Leu Thr Ala His Gln Gly Arg Val Gly Asn Ile Leu Gln
    50                  55                  60

Leu Gly Ser Lys Leu Ile Gly Thr Gly Lys Leu Ser Glu Asp Glu Glu
65                  70                  75                  80

Thr Glu Val Gln Glu Gln Met Asn Leu Leu Asn Ser Arg Trp Glu Cys
                85                  90                  95

Leu Arg Val Ala Ser Met Glu Lys Gln Ser Asn Leu His
            100                 105

<210> SEQ ID NO 76
<211> LENGTH: 112
<212> TYPE: PRT
<213> ORGANISM: Artificial Sequence
<220> FEATURE:
<223> OTHER INFORMATION: Modified Spectrin-16

<400> SEQUENCE: 76

Arg Val Leu Met Asp Leu Gln Asn Gln Lys Leu Thr Glu Ile Thr His
1               5                   10                  15

Val Ser Gln Ala Leu Leu Glu Val Glu Gln Leu Leu Asn Ala Pro Asp
            20                  25                  30

Leu Cys Ala Lys Asp Phe Glu Asp Leu Phe Lys Gln Glu Glu Ser Leu
        35                  40                  45

Lys Asn Ile Lys Asp Ser Leu Gln Gln Ser Ser Gly Arg Ile Asp Ile
    50                  55                  60

Ile His Ser Lys Lys Thr Ala Ala Leu Gln Ser Ala Thr Pro Val Glu
65                  70                  75                  80

Arg Val Lys Leu Gln Glu Ala Leu Ser Gln Leu Asp Phe Gln Trp Glu
                85                  90                  95

Lys Val Asn Lys Met Tyr Lys Asp Arg Gln Gly Arg Phe Asp Arg Ser
            100                 105                 110

<210> SEQ ID NO 77
<211> LENGTH: 107
<212> TYPE: PRT
<213> ORGANISM: Homo sapiens

<400> SEQUENCE: 77

Val Glu Lys Trp Arg Arg Phe His Tyr Asp Ile Lys Ile Phe Asn Gln
1               5                   10                  15

Trp Leu Thr Glu Ala Glu Gln Phe Leu Arg Lys Thr Gln Ile Pro Glu
            20                  25                  30

Asn Trp Glu His Ala Lys Tyr Lys Trp Tyr Leu Lys Glu Leu Gln Asp
        35                  40                  45

Gly Ile Gly Gln Arg Gln Thr Val Val Arg Thr Leu Asn Ala Thr Gly
    50                  55                  60

Glu Glu Ile Ile Gln Gln Ser Ser Lys Thr Asp Ala Ser Ile Leu Gln
65                  70                  75                  80

Glu Lys Leu Gly Ser Leu Asn Leu Arg Trp Gln Glu Val Cys Lys Gln
                85                  90                  95

Leu Ser Asp Arg Lys Lys Arg Leu Glu Glu Gln
            100                 105

<210> SEQ ID NO 78
<211> LENGTH: 41
<212> TYPE: PRT
<213> ORGANISM: Homo sapiens

<400> SEQUENCE: 78

Ala Pro Gly Leu Thr Thr Ile Gly Ala Ser Pro Thr Gln Thr Val Thr
1               5                   10                  15

Leu Val Thr Gln Pro Val Val Thr Lys Glu Thr Ala Ile Ser Lys Leu
            20                  25                  30

Glu Met Pro Ser Ser Leu Met Leu Glu
        35                  40

```
<210> SEQ ID NO 79
<211> LENGTH: 129
<212> TYPE: PRT
<213> ORGANISM: Homo sapiens

<400> SEQUENCE: 79

Ser Asp Gln Trp Lys Arg Leu His Leu Ser Leu Gln Glu Leu Leu Val
1               5                   10                  15

Trp Leu Gln Leu Lys Asp Asp Glu Leu Ser Arg Gln Ala Pro Ile Gly
            20                  25                  30

Gly Asp Phe Pro Ala Val Gln Lys Gln Asn Asp Val His Arg Ala Phe
        35                  40                  45

Lys Arg Glu Leu Lys Thr Lys Glu Pro Val Ile Met Ser Thr Leu Glu
    50                  55                  60

Thr Val Arg Ile Phe Leu Thr Glu Gln Pro Leu Glu Gly Leu Glu Lys
65                  70                  75                  80

Leu Tyr Gln Glu Pro Arg Glu Leu Pro Pro Glu Glu Arg Ala Gln Asn
                85                  90                  95

Val Thr Arg Leu Leu Arg Lys Gln Ala Glu Glu Val Asn Thr Glu Trp
            100                 105                 110

Glu Lys Leu Asn Leu His Ser Ala Asp Trp Gln Arg Lys Ile Asp Glu
        115                 120                 125

Thr

<210> SEQ ID NO 80
<211> LENGTH: 108
<212> TYPE: PRT
<213> ORGANISM: Homo sapiens

<400> SEQUENCE: 80

Leu Glu Arg Leu Gln Glu Leu Gln Glu Ala Thr Asp Glu Leu Asp Leu
1               5                   10                  15

Lys Leu Arg Gln Ala Glu Val Ile Lys Gly Ser Trp Gln Pro Val Gly
            20                  25                  30

Asp Leu Leu Ile Asp Ser Leu Gln Asp His Leu Glu Lys Val Lys Ala
        35                  40                  45

Leu Arg Gly Glu Ile Ala Pro Leu Lys Glu Asn Val Ser His Val Asn
    50                  55                  60

Asp Leu Ala Arg Gln Leu Thr Thr Leu Gly Ile Gln Leu Ser Pro Tyr
65                  70                  75                  80

Asn Leu Ser Thr Leu Glu Asp Leu Asn Thr Arg Trp Lys Leu Leu Gln
                85                  90                  95

Val Ala Val Glu Asp Arg Val Arg Gln Leu His Glu
            100                 105

<210> SEQ ID NO 81
<211> LENGTH: 72
<212> TYPE: PRT
<213> ORGANISM: Homo sapiens

<400> SEQUENCE: 81

Ala His Arg Asp Phe Gly Pro Ala Ser Gln His Phe Leu Ser Thr Ser
1               5                   10                  15

Val Gln Gly Pro Trp Glu Arg Ala Ile Ser Pro Asn Lys Val Pro Tyr
            20                  25                  30

Tyr Ile Asn His Glu Thr Gln Thr Thr Cys Trp Asp His Pro Lys Met
        35                  40                  45
```

Thr Glu Leu Tyr Gln Ser Leu Ala Asp Leu Asn Asn Val Arg Phe Ser
 50                  55                  60

Ala Tyr Arg Thr Ala Met Lys Leu
 65                  70

<210> SEQ ID NO 82
<211> LENGTH: 296
<212> TYPE: PRT
<213> ORGANISM: Homo sapiens

<400> SEQUENCE: 82

Arg Arg Leu Gln Lys Ala Leu Cys Leu Asp Leu Leu Ser Leu Ser Ala
 1               5                   10                  15

Ala Cys Asp Ala Leu Asp Gln His Asn Leu Lys Gln Asn Asp Gln Pro
                20                  25                  30

Met Asp Ile Leu Gln Ile Ile Asn Cys Leu Thr Thr Ile Tyr Asp Arg
            35                  40                  45

Leu Glu Gln Glu His Asn Asn Leu Val Asn Val Pro Leu Cys Val Asp
 50                  55                  60

Met Cys Leu Asn Trp Leu Leu Asn Val Tyr Asp Thr Gly Arg Thr Gly
 65                  70                  75                  80

Arg Ile Arg Val Leu Ser Phe Lys Thr Gly Ile Ile Ser Leu Cys Lys
                85                  90                  95

Ala His Leu Glu Asp Lys Tyr Arg Tyr Leu Phe Lys Val Ala Ser
            100                 105                 110

Ser Thr Gly Phe Cys Asp Gln Arg Arg Leu Gly Leu Leu His Asp
        115                 120                 125

Ser Ile Gln Ile Pro Arg Gln Leu Gly Glu Val Ala Ser Phe Gly Gly
130                 135                 140

Ser Asn Ile Glu Pro Ser Val Arg Ser Cys Phe Gln Phe Ala Asn Asn
145                 150                 155                 160

Lys Pro Glu Ile Glu Ala Ala Leu Phe Leu Asp Trp Met Arg Leu Glu
                165                 170                 175

Pro Gln Ser Met Val Trp Leu Pro Val Leu His Arg Val Ala Ala Ala
            180                 185                 190

Glu Thr Ala Lys His Gln Ala Lys Cys Asn Ile Cys Lys Glu Cys Pro
        195                 200                 205

Ile Ile Gly Phe Arg Tyr Arg Ser Leu Lys His Phe Asn Tyr Asp Ile
210                 215                 220

Cys Gln Ser Cys Phe Phe Ser Gly Arg Val Ala Lys Gly His Lys Met
225                 230                 235                 240

His Tyr Pro Met Val Glu Tyr Cys Thr Pro Thr Thr Ser Gly Glu Asp
                245                 250                 255

Val Arg Asp Phe Ala Lys Val Leu Lys Asn Lys Phe Arg Thr Lys Arg
            260                 265                 270

Tyr Phe Ala Lys His Pro Arg Met Gly Tyr Leu Pro Val Gln Thr Val
        275                 280                 285

Leu Glu Gly Asp Asn Met Glu Thr
290                 295

<210> SEQ ID NO 83
<211> LENGTH: 1311
<212> TYPE: PRT
<213> ORGANISM: Artificial Sequence
<220> FEATURE:
<223> OTHER INFORMATION: BXA-212372-J4V13

<400> SEQUENCE: 83

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415
```

```
Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Met Asp Leu Gln Asn Gln Lys Leu Thr Glu Ile Thr His Val Ser
    450                 455                 460

Gln Ala Leu Leu Glu Val Glu Gln Leu Asn Ala Pro Asp Leu Cys
465                 470                 475                 480

Ala Lys Asp Phe Glu Asp Leu Phe Lys Gln Glu Ser Leu Lys Asn
                485                 490                 495

Ile Lys Asp Ser Leu Gln Gln Ser Ser Gly Arg Ile Asp Ile His
                500                 505                 510

Ser Lys Lys Thr Ala Ala Leu Gln Ser Ala Thr Pro Val Glu Arg Val
        515                 520                 525

Lys Leu Gln Glu Ala Leu Ser Gln Leu Asp Phe Gln Trp Glu Lys Val
    530                 535                 540

Asn Lys Met Tyr Lys Asp Arg Gln Gly Arg Phe Asp Arg Ser Val Glu
545                 550                 555                 560

Lys Trp Arg Arg Phe His Tyr Asp Ile Lys Ile Phe Asn Gln Trp Leu
                565                 570                 575

Thr Glu Ala Glu Gln Phe Leu Arg Lys Thr Gln Ile Pro Glu Asn Trp
            580                 585                 590

Glu His Ala Lys Tyr Lys Trp Tyr Leu Lys Glu Leu Gln Asp Gly Ile
        595                 600                 605

Gly Gln Arg Gln Thr Val Val Arg Thr Leu Asn Ala Thr Gly Glu Glu
    610                 615                 620

Ile Ile Gln Gln Ser Ser Lys Thr Asp Ala Ser Ile Leu Gln Glu Lys
625                 630                 635                 640

Leu Gly Ser Leu Asn Leu Arg Trp Gln Glu Val Cys Lys Gln Leu Ser
                645                 650                 655

Asp Arg Lys Lys Arg Leu Glu Glu Gln Ala Pro Gly Leu Thr Thr Ile
                660                 665                 670

Gly Ala Ser Pro Thr Gln Thr Val Thr Leu Val Thr Gln Pro Val Val
        675                 680                 685

Thr Lys Glu Thr Ala Ile Ser Lys Leu Glu Met Pro Ser Ser Leu Met
    690                 695                 700

Leu Glu Ser Asp Gln Trp Lys Arg Leu His Leu Ser Leu Gln Glu Leu
705                 710                 715                 720

Leu Val Trp Leu Gln Leu Lys Asp Asp Glu Leu Ser Arg Gln Ala Pro
                725                 730                 735

Ile Gly Gly Asp Phe Pro Ala Val Gln Lys Gln Asn Asp Val His Arg
                740                 745                 750

Ala Phe Lys Arg Glu Leu Lys Thr Lys Glu Pro Val Ile Met Ser Thr
        755                 760                 765

Leu Glu Thr Val Arg Ile Phe Leu Thr Glu Gln Pro Leu Glu Gly Leu
    770                 775                 780

Glu Lys Leu Tyr Gln Glu Pro Arg Glu Leu Pro Pro Glu Glu Arg Ala
785                 790                 795                 800

Gln Asn Val Thr Arg Leu Leu Arg Lys Gln Ala Glu Glu Val Asn Thr
                805                 810                 815

Glu Trp Glu Lys Leu Asn Leu His Ser Ala Asp Trp Gln Arg Lys Ile
            820                 825                 830
```

```
Asp Glu Thr Leu Glu Arg Leu Gln Glu Leu Gln Ala Thr Asp Glu
            835                 840                 845

Leu Asp Leu Lys Leu Arg Gln Ala Glu Val Ile Lys Gly Ser Trp Gln
850                 855                 860

Pro Val Gly Asp Leu Leu Ile Asp Ser Leu Gln Asp His Leu Glu Lys
865                 870                 875                 880

Val Lys Ala Leu Arg Gly Glu Ile Ala Pro Leu Lys Glu Asn Val Ser
                885                 890                 895

His Val Asn Asp Leu Ala Arg Gln Thr Thr Leu Gly Ile Gln Leu
            900                 905                 910

Ser Pro Tyr Asn Leu Ser Thr Leu Glu Asp Leu Asn Thr Arg Trp Lys
            915                 920                 925

Leu Leu Gln Val Ala Val Glu Asp Arg Val Arg Gln Leu His Glu Ala
            930                 935                 940

His Arg Asp Phe Gly Pro Ala Ser Gln His Phe Leu Ser Thr Ser Val
945                 950                 955                 960

Gln Gly Pro Trp Glu Arg Ala Ile Ser Pro Asn Lys Val Pro Tyr Tyr
                965                 970                 975

Ile Asn His Glu Thr Gln Thr Thr Cys Trp Asp His Pro Lys Met Thr
            980                 985                 990

Glu Leu Tyr Gln Ser Leu Ala Asp Leu Asn Asn Val Arg Phe Ser Ala
            995                 1000                1005

Tyr Arg Thr Ala Met Lys Leu Arg Arg Leu Gln Lys Ala Leu Cys
    1010                1015                1020

Leu Asp Leu Leu Ser Leu Ser Ala Ala Cys Asp Ala Leu Asp Gln
    1025                1030                1035

His Asn Leu Lys Gln Asn Asp Gln Pro Met Asp Ile Leu Gln Ile
    1040                1045                1050

Ile Asn Cys Leu Thr Thr Ile Tyr Asp Arg Leu Glu Gln Glu His
    1055                1060                1065

Asn Asn Leu Val Asn Val Pro Leu Cys Val Asp Met Cys Leu Asn
    1070                1075                1080

Trp Leu Leu Asn Val Tyr Asp Thr Gly Arg Thr Gly Arg Ile Arg
    1085                1090                1095

Val Leu Ser Phe Lys Thr Gly Ile Ile Ser Leu Cys Lys Ala His
    1100                1105                1110

Leu Glu Asp Lys Tyr Arg Tyr Leu Phe Lys Gln Val Ala Ser Ser
    1115                1120                1125

Thr Gly Phe Cys Asp Gln Arg Arg Leu Gly Leu Leu His Asp
    1130                1135                1140

Ser Ile Gln Ile Pro Arg Gln Leu Gly Glu Val Ala Ser Phe Gly
    1145                1150                1155

Gly Ser Asn Ile Glu Pro Ser Val Arg Ser Cys Phe Gln Phe Ala
    1160                1165                1170

Asn Asn Lys Pro Glu Ile Glu Ala Ala Leu Phe Leu Asp Trp Met
    1175                1180                1185

Arg Leu Glu Pro Gln Ser Met Val Trp Leu Pro Val Leu His Arg
    1190                1195                1200

Val Ala Ala Ala Glu Thr Ala Lys His Gln Ala Lys Cys Asn Ile
    1205                1210                1215

Cys Lys Glu Cys Pro Ile Ile Gly Phe Arg Tyr Arg Ser Leu Lys
    1220                1225                1230

His Phe Asn Tyr Asp Ile Cys Gln Ser Cys Phe Phe Ser Gly Arg
```

```
                1235                1240                1245

Val Ala Lys Gly His Lys Met His Tyr Pro Met Val Glu Tyr Cys
                1250                1255                1260

Thr Pro Thr Thr Ser Gly Glu Asp Val Arg Asp Phe Ala Lys Val
                1265                1270                1275

Leu Lys Asn Lys Phe Arg Thr Lys Arg Tyr Phe Ala Lys His Pro
                1280                1285                1290

Arg Met Gly Tyr Leu Pro Val Gln Thr Val Leu Glu Gly Asp Asn
                1295                1300                1305

Met Glu Thr
                1310

<210> SEQ ID NO 84
<211> LENGTH: 1310
<212> TYPE: PRT
<213> ORGANISM: Artificial Sequence
<220> FEATURE:
<223> OTHER INFORMATION: BXA-212372-J4V12

<400> SEQUENCE: 84

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
                20                  25                  30

Gly Lys Gln His Ile Glu Asn Leu Phe Ser Asp Leu Gln Asp Gly Arg
            35                  40                  45

Arg Leu Leu Asp Leu Leu Glu Gly Leu Thr Gly Gln Lys Leu Pro Lys
50                  55                  60

Glu Lys Gly Ser Thr Arg Val His Ala Leu Asn Asn Val Asn Lys Ala
65                  70                  75                  80

Leu Arg Val Leu Gln Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
```

```
              275                 280                 285
Thr Ser Ser Pro Lys Pro Arg Phe Lys Ser Tyr Ala Tyr Thr Gln Ala
290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
                340                 345                 350

Ser Trp Leu Leu Ser Ala Glu Asp Thr Leu Gln Ala Gln Gly Glu Ile
                355                 360                 365

Ser Asn Asp Val Glu Val Val Lys Asp Gln Phe His Thr His Glu Gly
370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
                420                 425                 430

Cys Leu Arg Val Ala Ser Met Glu Lys Gln Ser Asn Leu His Arg Val
                435                 440                 445

Leu Met Asp Leu Gln Asn Gln Lys Thr Glu Ile Thr His Val Ser Gln
450                 455                 460

Ala Leu Leu Glu Val Glu Gln Leu Leu Asn Ala Pro Asp Leu Cys Ala
465                 470                 475                 480

Lys Asp Phe Glu Asp Leu Phe Lys Gln Glu Glu Ser Leu Lys Asn Ile
                485                 490                 495

Lys Asp Ser Leu Gln Gln Ser Ser Gly Arg Ile Asp Ile Ile His Ser
                500                 505                 510

Lys Lys Thr Ala Ala Leu Gln Ser Ala Thr Pro Val Glu Arg Val Lys
                515                 520                 525

Leu Gln Glu Ala Leu Ser Gln Leu Asp Phe Gln Trp Glu Lys Val Asn
530                 535                 540

Lys Met Tyr Lys Asp Arg Gln Gly Arg Phe Asp Arg Ser Val Glu Lys
545                 550                 555                 560

Trp Arg Arg Phe His Tyr Asp Ile Lys Ile Phe Asn Gln Trp Leu Thr
                565                 570                 575

Glu Ala Glu Gln Phe Leu Arg Lys Thr Gln Ile Pro Glu Asn Trp Glu
                580                 585                 590

His Ala Lys Tyr Lys Trp Tyr Leu Lys Glu Leu Gln Asp Gly Ile Gly
                595                 600                 605

Gln Arg Gln Thr Val Val Arg Thr Leu Asn Ala Thr Gly Glu Glu Ile
                610                 615                 620

Ile Gln Gln Ser Ser Lys Thr Asp Ala Ser Ile Leu Gln Glu Lys Leu
625                 630                 635                 640

Gly Ser Leu Asn Leu Arg Trp Gln Glu Val Cys Lys Gln Leu Ser Asp
                645                 650                 655

Arg Lys Lys Arg Leu Glu Glu Gln Ala Pro Gly Leu Thr Ile Gly
                660                 665                 670

Ala Ser Pro Thr Gln Thr Val Thr Leu Val Thr Gln Pro Val Val Thr
                675                 680                 685

Lys Glu Thr Ala Ile Ser Lys Leu Glu Met Pro Ser Ser Leu Met Leu
                690                 695                 700
```

```
Glu Ser Asp Gln Trp Lys Arg Leu His Leu Ser Leu Gln Glu Leu Leu
705                 710                 715                 720

Val Trp Leu Gln Leu Lys Asp Asp Glu Leu Ser Arg Gln Ala Pro Ile
            725                 730                 735

Gly Gly Asp Phe Pro Ala Val Gln Lys Gln Asn Asp Val His Arg Ala
        740                 745                 750

Phe Lys Arg Glu Leu Lys Thr Lys Glu Pro Val Ile Met Ser Thr Leu
            755                 760                 765

Glu Thr Val Arg Ile Phe Leu Thr Glu Gln Pro Leu Glu Gly Leu Glu
770                 775                 780

Lys Leu Tyr Gln Glu Pro Arg Glu Leu Pro Glu Glu Arg Ala Gln
785                 790                 795                 800

Asn Val Thr Arg Leu Leu Arg Lys Gln Ala Glu Glu Val Asn Thr Glu
                805                 810                 815

Trp Glu Lys Leu Asn Leu His Ser Ala Asp Trp Gln Arg Lys Ile Asp
            820                 825                 830

Glu Thr Leu Glu Arg Leu Gln Glu Leu Gln Glu Ala Thr Asp Glu Leu
        835                 840                 845

Asp Leu Lys Leu Arg Gln Ala Glu Val Ile Lys Gly Ser Trp Gln Pro
850                 855                 860

Val Gly Asp Leu Leu Ile Asp Ser Leu Gln Asp His Leu Glu Lys Val
865                 870                 875                 880

Lys Ala Leu Arg Gly Glu Ile Ala Pro Leu Lys Glu Asn Val Ser His
                885                 890                 895

Val Asn Asp Leu Ala Arg Gln Leu Thr Thr Leu Gly Ile Gln Leu Ser
            900                 905                 910

Pro Tyr Asn Leu Ser Thr Leu Glu Asp Leu Asn Thr Arg Trp Lys Leu
        915                 920                 925

Leu Gln Val Ala Val Glu Asp Arg Val Arg Gln Leu His Glu Ala His
    930                 935                 940

Arg Asp Phe Gly Pro Ala Ser Gln His Phe Leu Ser Thr Ser Val Gln
945                 950                 955                 960

Gly Pro Trp Glu Arg Ala Ile Ser Pro Asn Lys Val Pro Tyr Tyr Ile
                965                 970                 975

Asn His Glu Thr Gln Thr Thr Cys Trp Asp His Pro Lys Met Thr Glu
            980                 985                 990

Leu Tyr Gln Ser Leu Ala Asp Leu Asn Asn Val Arg Phe Ser Ala Tyr
        995                 1000                1005

Arg Thr Ala Met Lys Leu Arg Arg Leu Gln Lys Ala Leu Cys Leu
    1010                1015                1020

Asp Leu Leu Ser Leu Ser Ala Ala Cys Asp Ala Leu Asp Gln His
    1025                1030                1035

Asn Leu Lys Gln Asn Asp Gln Pro Met Asp Ile Leu Gln Ile Ile
    1040                1045                1050

Asn Cys Leu Thr Thr Ile Tyr Asp Arg Leu Glu Gln Glu His Asn
    1055                1060                1065

Asn Leu Val Asn Val Pro Leu Cys Val Asp Met Cys Leu Asn Trp
    1070                1075                1080

Leu Leu Asn Val Tyr Asp Thr Gly Arg Thr Gly Arg Ile Arg Val
    1085                1090                1095

Leu Ser Phe Lys Thr Gly Ile Ile Ser Leu Cys Lys Ala His Leu
    1100                1105                1110
```

-continued

```
Glu Asp Lys Tyr Arg Tyr Leu Phe Lys Gln Val Ala Ser Ser Thr
    1115                1120                1125

Gly Phe Cys Asp Gln Arg Arg Leu Gly Leu Leu Leu His Asp Ser
    1130                1135                1140

Ile Gln Ile Pro Arg Gln Leu Gly Glu Val Ala Ser Phe Gly Gly
    1145                1150                1155

Ser Asn Ile Glu Pro Ser Val Arg Ser Cys Phe Gln Phe Ala Asn
    1160                1165                1170

Asn Lys Pro Glu Ile Glu Ala Ala Leu Phe Leu Asp Trp Met Arg
    1175                1180                1185

Leu Glu Pro Gln Ser Met Val Trp Leu Pro Val Leu His Arg Val
    1190                1195                1200

Ala Ala Ala Glu Thr Ala Lys His Gln Ala Lys Cys Asn Ile Cys
    1205                1210                1215

Lys Glu Cys Pro Ile Ile Gly Phe Arg Tyr Arg Ser Leu Lys His
    1220                1225                1230

Phe Asn Tyr Asp Ile Cys Gln Ser Cys Phe Phe Ser Gly Arg Val
    1235                1240                1245

Ala Lys Gly His Lys Met His Tyr Pro Met Val Glu Tyr Cys Thr
    1250                1255                1260

Pro Thr Thr Ser Gly Glu Asp Val Arg Asp Phe Ala Lys Val Leu
    1265                1270                1275

Lys Asn Lys Phe Arg Thr Lys Arg Tyr Phe Ala Lys His Pro Arg
    1280                1285                1290

Met Gly Tyr Leu Pro Val Gln Thr Val Leu Glu Gly Asp Asn Met
    1295                1300                1305

Glu Thr
    1310

<210> SEQ ID NO 85
<211> LENGTH: 1309
<212> TYPE: PRT
<213> ORGANISM: Artificial Sequence
<220> FEATURE:
<223> OTHER INFORMATION: BXA-212372-J4V11

<400> SEQUENCE: 85

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140
```

```
Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
            165                 170                 175

Arg Pro Asp Leu Phe Asp Trp Asn Ser Val Val Cys Gln Gln Ser Ala
                180                 185                 190

Thr Gln Arg Leu Glu His Ala Phe Asn Ile Ala Arg Tyr Gln Leu Gly
            195                 200                 205

Ile Glu Lys Leu Leu Asp Pro Glu Asp Val Asp Thr Thr Tyr Pro Asp
210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Met Asp Leu Gln Asn Gln Lys Glu Ile Thr His Val Ser Gln Ala
450                 455                 460

Leu Leu Glu Val Glu Gln Leu Leu Asn Ala Pro Asp Leu Cys Ala Lys
465                 470                 475                 480

Asp Phe Glu Asp Leu Phe Lys Gln Glu Glu Ser Leu Lys Asn Ile Lys
                485                 490                 495

Asp Ser Leu Gln Gln Ser Ser Gly Arg Ile Asp Ile Ile His Ser Lys
            500                 505                 510

Lys Thr Ala Ala Leu Gln Ser Ala Thr Pro Val Glu Arg Val Lys Leu
        515                 520                 525

Gln Glu Ala Leu Ser Gln Leu Asp Phe Gln Trp Glu Lys Val Asn Lys
    530                 535                 540

Met Tyr Lys Asp Arg Gln Gly Arg Phe Asp Arg Ser Val Glu Lys Trp
545                 550                 555                 560

Arg Arg Phe His Tyr Asp Ile Lys Ile Phe Asn Gln Trp Leu Thr Glu
```

565                 570                 575
Ala Glu Gln Phe Leu Arg Lys Thr Gln Ile Pro Glu Asn Trp Glu His
                580                 585                 590

Ala Lys Tyr Lys Trp Tyr Leu Lys Glu Leu Gln Asp Gly Ile Gly Gln
                595                 600                 605

Arg Gln Thr Val Val Arg Thr Leu Asn Ala Thr Gly Glu Glu Ile Ile
            610                 615                 620

Gln Gln Ser Ser Lys Thr Asp Ala Ser Ile Leu Gln Glu Lys Leu Gly
625                 630                 635                 640

Ser Leu Asn Leu Arg Trp Gln Glu Val Cys Lys Gln Leu Ser Asp Arg
                645                 650                 655

Lys Lys Arg Leu Glu Glu Gln Ala Pro Gly Leu Thr Thr Ile Gly Ala
                660                 665                 670

Ser Pro Thr Gln Thr Val Thr Leu Val Thr Gln Pro Val Val Thr Lys
                675                 680                 685

Glu Thr Ala Ile Ser Lys Leu Glu Met Pro Ser Ser Leu Met Leu Glu
            690                 695                 700

Ser Asp Gln Trp Lys Arg Leu His Leu Ser Leu Gln Glu Leu Leu Val
705                 710                 715                 720

Trp Leu Gln Leu Lys Asp Asp Glu Leu Ser Arg Gln Ala Pro Ile Gly
                725                 730                 735

Gly Asp Phe Pro Ala Val Gln Lys Gln Asn Asp Val His Arg Ala Phe
                740                 745                 750

Lys Arg Glu Leu Lys Thr Lys Glu Pro Val Ile Met Ser Thr Leu Glu
                755                 760                 765

Thr Val Arg Ile Phe Leu Thr Glu Gln Pro Leu Glu Gly Leu Glu Lys
            770                 775                 780

Leu Tyr Gln Glu Pro Arg Glu Leu Pro Pro Glu Glu Arg Ala Gln Asn
785                 790                 795                 800

Val Thr Arg Leu Leu Arg Lys Gln Ala Glu Glu Val Asn Thr Glu Trp
                805                 810                 815

Glu Lys Leu Asn Leu His Ser Ala Asp Trp Gln Arg Lys Ile Asp Glu
                820                 825                 830

Thr Leu Glu Arg Leu Gln Glu Leu Gln Glu Ala Thr Asp Glu Leu Asp
            835                 840                 845

Leu Lys Leu Arg Gln Ala Glu Val Ile Lys Gly Ser Trp Gln Pro Val
850                 855                 860

Gly Asp Leu Leu Ile Asp Ser Leu Gln Asp His Leu Glu Lys Val Lys
                865     870                 875                 880

Ala Leu Arg Gly Glu Ile Ala Pro Leu Lys Glu Asn Val Ser His Val
                885                 890                 895

Asn Asp Leu Ala Arg Gln Leu Thr Thr Leu Gly Ile Gln Leu Ser Pro
            900                 905                 910

Tyr Asn Leu Ser Thr Leu Glu Asp Leu Asn Thr Arg Trp Lys Leu Leu
            915                 920                 925

Gln Val Ala Val Glu Asp Arg Val Arg Gln Leu His Glu Ala His Arg
            930                 935                 940

Asp Phe Gly Pro Ala Ser Gln His Phe Leu Ser Thr Ser Val Gln Gly
945                 950                 955                 960

Pro Trp Glu Arg Ala Ile Ser Pro Asn Lys Val Pro Tyr Tyr Ile Asn
                965                 970                 975

His Glu Thr Gln Thr Thr Cys Trp Asp His Pro Lys Met Thr Glu Leu
            980                 985                 990

Tyr Gln Ser Leu Ala Asp Leu Asn Asn Val Arg Phe Ser Ala Tyr Arg
        995                 1000                    1005

Thr Ala Met Lys Leu Arg Arg Leu Gln Lys Ala Leu Cys Leu Asp
    1010                1015                1020

Leu Leu Ser Leu Ser Ala Ala Cys Asp Ala Leu Asp Gln His Asn
    1025                1030                1035

Leu Lys Gln Asn Asp Gln Pro Met Asp Ile Leu Gln Ile Ile Asn
    1040                1045                1050

Cys Leu Thr Thr Ile Tyr Asp Arg Leu Glu Gln Glu His Asn Asn
    1055                1060                1065

Leu Val Asn Val Pro Leu Cys Val Asp Met Cys Leu Asn Trp Leu
    1070                1075                1080

Leu Asn Val Tyr Asp Thr Gly Arg Thr Gly Arg Ile Arg Val Leu
    1085                1090                1095

Ser Phe Lys Thr Gly Ile Ile Ser Leu Cys Lys Ala His Leu Glu
    1100                1105                1110

Asp Lys Tyr Arg Tyr Leu Phe Lys Gln Val Ala Ser Ser Thr Gly
    1115                1120                1125

Phe Cys Asp Gln Arg Arg Leu Gly Leu Leu Leu His Asp Ser Ile
    1130                1135                1140

Gln Ile Pro Arg Gln Leu Gly Glu Val Ala Ser Phe Gly Gly Ser
    1145                1150                1155

Asn Ile Glu Pro Ser Val Arg Ser Cys Phe Gln Phe Ala Asn Asn
    1160                1165                1170

Lys Pro Glu Ile Glu Ala Ala Leu Phe Leu Asp Trp Met Arg Leu
    1175                1180                1185

Glu Pro Gln Ser Met Val Trp Leu Pro Val Leu His Arg Val Ala
    1190                1195                1200

Ala Ala Glu Thr Ala Lys His Gln Ala Lys Cys Asn Ile Cys Lys
    1205                1210                1215

Glu Cys Pro Ile Ile Gly Phe Arg Tyr Arg Ser Leu Lys His Phe
    1220                1225                1230

Asn Tyr Asp Ile Cys Gln Ser Cys Phe Phe Ser Gly Arg Val Ala
    1235                1240                1245

Lys Gly His Lys Met His Tyr Pro Met Val Glu Tyr Cys Thr Pro
    1250                1255                1260

Thr Thr Ser Gly Glu Asp Val Arg Asp Phe Ala Lys Val Leu Lys
    1265                1270                1275

Asn Lys Phe Arg Thr Lys Arg Tyr Phe Ala Lys His Pro Arg Met
    1280                1285                1290

Gly Tyr Leu Pro Val Gln Thr Val Leu Glu Gly Asp Asn Met Glu
    1295                1300                1305

Thr

<210> SEQ ID NO 86
<211> LENGTH: 1309
<212> TYPE: PRT
<213> ORGANISM: Artificial Sequence
<220> FEATURE:
<223> OTHER INFORMATION: BXA-212372-J4V4

<400> SEQUENCE: 86

Met Leu Trp Trp Glu Glu Val Glu Asp Cys Tyr Glu Arg Glu Asp Val
1               5                   10                  15

```
Gln Lys Lys Thr Phe Thr Lys Trp Val Asn Ala Gln Phe Ser Lys Phe
             20                  25                  30
Gly Lys Gln His Ile Glu Asn Leu Phe Ser Asp Leu Gln Asp Gly Arg
             35                  40                  45
Arg Leu Leu Asp Leu Leu Glu Gly Leu Thr Gly Gln Lys Leu Pro Lys
 50                  55                  60
Glu Lys Gly Ser Thr Arg Val His Ala Leu Asn Asn Val Asn Lys Ala
 65                  70                  75                  80
Leu Arg Val Leu Gln Asn Asn Val Asp Leu Val Asn Ile Gly Ser
                 85                  90                  95
Thr Asp Ile Val Asp Gly Asn His Lys Leu Thr Leu Gly Leu Ile Trp
             100                 105                 110
Asn Ile Ile Leu His Trp Gln Val Lys Asn Val Met Lys Asn Ile Met
             115                 120                 125
Ala Gly Leu Gln Gln Thr Asn Ser Glu Lys Ile Leu Leu Ser Trp Val
             130                 135                 140
Arg Gln Ser Thr Arg Asn Tyr Pro Gln Val Asn Val Ile Asn Phe Thr
145                 150                 155                 160
Thr Ser Trp Ser Asp Gly Leu Ala Leu Asn Ala Leu Ile His Ser His
                 165                 170                 175
Arg Pro Asp Leu Phe Asp Trp Asn Ser Val Val Cys Gln Gln Ser Ala
             180                 185                 190
Thr Gln Arg Leu Glu His Ala Phe Asn Ile Ala Arg Tyr Gln Leu Gly
             195                 200                 205
Ile Glu Lys Leu Leu Asp Pro Glu Asp Val Asp Thr Thr Tyr Pro Asp
210                 215                 220
Lys Lys Ser Ile Leu Met Tyr Ile Thr Ser Leu Phe Gln Val Leu Pro
225                 230                 235                 240
Gln Gln Val Ser Ile Glu Ala Ile Gln Glu Val Glu Met Leu Pro Arg
                 245                 250                 255
Pro Pro Lys Val Thr Lys Glu Glu His Phe Gln Leu His His Gln Met
             260                 265                 270
His Tyr Ser Gln Gln Ile Thr Val Ser Leu Ala Gln Gly Tyr Glu Arg
             275                 280                 285
Thr Ser Ser Pro Lys Pro Arg Phe Lys Ser Tyr Ala Tyr Thr Gln Ala
290                 295                 300
Ala Tyr Val Thr Thr Ser Asp Pro Thr Arg Ser Pro Phe Pro Ser Gln
305                 310                 315                 320
His Leu Glu Ala Pro Glu Asp Lys Ser Phe Gly Ser Ser Leu Met Glu
             325                 330                 335
Ser Glu Val Asn Leu Asp Arg Tyr Gln Thr Ala Leu Glu Glu Val Leu
                 340                 345                 350
Ser Trp Leu Leu Ser Ala Glu Asp Thr Leu Gln Ala Gln Gly Glu Ile
             355                 360                 365
Ser Asn Asp Val Glu Val Lys Asp Gln Phe His Thr His Glu Gly
             370                 375                 380
Tyr Met Met Asp Leu Thr Ala His Gln Gly Arg Val Gly Asn Ile Leu
385                 390                 395                 400
Gln Leu Gly Ser Lys Leu Ile Gly Thr Gly Lys Leu Ser Glu Asp Glu
                 405                 410                 415
Glu Thr Glu Val Gln Glu Gln Met Asn Leu Leu Asn Ser Arg Trp Glu
             420                 425                 430
Cys Leu Arg Val Ala Ser Met Glu Lys Gln Ser Asn Leu His Arg Val
```

```
            435                 440                 445
Leu Met Asp Leu Thr Tyr Leu Thr Glu Ile Thr His Val Ser Gln Ala
450                 455                 460

Leu Leu Glu Val Glu Gln Leu Leu Asn Ala Pro Asp Leu Cys Ala Lys
465                 470                 475                 480

Asp Phe Glu Asp Leu Phe Lys Gln Glu Glu Ser Leu Lys Asn Ile Lys
                    485                 490                 495

Asp Ser Leu Gln Gln Ser Ser Gly Arg Ile Asp Ile Ile His Ser Lys
                500                 505                 510

Lys Thr Ala Ala Leu Gln Ser Ala Thr Pro Val Glu Arg Val Lys Leu
            515                 520                 525

Gln Glu Ala Leu Ser Gln Leu Asp Phe Gln Trp Lys Val Asn Lys
530                 535                 540

Met Tyr Lys Asp Arg Gln Gly Arg Phe Asp Arg Ser Val Glu Lys Trp
545                 550                 555                 560

Arg Arg Phe His Tyr Asp Ile Lys Ile Phe Asn Gln Trp Leu Thr Glu
                565                 570                 575

Ala Glu Gln Phe Leu Arg Lys Thr Gln Ile Pro Glu Asn Trp Glu His
                580                 585                 590

Ala Lys Tyr Lys Trp Tyr Leu Lys Glu Leu Gln Asp Gly Ile Gly Gln
                595                 600                 605

Arg Gln Thr Val Val Arg Thr Leu Asn Ala Thr Gly Glu Glu Ile Ile
610                 615                 620

Gln Gln Ser Ser Lys Thr Asp Ala Ser Ile Leu Gln Glu Lys Leu Gly
625                 630                 635                 640

Ser Leu Asn Leu Arg Trp Gln Glu Val Cys Lys Gln Leu Ser Asp Arg
                645                 650                 655

Lys Lys Arg Leu Glu Glu Gln Ala Pro Gly Leu Thr Thr Ile Gly Ala
                660                 665                 670

Ser Pro Thr Gln Thr Val Thr Leu Val Thr Gln Pro Val Val Thr Lys
                675                 680                 685

Glu Thr Ala Ile Ser Lys Leu Glu Met Pro Ser Ser Leu Met Leu Glu
690                 695                 700

Ser Asp Gln Trp Lys Arg Leu His Leu Ser Leu Gln Glu Leu Leu Val
705                 710                 715                 720

Trp Leu Gln Leu Lys Asp Asp Glu Leu Ser Arg Gln Ala Pro Ile Gly
                725                 730                 735

Gly Asp Phe Pro Ala Val Gln Lys Gln Asn Asp Val His Arg Ala Phe
                740                 745                 750

Lys Arg Glu Leu Lys Thr Lys Glu Pro Val Ile Met Ser Thr Leu Glu
            755                 760                 765

Thr Val Arg Ile Phe Leu Thr Glu Gln Pro Leu Glu Gly Leu Glu Lys
            770                 775                 780

Leu Tyr Gln Glu Pro Arg Glu Leu Pro Pro Glu Glu Arg Ala Gln Asn
785                 790                 795                 800

Val Thr Arg Leu Leu Arg Lys Gln Ala Glu Glu Val Asn Thr Glu Trp
                805                 810                 815

Glu Lys Leu Asn Leu His Ser Ala Asp Trp Gln Arg Lys Ile Asp Glu
            820                 825                 830

Thr Leu Glu Arg Leu Gln Glu Leu Gln Glu Ala Thr Asp Glu Leu Asp
                835                 840                 845

Leu Lys Leu Arg Gln Ala Glu Val Ile Lys Gly Ser Trp Gln Pro Val
850                 855                 860
```

-continued

```
Gly Asp Leu Leu Ile Asp Ser Leu Gln Asp His Leu Glu Lys Val Lys
865                 870                 875                 880

Ala Leu Arg Gly Glu Ile Ala Pro Leu Lys Glu Asn Val Ser His Val
                885                 890                 895

Asn Asp Leu Ala Arg Gln Leu Thr Thr Leu Gly Ile Gln Leu Ser Pro
            900                 905                 910

Tyr Asn Leu Ser Thr Leu Glu Asp Leu Asn Thr Arg Trp Lys Leu Leu
            915                 920                 925

Gln Val Ala Val Glu Asp Arg Val Arg Gln Leu His Glu Ala His Arg
        930                 935                 940

Asp Phe Gly Pro Ala Ser Gln His Phe Leu Ser Thr Ser Val Gln Gly
945                 950                 955                 960

Pro Trp Glu Arg Ala Ile Ser Pro Asn Lys Val Pro Tyr Tyr Ile Asn
                965                 970                 975

His Glu Thr Gln Thr Thr Cys Trp Asp His Pro Lys Met Thr Glu Leu
            980                 985                 990

Tyr Gln Ser Leu Ala Asp Leu Asn Asn Val Arg Phe Ser Ala Tyr Arg
            995                 1000                1005

Thr Ala Met Lys Leu Arg Arg Leu Gln Lys Ala Leu Cys Leu Asp
    1010                1015                1020

Leu Leu Ser Leu Ser Ala Ala Cys Asp Ala Leu Asp Gln His Asn
    1025                1030                1035

Leu Lys Gln Asn Asp Gln Pro Met Asp Ile Leu Gln Ile Ile Asn
    1040                1045                1050

Cys Leu Thr Thr Ile Tyr Asp Arg Leu Glu Gln Glu His Asn Asn
    1055                1060                1065

Leu Val Asn Val Pro Leu Cys Val Asp Met Cys Leu Asn Trp Leu
    1070                1075                1080

Leu Asn Val Tyr Asp Thr Gly Arg Thr Gly Arg Ile Arg Val Leu
    1085                1090                1095

Ser Phe Lys Thr Gly Ile Ile Ser Leu Cys Lys Ala His Leu Glu
    1100                1105                1110

Asp Lys Tyr Arg Tyr Leu Phe Lys Gln Val Ala Ser Ser Thr Gly
    1115                1120                1125

Phe Cys Asp Gln Arg Arg Leu Gly Leu Leu Leu His Asp Ser Ile
    1130                1135                1140

Gln Ile Pro Arg Gln Leu Gly Glu Val Ala Ser Phe Gly Gly Ser
    1145                1150                1155

Asn Ile Glu Pro Ser Val Arg Ser Cys Phe Gln Phe Ala Asn Asn
    1160                1165                1170

Lys Pro Glu Ile Glu Ala Ala Leu Phe Leu Asp Trp Met Arg Leu
    1175                1180                1185

Glu Pro Gln Ser Met Val Trp Leu Pro Val Leu His Arg Val Ala
    1190                1195                1200

Ala Ala Glu Thr Ala Lys His Gln Ala Lys Cys Asn Ile Cys Lys
    1205                1210                1215

Glu Cys Pro Ile Ile Gly Phe Arg Tyr Arg Ser Leu Lys His Phe
    1220                1225                1230

Asn Tyr Asp Ile Cys Gln Ser Cys Phe Phe Ser Gly Arg Val Ala
    1235                1240                1245

Lys Gly His Lys Met His Tyr Pro Met Val Glu Tyr Cys Thr Pro
    1250                1255                1260
```

```
Thr Thr Ser Gly Glu Asp Val Arg Asp Phe Ala Lys Val Leu Lys
    1265            1270            1275

Asn Lys Phe Arg Thr Lys Arg Tyr Phe Ala Lys His Pro Arg Met
1280            1285            1290

Gly Tyr Leu Pro Val Gln Thr Val Leu Glu Gly Asp Asn Met Glu
    1295            1300            1305

Thr

<210> SEQ ID NO 87
<211> LENGTH: 1308
<212> TYPE: PRT
<213> ORGANISM: Artificial Sequence
<220> FEATURE:
<223> OTHER INFORMATION: BXA-212372-J4

<400> SEQUENCE: 87

Met Leu Trp Trp Glu Val Glu Asp Cys Tyr Glu Arg Glu Asp Val
1               5                   10                  15

Gln Lys Lys Thr Phe Thr Lys Trp Val Asn Ala Gln Phe Ser Lys
                20                  25                  30

Gly Lys Gln His Ile Glu Asn Leu Phe Ser Asp Leu Gln Asp Gly Arg
            35                  40                  45

Arg Leu Leu Asp Leu Leu Glu Gly Leu Thr Gly Gln Lys Leu Pro Lys
50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
```

```
                305                 310                 315                 320
His Leu Glu Ala Pro Glu Asp Lys Ser Phe Gly Ser Ser Leu Met Glu
                    325                 330                 335

Ser Glu Val Asn Leu Asp Arg Tyr Gln Thr Ala Leu Glu Glu Val Leu
                    340                 345                 350

Ser Trp Leu Leu Ser Ala Glu Asp Thr Leu Gln Ala Gln Gly Glu Ile
                    355                 360                 365

Ser Asn Asp Val Glu Val Val Lys Asp Gln Phe His Thr His Glu Gly
                    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                    405                 410                 415

Glu Thr Glu Val Gln Glu Gln Met Asn Leu Leu Asn Ser Arg Trp Glu
                    420                 425                 430

Cys Leu Arg Val Ala Ser Met Glu Lys Gln Ser Asn Leu His Ser Tyr
                    435                 440                 445

Val Pro Ser Thr Tyr Leu Thr Glu Ile Thr His Val Ser Gln Ala Leu
                    450                 455                 460

Leu Glu Val Glu Gln Leu Leu Asn Ala Pro Asp Leu Cys Ala Lys Asp
465                 470                 475                 480

Phe Glu Asp Leu Phe Lys Gln Glu Glu Ser Leu Lys Asn Ile Lys Asp
                    485                 490                 495

Ser Leu Gln Gln Ser Ser Gly Arg Ile Asp Ile Ile His Ser Lys Lys
                    500                 505                 510

Thr Ala Ala Leu Gln Ser Ala Thr Pro Val Glu Arg Val Lys Leu Gln
                    515                 520                 525

Glu Ala Leu Ser Gln Leu Asp Phe Gln Trp Glu Lys Val Asn Lys Met
                    530                 535                 540

Tyr Lys Asp Arg Gln Gly Arg Phe Asp Arg Ser Val Glu Lys Trp Arg
545                 550                 555                 560

Arg Phe His Tyr Asp Ile Lys Ile Phe Asn Gln Trp Leu Thr Glu Ala
                    565                 570                 575

Glu Gln Phe Leu Arg Lys Thr Gln Ile Pro Glu Asn Trp Glu His Ala
                    580                 585                 590

Lys Tyr Lys Trp Tyr Leu Lys Glu Leu Gln Asp Gly Ile Gly Gln Arg
                    595                 600                 605

Gln Thr Val Val Arg Thr Leu Asn Ala Thr Gly Glu Glu Ile Ile Gln
                    610                 615                 620

Gln Ser Ser Lys Thr Asp Ala Ser Ile Leu Gln Glu Lys Leu Gly Ser
625                 630                 635                 640

Leu Asn Leu Arg Trp Gln Glu Val Cys Lys Gln Leu Ser Asp Arg Lys
                    645                 650                 655

Lys Arg Leu Glu Glu Gln Ala Pro Gly Leu Thr Thr Ile Gly Ala Ser
                    660                 665                 670

Pro Thr Gln Thr Val Thr Leu Val Thr Gln Pro Val Val Thr Lys Glu
                    675                 680                 685

Thr Ala Ile Ser Lys Leu Glu Met Pro Ser Ser Leu Met Leu Glu Ser
                    690                 695                 700

Asp Gln Trp Lys Arg Leu His Leu Ser Leu Gln Glu Leu Leu Val Trp
705                 710                 715                 720

Leu Gln Leu Lys Asp Asp Glu Leu Ser Arg Gln Ala Pro Ile Gly Gly
                    725                 730                 735
```

```
Asp Phe Pro Ala Val Gln Lys Gln Asn Asp Val His Arg Ala Phe Lys
            740                 745                 750

Arg Glu Leu Lys Thr Lys Glu Pro Val Ile Met Ser Thr Leu Glu Thr
            755                 760                 765

Val Arg Ile Phe Leu Thr Glu Gln Pro Leu Glu Gly Leu Glu Lys Leu
    770                 775                 780

Tyr Gln Glu Pro Arg Glu Leu Pro Pro Glu Arg Ala Gln Asn Val
785                 790                 795                 800

Thr Arg Leu Leu Arg Lys Gln Ala Glu Val Asn Thr Glu Trp Glu
                805                 810                 815

Lys Leu Asn Leu His Ser Ala Asp Trp Gln Arg Lys Ile Asp Glu Thr
            820                 825                 830

Leu Glu Arg Leu Gln Glu Leu Gln Glu Ala Thr Asp Glu Leu Asp Leu
            835                 840                 845

Lys Leu Arg Gln Ala Glu Val Ile Lys Gly Ser Trp Gln Pro Val Gly
            850                 855                 860

Asp Leu Leu Ile Asp Ser Leu Gln Asp His Leu Glu Lys Val Lys Ala
865                 870                 875                 880

Leu Arg Gly Glu Ile Ala Pro Leu Lys Glu Asn Val Ser His Val Asn
                885                 890                 895

Asp Leu Ala Arg Gln Leu Thr Thr Leu Gly Ile Gln Leu Ser Pro Tyr
            900                 905                 910

Asn Leu Ser Thr Leu Glu Asp Leu Asn Thr Arg Trp Lys Leu Leu Gln
            915                 920                 925

Val Ala Val Glu Asp Arg Val Arg Gln Leu His Glu Ala His Arg Asp
            930                 935                 940

Phe Gly Pro Ala Ser Gln His Phe Leu Ser Thr Ser Val Gln Gly Pro
945                 950                 955                 960

Trp Glu Arg Ala Ile Ser Pro Asn Lys Val Pro Tyr Tyr Ile Asn His
                965                 970                 975

Glu Thr Gln Thr Thr Cys Trp Asp His Pro Lys Met Thr Glu Leu Tyr
            980                 985                 990

Gln Ser Leu Ala Asp Leu Asn Asn Val Arg Phe Ser Ala Tyr Arg Thr
            995                 1000                1005

Ala Met Lys Leu Arg Arg Leu Gln Lys Ala Leu Cys Leu Asp Leu
    1010                1015                1020

Leu Ser Leu Ser Ala Ala Cys Asp Ala Leu Asp Gln His Asn Leu
    1025                1030                1035

Lys Gln Asn Asp Gln Pro Met Asp Ile Leu Gln Ile Ile Asn Cys
    1040                1045                1050

Leu Thr Thr Ile Tyr Asp Arg Leu Glu Gln Glu His Asn Asn Leu
    1055                1060                1065

Val Asn Val Pro Leu Cys Val Asp Met Cys Leu Asn Trp Leu Leu
    1070                1075                1080

Asn Val Tyr Asp Thr Gly Arg Thr Gly Arg Ile Arg Val Leu Ser
    1085                1090                1095

Phe Lys Thr Gly Ile Ile Ser Leu Cys Lys Ala His Leu Glu Asp
    1100                1105                1110

Lys Tyr Arg Tyr Leu Phe Lys Gln Val Ala Ser Ser Thr Gly Phe
    1115                1120                1125

Cys Asp Gln Arg Arg Leu Gly Leu Leu Leu His Asp Ser Ile Gln
    1130                1135                1140
```

```
Ile Pro Arg Gln Leu Gly Glu Val Ala Ser Phe Gly Gly Ser Asn
    1145                1150                1155

Ile Glu Pro Ser Val Arg Ser Cys Phe Gln Phe Ala Asn Asn Lys
    1160                1165                1170

Pro Glu Ile Glu Ala Ala Leu Phe Leu Asp Trp Met Arg Leu Glu
    1175                1180                1185

Pro Gln Ser Met Val Trp Leu Pro Val Leu His Arg Val Ala Ala
    1190                1195                1200

Ala Glu Thr Ala Lys His Gln Ala Lys Cys Asn Ile Cys Lys Glu
    1205                1210                1215

Cys Pro Ile Ile Gly Phe Arg Tyr Arg Ser Leu Lys His Phe Asn
    1220                1225                1230

Tyr Asp Ile Cys Gln Ser Cys Phe Phe Ser Gly Arg Val Ala Lys
    1235                1240                1245

Gly His Lys Met His Tyr Pro Met Val Glu Tyr Cys Thr Pro Thr
    1250                1255                1260

Thr Ser Gly Glu Asp Val Arg Asp Phe Ala Lys Val Leu Lys Asn
    1265                1270                1275

Lys Phe Arg Thr Lys Arg Tyr Phe Ala Lys His Pro Arg Met Gly
    1280                1285                1290

Tyr Leu Pro Val Gln Thr Val Leu Glu Gly Asp Asn Met Glu Thr
    1295                1300                1305

<210> SEQ ID NO 88
<211> LENGTH: 1328
<212> TYPE: PRT
<213> ORGANISM: Artificial Sequence
<220> FEATURE:
<223> OTHER INFORMATION: BXA-212372

<400> SEQUENCE: 88

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190
```

```
Thr Gln Arg Leu Glu His Ala Phe Asn Ile Ala Arg Tyr Gln Leu Gly
        195                 200                 205
Ile Glu Lys Leu Leu Asp Pro Glu Asp Val Asp Thr Thr Tyr Pro Asp
    210                 215                 220
Lys Lys Ser Ile Leu Met Tyr Ile Thr Ser Leu Phe Gln Val Leu Pro
225                 230                 235                 240
Gln Gln Val Ser Ile Glu Ala Ile Gln Glu Val Met Leu Pro Arg
                245                 250                 255
Pro Pro Lys Val Thr Lys Glu Glu His Phe Gln Leu His His Gln Met
            260                 265                 270
His Tyr Ser Gln Gln Ile Thr Val Ser Leu Ala Gln Gly Tyr Glu Arg
        275                 280                 285
Thr Ser Ser Pro Lys Pro Arg Phe Lys Ser Tyr Ala Tyr Thr Gln Ala
    290                 295                 300
Ala Tyr Val Thr Thr Ser Asp Pro Thr Arg Ser Pro Phe Pro Ser Gln
305                 310                 315                 320
His Leu Glu Ala Pro Glu Asp Lys Ser Phe Gly Ser Ser Leu Met Glu
                325                 330                 335
Ser Glu Val Asn Leu Asp Arg Tyr Gln Thr Ala Leu Glu Glu Val Leu
            340                 345                 350
Ser Trp Leu Leu Ser Ala Glu Asp Thr Leu Gln Ala Gln Gly Glu Ile
        355                 360                 365
Ser Asn Asp Val Glu Val Val Lys Asp Gln Phe His Thr His Glu Gly
    370                 375                 380
Tyr Met Met Asp Leu Thr Ala His Gln Gly Arg Val Gly Asn Ile Leu
385                 390                 395                 400
Gln Leu Gly Ser Lys Leu Ile Gly Thr Gly Lys Leu Ser Glu Asp Glu
                405                 410                 415
Glu Thr Glu Val Gln Glu Gln Met Asn Leu Leu Asn Ser Arg Trp Glu
            420                 425                 430
Cys Leu Arg Val Ala Ser Met Glu Lys Gln Ser Asn Leu His Ile His
        435                 440                 445
Thr Val Arg Glu Glu Thr Met Met Val Met Thr Glu Asp Met Pro Leu
    450                 455                 460
Glu Ile Ser Tyr Val Pro Ser Thr Tyr Leu Thr Glu Ile Thr His Val
465                 470                 475                 480
Ser Gln Ala Leu Leu Glu Val Glu Gln Leu Leu Asn Ala Pro Asp Leu
                485                 490                 495
Cys Ala Lys Asp Phe Glu Asp Leu Phe Lys Gln Glu Glu Ser Leu Lys
            500                 505                 510
Asn Ile Lys Asp Ser Leu Gln Gln Ser Ser Gly Arg Ile Asp Ile Ile
        515                 520                 525
His Ser Lys Lys Thr Ala Ala Leu Gln Ser Ala Thr Pro Val Glu Arg
    530                 535                 540
Val Lys Leu Gln Glu Ala Leu Ser Gln Leu Asp Phe Gln Trp Glu Lys
545                 550                 555                 560
Val Asn Lys Met Tyr Lys Asp Arg Gln Gly Arg Phe Asp Arg Ser Val
                565                 570                 575
Glu Lys Trp Arg Arg Phe His Tyr Asp Ile Lys Ile Phe Asn Gln Trp
            580                 585                 590
Leu Thr Glu Ala Glu Gln Phe Leu Arg Lys Thr Gln Ile Pro Glu Asn
        595                 600                 605
Trp Glu His Ala Lys Tyr Lys Trp Tyr Leu Lys Glu Leu Gln Asp Gly
```

-continued

```
           610                 615                 620
Ile Gly Gln Arg Gln Thr Val Arg Thr Leu Asn Ala Thr Gly Glu
625                 630                 635                 640

Glu Ile Ile Gln Gln Ser Ser Lys Thr Asp Ala Ser Ile Leu Gln Glu
                645                 650                 655

Lys Leu Gly Ser Leu Asn Leu Arg Trp Gln Glu Val Cys Lys Gln Leu
                660                 665                 670

Ser Asp Arg Lys Lys Arg Leu Glu Glu Gln Ala Pro Gly Leu Thr Thr
                675                 680                 685

Ile Gly Ala Ser Pro Thr Gln Thr Val Thr Leu Val Thr Gln Pro Val
                690                 695                 700

Val Thr Lys Glu Thr Ala Ile Ser Lys Leu Glu Met Pro Ser Ser Leu
705                 710                 715                 720

Met Leu Glu Ser Asp Gln Trp Lys Arg Leu His Leu Ser Leu Gln Glu
                725                 730                 735

Leu Leu Val Trp Leu Gln Leu Lys Asp Asp Glu Leu Ser Arg Gln Ala
                740                 745                 750

Pro Ile Gly Gly Asp Phe Pro Ala Val Gln Lys Gln Asn Asp Val His
                755                 760                 765

Arg Ala Phe Lys Arg Glu Leu Lys Thr Lys Glu Pro Val Ile Met Ser
770                 775                 780

Thr Leu Glu Thr Val Arg Ile Phe Leu Thr Glu Gln Pro Leu Glu Gly
785                 790                 795                 800

Leu Glu Lys Leu Tyr Gln Glu Pro Arg Glu Leu Pro Pro Glu Glu Arg
                805                 810                 815

Ala Gln Asn Val Thr Arg Leu Leu Arg Lys Gln Ala Glu Glu Val Asn
                820                 825                 830

Thr Glu Trp Glu Lys Leu Asn Leu His Ser Ala Asp Trp Gln Arg Lys
                835                 840                 845

Ile Asp Glu Thr Leu Glu Arg Leu Gln Glu Leu Gln Glu Ala Thr Asp
850                 855                 860

Glu Leu Asp Leu Lys Leu Arg Gln Ala Glu Val Ile Lys Gly Ser Trp
865                 870                 875                 880

Gln Pro Val Gly Asp Leu Leu Ile Asp Ser Leu Gln Asp His Leu Glu
                885                 890                 895

Lys Val Lys Ala Leu Arg Gly Glu Ile Ala Pro Leu Lys Glu Asn Val
                900                 905                 910

Ser His Val Asn Asp Leu Ala Arg Gln Leu Thr Thr Leu Gly Ile Gln
                915                 920                 925

Leu Ser Pro Tyr Asn Leu Ser Thr Leu Glu Asp Leu Asn Thr Arg Trp
930                 935                 940

Lys Leu Leu Gln Val Ala Val Glu Asp Arg Val Arg Gln Leu His Glu
945                 950                 955                 960

Ala His Arg Asp Phe Gly Pro Ala Ser Gln His Phe Leu Ser Thr Ser
                965                 970                 975

Val Gln Gly Pro Trp Glu Arg Ala Ile Ser Pro Asn Lys Val Pro Tyr
                980                 985                 990

Tyr Ile Asn His Glu Thr Gln Thr Thr Cys Trp Asp His Pro Lys Met
                995                 1000                1005

Thr Glu Leu Tyr Gln Ser Leu Ala Asp Leu Asn Asn Val Arg Phe
            1010                1015                1020

Ser Ala Tyr Arg Thr Ala Met Lys Leu Arg Arg Leu Gln Lys Ala
            1025                1030                1035
```

| | | | | | | | | | |
|---|---|---|---|---|---|---|---|---|---|
| Leu | Cys | Leu | Asp | Leu | Leu | Ser | Leu | Ser | Ala | Ala | Cys | Asp | Ala | Leu |
| | 1040 | | | | | 1045 | | | | 1050 | | | | |

Leu Cys Leu Asp Leu Leu Ser Leu Ser Ala Ala Cys Asp Ala Leu
     1040                    1045                1050

Asp Gln His Asn Leu Lys Gln Asn Asp Gln Pro Met Asp Ile Leu
    1055                    1060                1065

Gln Ile Ile Asn Cys Leu Thr Thr Ile Tyr Asp Arg Leu Glu Gln
    1070                    1075                1080

Glu His Asn Asn Leu Val Asn Val Pro Leu Cys Val Asp Met Cys
    1085                    1090                1095

Leu Asn Trp Leu Leu Asn Val Tyr Asp Thr Gly Arg Thr Gly Arg
    1100                    1105                1110

Ile Arg Val Leu Ser Phe Lys Thr Gly Ile Ile Ser Leu Cys Lys
    1115                    1120                1125

Ala His Leu Glu Asp Lys Tyr Arg Tyr Leu Phe Lys Gln Val Ala
    1130                    1135                1140

Ser Ser Thr Gly Phe Cys Asp Gln Arg Arg Leu Gly Leu Leu Leu
    1145                    1150                1155

His Asp Ser Ile Gln Ile Pro Arg Gln Leu Gly Glu Val Ala Ser
    1160                    1165                1170

Phe Gly Gly Ser Asn Ile Glu Pro Ser Val Arg Ser Cys Phe Gln
    1175                    1180                1185

Phe Ala Asn Asn Lys Pro Glu Ile Glu Ala Ala Leu Phe Leu Asp
    1190                    1195                1200

Trp Met Arg Leu Glu Pro Gln Ser Met Val Trp Leu Pro Val Leu
    1205                    1210                1215

His Arg Val Ala Ala Ala Glu Thr Ala Lys His Gln Ala Lys Cys
    1220                    1225                1230

Asn Ile Cys Lys Glu Cys Pro Ile Ile Gly Phe Arg Tyr Arg Ser
    1235                    1240                1245

Leu Lys His Phe Asn Tyr Asp Ile Cys Gln Ser Cys Phe Phe Ser
    1250                    1255                1260

Gly Arg Val Ala Lys Gly His Lys Met His Tyr Pro Met Val Glu
    1265                    1270                1275

Tyr Cys Thr Pro Thr Thr Ser Gly Glu Asp Val Arg Asp Phe Ala
    1280                    1285                1290

Lys Val Leu Lys Asn Lys Phe Arg Thr Lys Arg Tyr Phe Ala Lys
    1295                    1300                1305

His Pro Arg Met Gly Tyr Leu Pro Val Gln Thr Val Leu Glu Gly
    1310                    1315                1320

Asp Asn Met Glu Thr
    1325

<210> SEQ ID NO 89
<211> LENGTH: 426
<212> TYPE: DNA
<213> ORGANISM: Artificial Sequence
<220> FEATURE:
<223> OTHER INFORMATION: 5' UTR

<400> SEQUENCE: 89
ccgccttcgg caccattcct cacgacaccc aaatatggcg acgggtgagg aatggtgggg     60
agttattttt agagcggtga ggaaggtggg caggcagcag gtgttggcgc tctaaaaata    120
actcccggga gttattttta gagcggagga atggtggaca cccaaatatg gcgacggttc    180
ctcacccgtc gccatatttg ggtgtccgcc ctcggccggg gccgcattcc tgggggccgg    240

| gcggtgctcc cgcccgcctc gataaaaggc tccggggccg gcggcggccc acgagctacc | 300 |
| cggaggagcg ggaggcacgc gtctctaagg taaatataaa attttaagt gtataatgtg | 360 |
| ttaaactact gattctaatt gtttctctct tttagattcc aacctttgga actgatctag | 420 |
| accacc | 426 |

```
<210> SEQ ID NO 90
<211> LENGTH: 756
<212> TYPE: DNA
<213> ORGANISM: Artificial Sequence
<220> FEATURE:
<223> OTHER INFORMATION: ABD1

<400> SEQUENCE: 90
```

| atgctttggt gggaagaagt cgaggactgc tacgagcgcg aggacgtgca gaagaaaacc | 60 |
| ttcaccaaat gggtcaacgc ccagttcagc aagttcggca agcagcacat cgagaacctg | 120 |
| ttcagcgacc tgcaggatgg cagaaggctg ctggatctgc tggaaggcct gacaggccag | 180 |
| aagctgccta agagaaaggg cagcacaaga gtgcacgccc tgaacaacgt gaacaaggcc | 240 |
| ctgagagtgc tgcagaacaa caacgtggac ctggtcaaca tcggcagcac cgacatcgtg | 300 |
| gacggcaatc acaaactgac cctgggcctg atctggaaca tcatcctgca ctggcaagtg | 360 |
| aagaacgtga tgaagaacat catggccggc ctgcagcaga ccaacagcga aagattctg | 420 |
| ctgagctggg tccgacagag cacccggaac taccctcaag tgaacgtgat caacttcacc | 480 |
| acctcttgga gcgacggact ggccctgaat gccctgattc acagccacag acctgacctg | 540 |
| ttcgactgga atagcgtcgt gtgtcagcag agcgccacac agagactgga acacgccttc | 600 |
| aatatcgcca gataccagct gggcatcgag aaactgctgg accccgagga tgtggacacc | 660 |
| acctatcctg acaagaaatc catcctcatg tacatcacca gcctgttcca ggtgctgccc | 720 |
| cagcaagtgt ctatcgaggc cattcaagag gtcgag | 756 |

```
<210> SEQ ID NO 91
<211> LENGTH: 255
<212> TYPE: DNA
<213> ORGANISM: Artificial Sequence
<220> FEATURE:
<223> OTHER INFORMATION: Hinge 1

<400> SEQUENCE: 91
```

| atgctgccca gacctcctaa agtgaccaaa gaggaacact tccagctgca ccaccagatg | 60 |
| cactactctc agcagatcac cgtgtctctg gcccagggct acgagagaac aagcagcccc | 120 |
| aagcctcggt tcaagagcta cgcctataca caggccgcct acgtgaccac cagcgatccc | 180 |
| acaagaagcc catttccaag ccagcatctg gaagcccctg aggacaagag ctttggcagc | 240 |
| agcctgatgg aaagc | 255 |

```
<210> SEQ ID NO 92
<211> LENGTH: 327
<212> TYPE: DNA
<213> ORGANISM: Artificial Sequence
<220> FEATURE:
<223> OTHER INFORMATION: Spectrin-1

<400> SEQUENCE: 92
```

| gaagtgaacc tggatagata ccagacagcc ctggaagagg tgctgtcttg gctgctgtct | 60 |
| gccgaagata cactgcaggc tcagggcgag atcagcaacg acgtggaagt ggtcaaggac | 120 |
| cagttttcaca cccacgaggg ctacatgatg gacctgacag cccatcaggg cagagtgggc | 180 |

```
aatatcctgc agctgggctc taagctgatc ggcacaggca agctgagcga ggacgaagag    240
acagaggtgc aagagcagat gaacctgctg aacagcagat gggagtgtct gagagtggcc    300
agcatggaaa agcagagcaa cctgcac                                        327

<210> SEQ ID NO 93
<211> LENGTH: 336
<212> TYPE: DNA
<213> ORGANISM: Artificial Sequence
<220> FEATURE:
<223> OTHER INFORMATION: Modified Spectrin-16

<400> SEQUENCE: 93
cgggtcctga tggatctgca gaatcagaag ctgaccgaga tcacccacgt gtcacaggcc    60
ctgcttgaag tggaacagct gctgaacgcc cctgatctgt gcgccaagga cttcgaggat   120
ctgttcaagc aagaggaaag cctgaagaat atcaaggact ctctgcagca gtccagcggc   180
cggatcgaca tcatccacag caagaaaaca gctgccctgc agtccgccac acctgtggaa   240
agagtgaaac tgcaagaggc cctgtctcag ctggacttcc agtgggagaa agtgaacaag   300
atgtacaagg accggcaggg cagattcgac cgctct                             336

<210> SEQ ID NO 94
<211> LENGTH: 321
<212> TYPE: DNA
<213> ORGANISM: Artificial Sequence
<220> FEATURE:
<223> OTHER INFORMATION: Spectrin-17

<400> SEQUENCE: 94
gtggaaaaat ggcggagatt ccactacgac atcaagatct tcaaccagtg gctgacagag    60
gccgagcagt tcctgagaaa gacacagatc cccgagaact gggagcacgc caagtacaag   120
tggtatctga agaactgca ggacggcatc ggccagaggc agacagtcgt tagaacactg    180
aatgccaccg gcgaggaaat catccagcag agcagcaaga ccgacgccag catcctgcaa   240
gagaagctgg gcagcctgaa cctgagatgg caagaagtgt gcaagcagct gtccgaccgg   300
aagaagaggc tggaagaaca g                                             321

<210> SEQ ID NO 95
<211> LENGTH: 123
<212> TYPE: DNA
<213> ORGANISM: Artificial Sequence
<220> FEATURE:
<223> OTHER INFORMATION: Hinge 3

<400> SEQUENCE: 95
gcccctggcc tgacaacaat cggagcctct cctacacaga ccgtgacact ggtcacacag    60
cccgtggtca ccaaagagac agccatcagc aagctggaaa tgccctctag cctgatgctc   120
gag                                                                 123

<210> SEQ ID NO 96
<211> LENGTH: 387
<212> TYPE: DNA
<213> ORGANISM: Artificial Sequence
<220> FEATURE:
<223> OTHER INFORMATION: Spectrin-23

<400> SEQUENCE: 96
agcgaccagt ggaagagact gcacctgtct ctgcaagagc tgctcgtgtg gctgcagctg    60
```

| | |
|---|---|
| aaggacgatg aactgagcag acaggcccca atcggaggcg attttcctgc cgtgcagaaa | 120 |
| cagaacgacg tgcacagagc cttcaagcgg gaactgaaaa caaaagaacc cgtgatcatg | 180 |
| agcaccctgg aaaccgtgcg gatcttcctg acagagcagc ctctcgaagg cctggaaaag | 240 |
| ctgtaccaag agcctagaga gctgcctcct gaggaacggg cccagaatgt gaccagactg | 300 |
| ctgagaaagc aggccgaaga ggtcaacacc gaatgggaga agctgaacct gcacagcgcc | 360 |
| gactggcaga gaaagatcga cgagaca | 387 |

```
<210> SEQ ID NO 97
<211> LENGTH: 324
<212> TYPE: DNA
<213> ORGANISM: Artificial Sequence
<220> FEATURE:
<223> OTHER INFORMATION: Spectrin-24

<400> SEQUENCE: 97
```

| | |
|---|---|
| ctggaacggc tgcaagaact ccagaaagcc accgacgagc tggacctgaa actgaggcag | 60 |
| gctgaagtga tcaaaggcag ctggcagcca gtgggcgacc tgctgattga tagtctgcag | 120 |
| gaccacctgg aaaagtgaa ggccctgcgg ggagagatcg ccccactgaa agaaaacgtg | 180 |
| tcccacgtga acgacctggc cagacagctg acaaccctgg gaatccagct gtccccttac | 240 |
| aacctgtcca cactggaaga tctgaacacc cggtggaaac tgctccaggt ggccgtggaa | 300 |
| gatagagtgc gacagctgca cgag | 324 |

```
<210> SEQ ID NO 98
<211> LENGTH: 216
<212> TYPE: DNA
<213> ORGANISM: Artificial Sequence
<220> FEATURE:
<223> OTHER INFORMATION: Hinge 4

<400> SEQUENCE: 98
```

| | |
|---|---|
| gcccacagag attttggacc agccagccag cacttcctgt ctacatctgt gcaaggccct | 60 |
| tgggagagag ctatcagccc taacaaggtg ccctactaca tcaaccacga gacacagacc | 120 |
| acctgttggg atcaccccaa gatgaccgag ctgtatcaga gcctggccga cctgaacaat | 180 |
| gtgcgcttta gcgcctaccg gaccgccatg aagctg | 216 |

```
<210> SEQ ID NO 99
<211> LENGTH: 891
<212> TYPE: DNA
<213> ORGANISM: Artificial Sequence
<220> FEATURE:
<223> OTHER INFORMATION: CR

<400> SEQUENCE: 99
```

| | |
|---|---|
| cggagactgc agaaagccct gtgtctggac ctgctgtctc tgtctgcagc ctgtgatgcc | 60 |
| ctggaccagc acaacctgaa gcagaacgac cagcctatgg acatcctcca gatcatcaac | 120 |
| tgcctgacca ccatctacga ccggctggaa caagagcaca caacctcgt gaatgtgcc | 180 |
| ctgtgcgtgg acatgtgtct gaactggctg ctgaatgtgt acgacaccgg cagaaccggc | 240 |
| aggatcagag tgctgagctt caagaccggc atcatctccc tgtgcaaagc ccacctcgag | 300 |
| gacaagtaca gatacctgtt caaacaggtg gccagctcca ccggcttttg cgatcaaaga | 360 |
| aggctgggcc tgctgctgca cgacagcatc cagattccta acagctgggcg cgaagtggcc | 420 |
| tccttcggcg gatctaatat tgagcctagc gtgcggagct gcttccagtt cgccaacaac | 480 |
| aagcctgaga tcgaggccgc tctgttcctg gattggatgc gcctggaacc tcagagcatg | 540 |

```
gtttggctgc ctgtgctgca tagagtggcc gctgccgaaa cagccaagca ccaggccaag    600
tgcaacatct gcaaagagtg ccccatcatc ggcttccggt acagatccct gaagcacttc    660
aactacgata tctgccagag ctgtttcttc tctggccgcg tggccaaggg ccacaaaatg    720
cactacccca tggtggaata ctgcacccct accacatctg gcgaagatgt gcgggatttc    780
gccaaggtgc tgaaaaacaa gttccggacc aagcggtact tcgctaagca ccccagaatg    840
ggctatctgc ccgtgcagac agtgctcgag ggcgataaca tggaaacctg a             891

<210> SEQ ID NO 100
<211> LENGTH: 3936
<212> TYPE: DNA
<213> ORGANISM: Artificial Sequence
<220> FEATURE:
<223> OTHER INFORMATION: BXA-220931

<400> SEQUENCE: 100
atgctttggt gggaagaagt cgaggactgc tacgagcgcg aggacgtgca gaagaaaacc     60
ttcaccaaat gggtcaacgc ccagttcagc aagttcggca gcagcacat cgagaacctg    120 ttcagcgacc tgcaggatgg cagaaggctg ctggatctgc tggaaggcct gacaggccag    180
aagctgccta agagaaaggg cagcacaaga gtgcacgccc tgaacaacgt gaacaaggcc    240
ctgagagtgc tgcagaacaa caacgtggac ctggtcaaca tcggcagcac cgacatcgtg    300
gacggcaatc acaaactgac cctgggcctg atctggaaca tcatcctgca ctggcaagtg    360
aagaacgtga tgaagaacat catggccggc ctgcagcaga ccaacagcga aaagattctg    420
ctgagctggg tccgacagag caccccggaac taccctcaag tgaacgtgat caacttcacc    480
acctcttgga gcgacggact ggccctgaat gccctgattc acagccacag acctgacctg    540
ttcgactgga atagcgtcgt gtgtcagcag agcgccacac agagactgga acacgccttc    600
aatatcgcca gataccagct gggcatcgag aaactgctgg accccgagga tgtggacacc    660
acctatcctg acaagaaatc catcctcatg tacatccacc gcctgttcca ggtgctgccc    720
cagcaagtgt ctatcgaggc cattcaagag gtcgagatgc tgcccagacc tcctaaagtg    780
accaaagagg aacacttcca gctgcaccac cagatgcact actctcagca gatcaccgtg    840
tctctggccc agggctacga gagaacaagc agccccaagc ctcggttcaa gagctacgcc    900
tatacacagg ccgcctacgt gaccaccagc gatcccacaa gaagcccatt tccaagccag    960
catctggaag cccctgagga caagagcttt ggcagcagcc tgatggaaag cgaagtgaac   1020
ctggatagat accagacagc cctggaagag gtgctgtctt ggctgctgtc tgccgaagat   1080
acactgcagg ctcagggcga gatcagcaac gacgtggaag tggtcaagga ccagtttcac   1140
acccacgagg gctacatgat ggacctgaca gcccatcagg gcagagtggg caatatcctg   1200
cagctgggct ctaagctgat cggcacaggc aagctgagcg aggacgaaga gacagaggtg   1260
caagagcaga tgaacctgct gaacagcaga tgggagtgtc tgagagtggc agcatggaa    1320 aagcagagca acctgcaccg ggtcctgatg atctgcaga atcagaagct gaccgagatc   1380
acccacgtgt cacaggccct gcttgaagtg aacagctgc tgaacgcccc tgatctgtgc   1440
gccaaggact cgaggatct gttcaagcaa gaggaaagcc tgaagaatat caaggactct   1500
ctgcagcagt ccagcggccg gatcgacatc atccacagca gaaaacagc tgccctgcag   1560 tccgccacac ctgtggaaag agtgaaactg caagaggccc tgtctcagct ggacttccag   1620
tgggagaaag tgaacaagat gtacaaggac cggcagggca gattcgaccg ctctgtggaa   1680
```

```
aaatggcgga gattccacta cgacatcaag atcttcaacc agtggctgac agaggccgag    1740
cagttcctga gaaagacaca gatccccgag aactgggagc acgccaagta caagtggtat    1800
ctgaaagaac tgcaggacgg catcggccag aggcagacag tcgttagaac actgaatgcc    1860
accggcgagg aaatcatcca gcagagcagc aagaccgacg ccagcatcct gcaagagaag    1920
ctgggcagcc tgaacctgag atggcaagaa gtgtgcaagc agctgtccga ccggaagaag    1980
aggctggaag aacaggcccc tggcctgaca caatcggag cctctcctac acagaccgtg     2040
acactggtca cacagcccgt ggtcaccaaa gagacagcca tcagcaagct ggaaatgccc    2100
tctagcctga tgctcgagag cgaccagtgg aagagactgc acctgtctct gcaagagctg    2160
ctcgtgtggc tgcagctgaa ggacgatgaa ctgagcagac aggccccaat cggaggcgat    2220
tttcctgccg tgcagaaaca gaacgacgtg cacagagcct tcaagcggga actgaaaaca    2280
aaagaacccg tgatcatgag caccctggaa accgtgcgga tcttcctgac agagcagcct    2340
ctcgaaggcc tggaaaagct gtaccaagag cctagagagc tgcctcctga ggaacgggcc    2400
cagaatgtga ccagactgct gagaaagcag gccgaagagg tcaacaccga atgggagaag    2460
ctgaacctgc acagcgccga ctggcagaga aagatcgacg agacactgga acggctgcaa    2520
gaactccaag aagccaccga cgagctggac ctgaaactga ggcaggctga agtgatcaaa    2580
ggcagctggc agccagtggg cgacctgctg attgatagtc tgcaggacca cctggaaaaa    2640
gtgaaggccc tgcggggaga gatcgcccca ctgaaagaaa acgtgtccca cgtgaacgac    2700
ctggccagac agctgacaac cctgggaatc cagctgtccc cttacaacct gtccacactg    2760
gaagatctga acaccggtg gaaactgctc caggtggccg tggaagatag agtgcgacag    2820
ctgcacgagg cccacagaga ttttggacca gccagccagc acttcctgtc tacatctgtg    2880
caaggccctt gggagagagc tatcagccct aacaaggtgc cctactacat caaccacgag    2940
acacagacca cctgttggga tcaccccaag atgaccgagc tgtatcagag cctggccgac    3000
ctgaacaatg tgcgctttag cgcctaccgg accgccatga agctgcggag actgcagaaa    3060
gccctgtgtc tggacctgct gtctctgtct gcagcctgtg atgccctgga ccagcacaac    3120
ctgaagcaga acgaccagcc tatggacatc ctccagatca tcaactgcct gaccaccatc    3180
tacgaccggc tggaacaaga gcacaacaac ctcgtgaatg tgcccctgtg cgtggacatg    3240
tgtctgaact ggctgctgaa tgtgtacgac accggcagaa ccggcaggat cagagtgctg    3300
agcttcaaga ccggcatcat ctccctgtgc aaagcccacc tcgaggacaa gtacagatac    3360
ctgttcaaac aggtggccag ctccaccggc ttttgcgatc aaagaaggct gggcctgctg    3420
ctgcacgaca gcatccagat tcctagacag ctgggcgaag tggcctcctt cggcggatct    3480
aatattgagc ctagcgtgcg gagctgcttc cagttcgcca acaacaagcc tgagatcgag    3540
gccgctctgt tcctggattg gatgcgcctg gaacctcaga gcatggtttg gctgcctgtg    3600
ctgcatagag tggccgctgc cgaaacagcc aagcaccagg ccaagtgcaa catctgcaaa    3660
gagtgcccca tcatcggctt ccggtacaga tccctgaagc acttcaacta cgatatctgc    3720
cagagctgtt tcttctctgg ccgcgtggcc aagggccaca aaatgcacta ccccatggtg    3780
gaatactgca cccctaccac atctggcgaa gatgtgcggg atttcgccaa ggtgctgaaa    3840
aacaagttcc ggaccaagcg gtacttcgct aagcacccca gaatgggcta tctgcccgtg    3900
cagacagtgc tcgagggcga taacatggaa acctga                              3936

<210> SEQ ID NO 101
<211> LENGTH: 3936
```

```
<212> TYPE: DNA
<213> ORGANISM: Artificial Sequence
<220> FEATURE:
<223> OTHER INFORMATION: BXA-212372-J4V13

<400> SEQUENCE: 101
atgctgtggt gggaggaagt ggaagattgc tacgagcgcg aggacgtgca gaagaaaacc      60
ttcaccaaat gggtgaacgc ccagttcagc aagttcggca agcagcacat cgagaacctg     120
ttcagcgacc tgcaggacgg cagacggctg ctggacctgc tggaaggcct gaccggccag     180
aagctgccca agagaaggg cagcaccaga gtgcacgccc tgaacaacgt gaacaaggcc      240
ctgcgggtgc tgcagaacaa caacgtggac ctggtgaaca tcggcagcac cgacatcgtg     300
gacggcaacc acaagctgac cctgggcctg atctggaaca tcatcctgca ctggcaggtc     360
aaaaacgtga tgaagaacat catggccggc ctgcagcaga ccaacagcga agatcctg      420
ctgagctggg tgcgccagag cacccggaac taccccccagg tcaacgtgat caacttcacc    480
acctcttgga cgacggcct ggccctgaac gccctgatcc acagccaccg gcccgacctg      540
ttcgactgga acagcgtggt ctgccagcag agcgccaccc agcggctgga cacgccttc      600
aatatcgcca gataccagct gggcatcgag aagctgctgg atcccgagga cgtggacacc     660
acctaccccg acaagaaatc catcctgatg tatatcacca gcctgttcca ggtgctgccc     720
cagcaggtgt ccatcgaggc catccaggaa gtggaaatgc tgcccagacc ccccaaagtg     780
accaaagagg aacacttcca gctgcaccac cagatgcact cagccagca gatcaccgtg      840
tccctggctc agggctacga gcggaccagc agccccaagc cccggttcaa gagctacgcc     900
tacacccagg ccgcctacgt gaccaccagc gaccccacca aagcccatt ccccagccag      960
catctggaag cccccgagga caagagcttc ggcagcagcc tgatggaaag cgaagtgaac    1020
ctggacagat accagaccgc cctggaagag gtgctgtcct ggctgctgag cgccgaggat    1080
acactgcagg cccagggcga gatcagcaac gacgtggaag tggtgaaaga ccagttccac    1140
acccacgagg gctacatgat ggacctgacc gcccaccagg gcagagtggg caacatcctg    1200
cagctgggca gcaagctgat cggcaccggc aagctgagcg aggacgaaga gacagaggtg    1260
caggaacaga tgaacctgct gaacagcaga tgggagtgcc tgcgggtggc cagcatggaa    1320
aagcagagca acctgcaccg ggtcctgatg gatctgcaga atcagaagct gaccgagatc    1380
acccacgtgt cccaggctct gctggaagtg aacagctgc tgaacgcccc cgacctgtgc    1440
gccaaggact cgaggatct gttcaagcag gaagagagcc tgaagaatat caaggactcc    1500
ctgcagcagt ccagcggccg gatcgacatc atccacagca gaaaaacagc cgccctgcag    1560
tccgccaccc ccgtggaaag agtgaagctg caggaagccc tgagccagct ggacttccag    1620
tgggagaaag tgaacaagat gtacaaggac cggcagggca gattcgaccg cagcgtggaa    1680
aagtggcggc ggttccacta cgacatcaag atcttcaacc agtggctgac cgaggccgag    1740
cagttcctga aaagacccca gatccccgag aactgggagc acgccaagta caagtggtat    1800
ctgaaagagc tgcaggacgg catcggccag cggcagacag tggtccgcac cctgaatgcc    1860
accggcgagg aaatcatcca gcagagcagc aagaccgacg ccagcatcct gcaggaaaag    1920
ctgggcagcc tgaacctgcg gtgcaggaa gtgtgcaagc agctgagcga ccggaagaag    1980
cggctggaag aacaggcccc tggcctgacc acaatcggcg ccagccctac ccagaccgtg    2040
accctggtga cacagcccgt ggtgacaaaa gagacagcca tcagcaagct ggaaatgccc    2100
agcagcctga tgctggaaag cgaccagtgg aagcggctgc acctgagcct gcaggaactg    2160
```

| | |
|---|---|
| ctggtctggc tgcagctgaa ggacgacgag ctgagcagac aggcccccat cggcggcgat | 2220 |
| ttccccgccg tgcagaaaca gaacgacgtg caccgggcct tcaagcgcga gctgaaaaca | 2280 |
| aaagaacccg tgatcatgag caccctggaa accgtgcgga tcttcctgac cgagcagccc | 2340 |
| ctggaaggcc tggaaaagct gtaccaggaa cccagagagc tgcccccga ggaacgggcc | 2400 |
| cagaacgtga ccagactgct gcggaagcag gccgaagagg tcaacaccga gtgggagaag | 2460 |
| ctgaacctgc acagcgccga ctggcagcgg aagatcgacg agacactgga acggctgcag | 2520 |
| gaactgcagg aggccaccga cgagctggac ctgaagctga cagggccga agtgatcaag | 2580 |
| ggcagctggc agcccgtggg cgacctgctg atcgactccc tgcaggacca cctggaaaaa | 2640 |
| gtgaaggccc tgcggggcga gatcgccccc ctgaaagaaa acgtgtccca cgtgaacgac | 2700 |
| ctggcccggc agctgaccac cctgggcatc cagctgagcc cctacaacct gtccaccctg | 2760 |
| gaagatctga cacccggtg gaagctgctg caggtggccg tggaagatag agtgcggcag | 2820 |
| ctgcacgagg cccacagaga ctttggcct gccagccagc acttcctgag cacctctgtg | 2880 |
| cagggaccct gggagagagc catcagcccc aacaaggtgc cctactacat caaccacgag | 2940 |
| acacagacca cctgttggga ccaccccaag atgaccgagc tgtaccagag cctggccgac | 3000 |
| ctgaacaatg tgcggttcag cgcctaccgg accgccatga gctgaggcg gctgcagaaa | 3060 |
| gctctgtgcc tggatctgct gagcctgagc gccgcctgcg acgccctgga ccagcacaac | 3120 |
| ctgaagcaga acgaccagcc catggatatc ctgcagatca tcaactgcct gaccacaatc | 3180 |
| tacgacaggc tggaacagga acacaacaat ctggtcaacg tgcccctgtg cgtggacatg | 3240 |
| tgcctgaatt ggctgctgaa tgtgtacgac accggccgga ccgcagaat ccgggtgctg | 3300 |
| agcttcaaga ccggcatcat cagcctgtgc aaggcccacc tggaagataa gtaccgctac | 3360 |
| ctgttcaaac aggtggccag ctccaccggc ttttgcgacc agcggagact gggcctgctg | 3420 |
| ctgcacgaca gcatccagat ccccagacag ctgggcgagg tggcctcctt cggcggcagc | 3480 |
| aacattgagc ccagcgtgcg gagctgcttc cagttcgcca acaacaagcc cgagatcgag | 3540 |
| gccgccctgt cctggactg gatgagactg gaaccccaga gcatggtgtg gctgcccgtg | 3600 |
| ctgcatcggg tggccgctgc cgagacagcc aagcaccagg ccaagtgcaa catctgcaaa | 3660 |
| gagtgcccca tcatcggctt ccggtacaga agcctgaagc acttcaacta cgatatctgc | 3720 |
| cagagctgct tcttcagcgg cagagtggcc aagggccaca aaatgcacta ccccatggtg | 3780 |
| gaatactgca ccccaccac cagcggcgag gatgtgcggg acttcgccaa ggtgctgaaa | 3840 |
| aacaagttcc ggaccaagcg gtactttgcc aagcaccccc ggatgggcta cctgcccgtg | 3900 |
| cagacagtgc tggaaggcga caacatggaa acctga | 3936 |

<210> SEQ ID NO 102
<211> LENGTH: 3933
<212> TYPE: DNA
<213> ORGANISM: Artificial Sequence
<220> FEATURE:
<223> OTHER INFORMATION: BXA-212372-J4V12

<400> SEQUENCE: 102

| | |
|---|---|
| atgctgtggt gggaggaagt ggaagattgc tacgagcgcg aggacgtgca gaagaaaacc | 60 |
| ttcaccaaat gggtgaacgc ccagttcagc aagttcggca gcagcacat cgagaacctg | 120 |
| ttcagcgacc tgcaggacgg cagacggctg ctggacctgc tggaaggcct gaccggccag | 180 |
| aagctgccca agagaaggg cagcaccaga gtgcacgccc tgaacaacgt gaacaaggcc | 240 |
| ctgcgggtgc tgcagaacaa caacgtggac ctggtgaaca tcggcagcac cgacatcgtg | 300 |

```
gacggcaacc acaagctgac cctgggcctg atctggaaca tcatcctgca ctggcaggtc    360
aaaaacgtga tgaagaacat catggccggc ctgcagcaga ccaacagcga gaagatcctg    420
ctgagctggg tgcgccagag cacccggaac taccccccagg tcaacgtgat caacttcacc    480
acctcttgga gcgacggcct ggccctgaac gccctgatcc acagccaccg gcccgacctg    540
ttcgactgga acagcgtggt ctgccagcag agcgccaccc agcggctgga cacgccttc     600 aatatcgcca gataccagct gggcatcgag aagctgctgg atcccgagga cgtggacacc    660
acctaccccg acaagaaatc catcctgatg tatatcacca gcctgttcca ggtgctgccc    720
cagcaggtgt ccatcgaggc catccaggaa gtggaaatgc tgcccagacc ccccaaagtg    780
accaaagagg aacacttcca gctgcaccac cagatgcact acagccagca gatcaccgtg    840
tccctggctc agggctacga gcggaccagc agccccaagc cccggttcaa gagctacgcc    900
tacacccagg ccgcctacgt gaccaccagc gaccccacca gaagcccatt ccccagccag    960
catctggaag cccccgagga caagagcttc ggcagcagcc tgatggaaag cgaagtgaac   1020
ctggacagat accagaccgc cctggaagag gtgctgtcct ggctgctgag cgccgaggat   1080
acactgcagg cccagggcga gatcagcaac gacgtggaag tggtgaaaga ccagttccac   1140
acccacgagg gctacatgat ggacctgacc gcccaccagg gcagagtggg caacatcctg   1200
cagctgggca gcaagctgat cggcaccggc aagctgagcg aggacgaaga gacagaggtg   1260
caggaacaga tgaacctgct gaacagcaga tgggagtgcc tgcgggtggc cagcatggaa   1320
aagcagagca acctgcacag agtttaatg gatctccaga atcagaaaac cgagatcacc   1380
cacgtgtccc aggctctgct ggaagtggaa cagctgctga cgcccccga cctgtgcgcc   1440 aaggacttcg aggatctgtt caagcaggaa gagagcctga gaatatcaa ggactccctg   1500 cagcagtcca gcggccggat cgacatcatc cacagcaaga aaacagccgc cctgcagtcc   1560 gccaccccg tggaaagagt gaagctgcag gaagccctga ccagctgga cttccagtgg   1620 gagaaagtga acaagatgta caaggaccgg cagggcagat cgaccgcag cgtggaaaag   1680 tggcggcggt tccactacga catcaagatc ttcaaccagt ggctgaccga ggccgagcag   1740
ttcctgagaa agacccagat ccccgagaac tgggagcacg ccaagtacaa gtggtatctg   1800
aaagagctgc aggacggcat cggccagcgg cagacagtgg tccgcaccct gaatgccacc   1860
ggcgaggaaa tcatccagca gagcagcaag accgacgcca gcatcctgca ggaaaagctg   1920
ggcagcctga acctgcggtg caggaagtg tgcaagcagc tgagcgaccg gaagaagcgg   1980
ctggaagaac aggcccctgg cctgaccaca atcggcgcca gcctacccca gaccgtgacc   2040
ctggtgacac agcccgtggt gacaaaagag acagccatca gcaagctgga atgcccagc    2100 agcctgatgc tggaaagcga ccagtggaag cggctgcacc tgagcctgca ggaactgctg   2160
gtctggctgc agctgaagga cgacgagctg agcagacagg ccccatcgg cggcgattc   2220 cccgccgtgc agaaacagaa cgacgtgcac cgggccttca gcgcgagct gaaaacaaaa   2280 gaacccgtga tcatgagcac cctggaaacc gtgcggatct tcctgaccga gcagccctg   2340 gaaggcctgg aaaagctgta ccaggaaccc agagagctgc ccccgagga acgggcccag   2400 aacgtgacca gactgctgcg gaagcaggcc gaagaggtca caccgagtg ggagaagctg   2460 aacctgcaca gcgccgactg gcagcggaag atcgacgaga cactggaacg gctgcaggaa   2520
ctgcaggagg ccaccgacga gctggaccctg aagctgagac aggccgaagt gatcaagggc   2580
agctggcagc ccgtgggcga cctgctgatc gactcccctg caggaccacct ggaaaaagtg   2640
```

```
aaggccctgc ggggcgagat cgcccccctg aaagaaaacg tgtcccacgt gaacgacctg    2700
gcccggcagc tgaccaccct gggcatccag ctgagcccct acaacctgtc caccctggaa    2760
gatctgaaca cccggtggaa gctgctgcag gtggccgtgg aagatagagt gcggcagctg    2820
cacgaggccc acagagactt tggccctgcc agccagcact tcctgagcac ctctgtgcag    2880
ggaccctggg agagagccat cagccccaac aaggtgccct actacatcaa ccacgagaca    2940
cagaccacct gttgggacca ccccaagatg accgagctgt accagagcct ggccgacctg    3000
aacaatgtgc ggttcagcgc ctaccggacc gccatgaagc tgaggcggct gcagaaagct    3060
ctgtgcctgg atctgctgag cctgagcgcc gcctgcgacg ccctggacca gcacaacctg    3120
aagcagaacg accagcccat ggatatcctg cagatcatca actgcctgac cacaatctac    3180
gacaggctgg aacaggaaca caacaatctg gtcaacgtgc ccctgtgcgt ggacatgtgc    3240
ctgaattggc tgctgaatgt gtacgacacc ggccggaccg gcagaatccg ggtgctgagc    3300
ttcaagaccg gcatcatcag cctgtgcaag gcccacctgg aagataagta ccgctacctg    3360
ttcaaacagg tggccagctc caccggcttt tgcgaccagc ggagactggg cctgctgctg    3420
cacgacagca tccagatccc cagacagctg ggcgaggtgg cctccttcgg cggcagcaac    3480
attgagccca gcgtgcggag ctgcttccag ttcgccaaca caagcccga tcgaggcc     3540 gccctgttcc tggactggat gagactggaa ccccagagca tggtgtggct gcccgtgctg    3600
catcgggtgg ccgctgccga cagccaag caccaggcca agtgcaacat ctgcaaagag     3660
tgccccatca tcggcttccg gtacagaagc ctgaagcact tcaactacga tatctgccag    3720
agctgcttct tcagcggcag agtggccaag gccacaaaa tgcactaccc catggtggaa     3780
tactgcaccc ccaccaccag cggcgaggat gtgcgggact tcgccaaggt gctgaaaaac    3840
aagttccgga ccaagcggta ctttgccaag caccccggaa tgggctacct gcccgtgcag    3900
acagtgctgg aaggcgacaa catggaaacc tga    3933

<210> SEQ ID NO 103
<211> LENGTH: 3930
<212> TYPE: DNA
<213> ORGANISM: Artificial Sequence
<220> FEATURE:
<223> OTHER INFORMATION: BXA-212372-J4V11

<400> SEQUENCE: 103
atgctgtggt gggaggaagt ggaagattgc tacgagcgcg aggacgtgca agagaaaacc      60
ttcaccaaat gggtgaacgc ccagttcagc aagttcggca gcagcacat cgagaacctg      120 ttcagcgacc tgcaggacgg cagacggctg ctggacctgc tggaaggcct gaccggccag    180
aagctgccca agagaaggg cagcaccaga gtgcacgccc tgaacaacgt gaacaaggcc     240
ctgcgggtgc tgcagaacaa caacgtggac ctggtgaaca tcggcagcac cgacatcgtg    300
gacggcaacc acaagctgac cctgggcctg atctggaaca tcatcctgca ctggcaggtc    360
aaaaacgtga tgaagaacat catggccggc ctgcagcaga ccaacagcga agatcctg      420 ctgagctggg tgcgccagag cacccggaac tacccccagg tcaacgtgat caacttcacc    480
acctcttgga gcgacggcct ggccctgaac gccctgatcc acagccaccg gcccgacctg    540
ttcgactgga acagcgtggt ctgccagcag agcgccaccc agcggctgga acacgccttc    600
aatatcgccc ataccagct gggcatcgag aagctgctgg atcccgagga cgtggacacc    660
acctaccccg acaagaaatc catcctgatg tatatccaca gcctgttcca ggtgctgccc    720
cagcaggtgt ccatcgaggc catccaggaa gtggaaatgc tgcccagacc ccccaaagtg    780
```

-continued

```
accaaagagg aacacttcca gctgcaccac cagatgcact acagccagca gatcaccgtg    840
tccctggctc agggctacga gcggaccagc agccccaagc cccggttcaa gagctacgcc    900
tacacccagg ccgcctacgt gaccaccagc gacccacca gaagcccatt ccccagccag     960
catctggaag cccccgagga caagagcttc ggcagcagcc tgatggaaag cgaagtgaac   1020
ctggacagat accagaccgc cctggaagag gtgctgtcct ggctgctgag cgccgaggat   1080
acactgcagg cccagggcga gatcagcaac gacgtggaag tggtgaaaga ccagttccac   1140
acccacgagg gctacatgat ggacctgacc gcccaccagg gcagagtggg caacatcctg   1200
cagctgggca gcaagctgat cggcaccggc aagctgagcg aggacgaaga cagaggtg    1260
caggaacaga tgaacctgct gaacagcaga tgggagtgcc tgcgggtggc cagcatggaa   1320
aagcagagca acctgcacag agttttaatg gatctccaga atcagaaaga gatcacccac   1380
gtgtcccagg ctctgctgga agtggaacag ctgctgaacg cccccgacct gtgcgccaag   1440
gacttcgagg atctgttcaa gcaggaagag agcctgaaga atatcaagga ctccctgcag   1500
cagtccagcg gccggatcga catcatccac agcaagaaaa cagccgccct gcagtccgcc   1560
acccccgtgg aaagagtgaa gctgcaggaa gccctgagcc agctggactt ccagtgggag   1620
aaagtgaaca agatgtacaa ggaccggcag ggcagattcg accgcagcgt ggaaaagtgg   1680
cggcggttcc actacgacat caagatcttc aaccagtggc tgaccgaggc cgagcagttc   1740
ctgagaaaga cccagatccc cgagaactgg gagcacgcca agtacaagtg gtatctgaaa   1800
gagctgcagg acggcatcgg ccagcggcag acagtggtcc gcaccctgaa tgccaccggc   1860
gaggaaatca tccagcagag cagcaagacc gacgccagca tcctgcagga aaagctgggc   1920
agcctgaacc tgcggtggca ggaagtgtgc aagcagctga gcgaccggaa gaagcggctg   1980
gaagaacagg cccctggcct gaccacaatc ggcgccagcc tacccagac cgtgaccctg   2040
gtgacacagc ccgtggtgac aaaagagaca gccatcagca agctggaaat gcccagcagc   2100
ctgatgctgg aaagcgacca gtggaagcgg ctgcacctga gcctgcagga actgctggtc   2160
tggctgcagc tgaaggacga cgagctgagc agacaggccc ccatcggcgg cgatttcccc   2220
gccgtgcaga aacagaacga cgtgcaccgg gccttcaagc gcgagctgaa aacaaaagaa   2280
cccgtgatca tgagcaccct ggaaaccgtg cggatcttcc tgaccgagca gccctggaa   2340
ggcctggaaa agctgtacca ggaacccaga gagctgcccc cgaggaacg ggcccagaac   2400
gtgaccagac tgctgcggaa gcaggccgaa gaggtcaaca ccgagtggga agctgaac    2460
ctgcacagcg ccgactggca gcggaagatc gacgagacac tggaacggct gcaggaactg   2520
caggaggcca ccgacgagct ggacctgaag ctgagacagg ccgaagtgat caagggcagc   2580
tggcagcccg tgggcgacct gctgatcgac tccctgcagg accacctgga aaaagtgaag   2640
gccctgcggg gcgagatcgc ccccctgaaa gaaaacgtgt cccacgtgaa cgacctggcc   2700
cggcagctga ccaccctggg catccagctg agccccctaca acctgtccac cctggaagat   2760
ctgaacaccc ggtggaagct gctgcaggtg gccgtggaag atagagtgcg gcagctgcac   2820
gaggcccaca gagactttgg ccctgccagc cagcacttcc tgagcacctc tgtgcaggga   2880
ccctgggaga gagccatcag ccccaacaag gtgccctact acatcaacca cgagacacag   2940
accacctgtt gggaccaccc caagatgacc gagctgtacc agagcctggc cgacctgaac   3000
aatgtgcggt tcagcgccta ccggaccgcc atgaagctga ggcggctgca gaaagctctg   3060
tgcctggatc tgctgagcct gagcgccgcc tgcgacgccc tggaccagca caacctgaag   3120
```

| | |
|---|---|
| cagaacgacc agcccatgga tatcctgcag atcatcaact gcctgaccac aatctacgac | 3180 |
| aggctggaac aggaacacaa caatctggtc aacgtgcccc tgtgcgtgga catgtgcctg | 3240 |
| aattggctgc tgaatgtgta cgacaccggc cggaccggca gaatccgggt gctgagcttc | 3300 |
| aagaccggca tcatcagcct gtgcaaggcc cacctggaag ataagtaccg ctacctgttc | 3360 |
| aaacaggtgg ccagctccac cggcttttgc gaccagcgga gactgggcct gctgctgcac | 3420 |
| gacagcatcc agatccccag acagctgggc gaggtggcct ccttcggcgg cagcaacatt | 3480 |
| gagcccagcg tgcggagctg cttccagttc gccaacaaca agcccgagat cgaggccgcc | 3540 |
| ctgttcctgg actggatgag actggaaccc cagagcatgg tgtggctgcc cgtgctgcat | 3600 |
| cgggtggccg ctgccgagac agccaagcac caggccaagt gcaacatctg caaagagtgc | 3660 |
| cccatcatcg gcttccggta cagaagcctg aagcacttca actacgatat ctgccagagc | 3720 |
| tgcttcttca gcggcagagt ggccaagggc cacaaaatgc actaccccat ggtggaatac | 3780 |
| tgcacccccca ccaccagcgg cgaggatgtg cgggacttcg ccaaggtgct gaaaaacaag | 3840 |
| ttccggacca agcggtactt tgccaagcac ccccggatgg gctacctgcc cgtgcagaca | 3900 |
| gtgctggaag gcgacaacat ggaaacctga | 3930 |

<210> SEQ ID NO 104
<211> LENGTH: 3930
<212> TYPE: DNA
<213> ORGANISM: Artificial Sequence
<220> FEATURE:
<223> OTHER INFORMATION: BXA-212372-J4V4

<400> SEQUENCE: 104

| | |
|---|---|
| atgctgtggt gggaggaagt ggaagattgc tacgagcgcg aggacgtgca agagaaaacc | 60 |
| ttcaccaaat gggtgaacgc ccagttcagc aagttcggca gcagcacat cgagaacctg | 120 |
| ttcagcgacc tgcaggacgg cagacggctg ctggacctgc tggaaggcct gaccggccag | 180 |
| aagctgccca agagaaggg cagcaccaga gtgcacgccc tgaacaacgt gaacaaggcc | 240 |
| ctgcgggtgc tgcagaacaa caacgtggac ctggtgaaca tcggcagcac cgacatcgtg | 300 |
| gacggcaacc acaagctgac cctgggcctg atctggaaca tcatcctgca ctggcaggtc | 360 |
| aaaaacgtga tgaagaacat catggccggc ctgcagcaga ccaacagcga agatcctg | 420 |
| ctgagctggg tgcgccagag caccggaac taccccagg tcaacgtgat caacttcacc | 480 |
| acctcttgga gcgacggcct ggccctgaac gccctgatcc acagccaccg gcccgacctg | 540 |
| ttcgactgga cagcgtggt ctgccagcag agcgccaccc agcggctgga acacgccttc | 600 |
| aatatcgcca gataccagct gggcatcgag aagctgctgg atcccgagga cgtggacacc | 660 |
| acctaccccg acaagaaatc catcctgatg tatatccaca gcctgttcca ggtgctgccc | 720 |
| cagcaggtgt ccatcgaggc catccaggaa gtggaaatgc tgcccagacc ccccaaagtg | 780 |
| accaaagagg aacacttcca gctgcaccac cagatgcact acagccagca gatcaccgtg | 840 |
| tcctggct agggctacga gcggaccagc agccccaagc ccggttcaa gagctacgcc | 900 |
| tacacccagg ccgcctacgt gaccaccagc gaccccacca aagcccatt ccccagccag | 960 |
| catctggaag cccccgagga caagagcttc ggcagcagct gatggaaag cgaagtgaac | 1020 |
| ctggacagat accagaccgc cctggaagag gtgctgtcct ggctgctgag cgccgaggat | 1080 |
| acactgcagg cccagggcga gatcagcaac gacgtggaag tggtgaaaga ccagttccac | 1140 |
| acccacgagg gctacatgat ggacctgacc gcccaccagg cagagtggg caacatcctg | 1200 |
| cagctgggca gcaagctgat cggcaccggc aagctgagcg aggacgaaga cagaggtg | 1260 |

```
caggaacaga tgaacctgct gaacagcaga tgggagtgcc tgcgggtggc cagcatggaa    1320
aagcagagca acctgcacag agttttaatg gatctcacct acctgaccga gatcacccac    1380
gtgtcccagg ctctgctgga agtggaacag ctgctgaacg cccccgacct gtgcgccaag    1440
gacttcgagg atctgttcaa gcaggaagag agcctgaaga atatcaagga ctcccctgcag   1500 cagtccagcg gccggatcga catcatccac agcaagaaaa cagccgccct gcagtccgcc    1560
acccccgtgg aaagagtgaa gctgcaggaa gccctgagcc agctggactt ccagtgggag    1620
aaagtgaaca agatgtacaa ggaccggcag ggcagattcg accgcagcgt ggaaaagtgg    1680
cggcggttcc actacgacat caagatcttc aaccagtggc tgaccgaggc cgagcagttc    1740
ctgagaaaga cccagatccc cgagaactgg gagcacgcca agtacaagtg gtatctgaaa    1800
gagctgcagg acggcatcgg ccagcggcag acagtggtcc gcaccctgaa tgccaccggc    1860
gaggaaatca tccagcagag cagcaagacc gacgccagca tcctgcagga aaagctgggc    1920
agcctgaacc tgcggtggca ggaagtgtgc aagcagctga gcgaccggaa gaagcggctg    1980
gaagaacagg cccctggcct gaccacaatc ggcgccagcc tacccagac cgtgaccctg     2040 gtgacacagc ccgtggtgac aaaagagaca gccatcagca gctggaaat gcccagcagc    2100 ctgatgctgg aaagcgacca gtggaagcgg ctgcacctga gcctgcagga actgctggtc    2160
tggctgcagc tgaaggacga cgagctgagc agacaggccc ccatcggcgg cgatttcccc    2220
gccgtgcaga acagaacga cgtgcaccgg gccttcaagc gcgagctgaa acaaaagaa     2280 cccgtgatca tgagcaccct ggaaaccgtg cggatcttcc tgaccgagca gcccctggaa    2340
ggcctggaaa agctgtacca ggaacccaga gagctgcccc ccgaggaacg ggcccagaac    2400
gtgaccagac tgctgcggaa gcaggccgaa gaggtcaaca ccgagtggga agagctgaac    2460
ctgcacagcg ccgactggca gcggaagatc gacgagacac tggaacggct gcaggaactg    2520
caggaggcca ccgacgagct ggacctgaag ctgagacagg ccgaagtgat caagggcagc    2580
tggcagcccg tgggcgacct gctgatcgac tccctgcagg accacctgga aaaagtgaag    2640
gccctgcggg gcgagatcgc cccccctgaaa gaaaacgtgt cccacgtgaa cgacctggcc    2700
cggcagctga ccaccctggg catccagctg agccctaca acctgtccac cctggaagat   2760
ctgaacaccc ggtggaagct gctgcaggtg gccgtggaag atagagtgcg gcagctgcac    2820
gaggcccaca gagactttgg ccctgccagc cagcacttcc tgagcacctc tgtgcaggga    2880
ccctgggaga gagccatcag ccccaacaag gtgccctact acatcaacca cgagacacag    2940
accacctgtt gggaccaccc caagatgacc gagctgtacc agagcctggc cgacctgaac    3000
aatgtgcggt tcagcgccta ccggaccgcc atgaagctga ggcggctgca gaaagctctg    3060
tgcctggatc tgctgagcct gagcgccgcc tgcgacgccc tggaccagca aacctgaag    3120 cagaacgacc agcccatgga tatcctgcag atcatcaact gcctgaccac aatctacgac    3180
aggctggaac aggaacacaa caatctggtc aacgtgcccc tgtgcgtgga catgtgcctg    3240
aattggctgc tgaatgtgta cgacaccggc cggaccggca gaatccgggt gctgagcttc    3300
aagaccggca tcatcagcct gtgcaaggcc cacctggaag ataagtaccg ctacctgttc    3360
aaacaggtgg ccagctccac cggcttttgc gaccagcgga gactgggcct gctgctgcac    3420
gacagcatcc agatccccag acagctgggc gaggtggcct ccttcggcgg cagcaacatt    3480
gagcccagcg tgcggagctg cttccagttc gccaacaaca gcccgagat cgaggccgcc    3540 ctgttcctgg actggatgag actggaaccc cagagcatgg tgtggctgcc cgtgctgcat    3600
```

| | |
|---|---|
| cgggtggccg ctgccgagac agccaagcac caggccaagt gcaacatctg caaagagtgc | 3660 |
| cccatcatcg gcttccggta cagaagcctg aagcacttca actacgatat ctgccagagc | 3720 |
| tgcttcttca gcgcagagt ggccaagggc cacaaaatgc actaccccat ggtggaatac | 3780 |
| tgcaccccca ccaccagcgg cgaggatgtg cgggacttcg ccaaggtgct gaaaaacaag | 3840 |
| ttccggacca agcggtactt tgccaagcac ccccggatgg gctacctgcc cgtgcagaca | 3900 |
| gtgctggaag gcgacaacat ggaaacctga | 3930 |

<210> SEQ ID NO 105
<211> LENGTH: 3927
<212> TYPE: DNA
<213> ORGANISM: Artificial Sequence
<220> FEATURE:
<223> OTHER INFORMATION: BXA-212372-J4

<400> SEQUENCE: 105

| | |
|---|---|
| atgctgtggt gggaggaagt ggaagattgc tacgagcgcg aggacgtgca gaagaaaacc | 60 |
| ttcaccaaat gggtgaacgc ccagttcagc aagttcggca gcagcacat cgagaacctg | 120 |
| ttcagcgacc tgcaggacgg cagacggctg ctggacctgc tggaaggcct gaccggccag | 180 |
| aagctgccca agagaaggg cagcaccaga gtgcacgccc tgaacaacgt gaacaaggcc | 240 |
| ctgcgggtgc tgcagaacaa caacgtggac ctggtgaaca tcggcagcac cgacatcgtg | 300 |
| gacggcaacc acaagctgac cctgggcctg atctggaaca tcatcctgca ctggcaggtc | 360 |
| aaaaacgtga tgaagaacat catggccggc ctgcagcaga ccaacagcga gaagatcctg | 420 |
| ctgagctggg tgcgccagag cacccggaac taccccagg tcaacgtgat caacttcacc | 480 |
| acctcttgga gcgacggcct ggccctgaac gccctgatcc acagccaccg gcccgacctg | 540 |
| ttcgactgga cagcgtggt ctgccagcag agcgccaccc agcggctgga acacgccttc | 600 |
| aatatcgcca gataccagct gggcatcgag aagctgctgg atcccgagga cgtggacacc | 660 |
| acctaccccg acaagaaatc catcctgatg tatatcacca gcctgttcca ggtgctgccc | 720 |
| cagcaggtgt ccatcgaggc catccaggaa gtggaaatgc tgcccagacc ccccaaagtg | 780 |
| accaaagagg aacacttcca gctgcaccac cagatgcact acagccagca gatcaccgtg | 840 |
| tccctggctc agggctacga gcggaccagc agccccaagc cccggttcaa gagctacgcc | 900 |
| tacacccagg ccgcctacgt gaccaccagc gaccccacca aagcccatt ccccagccag | 960 |
| catctggaag cccccgagga caagagcttc ggcagcagcc tgatggaaag cgaagtgaac | 1020 |
| ctggacagat accagaccgc cctggaagag gtgctgtcct ggctgctgag cgccgaggat | 1080 |
| acactgcagg cccagggcga gatcagcaac gacgtggaag tggtgaaaga ccagttccac | 1140 |
| acccacgagg gctacatgat ggacctgacc gcccaccagg cagagtggg caacatcctg | 1200 |
| cagctgggca gcaagctgat cggcaccggc aagctgagcg aggacgaaga gacagaggtg | 1260 |
| caggaacaga tgaacctgct gaacagcaga tgggagtgcc tgcgggtggc cagcatggaa | 1320 |
| aagcagagca acctgcacag ctacgtgccc agcacctacc tgaccgagat cacccacgtg | 1380 |
| tcccaggctc tgctggaagt ggaacagctg ctgaacgccc ccgacctgtg cgccaaggac | 1440 |
| ttcgaggatc tgttcaagca ggaagagagc ctgaagaata tcaaggactc cctgcagcag | 1500 |
| tccagcggcc ggatcgacat catccacagc aagaaaacag ccgccctgca gtccgccacc | 1560 |
| cccgtggaaa gagtgaagct gcaggaagcc ctgagccagc tggacttcca gtgggagaaa | 1620 |
| gtgaacaaga tgtacaagga ccggcaggc agattcgacc gcagcgtgga aaagtggcgg | 1680 |
| cggttccact acgacatcaa gatcttcaac cagtggctga ccgaggccga gcagttcctg | 1740 |

```
agaaagaccc agatcccga gaactgggag cacgccaagt acaagtggta tctgaaagag    1800
ctgcaggacg gcatcggcca gcggcagaca gtggtccgca ccctgaatgc caccggcgag    1860
gaaatcatcc agcagagcag caagaccgac gccagcatcc tgcaggaaaa gctgggcagc    1920
ctgaacctgc ggtggcagga agtgtgcaag cagctgagcg accggaagaa gcggctggaa    1980
gaacaggccc ctggcctgac cacaatcggc gccagcccta cccagaccgt gaccctggtg    2040
acacagcccg tggtgacaaa agagacagcc atcagcaagc tggaaatgcc cagcagcctg    2100
atgctggaaa gcgaccagtg gaagcggctg cacctgagcc tgcaggaact gctggtctgg    2160
ctgcagctga aggacgacga gctgagcaga caggcccca tcggcggcga tttccccgcc    2220
gtgcagaaac agaacgacgt gcaccgggcc ttcaagcgcg agctgaaaac aaaagaaccc    2280
gtgatcatga gcaccctgga aaccgtgcgg atcttcctga ccgagcagcc cctgaaggc    2340
ctggaaaagc tgtaccagga acccagagag ctgcccccg aggaacgggc ccagaacgtg    2400
accagactgc tgcggaagca ggccgaagag gtcaacaccg agtgggagaa gctgaacctg    2460
cacagcgccg actggcagcg gaagatcgac gagacactgg aacggctgca ggaactgcag    2520
gaggccaccg acgagctgga cctgaagctg agacaggccg aagtgatcaa gggcagctgg    2580
cagcccgtgg gcgacctgct gatcgactcc ctgcaggacc acctggaaaa agtgaaggcc    2640
ctgcggggcg agatcgcccc cctgaaagaa aacgtgtccc acgtgaacga cctggcccgg    2700
cagctgacca ccctgggcat ccagctgagc ccctacaacc tgtccaccct ggaagatctg    2760
aacacccggt ggaagctgct gcaggtggcc gtggaagata gagtgcggca gctgcacgag    2820
gcccacagag actttggccc tgccagccag cacttcctga gcacctctgt gcagggaccc    2880
tgggagagag ccatcagccc caacaaggtg ccctactaca tcaaccacga gacacagacc    2940
acctgttggg accaccccaa gatgaccgag ctgtaccaga gcctggccga cctgaacaat    3000
gtgcggttca gcgcctaccg gaccgccatg aagctgaggc ggctgcagaa agctctgtgc    3060
ctggatctgc tgagcctgag cgccgcctgc gacgccctgg accagcacaa cctgaagcag    3120
aacgaccagc ccatggatat cctgcagatc atcaactgcc tgaccacaat ctacgacagg    3180
ctggaacagg aacacaacaa tctggtcaac gtgcccctgt gcgtggacat gtgcctgaat    3240
tggctgctga atgtgtacga caccggccgg accggcagaa tccgggtgct gagcttcaag    3300
accggcatca tcagcctgtg caaggcccac ctggaagata agtaccgcta cctgttcaaa    3360
caggtggcca gctccaccgg cttttgcgac agcggagac tgggcctgct gctgcacgac    3420
agcatccaga tccccagaca gctgggcgag gtggcctcct cggcggcag caacattgag    3480
cccagcgtgc ggagctgctt ccagttcgcc aacaacaagc ccgagatcga ggccgccctg    3540
ttcctggact ggatgagact ggaacccag agcatggtgt ggctgccgt gctgcatcgg    3600
gtggccgctg ccgagacagc caagcaccag gccaagtgca acatctgcaa agagtgcccc    3660
atcatcggct ccggtacag aagcctgaag cacttcaact acgatatctg ccagagctgc    3720
ttcttcagcg gcagagtggc caagggccac aaaatgcact accccatggt ggaatactgc    3780
accccccacca ccagcggcga ggatgtgcgg gacttcgcca aggtgctgaa aaacaagttc    3840
cggaccaagc ggtactttgc caagcacccc cggatgggct acctgccgt gcagacagtg    3900
ctggaaggcg acaacatgga aacctga                                       3927

<210> SEQ ID NO 106
<211> LENGTH: 3987
<212> TYPE: DNA
```

<213> ORGANISM: Artificial Sequence
<220> FEATURE:
<223> OTHER INFORMATION: BXA-212372

<400> SEQUENCE: 106

```
atgctgtggt gggaggaagt ggaagattgc tacgagcgcg aggacgtgca gaagaaaacc      60
ttcaccaaat gggtgaacgc ccagttcagc aagttcggca agcagcacat cgagaacctg     120
ttcagcgacc tgcaggacgg cagacggctg ctggacctgc tggaaggcct gaccggccag     180
aagctgccca agagaagggg cagcaccaga gtgcacgccc tgaacaacgt gaacaaggcc     240
ctgcgggtgc tgcagaacaa caacgtggac ctggtgaaca tcggcagcac cgacatcgtg     300
gacggcaacc acaagctgac cctgggcctg atctggaaca tcatcctgca ctggcaggtc     360
aaaaacgtga tgaagaacat catggccggc ctgcagcaga ccaacagcga agatcctg      420
ctgagctggg tgcgccagag caccggaac tacccccagg tcaacgtgat caacttcacc     480
acctcttgga gcgacggcct ggccctgaac gccctgatcc acagccaccg gcccgacctg     540
ttcgactgga acagcgtggt ctgccagcag agcgccaccc agcggctgga acacgccttc     600
aatatcgcca gataccagct gggcatcgag aagctgctgg atcccgagga cgtggacacc     660
acctaccccg acaagaaatc catcctgatg tatatccacca gcctgttcca ggtgctgccc     720
cagcaggtgt ccatcgaggc catccaggaa gtggaaatgc tgcccagacc ccccaaagtg     780
accaaagagg aacacttcca gctgcaccac cagatgcact acagccagca gatcaccgtg     840
tccctggctc agggctacga gcggaccagc agccccaagc ccggttcaa gagctacgcc      900
tacacccagg ccgcctacgt gaccaccagc gaccccacca agagcccatt ccccagccag     960
catctggaag cccccgagga caagagcttc ggcagcagcc tgatggaaag cgaagtgaac    1020
ctggacagat accagaccgc cctggaagag gtgctgtcct ggctgctgag cgccgaggat    1080
acactgcagg cccagggcga gatcagcaac gacgtggaag tggtgaaaga ccagttccac    1140
acccacgagg gctacatgat ggacctgacc gcccaccagg cagagtggg caacatcctg    1200
cagctgggca gcaagctgat cggcaccggc aagctgagcg aggacgaaga gacagaggtg    1260
caggaacaga tgaacctgct gaacagcaga tgggagtgcc tgcgggtggc cagcatggaa    1320
aagcagagca acctgcacat ccacaccgtg cgggaagaga caatgatggt gatgaccgag    1380
gacatgcccc tggaaatcag ctacgtgccc agcacctacc tgaccgagat cacccacgtg    1440
tcccaggctc tgctggaagt ggaacagctg ctgaacgccc ccgacctgtg cgccaaggac    1500
ttcgaggatc tgttcaagca ggaagagagc ctgaagaata tcaaggactc cctgcagcag    1560
tccagcggcc ggatcgacat catccacagc aagaaaacag ccgccctgca gtccgccacc    1620
cccgtggaaa gagtgaagct gcaggaagcc ctgagccagc tggacttcca gtgggagaaa    1680
gtgaacaaga tgtacaagga ccggcagggc agattcgacc gcagcgtgga aaagtggcgg    1740
cggttccact acgacatcaa gatcttcaac cagtggctga ccgaggccga gcagttcctg    1800
agaaagaccc agatccccga gaactgggag cacgccaagt acaagtggta tctgaaagag    1860
ctgcaggacg gcatcggcca gcggcagaca gtggtccgca ccctgaatgc caccggcgag    1920
gaaatcatcc agcagagcag caagaccgac gccagcatcc tgcaggaaaa gctgggcagc    1980
ctgaacctgc ggtggcagga agtgtgcaag cagctgagcg accggaagaa gcggctggaa    2040
gaacaggccc tggcctgac cacaatcggc gccagcccta cccagaccgt gaccctggtg    2100
acacagcccg tggtgacaaa agagacagcc atcagcaagt ggaaatgcc cagcagcctg    2160
atgctggaaa gcgaccagtg gaagcggctg cacctgagcc tgcaggaact gctggtctgg    2220
```

```
ctgcagctga aggacgacga gctgagcaga caggccccca tcggcggcga tttccccgcc    2280
gtgcagaaac agaacgacgt gcaccgggcc ttcaagcgcg agctgaaaac aaaagaaccc    2340
gtgatcatga gcaccctgga aaccgtgcgg atcttcctga ccgagcagcc cctggaaggc    2400
ctggaaaagc tgtaccagga acccagagag ctgcccccccg aggaacgggc ccagaacgtg    2460
accagactgc tgcggaagca ggccgaagag gtcaacaccg agtgggagaa gctgaacctg    2520
cacagcgccg actggcagcg gaagatcgac gagacactgg aacggctgca ggaactgcag    2580
gaggccaccg acgagctgga cctgaagctg agacaggccg aagtgatcaa gggcagctgg    2640
cagcccgtgg gcgacctgct gatcgactcc ctgcaggacc acctggaaaa agtgaaggcc    2700
ctgcggggcg agatcgcccc cctgaaagaa aacgtgtccc acgtgaacga cctggcccgg    2760
cagctgacca ccctgggcat ccagctgagc ccctacaacc tgtccaccct ggaagatctg    2820
aacacccggt ggaagctgct gcaggtggcc gtggaagata gagtgcggca gctgcacgag    2880
gcccacagag actttggccc tgccagccag cacttcctga gcacctctgt gcagggaccc    2940
tgggagagag ccatcagccc caacaaggtg ccctactaca tcaaccacga gacacagacc    3000
acctgttggg accaccccaa gatgaccgag ctgtaccaga gcctggccga cctgaacaat    3060
gtgcggttca gcgcctaccg gaccgccatg aagctgaggc ggctgcagaa agctctgtgc    3120
ctggatctgc tgagcctgag cgccgcctgc gacgccctgg accagcacaa cctgaagcag    3180
aacgaccagc ccatggatat cctgcagatc atcaactgcc tgaccacaat ctacgacagg    3240
ctgaacagaa acacaacaa tctggtcaac gtgcccctgt gcgtggacat gtgcctgaat    3300
tggctgctga atgtgtacga caccggccgg accggcagaa tccgggtgct gagcttcaag    3360
accggcatca tcagcctgtg caaggcccac ctggaagata gtaccgcta cctgttcaaa    3420 caggtggcca gctccaccgg cttttgcgac cagcggagac tgggcctgct gctgcacgac    3480
agcatccaga tccccagaca gctgggcgag gtggcctcct tcggcggcag caacattgag    3540
cccagcgtgc ggagctgctt ccagttcgcc aacaacaagc ccgagatcga ggccgccctg    3600
ttcctggact ggatgagact ggaaccccag agcatggtgt ggctgccccgt gctgcatcgg    3660 gtggccgctg ccgagacagc caagcaccag gccaagtgca acatctgcaa agagtgcccc    3720
atcatcggct ccggtacag aagcctgaag cacttcaact acgatatctg ccagagctgc    3780
ttcttcagcg gcagagtggc caaggccac aaaatgcact accccatggt ggaatactgc    3840
acccccacca ccagcggcga ggatgtgcgg gacttcgcca aggtgctgaa aaacaagttc    3900
cggaccaagc ggtactttgc caagcacccc cggatgggct acctgcccgt gcagacagtg    3960
ctggaaggcg acaacatgga aacctga                                        3987
```

<210> SEQ ID NO 107
<211> LENGTH: 10
<212> TYPE: RNA
<213> ORGANISM: Homo sapiens

<400> SEQUENCE: 107 gccrccaugg                                                              10

<210> SEQ ID NO 108
<211> LENGTH: 10
<212> TYPE: DNA
<213> ORGANISM: Homo sapiens

<400> SEQUENCE: 108

```
gccaccatgg                                                                10
```

<210> SEQ ID NO 109
<211> LENGTH: 322
<212> TYPE: DNA
<213> ORGANISM: Artificial Sequence
<220> FEATURE:
<223> OTHER INFORMATION: C5-12(T) Promoter

<400> SEQUENCE: 109

```
ccgccttcgg caccattcct cacgacaccc aaatatggcg acgggtgagg aatggtgggg      60
agttattttt agagcggtga ggaaggtggg caggcagcag gtgttggcgc tctaaaaata     120
actcccggga gttattttta gagcggagga atggtggaca cccaaatatg gcgacggttc     180
ctcacccgtc gccatatttg ggtgtccgcc ctcggccggg gccgcattcc tgggggccgg     240
gcggtgctcc cgcccgcctc gataaaaggc tccggggccg gcggcggccc acgagctacc     300
cggaggagcg ggaggcacgc gt                                              322
```

<210> SEQ ID NO 110
<211> LENGTH: 104
<212> TYPE: DNA
<213> ORGANISM: Simian virus 40

<400> SEQUENCE: 110

```
ctctaaggta aatataaaat ttttaagtgt ataatgtgtt aaactactga ttctaattgt      60
ttctctcttt tagattccaa cctttggaac tgatctagac cacc                      104
```

<210> SEQ ID NO 111
<211> LENGTH: 3936
<212> TYPE: DNA
<213> ORGANISM: Artificial Sequence
<220> FEATURE:
<223> OTHER INFORMATION: BXA-220931

<400> SEQUENCE: 111

```
atgctttggt gggaagaagt cgaggactgc tacgagcgcg aggacgtgca gaagaaaacc      60
ttcaccaaat gggtcaacgc ccagttcagc aagttcggca gcagcacat cgagaacctg     120
ttcagcgacc tgcaggatgg cagaaggctg ctggatctgc tggaaggcct gacaggccag     180
aagctgccta agagaaggg cagcacaaga gtgcacgccc tgaacaacgt gaacaaggcc     240
ctgagagtgc tgcagaacaa caacgtggac ctggtcaaca tcggcagcac cgacatcgtg     300
gacggcaatc acaaactgac cctgggcctg atctggaaca tcatcctgca ctggcaagtg     360
aagaacgtga tgaagaacat catggccggc ctgcagcaga ccaacagcga aagattctg      420
ctgagctggg tccgacagag cacccggaac taccctcaag tgaacgtgat caacttcacc     480
acctcttgga gcgacggact ggccctgaat gccctgattc acagccacag acctgacctg     540
ttcgactgga atagcgtcgt gtgtcagcag agcgccacac agagactgga acacgccttc     600
aatatcgcca gataccagct gggcatcgag aaactgctgg accccgagga tgtggacacc     660
acctatcctg acaagaaatc catcctcatg tacatcacca gcctgttcca ggtgctgccc     720
cagcaagtgt ctatcgaggc cattcaagag gtcgagatgc tgcccagacc tcctaaagtg     780
accaaagagg aacacttcca gctgcaccac cagatgcact actctcagca gatcaccgtg     840
tctctggccc agggctacga gagaacaagc agccccaagc tcggttcaa gagctacgcc     900
tatacacagg ccgcctacgt gaccaccagc gatcccacaa gaagcccatt ccaagccag      960
catctggaag cccctgagga caagagcttt ggcagcagcc tgatggaaag cgaagtgaac    1020
```

```
ctggatagat accagacagc cctggaagag gtgctgtctt ggctgctgtc tgccgaagat    1080
acactgcagg ctcagggcga gatcagcaac gacgtggaag tggtcaagga ccagtttcac    1140
acccacgagg gctacatgat ggacctgaca gcccatcagg gcagagtggg caatatcctg    1200
cagctgggct ctaagctgat cggcacaggc aagctgagcg aggacgaaga gacagaggtg    1260
caagagcaga tgaacctgct gaacagcaga tgggagtgtc tgagagtggc cagcatggaa    1320
aagcagagca acctgcaccg ggtcctgatg gatctgcaga atcagaagct gaccgagatc    1380
acccacgtgt cacaggccct gcttgaagtg aacagctgc tgaacgcccc tgatctgtgc    1440
gccaaggact tcgaggatct gttcaagcaa gaggaaagcc tgaagaatat caaggactct    1500
ctgcagcagt ccagcggccg gatcgacatc atccacagca gaaaacagc tgccctgcag    1560 tccgccacac ctgtggaaag agtgaaactg aagaggccc tgtctcagct ggacttccag    1620
tgggagaaag tgaacaagat gtacaaggac cggcagggca gattcgaccg ctctgtggaa    1680
aaatggcgga gattccacta cgacatcaag atcttcaacc agtggctgac agaggccgag    1740
cagttcctga gaaagacaca gatccccgag aactgggagc acgccaagta caagtggtat    1800
ctgaaagaac tgcaggacgg catcggccag aggcagacag tcgttagaac actgaatgcc    1860
accggcgagg aaatcatcca gcagagcagc aagaccgacg ccagcatcct gcaagagaag    1920
ctgggcagcc tgaacctgag atggcaagaa gtgtgcaagc agctgtccga ccggaagaag    1980
aggctggaag aacaggcccc tggcctgaca caatcggag cctctcctac acagaccgtg    2040
acactggtca cacagcccgt ggtcaccaaa gagacagcca tcagcaagct ggaaatgccc    2100
tctagcctga tgctcgagag cgaccagtgg aagagactgc acctgtctct gcaagagctg    2160
ctcgtgtggc tgcagctgaa ggacgatgaa ctgagcagac aggcccccaat cggaggcgat    2220 tttcctgccg tgcagaaaca gaacgacgtg cacagagcct caagcgggaa actgaaaaca    2280
aaagaacccg tgatcatgag caccctggaa accgtgcgga tcttcctgac agagcagcct    2340
ctcgaaggcc tggaaaagct gtaccaagag cctagagagc tgcctcctga ggaacgggcc    2400
cagaatgtga ccagactgct gagaaagcag gccgaagagg tcaacaccga atgggagaag    2460
ctgaacctgc acagcgccga ctggcagaga aagatcgacg agacactgga acggctgcaa    2520
gaactccaag aagccaccga cgagctggac ctgaaactga ggcaggctga agtgatcaaa    2580
ggcagctggc agccagtggg cgacctgctg attgatagtc tgcaggacca cctgaaaaaa    2640
gtgaaggccc tgcggggaga gatcgcccca ctgaaagaaa acgtgtccca cgtgaacgac    2700
ctggccagac agctgacaac cctgggaatc cagctgtccc cttacaacct gtccacactg    2760
gaagatctga caccccggtg gaaactgctc caggtggccg tggaagatag agtgcgacag    2820
ctgcacgagg cccacagaga ttttggacca gccagccagc acttcctgtc tacatctgtg    2880
caaggccctt gggagagagc tatcagccct aacaaggtgc cctactacat caaccacgag    2940
acacagacca cctgttggga tcaccccaag atgaccgagc tgtatcagag cctggccgac    3000
ctgaacaatg tgcgctttag cgcctaccgg accgccatga agctgcggag actgcagaaa    3060
gccctgtgtc tggacctgct gtctctgtct gcagcctgtg atgccctgga ccagcacaac    3120
ctgaagcaga acgaccagcc tatggacatc ctccagatca tcaactgcct gaccaccatc    3180
tacgaccggc tggaacaaga gcacaacaac ctcgtgaatg tgcccctgtg cgtggacatg    3240
tgtctgaact ggctgctgaa tgtgtacgac accggcagaa ccggcaggat cagagtgctg    3300
agcttcaaga ccggcatcat ctccctgtgc aaagcccacc tcgaggacaa gtacagatac    3360
```

```
ctgttcaaac aggtggccag ctccaccggc ttttgcgatc aaagaaggct gggcctgctg    3420
ctgcacgaca gcatccagat tcctagacag ctgggcgaag tggcctcctt cggcggatct    3480
aatattgagc ctagcgtgcg gagctgcttc cagttcgcca acaacaagcc tgagatcgag    3540
gccgctctgt tcctggattg gatgcgcctg gaacctcaga gcatggtttg gctgcctgtg    3600
ctgcatagag tggccgctgc cgaaacagcc aagcaccagg ccaagtgcaa catctgcaaa    3660
gagtgcccca tcatcggctt ccggtacaga tccctgaagc acttcaacta cgatatctgc    3720
cagagctgtt tcttctctgg ccgcgtggcc aagggccaca aaatgcacta ccccatggtg    3780
gaatactgca cccctaccac atctggcgaa gatgtgcggg atttcgccaa ggtgctgaaa    3840
aacaagttcc ggaccaagcg gtacttcgct aagcacccca gaatgggcta tctgcccgtg    3900
cagacagtgc tcgagggcga taacatggaa acctga                             3936
```

<210> SEQ ID NO 112
<211> LENGTH: 25
<212> TYPE: DNA
<213> ORGANISM: Homo sapiens

<400> SEQUENCE: 112

```
gaagtctttt ccacatggca gatga                                           25
```

<210> SEQ ID NO 113
<211> LENGTH: 49
<212> TYPE: DNA
<213> ORGANISM: Artificial Sequence
<220> FEATURE:
<223> OTHER INFORMATION: PolyA

<400> SEQUENCE: 113

```
aataaaagat ccttattttc attggatctg tgtgttggtt ttttgtgtg                 49
```

<210> SEQ ID NO 114
<211> LENGTH: 19
<212> TYPE: DNA
<213> ORGANISM: Mus musculus

<400> SEQUENCE: 114

```
aaggcctgac agggcaaaa                                                  19
```

<210> SEQ ID NO 115
<211> LENGTH: 22
<212> TYPE: DNA
<213> ORGANISM: Mus musculus

<400> SEQUENCE: 115

```
cagggcatga actcttgtgg at                                              22
```

<210> SEQ ID NO 116
<211> LENGTH: 15
<212> TYPE: DNA
<213> ORGANISM: Mus musculus

<400> SEQUENCE: 116

```
ctgccaaaag aaaaa                                                      15
```

<210> SEQ ID NO 117
<211> LENGTH: 17
<212> TYPE: DNA
<213> ORGANISM: Homo sapiens

<400> SEQUENCE: 117

```
<210> SEQ ID NO 118
<211> LENGTH: 19
<212> TYPE: DNA
<213> ORGANISM: Homo sapiens

<400> SEQUENCE: 118
ttgctgaact gggcgttga                                                      19

<210> SEQ ID NO 119
<211> LENGTH: 17
<212> TYPE: DNA
<213> ORGANISM: Homo sapiens

<400> SEQUENCE: 119
aaaccttcac caaatgg                                                        17

<210> SEQ ID NO 120
<211> LENGTH: 20
<212> TYPE: DNA
<213> ORGANISM: Homo sapiens

<400> SEQUENCE: 120
tggaagattg ctacgagcgc                                                     20

<210> SEQ ID NO 121
<211> LENGTH: 20
<212> TYPE: DNA
<213> ORGANISM: Homo sapiens

<400> SEQUENCE: 121
caggtcgctg aacaggttct                                                     20

<210> SEQ ID NO 122
<211> LENGTH: 21
<212> TYPE: DNA
<213> ORGANISM: Homo sapiens

<400> SEQUENCE: 122
gcaagttcgg caagcagcac a                                                   21
```

MINIATURIZED DYSTROPHINS HAVING SPECTRIN FUSION DOMAINS AND USES THEREOF

CROSS-REFERENCE TO RELATED APPLICATIONS

The present application claims benefit of U.S. Patent Application Ser. No. 63/017,148, filed Apr. 29, 2020, which is herein incorporated by reference in its entirety.

REFERENCE TO SEQUENCE LISTING

This application contains a Sequence Listing file entitled 13391_ST25.txt, with a file size of about 237,110 bytes and created on 2 Feb. 2022, has been submitted electronically in ASCII format and is hereby incorporated by reference in its entirety.

FIELD

The presently disclosed subject matter generally relates to polynucleotides, polypeptides, cells, vectors, uses, and kits relating to miniaturized dystrophin.

BACKGROUND OF THE DISCLOSURE

Duchenne muscular dystrophy (DMD) is a recessively-inherited muscle wasting disorder afflicting approximately 1 in 3,500 males. DMD is caused by mutations in the dystrophin gene, which is located on the X chromosome. Mutations in this gene lead to aberrant or absent expression of the dystrophin protein.

Dystrophin is a key component of a protein complex that is responsible for regulating muscle cell integrity and function. DMD patients typically lose the ability to physically support themselves during childhood and become progressively weaker over time. This progressive wasting of skeletal muscles and cardiac dysfunction typically leads to loss of ambulation and premature death, primarily due to cardiac or respiratory failure.

Some attempts have been made in the past to treat DMD. However, the available treatment options were significantly limited due to the large size of the wild type dystrophin cDNA (approximately 13.9 kb) which cannot be administered to and expressed in DMD patients using standard viral vectors, including Adeno-associated virus (AAV), which cannot transfer more than approximately 4.9 kb of heterologous DNA. Therefore, there is a need to develop a recombinant dystrophin gene that can be efficiently packaged into a vector for gene therapy.

Adeno-associated viral (AAV) vectors have been shown to be useful in gene therapeutic approaches aimed at correcting genetic deficiencies that result in reduced or completely abolished levels of protein expression (Nathwani et al., *Human Gene Therapy* 28:1004-1012 (2017); Keeler A. M. et al., *Clin. Transl. Sci.* 10:242-248 (2017)), and are potentially useful for gene knockdown, genome editing or modification, and non-coding RNA modulation (Valdmanis et al., *Human Gene Therapy* 28(4):361-372 (2017 April)).

Packaging the entire cDNA of the muscle-specific isoform of dystrophin into a single rAAV capsid cannot be achieved easily because of the large size of the dystrophin cDNA. Previous studies have focused on the development of smaller genetic constructs that express only particular domains of dystrophin. See U.S. Pat. Nos. 6,869,777 and 8,501,920, each of which is incorporated by reference. However, these approaches have had only limited success.

There remains a need for more precise and efficient gene therapy tools for treating patients with mutations in the dystrophin gene, and, in particular, a need to develop a recombinant dystrophin gene that can be efficiently packaged into a vector for gene therapy.

SUMMARY OF THE DISCLOSURE

The present disclosure provides a nucleic acid molecule comprising a nucleotide sequence, which encodes a miniaturized dystrophin polypeptide comprising a modified spectrin repeat 16 (R16) domain, wherein a part of spectrin repeat 16 (R16) domain is replaced by a corresponding part of a different spectrin repeat domain. In some embodiments, the different spectrin repeat domain is spectrin repeat 2 (R2) domain. In some embodiments the modified R16 domain comprises an amino acid sequence at least about 80%, at least about 85%, at least about 90%, at least about 95%, at least about 96%, at least about 97%, at least about 98%, at least about 99%, or about 100% identical to a sequence selected from the group consisting of SEQ ID NO: 68, 69, 70 and 71. In some embodiments, the miniaturized dystrophin polypeptide comprises from N terminus to C terminus a hinge 1 (H1) domain, a spectrin repeat 1 (R1) domain, the modified R16 domain, a spectrin repeat 17 (R17) domain, a hinge 3 (H3) domain, a spectrin repeat 23 (R23) domain, a spectrin repeat 24 (R24) domain, and a hinge 4 (H4) domain of dystrophin. In some embodiments, (i) the H1 domain and the R1 domain are fused directly, (ii) the R1 domain and the modified R16 domain are fused directly, (iii) the modified R16 domain and the R17 domain are fused directly, (iv) the R17 domain and the H3 domain are fused directly, (v) the H3 domain and the R23 domain are fused directly, (vi) the R23 domain and the R24 domain are fused directly, or (vii) the R24 domain and the H4 domain are fused directly, or (vii) any combination thereof. In some embodiments, the miniaturized dystrophin polypeptide does not comprise a spectrin repeat 2 (R2) domain, spectrin repeat 3 (R3) domain, spectrin repeat 4 (R4) domain, spectrin repeat 5 (R5) domain, spectrin repeat 6 (R6) domain, spectrin repeat 7 (R7) domain, spectrin repeat 8 (R8) domain, spectrin repeat 9 (R9) domain, spectrin repeat 10 (R10) domain, spectrin repeat 11 (R11) domain, spectrin repeat 12 (R12) domain, spectrin repeat 13 (R13) domain, spectrin repeat 14 (R14) domain, spectrin repeat 15 (R15) domain, spectrin repeat 18 (R18) domain, spectrin repeat 19 (R19) domain, spectrin repeat 20 (R20) domain, spectrin repeat 21 (R21) domain, and/or spectrin repeat 22 (R22) domain. In some embodiments, the miniaturized dystrophin polypeptide further comprises an ABD1 domain and/or a CR domain. In some embodiments, the miniaturized dystrophin polypeptide consists essentially of or consists of, from N terminus to C terminus, the ABD1 domain, the H1 domain, the R1 domain, the modified R16 domain, the R17 domain, the H3 domain, the R23 domain, the R24 domain, the H4 domain, and the CR domain of dystrophin. In some embodiments, the H1 domain is an amino acid sequence at least about 80%, at least about 85%, at least about 90%, at least about 95%, at least about 96%, at least about 97%, at least about 98%, at least about 99%, or about 100% identical to SEQ ID NO: 74. In some embodiments, the R1 domain is an amino acid sequence at least about 80%, at least about 85%, at least about 90%, at least about 95%, at least about 96%, at least about 97%, at least about 98%, at least about 99%, or about 100% identical to SEQ ID NO: 75. In some embodiments, the modified R16 domain is an amino acid sequence at least about 80%, at least about 85%, at least about 90%, at least about 95%, at least about 96%, at least about 97%, at least about 98%, at least about 99%, or about 100% identical to SEQ ID NO: 76. In some embodiments, the R17 domain is an amino acid sequence at least about 80%, at least about 85%, at least about 90%, at least about 95%, at least about 96%, at least about 97%, at least about 98%, at least about 99%, or about 100% identical to SEQ ID NO: 77. In some embodiments, the H3 domain is an amino acid sequence at least about 80%, at least about 85%, at least about 90%, at least about 95%, at least about 96%, at least about 97%, at least about 98%, at least about 99%, or about 100% identical to SEQ ID NO: 78. In some embodiments, the R23 domain is an amino acid sequence at least about 80%, at least about 85%, at least about 90%, at least about 95%, at least about 96%, at least about 97%, at least about 98%, at least about 99%, or about 100% identical to SEQ ID NO: 79. In some embodiments, the R24 domain is an amino acid sequence at least about 80%, at least about 85%, at least about 90%, at least about 95%, at least about 96%, at least about 97%, at least about 98%, at least about 99%, or about 100% identical to SEQ ID NO: 80. In some embodiments, the H4 domain is an amino acid sequence at least about 80%, at least about 85%, at least about 90%, at least about 95%, at least about 96%, at least about 97%, at least about 98%, at least about 99%, or about 100% identical to SEQ ID NO: 81. In some embodiments, the miniaturized dystrophin polypeptide further comprises at the N terminus an amino acid sequence at least about 80%, at least about 85%, at least about 90%, at least about 95%, at least about 96%, at least about 97%, at least about 98%, at least about 99%, or about 100% identical to SEQ ID NO: 73. In some embodiments, the miniaturized dystrophin polypeptide further comprises at the C terminus an amino acid sequence at least about 80%, at least about 85%, at least about 90%, at least about 95%, at least about 96%, at least about 97%, at least about 98%, at least about 99%, or about 100% identical to SEQ ID NO: 82. In some embodiments, the miniaturized dystrophin polypeptide comprises an amino acid sequence at least about 80%, at least about 85%, at least about 90%, at least about 95%, at least about 96%, at least about 97%, at least about 98%, at least about 99%, or about 100% identical to SEQ ID NO: 83. In some embodiments, the miniaturized dystrophin polypeptide comprises an amino acid sequence at least about 80%, at least about 85%, at least about 90%, at least about 95%, at least about 96%, at least about 97%, at least about 98%, at least about 99%, or about 100% identical to SEQ ID NO: 84. In some embodiments, the miniaturized dystrophin polypeptide comprises an amino acid sequence at least about 80%, at least about 85%, at least about 90%, at least about 95%, at least about 96%, at least about 97%, at least about 98%, at least about 99%, or about 100% identical to SEQ ID NO: 85. In some embodiments, the miniaturized dystrophin polypeptide comprises an amino acid sequence at least about 80%, at least about 85%, at least about 90%, at least about 95%, at least about 96%, at least about 97%, at least about 98%, at least about 99%, or about 100% identical to SEQ ID NO: 86. In some embodiments, the miniaturized dystrophin polypeptide comprises an amino acid sequence at least about 80%, at least about 85%, at least about 90%, at least about 95%, at least about 96%, at least about 97%, at least about 98%, at least about 99%, or about 100% identical to SEQ ID NO: 87. In some embodiments, the miniaturized dystrophin polypeptide exhibits a higher expression of the miniaturized dystrophin polypeptide than BXA-212372 (SEQ ID NO: 88). In some embodiments, the miniaturized dystrophin polypeptide expression is at least about 1.5 fold, at least about 1.6 fold, at least about 1.7 fold, at least about 1.8 fold, at least about 1.9 fold, at least about 2 fold, at least about 2.1 fold, at least about 2.2 fold, at least about 2.3 fold, at least about 2.4 fold, at least about 2.5 fold, at least about 2.6 fold, at least about 2.7 fold, at least about 2.8 fold, at least about 2.9 fold or at least about 3 fold higher than the BXA-212372 polypeptide (SEQ ID NO: 88) expression.

In some embodiments, the nucleic acid molecule disclosed herein further comprises a promoter. In some embodiments, the promoter is a tissue-specific promoter. In some embodiments, the promoter drives expression of the therapeutic protein in muscle cells, hepatocytes, endothelial cells, neuronal cells, sinusoidal cells, or any combination thereof. In some embodiments, the promoter is selected from the group consisting of a C5-12(T) promoter, an MLC2v-cTNT455 promoter, a mouse thyretin promoter (mTTR), an endogenous human factor VIII promoter (F8), a human alpha-1-antitrypsin promoter (hAAT), a human albumin minimal promoter, a mouse albumin promoter, a tristetraprolin (TTP) promoter, a CASI promoter, a synapsin 1 gene promoter, a CAG promoter, a cytomegalovirus (CMV) promoter, α1-antitrypsin (AAT), muscle creatine kinase (MCK), myosin heavy chain alpha (uMHC), myoglobin (MB), desmin (DES), SPc5-12, 2R5Sc5-12, dMCK, tMCK, and a phosphoglycerate kinase (PGK) promoter. In some embodiments, the promoter is a C5-12(T) promoter. In some embodiments, the nucleic acid molecule disclosed herein further comprises an intronic sequence. In some embodiments, the intronic sequence is positioned 5' to the nucleotide sequence encoding the miniaturized dystrophin polypeptide. In some embodiments, the intronic sequence is positioned 3' to the promoter. In some embodiments, the intronic sequence comprises a synthetic intronic sequence. In some embodiments, the nucleic acid molecule disclosed herein further comprises a post-transcriptional regulatory element. In some embodiments, the post-transcriptional regulatory element is positioned 3' to the nucleotide sequence encoding the miniaturized dystrophin polypeptide. In some embodiments, the post-transcriptional regulatory element comprises a mutated woodchuck hepatitis virus post-transcriptional regulatory element (WPRE), a microRNA binding site, or a DNA nuclear targeting sequence, or any combination thereof. In some embodiments, the nucleic acid molecule disclosed further comprises a 3'UTR poly(A) tail sequence. In some embodiments, the 3'UTR poly(A) tail sequence is selected from the group consisting of dystrophin poly(A), bGH poly(A), actin poly (A), hemoglobin poly(A), and any combination thereof. In some embodiments, the 3'UTR poly(A) tail sequence comprises dystrophin poly(A). In some embodiments, the nucleic acid molecule disclosed further comprises an enhancer sequence. In some embodiments, the nucleic acid molecule disclosed herein further comprises a first ITR and/or a second ITR. In some embodiments, the first ITR and the second ITR are identical. In some embodiments, the first ITR and/or the second ITR are derived from adeno-associated virus. In some embodiments, the nucleic acid molecule disclosed herein comprises a sequence encoding a heterologous moiety. In some embodiments, the heterologous moiety is selected from the group consisting of albumin or a fragment thereof, an immunoglobulin Fc region, the C-terminal peptide (CTP) of the R subunit of human chorionic gonadotropin, a PAS sequence, a HAP sequence, a transferrin or a fragment thereof, an albumin-binding moiety or a derivative thereof, and any combination thereof.

In some embodiments, provided is a vector comprising a nucleic acid molecule disclosed herein. In some embodiments, the vector is selected from the group consisting of a adenoviral vector, a retroviral vector, poxvirus vector, a baculovirus vector, a herpes viral vector. In some embodiments, the vector is an adeno-associated virus (AAV) vector. In some embodiments, the AAV vector is selected from AAV1, AAV2, AAV3, AAV4, AAV5, AAV6, AAV7, AAV8, AAV9, AAV10, and AAV11. In some embodiments, the AAV vector is AAV8 or AAV9. In some embodiments, the AAV vector is AAV9. In some embodiments, the AAV vector is AAV8.

In some embodiments, the nucleic acid molecule or vector disclosed herein is formulated with a delivery agent. In some embodiments, the delivery agent comprises a lipid nanoparticle. In some embodiments, the delivery agent is selected from the group consisting of liposomes, non-lipid polymeric molecules, endosomes, and any combination thereof. In some embodiments, the nucleic acid molecule or vector disclosed herein is formulated for intravenous, transdermal, intradermal, subcutaneous, pulmonary, or oral delivery, or any combination thereof. In some embodiments, the nucleic acid molecule or vector disclosed herein is formulated for intravenous delivery.

In some embodiments, provided is a polypeptide encoded by the nucleic acid molecule or vector disclosed herein.

In some embodiments, provided is a host cell comprising the nucleic acid molecule or vector disclosed herein. In some embodiments, the cell is a CHO cell, a HEK293 cell, a HBK cell, a COS cell, a NSO cell, or a HT1080 cell.

In some embodiments, provided is a pharmaceutical composition comprising (a) the nucleic, the vector, the polypeptide, or the host cell disclosed herein; and (b) a pharmaceutically acceptable excipient.

In some embodiments, provided is a kit, comprising the nucleic, the vector, the polypeptide, the host cell, or the pharmaceutical composition disclosed herein, and instructions for administering the nucleic, the vector, the polypeptide, the host cell, or the pharmaceutical composition to a subject in need thereof.

In some embodiments, provided is a method of producing a miniaturized dystrophin polypeptide, comprising: culturing the host cell disclosed herein under suitable conditions and recovering the miniaturized dystrophin polypeptide.

In some embodiments, provided is a method of expressing a miniaturized dystrophin polypeptide in a subject in need thereof, comprising administering to the subject the nucleic acid, the vector, the host cell, or the pharmaceutical composition disclosed herein.

In some embodiments, provided is a method of treating a subject having a disease or condition comprising administering to the subject the nucleic acid, the vector, the polypeptide, the host cell, or the pharmaceutical composition disclosed herein. In some embodiments, the disease or condition is a disease caused by dystrophin deficiency. In some embodiments, the disease is Sarcopenia, a heart disease, cachexia, Duchenne muscular dystrophy (DMD), Becker muscular dystrophy (BMD), X-linked dilated cardiomyopathy (XLDC), facioscapulohumeral muscular dystrophy, myotonic muscular dystrophy, limb-girdle muscular dystrophy, oculopharyngeal muscular dystrophy, Emery-Dreifuss muscular dystrophy, distal muscular dystrophy, and/or congenital muscular dystrophy. In some embodiments, the nucleic acid molecule, the vector, the polypeptide, the host cell, or the pharmaceutical composition is administered intravenously, transdermally, intradermally, subcutaneously, orally, or pulmonarily, or any combination thereof. In some embodiments, the method disclosed herein further comprises administering to the subject a second agent. In some embodiments, the subject is a human. In some embodiments, the administration of the nucleic acid molecule, the vector, the polypeptide, the host cell, or the pharmaceutical composition to the subject results in increased dystrophin protein expression, relative to dystrophin protein expression in the subject prior to the administration, wherein the dystrophin protein expression is increased by at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 20-fold, at least about 25-fold, at least about 30-fold, at least about 35-fold, at least about 40-fold, at least about 50-fold, at least about 60-fold, at least about 70-fold, at least about 80-fold, at least about 90-fold, or at least about 100-fold. In some embodiments, provided is a nucleic acid molecule comprising a nucleotide sequence, which encodes a miniaturized dystrophin polypeptide comprising an amino acid sequence of SEQ ID NO: 83. In some embodiments, provided is a nucleic acid molecule comprising a nucleotide sequence, which encodes a miniaturized dystrophin polypeptide consisting of the amino acid sequence of SEQ ID NO: 83.

In some embodiments, the nucleic acid molecule, the vector, the polypeptide, the host cell, the pharmaceutical composition, the kit, or the method disclosed herein, comprises a nucleotide sequence encoding a miniaturized dystrophin polypeptide comprising an amino acid sequence of SEQ ID NO: 83.

In some embodiments, the nucleic acid molecule encodes miniaturized dystrophin polypeptide BXA-220931 (SEQ ID NO: 83).

In some embodiments, provided is a nucleic acid molecule comprising a nucleotide sequence comprising in order a C5-12(T) promoter of SEQ ID NO: 109, an SV40 intron of SEQ ID NO: 110, a coding sequence for miniaturized dystrophin BXA-220931 of SEQ ID NO: 111, a 3' UTR of SEQ ID NO: 112, and a polyA sequence of SEQ ID NO: 113.

In some embodiments, the nucleic acid molecule, the vector, the polypeptide, the host cell, the pharmaceutical composition, the kit, or the method disclosed herein, comprises a nucleotide sequence comprising in order a C5-12(T) promoter of SEQ ID NO: 109, an SV40 intron of SEQ ID NO: 110, a coding sequence for miniaturized dystrophin BXA-220931 of SEQ ID NO: 111, a 3' UTR of SEQ ID NO: 112, and a polyA sequence of SEQ ID NO: 113.

BRIEF DESCRIPTION OF THE DRAWINGS

FIG. 5A shows a histogram indicating the proportion of samples, among the 40-samples cell panel tested, that were pulsed with various junction peptides as indicated and had CD4$^+$ proliferating cells (each square represents one patient sample). FIG. 5B shows a histogram indicating the proportion of samples, among the 40-samples cell panel tested, that were pulsed with various junction peptides as indicated and had CD8$^+$ proliferating cells (each square represents one patient sample).

FIG. 7A shows the effect of the indicated promoters on GFP expression. Expression is relative to the use of a CMV promoter (left-most data point). FIG. 7B shows the effect of the indicated introns/5'UTR on GFP expression. Expression is relative to expression resulting from the lack of an intron (left-most data point) Significance with respect to CMV promoter (FIG. 7A) and no intron (FIG. 7B): P<0.01, *P<0.001 (one-way ANOVA with post-hoc Tukey test). Bar graphs reflect the means+/−standard deviations.

FIG. 8A shows immuno-fluorescence visualization of expression of miniaturized dystrophin polypeptide and wheat germ-agglutinin (WGA) in muscle tissue of mdx$^{scsn}$ mice treated with AAV9-BXA-212372-J4V4. FIG. 8B shows immuno-fluorescence visualization of expression of miniaturized dystrophin polypeptide and wheat germ-agglutinin (WGA) in muscle tissue of mdx$^{scsn}$ mice treated with AAV9-BXA-212372-J4V11. FIG. 8C shows immuno-fluorescence visualization of expression of miniaturized dystrophin polypeptide and wheat germ-agglutinin (WGA) in muscle tissue of mdx$^{scsn}$ mice treated with AAV9-BXA-212372-J4V12. FIG. 8D shows immuno-fluorescence visualization of expression of miniaturized dystrophin polypep-tide and wheat germ-agglutinin (WGA) in muscle tissue of mdx$^{scsn}$ mice treated with AAV9-BXA-212372-J4V13 (BXA-220931). No dystrophin protein aggregates are detectable.

FIG. 10A shows a schematic illustrating the experimental setup and impulse conduction across a microelectrode array in tissue culture. FIG. 10B shows a graphic wherein the conduction velocity of the tested iCMs expressing miniaturized dystrophin polypeptide of BXA-220931 is plotted as a function of time post transfection. BXA-220931 increased conduction velocity of the tested iCMs. Untreated iCMs served as controls. Significance: *P<0.05, P<0.01, *P<0.001 (one-way ANOVA with post-hoc Tukey test). FIG. 10C shows a histogram indicating the expression of miniaturized dystrophin polypeptide BXA-220931 in cells in which conduction velocity was measured. Untreated iCMs served as controls. Bar graphs reflect the means+/−standard deviations.

FIG. 11A shows a histogram indicating the relative amount of vector genomes (VG) per μg genomic DNA in muscle tissue of mdx$^{scsn}$ mice treated with AAV9-BXA-220931 or AAV9-BXA-212374. FIG. 11B shows a histogram indicating the relative amount of miniaturized dystrophin mRNA in muscle tissue of mdx$^{scsn}$ mice treated with AAV9-BXA-220931 or AAV9-BXA-212374. FIG. 11C shows a histogram indicating the relative amount of miniaturized dystrophin protein in muscle tissue of mdx$^{scsn}$ mice treated with AAV9-BXA-220931 or AAV9-BXA-212374. Miniaturized dystrophin mRNA and protein expression remained above wild-type dystrophin levels. Wild-type mice and untreated mdx$^{scsn}$ mice served as controls. Bar graphs reflect the means+/−standard deviations.

FIG. 12A shows immuno-fluorescence visualization of expression of miniaturized dystrophin polypeptides and α2-Laminin in diaphragm muscle tissue of mice treated with AAV9-BXA-220931 or AAV9-BXA-212374. Nuclei were visualized with DAPI. The miniaturized dystrophin co-localized with α2-Laminin, a general marker for muscle sarcolemma. FIG. 12B shows a histogram indicating the relative number of cells in various muscles positive for miniaturized dystrophin (+ve=positive). Wild-type mice and untreated mdx$^{scsn}$ mice stained for dystrophin and α2-Laminin served as controls. Bar graphs reflect the means+/−standard deviations.

FIG. 14A shows a histogram indicating the relative amount of vector genomes (VG) per µg genomic DNA in muscle tissue of mdx$^{scsn}$ mice treated with AAV9-BXA-220931 or AAV9-BXA-212374. FIG. 14B shows a histogram indicating the relative amount of miniaturized dystrophin mRNA in muscle tissue of mdx$^{scsn}$ mice treated with AAV9-BXA-220931 or AAV9-BXA-212374. FIG. 14C shows a histogram indicating the relative amount of miniaturized dystrophin protein in muscle tissue of mdx$^{scsn}$ mice treated with AAV9-BXA-220931 or AAV9-BXA-212374. Miniaturized dystrophin mRNA and protein expression remained above wild-type dystrophin levels. Wild-type mice and untreated mdx$^{scsn}$ mice served as controls. Bar graphs reflect the means+/−standard deviations.

FIG. 15A shows immunofluorescence visualization of miniaturized dystrophin and laminin in the tibialis anterior muscle of 12 weeks old mdx$^{scsn}$ mice treated with AAV9-BXA-220931. Nuclei were visualized with DAPI. Miniaturized dystrophin remained on the sarcolemma of nearly every muscle fiber similar to dystrophin in wild-type mice. Untreated mdx$^{scsn}$ mice stained for dystrophin and laminin served as controls. FIG. 15B shows a histogram indicating the proportion of cells in various muscles positive for miniaturized dystrophin in mdx$^{scsn}$ mice treated with AAV9-BXA-220931 or AAV9-BXA-212374 (+ve=positive). FIG. 15C shows a histogram indicating the proportion of muscle cells with central nuclei in mdx$^{scsn}$ mice treated with AAV9-BXA-220931 or AAV9-BXA-212374. Wild-type mice and untreated mdx$^{scsn}$ mice served as controls. Bar graphs reflect the means+/−standard deviations.

DETAILED DESCRIPTION OF THE DISCLOSURE

Overview

Figure 1:
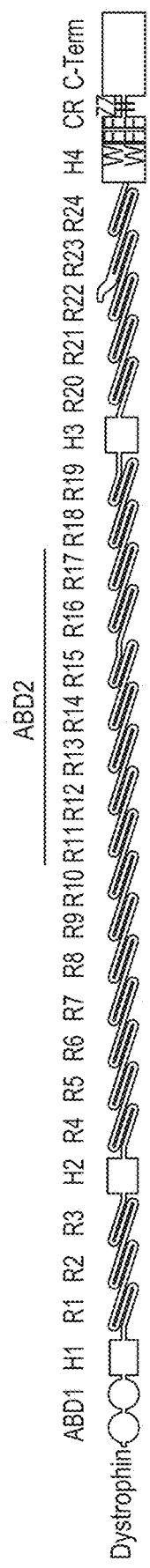
FIG. 1 shows a schematic diagram of the full length human Dystrophin protein. ABD1: actin-binding domain-1; H # (e.g., H1): hinge region; R # (e.g., R1): spectrin-like repeat domains; ABD2: actin-binding domain-2; CR: cysteine-rich domain; C-term: C-terminal domain of the protein.

The present disclosure relates to novel miniaturized dystrophins or the genes encoding the same. The miniaturized dystrophins can be operatively linked to a regulatory cassette. The present disclosure also relates to methods of treating a subject having muscular dystrophy, sarcopenia, heart failure, or cachexia. Further, the present disclosure relates to methods of prophylactically treating a subject at risk of developing muscular dystrophy, sarcopenia, heart failure, or cachexia. The methods for treating a subject having, or at risk of developing, muscular dystrophy, sarcopenia, heart failure, or cachexia can comprise administering a pharmaceutical composition including a miniaturized dystrophin gene and a delivery vehicle to the subject.

Definitions

In order that the present disclosure can be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone). It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

Dystrophin (DMD) is a large human X-linked gene that encodes Dystrophin. The protein Dystrophin is a 427 kDa cytoskeletal protein that localizes to the cytoplasmic face of the sarcolemma and is enriched at costameres in muscle fibers. The Dystrophin protein has four main functional domains: an actin-binding amino-terminal domain (ABD1); a central rod domain comprising a series of rods, called "spectrin repeat domains" and hinges; a cysteine-rich domain; and a carboxyl-terminus.

As used herein, the term "miniaturized dystrophin polypeptide" or "miniaturized dystrophin peptide" refers to a polypeptide that is smaller in size than the full-length wild-type dystrophin polypeptide. In some embodiments, the miniaturized dystrophin polypeptide is capable of altering (increasing or decreasing, as the case may be) a measurable value of muscle physiology or anatomy in a DMD animal model by at least approximately 10 or 20% of the wild type value, such that the value is closer to the wild-type value (e.g., a mdx mouse has a measurable value of muscle physiology or anatomy that is 50% of the wild-type value, and this value is increased to at least 60% of the wild-type value; or a mdx mouse has a measurable value of muscle physiology or anatomy that is 150% of the wild-type value, and this value is decreased to at most 140% of the wild-type value). In certain embodiments, the miniaturized dystrophin polypeptide is capable of altering a measurable value of muscle physiology or anatomy in a DMD animal model by at least approximately 30% of the wild type value. In some embodiments, the miniaturized dystrophin polypeptide is capable of altering a measurable value of muscle physiology or anatomy in a DMD animal model to a level similar to the wild-type value (e.g., ±4%). As used herein, the term "spectrin repeats" or "spectrin-like repeats" refers to peptides composed of approximately 100 amino acids that are responsible for the rod-like shape of many structural proteins including, but not limited to, dystrophin, wherein the spectrin repeats are typically present in multiple copies. Spectrin repeats can include mutations of the natural peptide sequences, such as conservative and/or non-conservative changes in amino acid sequence, as well as the addition or deletion of up to 1, 2, 3, 4, 5, 6, 7, 8, 9, or 10 amino acids to/from the end of a spectrin repeat or within the spectrin repeat. In some embodiments, each spectrin repeat (each of R1 to R24) has at least 70%, at least 75%, at least 80%, at least 85%, at least 90%, at least 95%, at least 96%, at least 97%, at least 98%, at least 99%, or 100% sequence identity to the naturally occurring spectrin repeat (each of the naturally occurring R1 to R24).

As used herein, the term "spectrin repeat encoding sequences" refers to nucleic acid sequences encoding spectrin repeat peptides. This term includes natural and synthetic nucleic acid sequences encoding the spectrin repeats (e.g., both the naturally occurring and mutated spectrin repeat peptides).

As used herein, the term "spectrin repeat domain" refers to the region in a miniaturized dystrophin polypeptide that contains the spectrin repeats of the miniaturized dystrophin polypeptide.

The term "fused" refers to a first amino acid sequence that is linked in frame to a second amino acid sequence with which it is not normally linked in nature, forming a "fusion" protein/polypeptide. These fused amino acid sequences which normally exist in separate proteins can be brought together in the fusion polypeptide, or the amino acid sequences which normally exist in the same protein can be placed in a new arrangement in the fusion polypeptide. A fusion protein is created, for example, by chemical peptide synthesis, or by recombinant DNA technology whereby a polynucleotide is created, and then translated, in which the peptide regions are encoded in the desired relationship. A fusion protein can also comprise a second amino acid sequence associated with the first amino acid sequence by a covalent, non-peptide bond or by a non-covalent bond. In some embodiments, "fusion" between two polypeptides is achieved by a linker. Linkers can be amino acids or other chemical structures. In some embodiments, linkers can be synthetic. In some embodiments, "fusion" between two polypeptides is a direct fusion, i.e., without intervening linker. The term "fused directly" or "direct fusion" refers to a linkage between two polypeptide chains by a peptide bond. For example, a first amino acid is "fused directly" to a second amino acid when the first amino acid is "fused" to a second amino acid by a peptide bond.

"Heterologous" and "heterologous moiety" in reference to a polypeptide moiety or polynucleotide moiety that is part of a larger polypeptide or polynucleotide, respectively, describes a polypeptide or polynucleotide that originates from a different polypeptide or polynucleotide than the remaining part of the polypeptide or polynucleotide molecule. The additional heterologous component of the polypeptide or polynucleotide can originate from the same organism as the remaining polypeptide or polynucleotide, respectively, described herein, or the additional components can be from a different organism. For instance, a heterologous polypeptide can be synthetic, or derived from a different species, different cell type of an individual, or the same or different type of cell of distinct individuals. In one aspect, a heterologous moiety is a polypeptide fused to another polypeptide to produce a polypeptide. In another aspect, a heterologous moiety is a non-polypeptide such as PEG conjugated to a polypeptide or protein.

As used herein, the terms "muscle cell" refers to a cell derived from muscle tissue, including, but not limited to, cells derived from skeletal muscle, smooth muscle (e.g. from the digestive tract, urinary bladder, and blood vessels), and cardiac muscle. The term includes muscle cells in vitro, ex vivo, and in vivo. Thus, for example, an isolated cardiomyocyte would constitute a muscle cell, as would a cell as it exists in muscle tissue present in a subject in vivo. This term also encompasses both terminally differentiated and nondifferentiated muscle cells, such as myocytes, myotubes, myoblasts, cardiomyocytes, and cardiomyoblasts.

As used herein, the term "muscle-specific" in reference to a gene regulatory element (e.g., enhancer sequence, promoter sequence) means that the regulatory element drives transcriptional activity primarily in muscle cells or tissue (e.g., 20:1) compared to the transcriptional activity driven by the regulatory element in other tissues. Assays to determine the muscle-specificity of a regulatory element are known in the art (e.g., in vitro assay using murine muscle cells and liver cells transfected with an expression vector comprising the regulatory element to be tested driving expression of a beta-galactoside reporter).

As used herein, the term "adeno-associated virus" or "AAV" includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, primate AAV, non-primate AAV, and ovine AAV, those AAV serotypes and clades disclosed by Gao et al. (J. Virol. 78:6381 (2004)) and Moris et al. (Virol. 33:375 (2004)), and any other AAV now known or later discovered. See, e.g., Fields et al. VIROLOGY, volume 2, chapter 69 (4th ed., Lippincott-Raven Publishers). AAV refers to a Dependoparvovirus within the Parvoviridae family of viruses. For example, the AAV can be an AAV derived from a naturally occurring "wild-type" virus, an AAV derived from a recombinant AAV (rAAV) genome packaged into a capsid derived from capsid proteins encoded by a naturally occurring cap gene and/or a rAAV genome packaged into a capsid derived from capsid proteins encoded by a non-natural capsid cap gene. As used herein, "A. AV" can be used to refer to the virus itself or derivatives thereof. The term covers all subtypes and both naturally occurring and recombinant forms, except where expressly indicated otherwise. "Primate AAV" refers to AAV that infect primates, "non-primate AAV" refers to AAV that infects animals other than primates, "bovine AAV" refers to AAV that infect bovine mammals, etc. See, e.g., BERNARD N. FIELDS et al., VIROLOGY, volume 2 chapter 69 (3 d ed., Lippincott-Raven Publishers).

The term "rAAV" refers to a "recombinant AAV." In some embodiments, a recombinant AAV has an AAV genome in which part or all of the rep and cap genes have been replaced with heterologous polynucleotide sequences.

An "AAV vector" or "adeno-associated virus vector" as used herein refers to an rAAV comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two, AAV inverted terminal repeat sequences (ITRs).

A "capsid-free" or "capsid-less" (or variations thereof) viral (e.g., AAV) genome or nucleic acid molecule refers to a genome or nucleic acid molecule free from a capsid. In some embodiments, the capsid-less genome or nucleic acid molecule does not contain sequences encoding, for example, an AAV Rep protein.

An "AAV" or "AAV viral particle" or "AAV vector" or "rAAV vector particle" refers to a viral particle composed of at least one AAV capsid protein (typically of all of the capsid proteins of a wild-type AAV) and an encapsidated polynucleotide. If the particle comprises a heterologous polynucleotide (i.e. a polynucleotide other than a wild-type AAV genome, such as a transgene to be delivered to a mammalian cell), it is typically referred to as an "rAAV vector particle" or simply an "AAV vector."

A "helper virus" for AAV refers to a virus that allows AAV (e.g., wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV), all of which are also available from depositories such as ATCC.

As used herein, the term "inverted terminal repeat" (or "ITR") refers to a single stranded sequence of nucleotides followed downstream by its reverse complement. The intervening sequence of nucleotides between the initial sequence and the reverse complement can be any length including zero. The AAV genome typically comprises inverted terminal repeats (ITRs) at both ends, wherein each end typically is palindromic and can form a hairpin.

The terms "polynucleotide" and "nucleic acid" are used interchangeably herein and refer to a biopolymer composed of a plurality of nucleotide monomers covalently bonded in a chain The term "tropism" as used herein refers to a virus's (e.g., AAV's) ability to infect only one or more particular cell types and its ability to interact only with specific cell surface moieties to achieve cell entry, optionally and preferably followed by expression (e.g., transcription and, optionally, translation) of sequences carried by the virus (e.g., AAV) into the cell (e.g., for a recombinant virus, expression of the heterologous nucleotide sequence(s)).

As used herein, the term "transduction" refers to the entry of the virus (e.g., AAV) into the cell and the transfer of genetic material contained within the virus into the cell to obtain expression from the virus genome. Typically, a virus (e.g., AAV) enters cells in accordance with its tropism.

"Administering" refers to the physical introduction of a therapeutic agent to a subject, using any of the various methods and delivery systems known to those skilled in the art. Exemplary routes of administration, e.g., for an AAV therapy, include intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural, intrasterna, oral, rectal, topical, epidermal, mucosal, intranasal, vaginal, rectal, and sublingual administration. Administering can also be performed, for example, once, a plurality of times, and/or over one or more extended periods.

"Treatment" or "therapy" of a subject refers to any type of intervention or process performed on, or the administration of an active agent to, a subject with the objective of reversing, alleviating, ameliorating, inhibiting, slowing down, or preventing the onset, progression, development, severity, or recurrence of a symptom, complication, condition, or biochemical indicia associated with a disease.

A "therapeutically effective amount," "therapeutic dose," "effective dose," or "effective dosage," as used herein, means an amount or a dose that achieves a therapeutic goal, as described herein. One of ordinary skill in the art will further understand that a therapeutically effective amount etc. can be administered in a single dose, or can be achieved by administration of multiple doses (i.e., 1, 2, 3, 4, 5, 6, 7, 8, 9, 10 or more doses). The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

A "subject" includes any human or non-human animal. The term "nonhuman animal" includes, but is not limited to, vertebrates such as nonhuman primates, sheep, dogs, and rodents such as mice, rats, and guinea pigs. In some embodiments, the subject is a human. The terms "subject" and "patient" are used interchangeably herein.

As used herein, the terms "ug" and "uM" are used interchangeably with "µg" and "µM," respectively.

The use of the alternative (e.g., "or") should be understood to mean either one, both, or any combination thereof of the alternatives. As used herein, the indefinite articles "a" or "an" should be understood to refer to "one or more" of any recited or enumerated component or entity.

Approximately or about: As used herein, the term "approximately" or "about," as applied to one or more values of interest, refers to a value that is similar to a stated reference value and within a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). When the term "approximately" or "about" is applied herein to a particular value, the value without the term "approximately" or "about" is also disclosed herein.

As described herein, any concentration range, percentage range, ratio range, or integer range is to be understood to include the value of any integer within the recited range and, when appropriate, fractions thereof (such as one tenth and one hundredth of an integer), unless otherwise indicated.

Various aspects of the disclosure are described in further detail in the following subsections.

Polynucleotides and Polypeptides

Miniaturized Dystrophin

The present disclosure is directed to a nucleic acid molecule comprising a nucleotide sequence, which encodes a miniaturized dystrophin polypeptide. In some embodiments, the miniaturized dystrophin polypeptide comprises at least three hinge domains of dystrophin and at least five Spectrin repeat domains.

Dystrophin is a rod-shaped cytoplasmic protein that connects the cytoskeleton of a muscle fiber to the surrounding extracellular matrix through the cell membrane. This protein is located primarily in muscles used for movement (skeletal muscles) and in heart (cardiac) muscle. Small amounts of dystrophin are present in nerve cells in the brain. In skeletal and cardiac muscles, dystrophin is part of a group of proteins (a protein complex) that work together to strengthen muscle fibers and protect them from injury as muscles contract and relax. The dystrophin complex acts as an anchor, connecting each muscle cell's structural framework (cytoskeleton) with the lattice of proteins and other molecules outside the cell (extracellular matrix). The dystrophin complex can also play a role in cell signaling by interacting with proteins that send and receive chemical signals.

The DMD gene, encoding the full length dystrophin protein, is one of the longest human genes known, covering 2.3 megabases (0.08% of the human genome) at locus Xp21. The primary transcript in muscle measures about 2,100 kilobases and takes 16 hours to transcribe; the mature mRNA measures 14.0 kilobases. The 79-exon muscle transcript codes for a protein of 3685 amino acid residues.

Disclosed herein are amino acid and nucleotide sequences for dystrophin. The amino acid sequence constituting human wild type dystrophin, isoform Dp427m, is known as UniProt identifier No. NP_003997.1 and shown in Table 1.

TABLE 1

Amino Acids sequence of full-length Dystrophin Protein (NP_003997.1).

SEQ ID NO: 1
MLWWEEVEDCYEREDVQKKTFTKWVNAQFSKFGKQHIENLFSDLQDGRRLL
DLLEGLTGQKLPKEKGSTRVHALNNVNKALRVLQNNNVDLVNIGSTDIVDG
NHKLTLGLIWNIILHWQVKNVMKNIMAGLQQTNSEKILLSWVRQSTRNYPQ
VNVINFTTSWSDGLALNALIHSHRPDLFDWNSVVCQQSATQRLEHAFNIAR
YQLGIEKLLDPEDVDTTYPDKKSILMYITSLFQVLPQQVSIEAIQEVEMLP
RPPKVTKEEHFQLHHQMHYSQQITVSLAQGYERTSSPKPRFKSYAYTQAAY
VTTSDPTRSPFPSQHLEAPEDKSFGSSLMESEVNLDRYQTALEEVLSWLLS
AEDTLQAQGEISNDVEVVKDQFHTHEGYMMDLTAHQGRVGNILQLGSKLIG
TGKLSEDEETEVQEQMNLLNSRWECLRVASMEKQSNLHRVLMDLQNQKLKE
LNDWLTKTEERTRKMEEEPLGPDLEDLKRQVQQHKVLQEDLEQEQVRVNSL
THMVVVVDESSGDHATAALEEQLKVLGDRWANICRWTEDRWVLLQDILLKW
QRLTEEQCLFSAWLSEKEDAVNKIHTTGFKDQNEMLSSLQKLAVLKADLEK
KKQSMGKLYSLKQDLLSTLKNKSVTQKTEAWLDNFARCWDNLVQKLEKSTA
QISQAVTTTQPSLTQTTVMETVTTVTTREQILVKHAQEELPPPPPQKKRQI
TVDSEIRKRLDVDITELHSWITRSEAVLQSPEFAIFRKEGNFSDLKEKVNA
IEREKAEKFRKLQDASRSAQALVEQMVNEGVNADSIKQASEQLNSRWIEFC
QLLSERLNWLEYQNNIIAFYNQLQQLEQMTTTAENWLKIQPTTPSEPTAIK
SQLKICKDEVNRLSGLQPQIERLKIQSIALKEKGQGPMFLDADFVAFTNHF
KQVFSDVQAREKELQTIFDTLPPMRYQETMSAIRTWVQQSETKLSIPQLSV
TDYEIMEQRLGELQALQSSLQEQQSGLYYLSTTVKEMSKKAPSEISRKYQS
EFEEIEGRWKKLSSQLVEHCQKLEEQMNKLRKIQNHIQTLKKWMAEVDVFL
KEEWPALGDSEILKKQLKQCRLLVSDIQTIQPSLNSVNEGGQKIKNEAEPE
FASRLETELKELNTQWDHMCQQVYARKEALKGGLEKTVSLQKDLSEMHEWM
TQAEEEYLERDFEYKTPDELQKAVEEMKRAKEEAQQKEAKVKLLTESVNSV
IAQAPPVAQEALKKELETLTTNYQWLCTRLNGKCKTLEEVWACWHELLSYL
EKANKWLNEVEFKLKTTENIPGGAEEISEVLDSLENLMRHSEDNPNQIRIL
AQTLTDGGVMDELINEELETFNSRWRELHEEAVRRQKLLEQSIQSAQETEK
SLHLIQESLTFIDKQLAAYIADKVDAAQMPQEAQKIQSDLTSHEISLEEMK
KHNQGKEAAQRVLSQIDVAQKKLQDVSMKFRLFQKPANFEQRLQESKMILD
EVKMHLPALETKSVEQEVVQSQLNHCVNLYKSLSEVKSEVEMVIKTGRQIV
QKKQTENPKELDERVTALKLHYNELGAKVTERKQQLEKCLKLSRKMRKEMN
VLTEWLAATDMELTKRSAVEGMPSNLDSEVAWGKATQKEIEKQKVHLKSIT
EVGEALKTVLGKKETLVEDKLSLLNSNWIAVTSRAEEWLNLLLEYQKHMET
FDQNVDHITKWIIQADTLLDESEKKKPQQKEDVLKRLKAELNDIRPKVDST
RDQAANLMANRGDHCRKLVEPQISELNHRFAAISHRIKTGKASIPLKELEQ
FNSDIQKLLEPLEAEIQQGVNLKEEDFNKDMNEDNEGTVKELLQRGDNLQQ
RITDERKREEIKIKQQLLQTKHNALKDLRSQRRKKALEISHQWYQYKRQAD
DLLKCLDDIEKKLASLPEPRDERKIKEIDRELQKKKEELNAVRRQAEGLSE
DGAAMAVEPTQIQLSKRWREIESKFAQFRRLNFAQIHTVREETMMVMTEDM
PLEISYVPSTYLTEITHVSQALLEVEQLLNAPDLCAKDFEDLFKQEESLKN
IKDSLQQSSGRIDIIHSKKTAALQSATPVERVKLQEALSQLDFQWEKVNKM
YKDRQGRFDRSVEKWRRFHYDIKIFNQWLTEAEQFLRKTQIPENWEHAKYK
WYLKELQDGIGQRQTVVRTLNATGEEIIQQSSKTDASILQEKLGSLNLRWQ
EVCKQLSDRKKRLEEQKNILSEFQRDLNEFVLWLEEADNIASIPLEPGKEQ
QLKEKLEQVKLLVEELPLRQGILKQLNETGGPVLVSAPISPEEQDKLENKL
KQTNLQWIKVSRALPEKQGEIEAQIKDLGQLEKKLEDLEEQLNHLLLWLSP
IRNQLEIYNQPNQEGPFDVQETEIAVQAKQPDVEEILSKGQHLYKEKPATQ
PVKRKLEDLSSEWKAVNRLLQELRAKQPDLAPGLTTIGASPTQTVTLVTQP
VVTKETAISKLEMPSSLMLEVPALADFNRAWTELTDWLSLLDQVIKSQRVM
VGDLEDINEMIIKQKATMQDLEQRRPQLEELITAAQNLKNKTSNQEARTII
TDRIERIQNQWDEVQEHLQNRRQQLNEMLKDSTQWLEAKEEAEQVLGQARA
KLESWKEGPYTVDAIQKKITETKQLAKDLRQWQTNVDVANDLALKLLRDYS
ADDTRKVHMITENINASWRSIHKRVSEREAALEETHRLLQQFPLDLEKFLA
WLTEAETTANVLQDATRKERLLEDSKGVKELMKQWQDLQGEIEAHTDVYHN
LDENSQKILRSLEGSDDAVLLQRRLDNMNFKWSELRKKSLNIRSHLEASSD
QWKRLHLSLQELLVWLQLKDDELSRQAPIGGDFPAVQKQNDVHRAFKRELK
TKEPVIMSTLETVRIFLTEQPLEGLEKLYQEPRELPPEERAQNVTRLLRKQ
AEEVNTEWEKLNLHSADWQRKIDETLERLQELQEATDELDLKLRQAEVIKG
SWQPVGDLLIDSLQDHLEKVKALRGEIAPLKENVSHVNDLARQLTTLGIQL
SPYNLSTLEDLNTRWKLLQVAVEDRVRQLHEAHRDFGPASQHFLSTSVQGP
WERAISPNKVPYYINHETQTTCWDHPKMTELYQSLADLNNVRFSAYRTAMK
LRRLQKALCLDLLSLSAACDALDQHNLKQNDQPMDILQIINCLTTIYDRLE
QEHNNLVNVPLCVDMCLNWLLNVYDTGRTGRIRVLSFKTGIISLCKAHLED
KYRYLFKQVASSTGFCDQRRLGLLLHDSIQIPRQLGEVASFGGSNIEPSVR
SCFQFANNKPEIEAALFLDWMRLEPQSMVWLPVLHRVAAAETAKHQAKCNI
CKECPIIGFRYRSLKHFNYDICQSCFFSGRVAKGHKMHYPMVEYCTPTTSG
EDVRDFAKVLKNKFRTKRYFAKHPRMGYLPVQTVLEGDNMETPVTLINFWP
VDSAPASSPQLSHDDTHSRIEHYASRLAEMENSNGSYLNDSISPNESIDDE
HLLIQHYCQSLNQDSPLSQPRSPAQILISLSESEERGELERILADLEEENRN
LQAEYDRLKQQHEHKGLSPLPSPPEMMPTSPQSPRDAELIAEAKLLRQHKG
RLEARMQILEDHNKQLESQLHRLRQLLEQPQAEAKVNGTTVSSPSTSLQRS
DSSQPMLLRVVGSQTSDSMGEEDLLSPPQDTSTGLEEVMEQLNNSFPSSRG
RNTPGKPMREDTM

Various other dystrophin isoforms are known in the art that result from alternative splicing. In some embodiments, the constructs comprise the nucleotide sequences recited in Table 2, or parts thereof.

Also disclosed herein is a nucleotide sequence encoding the full-length dystrophin protein.

TABLE 2

Nucleotide sequence of full-length Dystrophin Protein (isoform Dp427m).

```
SEQ ID NO: 2
GGGATTCCCTCACTTTCCCCCTACAGGACTCAGATCTGGGAGGCAATTACC
TTCGGAGAAAAACGAATAGGAAAAACTGAAGTGTTACTTTTTTTAAAGCTG
CTGAAGTTTGTTGGTTTCTCATTGTTTTTAAGCCTACTGGAGCAATAAAGT
TTGAAGAACTTTTACCAGGTTTTTTTTATCGCTGCCTTGATATACACTTTT
CAAAATGCTTTGGTGGGAAGAAGTAGAGGACTGTTATGAAAGAGAAGATGT
TCAAAAGAAAACATTCACAAAATGGGTAAATGCACAATTTTCTAAGTTTGG
GAAGCAGCATATTGAGAACCTCTTCAGTGACCTACAGGATGGGAGGCGCCT
CCTAGACCTCCTCGAAAGGCCTGACAGGGCAAAAACTGCCAAAAGAAAAAG
ATCCACAAGAGTTCATGCCCTGAACAATGTCAACAAGGCACTGCGGGTTTT
GCAGAACAATAATGTTGATTTAGTGAATATTGGAAGTACTGACATCGTAGA
TGGAAATCATAAACTGACTCTTGGTTTGATTTGGAATATAATCCTCCACTG
GCAGGTCAAAAATGTAATGAAAAATATCATGGCTGGATTGCAACAAACCAA
CAGTGAAAAGATTCTCCTGAGCTGGGTCCGACAATCAACTCGTAATTATCC
ACAGGTTAATGTAATCAACTTCACCACCAGCTGGTCTGATGGCCTGGCTTT
GAATGCTCTCATCCATAGTCATAGGCCAGACCTATTTGACTGGAATAGTGT
GGTTTGCCAGCAGTCAGCCACACAACGACTGGAACATGCATTCAACATCGC
CAGATATCAATTAGGCATAGAGAAACTACTCGATCCTGAAGATGTTGATAC
CACCTATCCAGATAAGAAGTCCATCTTAATGTACATCACATCACTCTTCCA
AGTTTTGCCTCAACAAGTGAGCATTGAAGCCATCCAGGAAGTGGAAATGTT
GCCAAGGCCACCTAAAGTGACTAAAGAAGAACATTTTCAGTTACATCATCA
AATGCACTATTCTCAACAGATCACGGTCAGTCTAGCACAGGGATATGAGAG
AACTTCTTCCCCTAAGCCTCGATTCAGAGCTATGCTCTACACACAGGCTGC
TTATGTCACCACCTCTGACCCTACACGGAGCCCATTTCCTTCACAGCATTT
GGAAGCTCCTGAAGACAAGTCATTTGGCAGTTCATTGATGGAGAGTGAAGT
AAACCTGGACCGTTATCAAACAGCTTTTAGAAGAAGTATTATCGTGGCTTCT
TTCTGCTGAGGACACATTGCAAGCACAAGGAGAGATTTCTAATGATGTGGA
AGTGGTGAAAGACCAGTTTCATACTCATGAGGGGTACATGATGGATTTGAC
AGCCCATCAGGGCCGGGTTGGTAATATTCTACAATTGGGAAGTAAGCTGAT
TGGAACAGGAAAATTATCAGAAGATGAAGAAACTGAAGTACAGAGCAGAT
GAATCTCCTAAATTCAAGATGGGAATGCCTCAGGGTAGCTAGCATGGAAAA
ACAAAGCAATTTACATAGAGTTTTAATGGATCTCCAGAATCAGAAACTGAA
AGAGTTGAATGACTGGCTAACAAAAACAGAAGAAAGAACAAGGAAAATGGA
GGAAGAGCCTCTTGGACCTGATCTTGAAGACCTAAAACGCCAAGTACAAC
ACATAAGGTGCTTCAAGGAAGACTAGAACAAGAACAAGTCAGGGTCAATTC
TCTCACTCACATGGTGGTGGTAGTTGATGAATCTAGTGGAGATCACGCAAC
TGCTGCTTTGGAAGAACAACTTAAGGTATTGGGAGATCGATGGGCAAACAT
CTGTAGATGGACAGAGACCGCTGGGTTCTTTTTACAAGACATCCTTCTCAA
ATGGCAACGTCTTACTGAAGAACAGTGCCTTTTTAGTGCATGGCTTTCAGA
AAAAGAAGATGCAGTGAACAAGATTCACACAACTGGCTTTAAAGATCAAAA
TGAAATGTTATCAAGTCTTCAAAAACTGGCCGTTTTAAAAGCGGATCTAGA
AAAGAAAAGCAATCCATGGGCAAACTGTATTCACTCAAACAAGATCTTCT
TTCAACACTGAAGAATAAGTCAGTGACCCAGAAGACGGAAGCATGGCTGGA
TAACTTTGCCCGGTGTTGGGATAATTTAGTCCAAAAACTTGAAAAGAGTAC
AGCACAGATTTCACAGGCTGTCACCACCACTCAGCCATCACTAACACAGAC
AACTGTAATGGAAACAGTAACTACGGTGACCACAAGGGAACAGATCCTGGT
AAAGCATGCTCAAGAGGAACTTCCACCACCACCTCCCCAAAAGAAGAGGCA
GATTACTGTGGATTCTGAAATTAGGAAAAGGTTGGATGTTGATATAACTGA
ACTTCACAGCTGGATTACTCGCTCAGAAGCTGTGTTGCAGAGTCCTGAATT
TGCAATCTTTCGGAAGGAAGGCAACTTCTCAGACTTAAAAGAAAAGTCAA
TGCCATAGAGCGAGAAAAAGCTGAGAAGTTCAGAAAACTGCAAGATGCCAG
CAGATCAGCTCAGGCCCTGGTGGAACAGATGGTGAATGAGGGTGTTAATGC
AGATAGCATCAAACAAGCCTCAGAACAACTGAACAGCCGGTGGATCGAATT
CTGCCAGTTGCTAAGTGAGAGACTTAACTGGCTGGAGTATCAGAACAACAT
CATCGCTTTCTATAATCAGCTACAACAATTTGGAGCAGATCAACTACTGC
TGAAAACTGGTTGAAAATCCAACCCACCACCCATCAGAGCCAACAGCAAT
TAAAAGTCAGTTAAAAATTTGTAAGGATGAAGTCAACCGGCTATCAGGTCT
TCAACCTCAAATTGAACGATTAAAAATTCAAAGCATAGCCCTGAAAGAGAA
AGGACAAGGACCCATGTTCCTGGATGCAGACTTTGTGGCCTTTACAAATCA
TTTTAAGCAAGTCTTTTCTGATGTGCAGGCCAGAGAGAAAGAGCTACAGAC
AATTTTTGACACTTTGCCACCAATGCGCTATCAGGAGACCATGAGTGCCAT
CAGGACATGGGTCCAGCAGTCAGAAACCAAACTCTCCATACCTCAACTTAG
TGTCACCGACTATGAAATCATGGAGCAGAGATCGGGGAATTGCAGGCTTT
ACAAAGTTCTCTGCAAGAGCACAAAAGTGGCCTATACTATCTCAGCACCAC
TGTGAAAGATGTCGAAGAAAGCGCCCTCTGAATTAGCCGGAAATATCA
ATCAGAATTTGAAGAAATTGAGGGACGCTGGAAGAAGCTCTCCTCCCAGCT
GGTTGAGCATTGTCAAAAGCTAGAGGAGCAAATGAATAAACTCCGAAAAAT
TCAGAATCACATACAAACCCTGAAGAAATGGATGGCTGAAGTTGATGTTTT
```

TABLE 2-continued

Nucleotide sequence of full-length Dystrophin Protein (isoform Dp427m).

```
TCTGAAGGAGGAATGGCCTGCCCTTGGGGATTCAGAAATTCTAAAAAAGCA
GCTGAAACAGTGCAGACTTTTAGTCAGTGATATTCAGACAATTCAGCCCAG
TCTAAACAGTGTCAATGAAGGTGGGCAGAAGATAAAGAATGAAGCAGAGCC
AGAGTTTGCTTCGAGACTTGAGACAGAACTCAAAGAACTTAACACTCAGTG
GGATCACATGTGCCAACAGGTCTATGCCAGAAAGGAGGCCTTGAAGGGAGG
TTTGGAGAAAACTGTAAGCCTCCAGAAAGATCTATCAGAGATGCACGAATG
GATGACACAAGCTGAAGAAGAGTATCTTGAGAGAGATTTTGAATATAAAAC
TCCAGATGAATTACAGAAAGCAGTTGAAGAGATGAAGAGAGCTAAAGAAGA
GGCCCAACAAAAAGAAGCGAAAGTGAAACTCCTTACTGAGTCTGTAAATAG
TGTCATAGCTCAAGCTCCACCTGTAGCACAAGAGGCCTTAAAAAAGGAACT
TGAAACTCTAACCACCAACTACCAGTGGCTCTGCACTAGGCTGAATGGGAA
ATGCAAGACTTTGGAAGAAGTTTGGGCATGTTGGCATGAGTTATTGTCATA
CTTGGAGAAAGCAAACAAGTGGCTAAATGAAGTAGAATTTAAACTTAAAAC
CACTGAAAACATTCCTGGCGGAGCTGAGGAAATCTCTGAGGTGCTAGATTC
ACTTGAAAATTTGATGCGACATTCAGAGGATAACCCAAATCAGATTCGCAT
ATTGGCACAGACCCTAACAGATGGCGGAGTCATGGATGAGCTAATCAATGA
GGAACTTGAGACATTTAATTCTCGTTGGAGGGAACTACATGAAGAGGCTGT
AAGGAGGCAAAAGTTGCTTGAACAGAGCATCCAGTCTGCCCAGGAGACTGA
AAAATCCTTACACTTAATCCAGGAGTCCCTCACATTCATTGACAAGCAGTT
GGCAGCTTATATTGCAGACAAGGTGGACGCAGCTCAAATGCCTCAGGAAGC
CCAGAAAATCCAATCTGATTTGACAAGTCATGAGATCAGTTTAGAAGAAAT
GAAGAAACATAATCAGGGGAGGAGGCTGCCCAAAGAGTCCTGTCTCAGAT
TGATGTTGACAGAAAAAATTACAAGATGCTCCATGAAGTTTCGATTATT
CCAGAAACCAGCCAATTTTGAGCAGCGTCTACAAGAAAGTAAGATGATTTT
AGATGAAGTGAAGATGCACTTGCCTGCATTGGAAACAAAGAGTGTGGAACA
GGAAGTAGTACAGTCACAGCTAAATCATTGTGTGAACTTGTATAAAAGTCT
GAGTGAAGTGAAGTCTGAAGTGGAAATGGTGATAAAGACTGGACGTCAGAT
TGTACAGAAAAAGCAGACGGAAAATCCCAAAGAACTTGATGAAAGAGTAAC
AGCTTTGAAATTGCATTATAATGAGCTGGGAGCAAAGGTAACAGAAAGAAA
GCAACAGTTGGAGAAATGCTTGAAATTGTCCCGTAAGATGCGAAAGGAAAT
GAATGTCTTGACAGAATGGCTGGCAGCTACAGATATGGAATTGACAAAGAG
ATCAGCAGTTGAAGGAATGCCTAGTAATTTGGATTCTGAAGTTGCCTGGGG
AAAGGCTACTCAAAAAGAGATTGAGAAACAGAAGGTGCACCTGAAGAGTAT
CACAGAGGTAGGAGAGGCCTTGAAAACAGTTTTGGGCAAGAAGGAGACGTT
GGTGGAAGATAAACTCAGTCTTCTGAATAGTAACTGGATAGCTGTCACCTC
CCGAGCAGAAGAGTGGTTAAATCTTTTGTTGGAATACCAGAAACACATGA
AACTTTTGACCAGAATGTGGACCACATCACAAAGTGGATCATTCAGGCTGA
CACACTTTTGGATGAATCAGAGAAAAAGAAACCCCAGCAAAAAGAAGACGT
GCTTAAGCGTTTAAAGGCAGAACTTGAATGACATACGCCCAAAGGTGACTC
TACACGTGACCAAGCAGCAAACTTGATGGCAAACCGCGGTGACCACTGCAG
GAAATTAGTAGAGCCCCAAATCTCAGAGCTCAACCATCGATTTGCAGCCAT
TTCACACAGAATTAAGACTGGAAAGGCCTCCATTCCTTTGAAGGAATTGGA
GCAGTTTAACTCAGATATACAAAAATTGCTTGAACCACTGGAGGCTGAAAT
TCAGCAGGGGGTGAATCTGAAAGAGGAAGACTTCAATAAAGATATGAATGA
AGACAATGAGGGTACTGTAAAAGAATTGTTGCAAAGAGGAGACAACTTACA
ACAAAGAATCACAGATGAGAGAAAGAGAGGAAATAAAGATAAAACAGCA
GCTGTTACAGAAAACATAATGCTCTCAAGGATTTGAGGTCTCAAAGAAG
AAAAAAGGCTCTAGAAATTTCTCATCAGTGGTATCAGTACAAGAGGCAGGC
TGATGATCTCCTGAAATGCTTGGATGACATTGAAAAAAAATTAGCCAGCCT
ACCTGAGCCCAGAGATGAAAGGAAATAAAGGAAATTGATCGGGAATTGCA
GAAGAAGAAAGAGGAGCTGAATGCAGTGCGTAGGCAAGCTGAAGGTCTGTC
TGAGGATGGGGCCGCAATGGCAGTGGAGCCAACTCAGATCCAGCTCAGCAA
GCGCTGGCGGGAAATTGAGAGCAAATTTGCTCAGTTTCGAAGACTCAACTT
TGCACAAATTCACACTGTCCGTGAAGAAACGATGATGGTGATGACTGAAGA
CATGCCTTTGGAAATTTCTTATGTGCCTTCTACTTATTTGACTGAAATCAC
TCATGTCTCACAAGCCCTATTAGAAGTGGAACAACTTCTCAATGCTCCTGA
CCTCTGTGCTAAGGACTTTGAAGATCTCTTTAAGCAAGAGGAGTCTCTGAA
GAATATAAAAGATAGTCTACAACAAAGCTCAGGTCGGATTGACATTATTCA
TAGCAAGAAGACAGCAGCATTGCAAAGTGCAACGCCTGTGGAAAGGGTGAA
GCTACAGGAAGCTCTCTCCAGCTTGATTTCCAATGGGAAAAAGTTAACAA
AATGTACAAGGACCGACAACAAGGGCGATTTGACAGATCTGTTGAGAATGGCG
GCGTTTTCATTATGATATAAAGATATTTAATCAGTGGCTAACAGAAGCTGA
ACAGTTTCTCAGAAAGACACAAATTCCTGAGAATTGGGAACATGCTAAATA
CAAATGGTATCTTAAGGAACTCCAGGATGGCATTGGGCAGCGGCAAACTGT
TGTCAGAACATTGAATGCAACTGGGGAAGAAATAATTCAGCAATCCTCAAA
AACAGATGCCAGTATTCTACAGGAAAAATTGGGAAGCCTGAATCTGCGGTG
GCAGGAGGTCTGCAAACAGCTGTCAGACAGAAAAAGAGGCTAGAAGAACA
AAAGAATATTCTTGTCAGAATTTCAAAGAGATTTAAATGAATTTGTTTTATG
GTTGGAGGAAGCAGATAACATTGCTAGTATCCCACTTGAACCTGGAAAAGA
GCAGCAACTAAAAGAAAAGCTTGAGCAAGTCAAGTTACTGGTGGAAGAGTT
GCCCCTGCGCCAGGGAATTCTCAAACAATTAAATGAAACTGGAGGACCCGT
GCTTGTAAGTGCTCCCATAAGCCCAGAAGGACAAGATAAACTTGAAAATAA
GCTCAAGCAGACAAATCTCCAGTGGATAAAGGTTTCCAGAGCTTTACCTGA
GAAACAAGGAGAAATTGAAGCTCAAATAAAAGACCTTGGGCAGCTTGAAAA
AAAGCTTGAAGACCTTGAAGAGCAGTTAAATCATCTGCTGCTGTGGTTATC
TCCTATTAGGAATCAGTTGGAAATTTATAACCAACCAAACCAAGAAGGACC
ATTTGACGTTCAGGAAACTGAAATAGCAGTTCAAGCTAAACAACCGGATGT
```

TABLE 2-continued

Nucleotide sequence of full-length Dystrophin Protein (isoform Dp427m).

```
GGAAGAGATTTTGTCTAAAGGGCAGCATTTGTACAAGGAAAAACCAGCCAC
TCAGCCAGTGAAGAGGAAGTTAGAAGATCTGAGCTCTGAGTGGAAGGCGGT
AAACCGTTTACTTCAAGAGCTGAGGGCAAAGCAGCCTGACCTAGCTCCTGG
ACTGACCACTATTGGAGCCTCTCCTACTCAGACTGTTACTCTGGTGACACA
ACCTGTGGTTACTAAGGAAACTGCCATCTCCAAACTAGAAATGCCATCTTC
CTTGATGTTGGAGGTACCTGCTCTGGCAGATTTCAACCGGGCTTGGACAGA
ACTTACCGACTGGCTTTCTCTGCTTGATCAAGTTATAAAATCACAGAGGGT
GATGGTGGGTGACCTTGAGGATATCAACGAGATGATCATCAAGCAGAAGGC
AACAATGCAGGATTTGGAACAGAGGCGTCCCCAGTTGGAAGAACTCATTAC
CGCTGCCCAAAATTTGAAAAACAAGACCAGCAATCAAGAGGCTAGAACAAT
CATTACGGATCGAATTGAAAGAATTCAGAATCAGTGGGATGAAGTACAAGA
ACACCTTCAGAACCGGAGGCAACAGTTGAATGAAATGTTAAAGGATTCAAC
ACAATGGCTGGAAGCTAAGGAAGAAGCTGAGCAGGTCTTAGGACAGGCCAG
AGCCAAGCTTGAGTCATGGAAGGAGGGTCCCTATACAGTAGATGCAATCCA
AAAGAAAATCACAGAAACCAAGCAGTTGGCCAAAGACCTCCGCCAGTGGCA
GACAAATGTAGATGTGGCAAATGACTTGGCCCTGAAACTTCTCCGGGATTA
TTCTGCAGATGATACCAGAAAAGTCCACATGATAACAGAGAATATCAATGC
CTCTTGGAGAAGCATTCATAAAAGGGTGAGTGAGCGAGAGGCTGCTTTGGA
AGAAACTCATAGATTACTGCAACAGTTCCCCCTGGACCTGGAAAAGTTTCT
TGCCTGGCTTACAGAAGCTGAAACAACTGCCAATGTCCTACAGGATGCTAC
CCGTAAGGAAAGGCTCCTAGAAGACTCCAAGGGAGTAAAAGAGCTGATGAA
ACAATGGCAAGACCTCCAAGGTGAAATTGAAGCTCACACAGATGTTTATCA
CAACCTGGATGAAAACAGCCAAAAAATCCTGAGATCCCTGGAAGGTTCCGA
TGATGCAGTCCTGTTACAAAGACGTTTGGATAACATGAACTTCAAGTGGAG
TGAACTTCGGAAAAAGTCTCTCAACATTAGGTCCCATTTGGAAGCCAGTTC
TGACCAGTGGAAGCGTCTGCACCTTTCTCTGCAGGAACTTCTGGTGTGGCT
ACAGCTGAAAGATGATGAATTAAGCCGGCAGGCACCTATTGGAGGCGACTT
TCCAGCAGTTCAGAAGCAGAACGATGTACATAGGGCCTTCAAGAGGGAATT
GAAAACTAAAGAACCTGTAATCATGAGTACTCTTGAGACTGTACGAATATT
TCTGACAGAGCAGCCTTTGGAAGGACTAGAGAAACTCTACCAGGAGCCCAG
AGAGCTGCCTCCTGAGGAGAGAGCCCAGAATGTCACTCGGCTTCTACGAAA
GCAGGCTGAGGAGGTCAATACTGAGTGGGAAAAATTGAACCTGCACTCCGC
TGACTGGCAGAGAAAAATAGATGAGACCCTTGAAAGACTCCAGGAACTTCA
AGAGGCCACGGATGAGCTGGACCTCAAGCTGCGCCAAGCTGAGGTGATCAA
GGGATCCTGGCAGCCCGTGGGCGATCTCCTCATTGACTCTCTCCAAGATCA
CCTCGAGAAAGTCAAGGCACTTCGAGGAGAAATTGCGCCTCTGAAAGAGAA
CGTGAGCCACGTCAATGACCTTGCTCGCCAGCTTACCACTTTGGGCATTCA
GCTCTCACCGTATAACCTCAGCACTCTGGAAGACCTGAACACCAGATGGAA
GCTTCTGCAGGTGGCCGTCGAGGACCGAGTCAGGCAGCTGCATGAAGCCCA
CAGGGACTTTGGTCCAGCATCTCAGCACTTTCTTTCCACGTCTGTCCAGGG
TCCCTGGGAGAGAGCCATCTCGCCAAACAAAGTGCCCTACTATATCAACCA
CGAGACTCAAACAACTTGCTGGGACCATCCCAAAATGACAGAGCTCTACCA
GTCTTTAGCTGACCTGAATAATGTCAGATTCTCAGCTTATAGGACTGCCAT
GAAACTCCGAAGACTGCAGAAGGCCCTTTGCTTGGATCTCTTGAGCCTGTC
AGCTGCATGTGATGCCTTGGACCAGCACAACCTCAAGCAAAATGACCAGCC
CATGGATATCCTGCAGATTATTAATTGTTTGACCACTATTTATGACCGCCT
GGAGCAAGAGCACAACAATTTGGTCAACGTCCCTCTCTGCGTGGATATGTG
TCTGAACTGGCTGCTGAATGTTTATGATACGGGACGAACAGGGAGGATCCG
TGTCCTGTCTTTTAAAACTGGCATCATTTCCCTGTGTAAAGCACATTTGGA
AGACAAGTACAGATACCTTTTCAAGCAAGTGGCAAGTTCAACAGGATTTTG
TGACCAGCGCAGGCTGGGCCTCCTTCTGCATGATTCTATCCAAATTCCAAG
ACAGTTGGGTGAAGTTGCATCCTTTGGGGGCAGTAACATTGAGCCAAGTGT
CCGGAGCTGCTTCCAATTTGCTAATAATAAGCCAGAGATCGAAGCGGCCCT
CTTCCTAGACTGGATGAGACTGGAACCCCAGTCCATGGTGTGGCTGCCCGT
CCTGCACAGAGTGGCTGCTGCAGAAACTGCCAAGCATCAGGCCAATGTAA
CATCTGCAAAGAGTGTCCAATCATTGGATTCAGGTACAGGAGTCTAAAGCA
CTTTAATTATGACATCTGCCAAAGCTGCTTTTTTCTGGTCGAGTTGCAAA
AGGCCATAAAATGCACTATCCCATGGTGGAATATTGCACTCCGACTACATC
AGGAGAAGATGTTCGAGACTTTGCCAAGGTACTAAAAAACAAATTTCGAAC
CAAAAGGTATTTTGCGAAGCATCCCCGAATGGGCTACCTGCCAGTGCAGA
TGTCTTAGAGGGGGACAACATGGAAACTCCCGTTACTCTGATCAACTTCTG
GCCAGTAGATTCTGCGCCTGCCTCGTCCCCTCAGCTTTCACACGATGATAC
TCATTCACGCATTGAACATTATGCTAGCAGGCTAGCAGAAATGGAAACAG
CAATGGATCTTATCTAAATGATAGCATCTCTCCTAATGAGAGCATAGATGA
TGAACATTTGTTAATCCAGCATTACTGCCAAAGTTTGAACCAGGACTCCCC
CCTGAGCCAGCCTCGTAGTCCTGCCCAGATCTTGATTTCCTTAGAGAGTGA
GGAAAGAGGGGAGCTAGAGAGAATCCTAGCAGATCTTGAGGAAGAAAACAG
GAATCTGCAAGCAGAATATGACCGTCTAAAGCAGCAGCACGAACATAAAGG
CCTGTCCCCACTGCCGTCCCCTCCTGAAATGATGCCCACCTCTCCCCAGAG
TCCCCGGGATGCTGAGCTCATTGCTGAGGCCAAGCTACTGCGTCAACACAA
AGGCCGCCTGGAAGCCAGGATGCAAATCCTGGAAGACCACAATAAACAGCT
GGAGTCACAGTTACACAGGCTAAGGCAGCTGGGTGAGCAACCCCAGGCAGA
GGCCAAAGTGAATGGCACAACGGTGTCCTCTCCTTCTACCTCTCTACAGAG
GTCCGACAGCAGTCAGCCTATGCTGCTCCGAGTGGTTGGCAGTCAAACTTC
GGACTCCATGGGTGAGGAAGATCTTCTCAGTCCTCCCCAGGACACAAGCAC
AGGGTTAGAGGAGGTGATGGAGCAACTCAACAACTCCTTCCCTAGTTCAAG
AGGAAGAAATACCCCTGGAAAGCCAATGAGAGAGGACACAATGTAGGAAGT
CTTTTCCACATGGCAGATGATTTGGGCAGAGCGATGGAGTCCTTAGTATCA
GTCATGACAGATGAAGAAGGAGCAGAATAAATGTTTTACAACTCCTGATTC
CCGCATGGTTTTTATAATATTCATACAACAAAGAGGATTAGACAGTAAGAG
TTTACAAGAAATAAATCTATATTTTTGTGAAGGGTAGTGGTATTATACTGT
AGATTTCAGTAGTTTCTAAGTCTGTTATTGTTTTGTTAACAATGGCAGGTT
TTACACGTCTATGCAATTGTACAAAAAAGTTATAAGAAAACTACATGTAAA
ATCTTGATAGCTAAATAACTTGCCATTTCTTTATATGGAACGCATTTTGGG
TTGTTTAAAAATTTATAACAGTTATAAAGAAAGATTGTAAACTAAAGTGTG
CTTTATAAAAAAAGTTGTTTATAAAAACCCCTAAAAACAAAACAAACACA
CACACACACACATACACACACACACACAAAACTTTGAGGCAGCGCATTGTT
TTGCATCCTTTTGGCGTGATATCCATATGAAATTCATGGCTTTTTCTTTTT
TTGCATATTAAAGATAAGACTTCCTCTACCACCACACCCAAATGACTACTAC
ACACTGCTCATTTGAGAACTGTCAGCTGAGTGGGGCAGGCTTGAGTTTTCA
TTTCATATATCTATATGTCTATAAGTATATAAATACTATAGTTATATAGAT
AAAGAGATACGAATTTCTATAGACTGACTTTTTCCATTTTTTAAATGTTCA
TGTCACATCCTAATAGAAAGAAATTACTTCTAGTCAGTCATCCAGGCTTAC
CTGCTTGGTCTAGAATGGATTTTTCCCGGAGCCGGAAGCCAGGAGGAAACT
ACACCACACTAAAACATTGTCTACAGCTCCAGATGTTTCTCATTTTAAACA
ACTTTCCACTGACAACGAAAGTAAAGTAAAGTATTGGATTTTTTAAAGGG
AACATGTGAATGAATACACAGGACTTATTATATCAGAGTGAGTAATCGGTT
GGTTGGTTGATTGATTGATTGATTGATACATTCAGCTTCCTGCTGCTAGCA
ATGCCACGATTTAGATTTAATGATGCTTCAGTGGAAATCAATCAGAAGGTA
TTCTGACCTTGTGAACATCAGAAGGTATTTTTAACTCCCAAGCAGTAGCA
GGACGATGATAGGGCTGGAGGGCTATGGATTCCCAGCCCATCCCTGTGAAG
GAGTAGGCCACTCTTTAAGTGAAGGATTGGATGATTGTTCATAATACATAA
AGTTCTCTGTAATTACAACTAAATTATTATGCCCTCTTCTCACAGTCAAAA
GGAACTGGGTGGTTTGGTTTTTGTTGCTTTTTAGATTTATTGTCCCATGT
GGGATGAGTTTTTAAATGCCACAAGACATAATTTAAAATAAATAAACTTTG
GGAAAAGGTGTAAGACAGTAGCCCCATCACATTTGTGATACTGACAGGTAT
CAACCCAGAAGCCCATGAACTGTGTTTCCATCCTTTGCATTTCTCTGCGAG
TAGTTCCACACAGGTTTGTAAGTAAGTAAGAAAGAAGGCAAATTGATTCAA
ATGTTACAAAAAAACCCTTCTTGGTGGATTAGACAGGTTAAATATATAAAC
AAACAAACAAAAATTGCTCAAAAAAGAGGAGAAAAGCTCAAGAGGAAAAGC
TAAGGACTGGTAGGAAAAAGCTTTACTCTTTCATGCCATTTTATTTCTTTT
TGATTTTTAAATCATTCATTCAATAGATACCACCGTGTGACCTATAATTTT
GCAAATCTGTTACCTCTGACATCAAGTGTAATTAGCTTTTGGAGAGTGGGC
TGACATCAAGTGTAATTAGCTTTTGGAGAGTGGGTTTTGTCCATTATTAAT
AATTAATTAATTAACATCAAACACGGCTTCTCATGCTATTTCTACCTCACT
TTGGTTTTGGGGTGTTCCTGATAATTGTGCACACCTGAGTTCACAGCTTCA
CCACTTGTCCATTGCGTTATTTCTTTTTCCTTTATAATTCTTTCTTTTTC
CTTCATAATTTTCAAAAGAAAACCCAAAGCTCTAAGGTAACAAATTACCAA
ATTACATGAAGATTTGGTTTTTGTCTTGCATTTTTTTCCTTTATGTGACGC
TGGACCTTTTCTTTACCCAAGGATTTTTAAAACTCAGATTTAAAACAAGGG
GTTACTTTACATCCTACTAAGAAGTTTAAGTAAGTAAGTTTCATTCTAAAA
TCAGAGGTAAATAGAGTGCATAAATAATTTTGTTTTAATCTTTTTGTTTTT
CTTTTAGACACATTAGCTCTGGAGTGGAGTCTGTCATAATATTTGAACAAAA
ATTGAGAGCTTTATTGCTGCATTTTAAGCATAATTAATTTGGACATTATTT
CGTGTTGTGTTCTTTATAACCACCGAGTATTAAACTGTAAATCATAATGTA
ACTGAAGCATAAACATCACATGGCATGTTTTGTCATTGTTTTCAGGTACTG
AGTTCTTACTTGAGTATCATAATATATTGTGTTTAACACCAACACTGTAA
CATTTACGAATTATTTTTTAAACTTCAGTTTTACTGCATTTTCACAACAT
ATCAGACTTCACCAAATATATGCCTTACTATTGTATTATAGTACTGCTTTA
CTGTGTATCTCAATAAAGCACGCAGTTATGTTAC
```

The wild type, full length dystrophin protein (isoform Dp427m) contains 24 spectrin like repeats, at least four hinge regions, actin binding domain (ABD1), Cysteine rich domain (CR), and C terminal Domain (C-term.). The polypeptide sequence of each domain is shown in Table 3, and the nucleotide sequence of each domain is shown in Table 4.

TABLE 3

Amino Acid Sequences of Dystrophin Domains

| Description and Sequence Identifier | Sequence |
|---|---|
| ABD1 (SEQ ID NO: 3) | MLWWEEVEDCYEREDVQKKTFTKWVNAQFSKFGKQHIENLFSDLQDG RRLLDLLEGLTGQKLPKEKGSTRVHALNNVNKALRVLQNNNVDLVNIG STDIVDGNHKLTLGLIWNIILHWQVKNVMKNIMAGLQQTNSEKIL LSWVRQSTRNYPQVNVINFTTSWSDGLALNALIHSHRPDLFDWNSVVC QQSATQRLEHAFNIARYQLGIEKLLDPEDVDTTYPDKKSILMYITSLFQV LPQQVSIEAIQEVE |
| Hinge 1 (SEQ ID NO: 4) | MLPRPPKVTKEEHFQLHHQMHYSQQITVSLAQGYERTSSPKPRFKSYAY TQAAYVTTSDPTRSPFPSQHLEAPEDKSFGSSLMES |
| Spectrin repeat 1 (SEQ ID NO: 5) | EVNLDRYQTALEEVLSWLLSAEDTLQAQGEISNDVEVVKDQFHTHEGY MMDLTAHQGRVGNILQLGSKLIGTGKLSEDEETEVQEQMNLLNSRWEC LRVASMEKQSNLH |
| Spectrin repeat 2 (SEQ ID NO: 6) | RVLMDLQNQKLKELNDWLTKTEERTRKMEEEPLGPDLEDLKRQVQQH KVLQEDLEQEQVRVNSLTHMVVVVDESSGDHATAALEEQLKVLGDRW ANICRWTEDRWVLLQDI |
| Spectrin repeat 3 (SEQ ID NO: 7) | LLKWQRLTEEQCLFSAWLSEKEDAVNKIHTTGFKDQNEMLSSLQKLAV LKADLEKKKQSMGKLYSLKQDLLSTLKNKSVTQKTEAWLDNFARCWD NLVQKLEKSTAQISQA |
| Hinge 2 (SEQ ID NO: 8) | VTTTQPSLTQTTVMETVTTVTTREQILVKHAQEELPPPPPQKKRQITVD |
| Spectrin repeat 4 (SEQ ID NO: 9) | SEIRKRLDVDITELHSWITRSEAVLQSPEFAIFRKEGNFSDLKEKVNAIER EKAEKFRKLQDASRSAQALVEQMVNEGVNADSIKQASEQLNSRWIEFC QLLSERLNWLEY |
| Spectrin repeat 5 (SEQ ID NO: 10) | QNNIIAFYNQLQQLEQMTTTAENWLKIQPTTPSEPTAIKSQLKICKDEVN RLSGLQPQIERLKIQSIALKEKGQGPMFLDADFVAFTNHFKQVFSDVQA REKELQTIFD |
| Spectrin repeat 6 (SEQ ID NO: 11) | TLPPMRYQETMSAIRTWVQQSETKLSIPQLSVTDYEIMEQRLGELQALQ SSLQEQQSGLYYLSTTVKEMSKKAPSEISRKYQSEFEEIEGRWKKLSSQL VEHCQKLEEQ |
| Spectrin repeat 7 (SEQ ID NO: 12) | MNKLRKIQNHIQTLKKWMAEVDVFLKEEWPALGDSEILKKQLKQCRLL VSDIQTIQPSLNSVNEGGQKIKNEAEPEFASRLETELKELNTQWDHMCQ QVYARKEALKGG |
| Spectrin repeat 8 (SEQ ID NO: 13) | LEKTVSLQKDLSEMHEWMTQAEEEYLERDFEYKTPDELQKAVEEMKR AKEEAQQKEAKVKLLTESVNSVIAQAPPVAQEALKKELETLTTNYQWL CTRLNGKCKTLEEV |
| Spectrin repeat 9 (SEQ ID NO: 14) | WACWHELLSYLEKANKWLNEVEFKLKTTENIPGGAEEISEVLDSLENL MRHSEDNPNQIRILAQTLTDGGVMDELINEELETFNSRWRELHEEAVRR QKLLEQS |
| Spectrin repeat 10 (SEQ ID NO: 15) | IQSAQETEKSLHLIQESLTFIDKQLAAYIADKVDAAQMPQEAQKIQSDLT SHEISLEEMKKHNQGKEAAQRVLSQIDVAQKKLQDVSMKFRL |
| Spectrin repeat 11 (SEQ ID NO: 16) | FQKPANFEQRLQESKMILDEVKMHLPALETKSVEQEVVQSQLNHCVNL YKSLSEVKSEVEMVIKTGRQIVQKKQTENPKELDERVTALKLHYNELG AKVTERKQQLEKC |
| Spectrin repeat 12 (SEQ ID NO: 17) | LKLSRKMRKEMNVLTEWLAATDMELTKRSAVEGMPSNLDSEVAWGK ATQKEIEKQKVHLKSITEVGEALKTVLGKKETLVEDKLSLLNSNWIAVT SRAEEWLNLLLEY |
| Spectrin repeat 13 (SEQ ID NO: 18) | QKHMETFDQNVDHITKWIIQADTLLDESEKKKPQQKEDVLKRLKAELN DIRPKVDSTRDQAANLMANRGDHCRKLVEPQISELNHRFAAISHRIKTG KASIPLK |
| Spectrin repeat 14 (SEQ ID NO: 19) | ELEQFNSDIQKLLEPLEAEIQQGVNLKEEDFNKDMNEDNEGTVKELLQR GDNLQQRITDERKREEIKIKQQLLQTKHNALKDLRSQRRKKALEI |

TABLE 3-continued

Amino Acid Sequences of Dystrophin Domains

| Description and Sequence Identifier | Sequence |
|---|---|
| Spectrin repeat 15 (SEQ ID NO: 20) | SHQWYQYKRQADDLLKCLDDIEKKLASLPEPRDERKIKEIDRELQKKKE ELNAVRRQAEGLSEDGAAMAVEPTQIQLSKRWREIESKFAQFRRLNFA Q |
| L3 (20-mer linker) (SEQ ID NO: 21) | IHTVREETMMVMTEDMPLEI |
| Spectrin repeat 16 (SEQ ID NO: 22) | SYVPSTYLTEITHVSQALLEVEQLLNAPDLCAKDFEDLFKQEESLKNIKD SLQQSSGRIDIIHSKKTAALQSATPVERVKLQEALSQLDFQWEKVNKMY KDRQGRFDRS |
| Spectrin repeat 17 (SEQ ID NO: 23) | VEKWRRFHYDIKIFNQWLTEAEQFLRKTQIPENWEHAKYKWYLKELQ DGIGQRQTVVRTLNATGEEIIQQSSKTDASILQEKLGSLNLRWQEVCKQ LSDRKKRLEEQ |
| Spectrin repeat 18 (SEQ ID NO: 24) | KNILSEFQRDLNEFVLWLEEADNIASIPLEPGKEQQLKEKLEQVKLLVEE LPLRQGILKQLNETGGPVLVSAPISPEEQDKLENKLKQTNLQWIKVSRA LPEKQGEIEAQIKDLGQL |
| Spectrin repeat 19 (SEQ ID NO: 25) | EKKLEDLEEQLNHLLLWLSPIRNQLEIYNQPNQEGPFDVQETEIAVQAK QPDVEEILSKGQHLYKEKPATQPVKRKLEDLSSEWKAVNRLLQELRAK QPDL |
| Hinge 3 (SEQ ID NO: 26) | APGLTTIGASPTQTVTLVTQPVVTKETAISKLEMPSSLMLE |
| Spectrin repeat 20 (SEQ ID NO: 27) | VPALADFNRAWTELTDWLSLLDQVIKSQRVMVGDLEDINEMIIKQKAT MQDLEQRRPQLEELITAAQNLKNKTSNQEARTIITDRIERIQNQWDEVQ EHLQNRRQQLNEM |
| Spectrin repeat 21 (SEQ ID NO: 28) | LKDSTQWLEAKEEAEQVLGQARAKLESWKEGPYTVDAIQKKITETKQL AKDLRQWQTNVDVANDLALKLLRDYSADDTRKVHMITENINASWRSI HKRVSEREAALEET |
| Spectrin repeat 22 (SEQ ID NO: 29) | HRLLQQFPLDLEKFLAWLTEAETTANVLQDATRKERLLEDSKGVKELM KQWQDLQGEIEAHTDVYHNLDENSQKILRSLEGSDDAVLLQRRLDNM NFKWSELRKKSLNIRSHLEAS |
| Spectrin repeat 23 (SEQ ID NO: 30) | SDQWKRLHLSLQELLVWLQLKDDELSRQAPIGGDFPAVQKQNDVHRA FKRELKTKEPVIMSTLETVRIFLTEQPLEGLEKLYQEPRELPPEERAQNV TRLLRKQAEEVNTEWEKLNLHSADWQRKIDET |
| Spectrin repeat 24 (SEQ ID NO: 31) | LERLQELQEATDELDLKLRQAEVIKGSWQPVGDLLIDSLQDHLEKVKA LRGEIAPLKENVSHVNDLARQLTTLGIQLSPYNLSTLEDLNTRWKLLQV AVEDRVRQLHE |
| Hinge 4 (SEQ ID NO: 32) | AHRDFGPASQHFLSTSVQGPWERAISPNKVPYYINHETQTTCWDHPKM TELYQSLADLNNVRFSAYRTAMKL |
| CR (SEQ ID NO: 33) | RRLQKALCLDLLSLSAACDALDQHNLKQNDQPMDILQIINCLTTIYDRL EQEHNNLVNVPLCVDMCLNWLLNVYDTGRTGRIRVLSFKTGIISLCKA HLEDKYRYLFKQVASSTGFCDQRRLGLLLHDSIQIPRQLGEVASFGGSNI EPSVRSCFQFANNKPEIEAALFLDWMRLEPQSMVWLPVLHRVAAAETA KHQAKCNICKECPIIGFRYRSLKHFNYDICQSCFFSGRVAKGHKMHYPM VEYCTPTTSGEDVRDFAKVLKNKFRTKRYFAKHPRMGYLPVQTVLEGD NMET |
| C-term (SEQ ID NO: 34) | PVTLINFWPVDSAPASSPQLSHDDTHSRIEHYASRLAEMENSNGSYLND SISPNESIDDEHLLIQHYCQSLNQDSPLSQPRSPAQILISLESE- ERGELERIL |

TABLE 3-continued

Amino Acid Sequences of Dystrophin Domains

| Description and Sequence Identifier | Sequence |
|---|---|
| | ADLEEENRNLQAEYDRLKQQHEHKGLSPLPSPPEMMPTSPQSPRDAELI<br>AEAKLLRQHKGRLEARMQILEDHNKQLESQLHRLRQLLEQPQAEAKVN<br>GTTVSSPSTSLQRSDSSQPMLLRVVGSQTSDSMGEEDLLSPPQDTSTGLE<br>EVMEQLNNSFPSSRGRNTPGKPMREDTM |

TABLE 4

Nucleotide Sequences Encoding Dystrophin Domains

| Description and Sequence Identifier | Sequence |
|---|---|
| 5' untranslated region (SEQ ID NO: 35) | gggattccct cactttcccc ctacaggact cagatctggg aggcaattac cttcggagaa 60<br>aaacgaatag gaaaaactga agtgttactt ttttaaagc tgctgaagtt tgttggtttc 120<br>tcattgtttt taagcctact ggagcaataa agtttgaaga acttttacca ggttttttt 180<br>atcgctgcct tgatatacac ttttcaaa 208 |
| ABD1 (SEQ ID NO: 36) | atgctttggt gggaagaagt agaggactgt tatgaaagag aagatgttca aaagaaaaca 60<br>ttcacaaaat gggtaaatgc acaattttct aagtttggga agcagcatat tgagaacctc 120<br>ttcagtgacc tacaggatgg gaggcgcctc ctagacctcc tcgaaggcct gacagggcaa 180<br>aaactgccaa agaaaaagg atccacaaga gttcatgccc tgaacaatgt caacaaggca 240<br>ctgcgggttt tgcagaacaa taatgttgat ttagtgaata ttggaagtac tgacatcgta 300<br>gatggaaatc ataaactgac tcttggtttg atttggaata taatcctcca ctggcaggtc 360<br>aaaaatgtaa tgaaaatat catggctgga ttgcaacaaa ccaacagtga aaagattctc 420<br>ctgagctggg tccgacaatc aactcgtaat tatccacagg ttaatgtaat caacttcacc 480<br>accagctggt ctgatggcct ggctttgaat gctctcatcc atagtcatag gccagaccta 540<br>tttgactgga atagtgtggt ttgccagcag tcagccacac aacgactgga acatgcattc 600<br>aacatcgcca gatatcaatt aggcatagag aaaactactcg atcctgaaga tgttgatacc 660<br>acctatccag ataagaagtc catcttaatg tacatcacat cactcttcca agttttgcct 720<br>caacaagtga gcattgaagc catccaggaa gtggaa 756 |
| Hinge 1 (SEQ ID NO: 37) | atgttgccaa ggccacctaa agtgactaaa aagaacatt ttcagttaca tcatcaaatg 60<br>cactattctc aacagatcac ggtcagtcta gcacagggat atgagagaac ttcttcccct 120<br>aagcctcgat tcaagagcta tgcctacaca caggctgctt atgtcaccac ctctgaccct 180<br>acacggagcc catttccttc acagcatttg gaagctcctg aagacaagtc atttggcagt 240<br>tcattgatgg agagt 255 |
| Spectrin repeat 1 (SEQ ID NO: 38) | gaagtaaacc tggaccgtta tcaaacagct ttagaagaag tattatcgtg gcttctttct 60<br>gctgaggaca cattgcaagc acaaggagag atttctaatg atgtggaagt ggtgaaagac 120<br>cagtttcata ctcatgaggg gtacatgatg gatttgcag cccatcaggg ccgggttggt 180<br>aatattctac aattgggaag taagctgatt ggaacaggaa aattatcaga agatgaagaa 240<br>actgaagtac aagagcagat gaatctccta aattcaagat gggaatgcct cagggtagct 300<br>agcatggaaa aacaaagcaa tttacat 327 |
| Spectrin repeat 2 (SEQ ID NO: 39) | agagttttaa tggatctcca gaatcagaaa ctgaaagagt tgaatgactg gctaacaaaa 60<br>acagaagaaa gaacaaggaa aatgggagga gagcctcttg gacctgatct tgaagaccta 120<br>aaacgccaag tacaacaaca taaggtgctt caagaagatc tagaacaaga acaagtcagg 180<br>gtcaattctc tcactcacat ggtggtggta gttgatgaat ctagtggaga tcacgcaact 240<br>gctgctttgg aagaacaact taaggtattg ggagatcgat gggcaaacat ctgtagatgg 300<br>acagaagacc gctgggttct tttacaagac atc 333 |
| Spectrin repeat 3 (SEQ ID NO: 40) | cttctcaaat ggcaacgtct tactgaagaa cagtgccttt ttagtgcatg gctttcagaa 60<br>aaagaagatg cagtgaacaa gattcacaca actggcttta agatcaaaa tgaaatgtta 120<br>tcaagtcttc aaaaactggc cgttttaaaa gcggatcag aaaagaaaaa gcaatccatg 180<br>ggcaaactgt attcactcaa acaagatctt ctttcaacac tgaagaataa gtcagtgacc 240<br>cagaagacgg aagcatggct ggataacttt gcccggtgtt gggataattt agtccaaaaa 300<br>cttgaaaaga gtacagcaca gatttcacag gct 333 |
| Hinge 2 (SEQ ID NO: 41) | gtcaccacca ctcagccatc actaacacag acaactgtaa tggaaacagt aactacggtg 60<br>accacaaggg aacagatcct ggtaaagcat gctcaagagg aacttccacc accacctccc 120<br>caaaagaaga ggcagattac tgtggat 147 |
| Spectrin repeat 4 (SEQ ID NO: 42) | tctgaaatta ggaaaaggtt ggatgttgat ataactgaac ttcacagctg gattactcgc 60<br>tcagaagctg tgttcagag tcctgaattt gcaatctttc ggaaggaagg caacttctca 120<br>gacttaaaag aaaaagtcaa tgccataggc cgagaaaaag ctgaaaactg 180<br>caagatgcca gcagatcagc tcaggccctg gtgaacaga tggtgaatga gggtgttaat 240<br>gcagatagca tcaaacaagc ctcagaacaa ctgaacagcc ggtggatcga attctgccag 300<br>ttgctaagtg agagacttaa ctggctggag tat 333 |

TABLE 4-continued

Nucleotide Sequences Encoding Dystrophin Domains

| Description and Sequence Identifier | Sequence |
|---|---|
| Spectrin repeat 5 (SEQ ID NO: 43) | cagaacaaca tcatcgcttt ctataatcag ctacaacaat tggagcagat gacaactact 60<br>gctgaaaact ggttgaaaat ccaacccacc accccatcag agccaacagc aattaaaagt 120<br>cagttaaaaa tttgtaagga tgaagtcaac cggctatcag gtcttcaacc tcaaattgaa 180<br>cgattaaaaa ttcaaagcat agccctgaaa gagaaaggac aaggacccat gttcctggat 240<br>gcagactttg tggcctttac aaatcatttt aagcaagtct tttctgatgt gcaggccaga 300<br>gagaaagagc tacagacaat ttttgac 327 |
| Spectrin repeat 6 (SEQ ID NO: 44) | actttgccac caatgcgcta tcaggagacc atgagtgcca tcaggacatg ggtccagcag 60<br>tcagaaacca aactctccat acctcaactt agtgtcaccg actatgaaat catggagcag 120<br>agactcgggg aattgcaggc tttacaaagt tctctgcaag agcaacaaag tggcctatac 180<br>tatctcagca ccactgtgaa agagatgtcg aagaaagcgc cctctgaaat tagccggaaa 240<br>tatcaatcag aatttgaaga aattgaggga cgctggaaga agctctcctc ccagctggtt 300<br>gagcattgtc aaaagctaga ggagcaa 327 |
| Spectrin repeat 7 (SEQ ID NO: 45) | atgaataaac tccgaaaaat tcagaatcac atacaaaccc tgaagaaatg gatggctgaa 60<br>gttgatgttt ttctgaagga ggaatggcct gcccttgggg attcagaaat tctaaaaaag 120<br>cagctgaaac agtgcagact tttagtcagt gatattcaga caattcagcc cagtctaaac 180<br>agtgtcaatg aaggtgggca gaagataaag aatgaagcag agccagagtt tgcttcgaga 240<br>cttgagacag aactcaaaga acttaacact cagtgggatc acatgtgcca acaggtctat 300<br>gccagaaagg aggccttgaa gggaggt 327 |
| Spectrin repeat 8 (SEQ ID NO: 46) | ttggagaaaa ctgtaagcct ccagaaagat ctatcagaga tgcacgaatg gatgacacaa 60<br>gctgaagaag agtatcttga gagagatttt gaatataaaa ctccagatga attacagaaa 120<br>gcagttgaag agatgaagag agctaaagaa gaggcccaac aaaaagaagc gaaagtgaaa 180<br>ctccttactg agtctgtaaa tagtgtcata gctcaagctc cacctgtagc caagaggcc 240<br>ttaaaaaagg aacttgaaac tctaaccacc aactaccagt ggctctgcac taggctgaat 300<br>gggaaatgca agactttgga agaagtt 327 |
| Spectrin repeat 9 (SEQ ID NO: 47) | tgggcatgtt ggcatgagtt attgtcatac ttggagaaag caaacaagtg gctaaatgaa 60<br>gtagaattta aacttaaaac cactgaaaac attcctggcg gagctgagga atctctgag 120<br>gtgctagatt cacttgaaaa tttgatgcga cattcagagg ataacccaaa tcagattcgc 180<br>atattggcac agacccctaac agatggcgga gtcatggatg agctaatcaa tgaggaactt 240<br>gagacattta attctcgttg gagggaacta catgaagagg ctgtaaggag gcaaaagttg 300<br>cttgaacaga gc 312 |
| Spectrin repeat 10 (SEQ ID NO: 48) | atccagtctg cccaggagac tgaaaaatcc ttacacttaa tccaggagtc cctcacattc 60<br>attgacaagc agttggcagc ttatattgca gacaaggtgg acgcagctca aatgcctcag 120<br>gaagcccaga aaatccaatc tgatttgaca agtcatgaga tcagtttaga agaaatgaag 180<br>aaacataatc aggggaagga ggctgcccaa agagtcctgt ctcagattga tgttgcacag 240<br>aaaaaattac aagatgtctc catgaagttt cgatta 276 |
| Spectrin repeat 11 (SEQ ID NO: 49) | ttccagaaac cagccaattt tgagcagcgt ctacaagaaa gtaagatgat tttagatgaa 60<br>gtgaagatgc acttgcctgc attggaaaca aagagtgtag aacaggaagt agtacagtca 120<br>cagctaaatc attgtgtgaa cttgtataaa agtctgagtg aagtgaagtc tgaagtggaa 180<br>atggtgatga agactggacg tcagattgta cagaaaaagc agacggaaaa tcccaaagaa 240<br>cttgatgaaa gagtaacagc tttgaaattg cattataatg agctgggagc aaaggtaaca 300<br>gaaagaaagc aacagttgga gaaatgc 327 |
| Spectrin repeat 12 (SEQ ID NO: 50) | ttgaaattgt cccgtaagat gcgaaaggaa atgaatgtct tgacagaatg gctggcagct 60<br>acagatatgg aattgacaaa gagatcagca gttgaaggaa tgcctagtaa tttggattct 120<br>gaagttgcct ggggaaaggc tactcaaaaa gagattgaga acagaaggt gcacctgaag 180<br>agtatcacag aggtaggaga ggccttgaaa acagttttgg gcaagaagga cgttggtg 240<br>gaagataaac tcagtcttct gaatagtaac tggatagctg tcacctcccg agcagaagag 300<br>tggttaaatc ttttgttgga atac 324 |
| Spectrin repeat 13 (SEQ ID NO: 51) | cagaaacaca tggaaacttt tgaccagaat gtggaccaca tcacaaagtg gatcattcag 60<br>gctgacacac ttttggatga atcagaaaa aagaaacccc agcaaaaaga gacgtgctt 120<br>aagcgtttaa aggcagaact gaatgacata cgcccaaagg tggactctac acgtgaccaa 180<br>gcagcaaact tgatggcaaa ccgcggtgac cactgcagga attagtaga gccccaaatc 240<br>tcagagctca accatcgatt tgcagccatt tcacacagaa ttaagactgg aaaggcctcc 300<br>attcctttga ag 312 |
| Spectrin repeat 14 (SEQ ID NO: 52) | gaattggagc agtttaactc agatatacaa aaattgcttg aaccactgga ggctgaaatt 60<br>cagcagggg tgaatctgaa gaggaagga ttcaataaag atatgaatga agcaatgag 120<br>ggtactgtaa aagaattgtt gcaagagga gacaacttac aacaaagaat cacagatgag 180<br>agaaagagag aggaaataaa gataaaacag cagctgttac agacaaaaca taatgctctc 240<br>aaggatttga ggtctcaaag aagaaaaag gctctagaaa tt 282 |
| Spectrin repeat 15 (SEQ ID NO: 53) | tctcatcagt ggtatcagta caagaggcag gctgatgatc tcctgaaatg cttggatgac 60<br>attgaaaaaa aattagccag cctacctgag cccagagatg aaaggaaat aaaggaaatt 120<br>gatcgggaat tgcagaagaa gaaagaggag ctgaatgcag tgcgtaggca agctgagggc 180<br>ttgtctgagg atgggccgc aatggcagtg gagccaactc agatccagct cagcaagcgc 240<br>tggcgggaaa ttgagagcaa atttgctcag tttcgaagac tcaactttgc acaa 294 |

TABLE 4-continued

Nucleotide Sequences Encoding Dystrophin Domains

| Description and Sequence Identifier | Sequence |
|---|---|
| L3 (20-mer linker) (SEQ ID NO: 54) | attcacactg tccgtgaaga aacgatgatg gtgatgactg aagacatgcc tttggaaatt 60 |
| Spectrin repeat 16 (SEQ ID NO: 55) | tcttatgtgc cttctactta tttgactgaa atcactcatg tctcacaagc cctattagaa 60<br>gtggaacaac ttctcaatgc tcctgacctc tgtgctaagg actttgaaga tctctcttaag 120<br>caagaggagt ctctgaagaa tataaaagat agtctacaac aaagctcagg tcggattgac 180<br>attattcata gcaagaagac agcagcattg caaagtgcaa cgcctgtgga aagggtgaag 240<br>ctacaggaag ctctctccca gcttgatttc caatgggaaa aagttaacaa aatgtacaag 300<br>gaccgacaag ggcgatttga cagatct 327 |
| Spectrin repeat 17 (SEQ ID NO: 56) | gttgagaaat ggcggcgttt tcattatgat ataaagatat ttaatcagtg gctaacagaa 60<br>gctgaacagt ttctcagaaa gacacaaatt cctgagaatt gggaactagc taaatacaaa 120<br>tggtatctta aggaactcca ggatggcatt gggcagcggc aaactgttgt cagaacattg 180<br>aatgcaactg gggaagaaat aattcagcaa tcctcaaaaa cagatgccag tattctacag 240<br>gaaaaattgg gaagcctgaa tctgcggtgg caggaggtct gcaaacagct gtcagacaga 300<br>aaaaagaggc tagaagaaca a 321 |
| Spectrin repeat 18 (SEQ ID NO: 57) | aagaatatct tgtcagaatt tcaaagagat ttaaatgaat ttgttttatg gttggaggaa 60<br>gcagataaca ttgctagtat cccacttgaa cctggaaaag agcagcaact aaaagaaaag 120<br>cttgagcaag tcaagttact ggtggaagaa ttgcccctgc gcagggaat tctcaaacaa 180<br>ttaaatgaaa ctggaggacc cgtgcttgta agtgctccca agcccaga agagcaagat 240<br>aaacttgaaa ataagctcaa gcagacaaat ctccagtgga taaaggtttc cagagcttta 300<br>cctgagaaac aaggagaaat tgaagctcaa ataaaagacc ttgggcagct t 351 |
| Spectrin repeat 19 (SEQ ID NO: 58) | gaaaaaaagc ttgaagacct tgaagagcag ttaaatcatc tgctgctgtg gttatctcct 60<br>attaggaatc agttggaaat ttataaccaa ccaaaccaag aaggaccatt tgacgttcag 120<br>gaaactgaaa tagcagttca agctaaacaa ccggatgtgg aagagatttt gtctaaaggg 180<br>cagcatttgt acaaggaaaa accagccact cagccagtga agaggaagtt agaagatctg 240<br>agctctgagt ggaaggcggt aaaccgttta cttcaagagc tgagggcaaa gcagcctgac 300<br>cta 303 |
| Hinge 3 (SEQ ID NO: 59) | gctcctggac tgaccactat ggagcctct cctactcaga ctgttactct ggtgacacaa 60<br>cctgtggtta ctaaggaaac tgccatctcc aaactagaaa tgccatcttc cttgatgttg 120<br>gag 123 |
| Spectrin repeat 20 (SEQ ID NO: 60) | gtacctgctc tggcagattt caaccgggct tggacagaac ttaccgactg gctttctctg 60<br>cttgatcaag ttataaaatc acagagggtg atggtgggtg accttgagga tatcaacgag 120<br>atgatcatca gcagaaggc aacaatgcag gatttggaac agaggcgtcc ccagttcgaa 180<br>gaactcatta ccgctgccca aatttgaaa aacaagacca gcaatcaaga ggctagaaca 240<br>atcattacgg atcgaattga aagaattcag aatcagtggg atgaagtaca agaacacctt 300<br>cagaaccgga ggcaacagtt gaatgaaatg 330 |
| Spectrin repeat 21 (SEQ ID NO: 61) | ttaaaggatt caacacaatg gctggaagct aaggaagaag ctgagcaggt cttaggacag 60<br>gccagagcca agcttgagtc atggaaggag ggtccctata cagtagatgc aatccaaaag 120<br>aaaatcacag aaaccaagca gttggcaaa gacctccgcc agtggcagac aaatgtagat 180<br>gtggcaaatg acttggccct gaaacttctc cgggattatt ctgcagatga taccagaaaa 240<br>gtccacatga taacagagaa tatcaatgcc tcttggagaa gcattcataa aaggtgagt 300<br>gagcgagagg ctgctttgga agaaact 327 |
| Spectrin repeat 22 (SEQ ID NO: 62) | catagattac tgcaacagtt cccctggac ctggaaaagt ttcttgcctg gcttacagaa 60<br>gctgaaacaa ctgccaatgt cctacaggat gctacccgta aggaaaggcc cctagaagac 120<br>tccaagggag taaaagagct gatgaaacaa tggcaagacc tccaaggtga aattgaagct 180<br>cacacagatg tttatcacaa cctggatgaa aacagccaaa aaatcctgag atccctggaa 240<br>ggttccgatg atgcagtcct gttacaaaga cgtttggata acatgaactt caagtggagt 300<br>gaacttcgga aaaagtctct caacattagg tcccatttgg aagccagt 348 |
| Spectrin repeat 23 (SEQ ID NO: 63) | tctgaccagt ggaagcgtct gcacctttct ctgcaggaac ttctggtgtg gctacagctg 60<br>aaagatgatg aattaagccg gcaggcacct acttcgaagg acttcagag agttcagaag 120<br>cagaacgatg tacataggc cttcaagagg gaattgaaaa ctaaagaacc tgtaatcatg 180<br>agtactcttg agactgtacg aatatttctg acagagcagc ctttggaagg actagagaaa 240<br>ctctaccagg agcccagaga gctgcctcct gaggagagag cccagaatgt cactcggctt 300<br>ctacgaaagc aggctgagga ggtcaatact gagtgggaaa aattgaacct gcactccgct 360<br>gactggcaga gaaaaataga tgagacc 387 |
| Spectrin repeat 24 (SEQ ID NO:64) | cttgaaagac tccaggaact tcaagaggcc acggatgagc tggacctcaa gctgcgccaa 60<br>gctgaggtga tcaagggatc ctggcagccc gtggcagatc tcctcattga tctctccaa 120<br>gatcacctcg agaaagtcaa ggcacttcga ggagaaattg gcctctacaa agaacctgtg 180<br>agccacgtca atgaccttgc tcgccagctt accactttgg gcattcagct ctcaccgtat 240<br>aacctcagca ctctggaaga cctgaacacc agatggaagc ttctgcaggt ggccgtcgag 300<br>gaccgagtca ggcagctgca tgaa 324 |

TABLE 4-continued

Nucleotide Sequences Encoding Dystrophin Domains

| Description and Sequence Identifier | Sequence | | | | | |
|---|---|---|---|---|---|---|
| Hinge 4 (SEQ ID NO: 65) | gcccacaggg | actttggtcc | agcatctcag | cactttcttt | ccacgtctgt | ccagggtccc 60 |
| | tgggagagag | ccatctcgcc | aaacaaagtg | ccctactata | tcaaccacga | gactcaaaca 120 |
| | acttgctggg | accatcccaa | aatgacagag | ctctaccagt | ctttagctga | cctgaataat 180 |
| | gtcagattct | cagcttatag | gactgccatg | aaactc 216 | | |
| CR (SEQ ID NO: 66) | cgaagactgc | agaaggccct | ttgcttggat | ctcttgagcc | tgtcagctgc | atgtgatgcc 60 |
| | ttggaccagc | acaacctcaa | gcaaaatgac | cagcccatgg | atatcctgca | gattattaat 120 |
| | tgtttgacca | ctatttatga | ccgcctggag | caagagcaca | acaatttggt | caacgtccct 180 |
| | ctctgcgtgg | atatgtgtct | gaactggctg | ctgaatgttt | atgatacggg | acgaacaggg 240 |
| | aggatccgtg | tcctgtcttt | taaaactggc | atcatttccc | tgtgtaaagc | acatttggaa 300 |
| | gacaagtaca | gatacctttt | caagcaagtg | gcaagttcaa | caggattttg | tgaccagcgc 360 |
| | aggctgggcc | tccttctgca | tgattctatc | caaattccaa | gacagttggg | tgaagttgca 420 |
| | tcctttgggg | gcagtaacat | tgagccaagt | gtccggagct | gcttccaatt | tgctaataat 480 |
| | aagccagaga | tcgaagcggc | cctcttccta | gactggatga | gactggaacc | ccagtccatg 540 |
| | gtgtggctgc | ccgtcctgca | cagagtggct | gctgcagaaa | ctgccaagca | tcaggccaaa 600 |
| | tgtaacatct | gcaaagagtg | tccaatcatt | ggattcaggt | acaggagtct | aaagcacttt 660 |
| | aattatgaca | tctgccaaag | ctgctttttt | tctggtcgag | ttgcaaaagg | ccataaaatg 720 |
| | cactatccca | tggtggaata | ttgcactccg | actacatcgg | gagaagatgt | tcgagacttt 780 |
| | gccaaggtac | taaaaaacaa | atttcgaacc | aaaaggtatt | ttgcgaagca | tccccgaatg 840 |
| | ggctacctgc | cagtgcagac | tgtcttagag | ggggacaaca | tggaaact | |
| C-term (SEQ ID NO: 67) | cccgttactc | tgatcaactt | ctggccagta | gattctgcgc | ctgcctcgtc | ccctcagctt 60 |
| | tcacacgatg | atactcattc | acgcattgaa | cattatgcta | gcaggctagc | agaaatgaa 120 |
| | aacagcaatg | gatcttatct | aaatgatagc | atctctccta | atgagagcat | agatgatgaa 180 |
| | catttgttaa | tccagcatta | ctgccaaagt | ttgaaccagg | actccccct | gagccagcct 240 |
| | cgtagtcctg | cccagatctt | gatttcctta | gagagtgagg | aaagagggga | gctagagaga 300 |
| | atcctagcag | atcttgagga | agaaaacagg | aatctgcaag | cagaatatga | ccgtctaaag 360 |
| | cagcagcacg | aacataaagg | cctgtcccca | ctgccgtccc | ctcctgaaat | gatgcccacc 420 |
| | tctccccaga | gtccccggga | tgctgagctc | attgctgagg | ccaagctact | gcgtcaacac 480 |
| | aaaggccgcc | tggaagccag | gatgcaaatc | ctggaagacc | acaataaaca | gctggagtca 540 |
| | cagttacaca | ggctaaggca | gctgctggag | caaccccagg | cagaggccaa | agtgaatggc 600 |
| | acaacggtgt | cctctccttc | tacctctcta | cagaggtccg | acagcagtca | gcctatgctg 660 |
| | ctccgagtgg | ttggcagtca | aacttcggac | tccatgggtg | aggaagatct | tctcagtcct 720 |
| | ccccaggaca | caagcacagg | gttagaggag | gtgatggagc | aactcaacaa | ctccttccct 780 |
| | agttcaagag | gaagaaatac | ccctggaaag | ccaatgagag | aggacacaat | gtag |

The present disclosure is directed to a miniaturized dystrophin polypeptide that is smaller than the full-length dystrophin protein, i.e., isoform Dp427m, and that is not identical to the naturally occurring dystrophin protein isoforms, or a nucleic acid molecule comprising a nucleotide sequence encoding the miniaturized dystrophin polypeptide. When the present disclosure discloses miniaturized dystrophin polypeptides, the present disclosure also discloses nucleic acid molecule comprising a nucleotide sequence encoding the corresponding disclosed miniaturized dystrophin polypeptide, and vice versa. In some embodiments, the nucleic acid molecule encoding the miniaturized dystrophin polypeptide is suitable for gene therapy. Accordingly, the nucleic acid molecule encoding the miniaturized dystrophin polypeptide is constructed not only to fit into a gene therapy vector, e.g., AAV vector, or to be suitable for recombinant expression, but also to reduce any unwanted immune response (e.g., humoral immune response and/or cellular immune response, e.g., CD4 and/or CD8) against the miniaturized dystrophin polypeptide when administered or expressed in vivo.

In some embodiments, the miniaturized dystrophin polypeptide of the present disclosure comprises a junction N-terminal to a unmodified or modified spectrin repeat 16 (R16) domain that varies from the wild-type junction. In some embodiments, the miniaturized dystrophin polypeptide of the present disclosure comprises a modified spectrin repeat 16 (R16) domain, wherein a part of spectrin repeat 16 (R16) domain is replaced by a corresponding part of a different spectrin repeat domain. In some embodiments, the different spectrin repeat domain is spectrin repeat 2 (R2) domain. In some embodiments, the modified R16 domain comprises an amino acid sequence at least about 80%, at least about 85%, at least about 90%, at least about 95%, at least about 96%, at least about 97%, at least about 98%, at least about 99%, or about 100% identical to a sequence selected from the group consisting of SEQ ID NO: 68, 69, 70, 71 and 72. The term junction J4 (or J4 junction), as used herein, refers to the peptide sequence surrounding the junction between spectrin repeat 1 (R1) domain and spectrin repeat 16 (R16) domain. The variants of junction J4 disclosed herein, i.e., J4V4, J4V11, J4V12 and J4V13, are J4 junctions in which, to different degrees, the N-terminal part of spectrin repeat 16 (R16) domain has been replaced by certain N-terminal parts of spectrin repeat 2 (R2).

TABLE 5

Partial amino acid sequence of modified R16 domains/Junction J4 Variants.

| SEQ ID NO: | Description | Sequence |
|---|---|---|
| 68 | Modified Spectrin-16 (junction J4V13) | MDLQNQKLTEITHVSQ |

TABLE 5-continued

Partial amino acid sequence of modified R16 domains/Junction J4 Variants.

| SEQ ID NO: | Description | Sequence |
|---|---|---|
| 69 | Modified Spectrin-16 (junction J4V12) | LMDLQNQKTEITHVSQ |
| 70 | Modified Spectrin-16 (junction J4V11) | LMDLQNQKEITHVSQA |
| 71 | Modified Spectrin-16 (junction J4V4) | LHRVLMDLTYLTEITH |
| 72 | Modified Spectrin-16 (junction J4) | MEKQSNLHSYVPSTYL |

In some embodiments, the miniaturized dystrophin polypeptide comprises from N terminus to C terminus a hinge 1 (H1) domain, a spectrin repeat 1 (R1) domain, the modified R16 domain, a spectrin repeat 17 (R17) domain, a hinge 3 (H3) domain, a spectrin repeat 23 (R23) domain, a spectrin repeat 24 (R24) domain, and a hinge 4 (H4) domain of dystrophin. In some embodiments, (i) the H1 domain and the R1 domain are fused directly, (ii) the R1 domain and the modified R16 domain are fused directly, (iii) the modified R16 domain and the R17 domain are fused directly, (iv) the R17 domain and the H3 domain are fused directly, (v) the H3 domain and the R23 domain are fused directly, (vi) the R23 domain and the R24 domain are fused directly, or (vii) the R24 domain and the H4 domain are fused directly, or (vii) any combination thereof. In some embodiments, the miniaturized dystrophin polypeptide does not comprise a spectrin repeat 2 (R2) domain, spectrin repeat 3 (R3) domain, spectrin repeat 4 (R4) domain, spectrin repeat 5 (R5) domain, spectrin repeat 6 (R6) domain, spectrin repeat 7 (R7) domain, spectrin repeat 8 (R8) domain, spectrin repeat 9 (R9) domain, spectrin repeat 10 (R10) domain, spectrin repeat 11 (R11) domain, spectrin repeat 12 (R12) domain, spectrin repeat 13 (R13) domain, spectrin repeat 14 (R14) domain, spectrin repeat 15 (R15) domain, spectrin repeat 18 (R18) domain, spectrin repeat 19 (R19) domain, spectrin repeat 20 (R20) domain, spectrin repeat 21 (R21) domain, and/or spectrin repeat 22 (R22) domain. In some embodiments, the miniaturized dystrophin polypeptide further comprises an ABD1 domain and/or a CR domain. In some embodiments, the miniaturized dystrophin polypeptide consists essentially of or consists of, from N terminus to C terminus, the ABD1 domain, the H1 domain, the R1 domain, the modified R16 domain, the R17 domain, the H3 domain, the R23 domain, the R24 domain, the H4 domain, and the CR domain of dystrophin.

Each domain in the miniaturized dystrophin polypeptides can have one or more changes from the corresponding wild-type domain.

For example, the miniaturized dystrophin BXA-212372-J4V13 (BXA-220931) consists of the following protein domains in order:

TABLE 6

Amino acid sequence and domain structure of miniaturized dystrophin polypeptide BXA-212372-J4V13 (BXA-220931).

| SEQ ID NO: | Description | Sequence |
|---|---|---|
| 73 | ABD1 | MLWWEEVEDCYEREDVQKKTFTKWVNAQFSKFGKQHIEN LFSDLQDGRRLLDLLEGLTGQKLPKEKGSTRVHALNNVNK ALRVLQNNNVDLVNIGSTDIVDGNHKLTLGLIWNIILHWQV KNVMKNIMAGLQQTNSEKILLSWVRQSTRNYPQVNVINFT TSWSDGLALNALIHSHRPDLFDWNSVVCQQSATQRLEHAF NIARYQLGIEKLLDPEDVDTTYPDKKSILMYITSLFQVLPQQ VSIEAIQEVE |
| 74 | Hinge 1 | MLPRPPKVTKEEHFQLHHQMHYSQQITVSLAQGYERTSSP KPRFKSYAYTQAAYVTTSDPTRSPFPSQHLEAPEDKSFGSSL MES |
| 75 | Spectrin-1 | EVNLDRYQTALEEVLSWLLSAEDTLQAQGEISNDVEVVKD QFHTHEGYMMDLTAHQGRVGNILQLGSKLIGTGKLSEDEE TEVQEQMNLLNSRWECLRVASMEKQSNLH |
| 76 | Modified Spectrin-16 | RVLMDLQNQKLTEITHVSQALLEVEQLLNAPDLCAKDFED LFKQEESLKNIKDSLQQSSGRIDIIHSKKTAALQSATPVERV KLQEALSQLDFQWEKVNKMYKDRQGRFDRS |
| 77 | Spectrin-17 | VEKWRRFHYDIKIFNQWLTEAEQFLRKTQIPENWEHAKYK WYLKELQDGIGQRQTVVRTLNATGEEIIQQSSKTDASILQE KLGSLNLRWQEVCKQLSDRKKRLEEQ |
| 78 | Hinge 3 | APGLTTIGASPTQTVTLVTQPVVTKETAISKLEMPSSLMLE |
| 79 | Spectrin-23 | SDQWKRLHLSLQELLVWLQLKDDELSRQAPIGGDFPAVQK QNDVHRAFKRELKTKEPVIMSTLETVRIFLTEQPLEGLEKL YQEPRELPPEERAQNVTRLLRKQAEEVNTEWEKLNLHSAD WQRKIDET |

TABLE 6-continued

Amino acid sequence and domain structure of miniaturized dystrophin polypeptide BXA-212372-J4V13 (BXA-220931).

| SEQ ID NO: | Description | Sequence |
|---|---|---|
| 80 | Spectrin-24 | LERLQELQEATDELDLKLRQAEVIKGSWQPVGDLLIDSLQD HLEKVKALRGEIAPLKENVSHVNDLARQLTTLGIQLSPYNL STLEDLNTRWKLLQVAVEDRVRQLHE |
| 81 | Hinge 4 | AHRDFGPASQHFLSTSVQGPWERAISPNKVPYYINHETQTT CWDHPKMTELYQSLADLNNVRFSAYRTAMKL |
| 82 | CR | RRLQKALCLDLLSLSAACDALDQHNLKQNDQPMDILQIINC LTTIYDRLEQEHNNLVNVPLCVDMCLNWLLNVYDTGRTG RIRVLSFKTGIISLCKAHLEDKYRYLFKQVASSTGFCDQRRL GLLLHDSIQIPRQLGEVASFGGSNIEPSVRSCFQFANNKPEIE AALFLDWMRLEPQSMVWLPVLHRVAAAETAKHQAKCNIC KECPIIGFRYRSLKHFNYDICQSCFFSGRVAKGHKMHYPMV EYCTPTTSGEDVRDFAKVLKNKFRTKRYFAKHPRMGYLPV QTVLEGDNMET |

In some embodiments, the H1 domain is an amino acid sequence at least about 80%, at least about 85%, at least about 90%, at least about 95%, at least about 96%, at least about 97%, at least about 98%, at least about 99%, or about 100% identical to SEQ ID NO: 74. In some embodiments, the R1 domain is an amino acid sequence at least about 80%, at least about 85%, at least about 90%, at least about 95%, at least about 96%, at least about 97%, at least about 98%, at least about 99%, or about 100% identical to SEQ ID NO: 75. In some embodiments, the modified R16 domain is an amino acid sequence at least about 80%, at least about 85%, at least about 90%, at least about 95%, at least about 96%, at least about 97%, at least about 98%, at least about 99%, or about 100% identical to SEQ ID NO: 76. In some embodiments, the R17 domain is an amino acid sequence at least about 80%, at least about 85%, at least about 90%, at least about 95%, at least about 96%, at least about 97%, at least about 98%, at least about 99%, or about 100% identical to SEQ ID NO: 77. In some embodiments, the H3 domain is an amino acid sequence at least about 80%, at least about 85%, at least about 90%, at least about 95%, at least about 96%, at least about 97%, at least about 98%, at least about 99%, or about 100% identical to SEQ ID NO: 78. In some embodiments, the R23 domain is an amino acid sequence at least about 80%, at least about 85%, at least about 90%, at least about 95%, at least about 96%, at least about 97%, at least about 98%, at least about 99%, or about 100% identical to SEQ ID NO: 79. In some embodiments, the R24 domain is an amino acid sequence at least about 80%, at least about 85%, at least about 90%, at least about 95%, at least about 96%, at least about 97%, at least about 98%, at least about 99%, or about 100% identical to SEQ ID NO: 80. In some embodiments, the H4 domain is an amino acid sequence at least about 80%, at least about 85%, at least about 90%, at least about 95%, at least about 96%, at least about 97%, at least about 98%, at least about 99%, or about 100% identical to SEQ ID NO: 81. In some embodiments, the miniaturized dystrophin polypeptide further comprises at the N terminus an amino acid sequence at least about 80%, at least about 85%, at least about 90%, at least about 95%, at least about 96%, at least about 97%, at least about 98%, at least about 99%, or about 100% identical to SEQ ID NO: 73. In some embodiments, the miniaturized dystrophin polypeptide further comprises at the C terminus an amino acid sequence at least about 80%, at least about 85%, at least about 90%, at least about 95%, at least about 96%, at least about 97%, at least about 98%, at least about 99%, or about 100% identical to SEQ ID NO: 82.

The various miniaturized dystrophin polypeptides of the present disclosure are shown in Table 7.

TABLE 7

Amino Acid Sequences of miniaturized dystrophin constructs.

| SEQ ID NO and Description | Sequence |
|---|---|
| SEQ ID NO: 83 BXA-212372-J4V13 (BXA-220931) | MLWWEEVEDCYEREDVQKKTFTKWVNAQFSKFGKQHIENLFSDLQDG RRLLDLLEGLTGQKLPKEKGSTRVHALNNVNKALRVLQNNNVDLVNIG STDIVDGNHKLTLGLIWNIILHWQVKNVMKNIMAGLQQTNSEKILLSWV RQSTRNYPQVNVINFTTSWSDGLALNALIHSHRPDLFDWNSVVCQQSAT QRLEHAFNIARYQLGIEKLLDPEDVDTTYPDKKSILMYITSLFQVLPQQV SIEAIQEVEMLPRPPKVTKEEHFQLHHQMHYSQQITVSLAQGYERTSSPK PRFKSYAYTQAAYVTTSDPTRSPFPSQHLEAPEDKSFGSSLMESEVNLDR YQTALEEVLSWLLSAEDTLQAQGEISNDVEVVKDQFHTHEGYMMDLTA HQGRVGNILQLGSKLIGTGKLSEDEETEVQEQMNLLNSRWECLRVASM EKQSNLHRVLMDLQNQKLTEITHVSQALLEVEQLLNAPDLCAKDFEDLF KQEESLKNIKDSLQQSSGRIDIIHSKKTAALQSATPVERVKLQEALSQLDF QWEKVNKMYKDRQGRFDRSVEKWRRFHYDIKIFNQWLTEAEQFLRKT QIPENWEHAKYKWYLKELQDGIGQRQTVVRTLNATGEEIIQQSSKTDAS ILQEKLGSLNLRWQEVCKQLSDRKKRLEEQAPGLTTIGASPTQTVTLVT QPVVTKETAISKLEMPSSLMLESDQWKRLHLSLQELLVWLQLKDDELSR QAPIGGDFPAVQKQNDVHRAFKRELKTKEPVIMSTLETVRIFLTEQPLEG |

TABLE 7-continued

Amino Acid Sequences of miniaturized dystrophin constructs.

| SEQ ID NO and Description | Sequence |
|---|---|
| | LEKLYQEPRELPPEERAQNVTRLLRKQAEEVNTEWEKLNLHSADWQRK<br>IDETLERLQELQEATDELDLKLRQAEVIKGSWQPVGDLLIDSLQDHLEKV<br>KALRGEIAPLKENVSHVNDLARQLTTLGIQLSPYNLSTLEDLNTRWKLL<br>QVAVEDRVRQLHEAHRDFGPASQHFLSTSVQGPWERAISPNKVPYYINH<br>ETQTTCWDHPKMTELYQSLADLNNVRFSAYRTAMKLRRLQKALCDLL<br>SLSAACDALDQHNLKQNDQPMDILQIINCLTTIYDRLEQEHNNLVNVPL<br>CVDMCLNWLLNVYDTGRTGRIRVLSFKTGIISLCKAHLEDKYRYLFKQV<br>ASSTGFCDQRRLGLLLHDSIQIPRQLGEVASFGGSNIEPSVRSCFQFANNK<br>PEIEAALFLDWMRLEPQSMVWLPVLHRVAAAETAKHQAKCNICKECPII<br>GFRYRSLKHFNYDICQSCFFSGRVAKGHKMHYPMVEYCTPTTSGEDVR<br>DFAKVLKNKFRTKRYFAKHPRMGYLPVQTVLEGDNMET |
| SEQ ID NO: 84 - BXA-212372-J4V12 | MLWWEEVEDCYEREDVQKKTFTKWVNAQFSKFGKQHIENLFSDLQDG<br>RRLLDLLEGLTGQKLPKEKGSTRVHALNNVNKALRVLQNNNVDLVNIG<br>STDIVDGNHKLTLGLIWNIILHWQVKNVMKNIMAGLQQTNSEKILLSWV<br>RQSTRNYPQVNVINFTTSWSDGLALNALIHSHRPDLFDWNSVVCQQSAT<br>QRLEHAFNIARYQLGIEKLLDPEDVDTTYPDKKSILMYITSLFQVLPQQV<br>SIEAIQEVEMLPRPPKVTKEEHFQLHHQMHYSQQITVSLAQGYERTSSPK<br>PRFKSYAYTQAAYVTTSDPTRSPFPSQHLEAPEDKSFGSSLMESEVNLDR<br>YQTALEEVLSWLLSAEDTLQAQGEISNDVEVVKDQFHTHEGYMMDLTA<br>HQGRVGNILQLGSKLIGTKLSEDEETEVQEQMNLLNSRWECLRVASM<br>EKQSNLHRVLMDLQNQKTEITHVSQALLEVEQLLNAPDLCAKDFEDLFK<br>QEESLKNIKDSLQQSSGRIDIIHSKKTAALQSATPVERVKLQEALSQLDFQ<br>WEKVNKMYKDRQGRFDRSVEKWRRFHYDIKIFNQWLTEAEQFLRKTQI<br>PENWEHAKYKWYLKELQDGIGQRQTVVRTLNATGEEIIQQSSKTDASIL<br>QEKLGSLNLRWQEVCKQLSDRKKRLEEQAPGLTTIGASPTQTVTLVTQP<br>VVTKETAISKLEMPSSLMLESDQWKRLHLSLQELLVWLQLKDDELSRQ<br>APIGGDFPAVQKQNDVHRAFKRELKTKEPVIMSTLETVRIFLTEQPLEGL<br>EKLYQEPRELPPEERAQNVTRLLRKQAEEVNTEWEKLNLHSADWQRKI<br>DETLERLQELQEATDELDLKLRQAEVIKGSWQPVGDLLIDSLQDHLEKV<br>KALRGEIAPLKENVSHVNDLARQLTTLGIQLSPYNLSTLEDLNTRWKLL<br>QVAVEDRVRQLHEAHRDFGPASQHFLSTSVQGPWERAISPNKVPYYINH<br>ETQTTCWDHPKMTELYQSLADLNNVRFSAYRTAMKLRRLQKALCDLL<br>SLSAACDALDQHNLKQNDQPMDILQIINCLTTIYDRLEQEHNNLVNVPL<br>CVDMCLNWLLNVYDTGRTGRIRVLSFKTGIISLCKAHLEDKYRYLFKQV<br>ASSTGFCDQRRLGLLLHDSIQIPRQLGEVASFGGSNIEPSVRSCFQFANNK<br>PEIEAALFLDWMRLEPQSMVWLPVLHRVAAAETAKHQAKCNICKECPII<br>GFRYRSLKHFNYDICQSCFFSGRVAKGHKMHYPMVEYCTPTTSGEDVR<br>DFAKVLKNKFRTKRYFAKHPRMGYLPVQTVLEGDNMET |
| SEQ ID NO: 85 - BXA-212372-J4V11 | MLWWEEVEDCYEREDVQKKTFTKWVNAQFSKFGKQHIENLFSDLQDG<br>RRLLDLLEGLTGQKLPKEKGSTRVHALNNVNKALRVLQNNNVDLVNIG<br>STDIVDGNHKLTLGLIWNIILHWQVKNVMKNIMAGLQQTNSEKILLSWV<br>RQSTRNYPQVNVINFTTSWSDGLALNALIHSHRPDLFDWNSVVCQQSAT<br>QRLEHAFNIARYQLGIEKLLDPEDVDTTYPDKKSILMYITSLFQVLPQQV<br>SIEAIQEVEMLPRPPKVTKEEHFQLHHQMHYSQQITVSLAQGYERTSSPK<br>PRFKSYAYTQAAYVTTSDPTRSPFPSQHLEAPEDKSFGSSLMESEVNLDR<br>YQTALEEVLSWLLSAEDTLQAQGEISNDVEVVKDQFHTHEGYMMDLTA<br>HQGRVGNILQLGSKLIGTKLSEDEETEVQEQMNLLNSRWECLRVASM<br>EKQSNLHRVLMDLQNQKEITHVSQALLEVEQLLNAPDLCAKDFEDLFK<br>QEESLKNIKDSLQQSSGRIDIIHSKKTAALQSATPVERVKLQEALSQLDFQ<br>WEKVNKMYKDRQGRFDRSVEKWRRFHYDIKIFNQWLTEAEQFLRKTQI<br>PENWEHAKYKWYLKELQDGIGQRQTVVRTLNATGEEIIQQSSKTDASIL<br>QEKLGSLNLRWQEVCKQLSDRKKRLEEQAPGLTTIGASPTQTVTLVTQP<br>VVTKETAISKLEMPSSLMLESDQWKRLHLSLQELLVWLQLKDDELSRQ<br>APIGGDFPAVQKQNDVHRAFKRELKTKEPVIMSTLETVRIFLTEQPLEGL<br>EKLYQEPRELPPEERAQNVTRLLRKQAEEVNTEWEKLNLHSADWQRKI<br>DETLERLQELQEATDELDLKLRQAEVIKGSWQPVGDLLIDSLQDHLEKV<br>KALRGEIAPLKENVSHVNDLARQLTTLGIQLSPYNLSTLEDLNTRWKLL<br>QVAVEDRVRQLHEAHRDFGPASQHFLSTSVQGPWERAISPNKVPYYINH<br>ETQTTCWDHPKMTELYQSLADLNNVRFSAYRTAMKLRRLQKALCDLL<br>SLSAACDALDQHNLKQNDQPMDILQIINCLTTIYDRLEQEHNNLVNVPL<br>CVDMCLNWLLNVYDTGRTGRIRVLSFKTGIISLCKAHLEDKYRYLFKQV<br>ASSTGFCDQRRLGLLLHDSIQIPRQLGEVASFGGSNIEPSVRSCFQFANNK<br>PEIEAALFLDWMRLEPQSMVWLPVLHRVAAAETAKHQAKCNICKECPII<br>GFRYRSLKHFNYDICQSCFFSGRVAKGHKMHYPMVEYCTPTTSGEDVR<br>DFAKVLKNKFRTKRYFAKHPRMGYLPVQTVLEGDNMET |
| SEQ ID NO: 86 - BXA-212372-J4V4 | MLWWEEVEDCYEREDVQKKTFTKWVNAQFSKFGKQHIENLFSDLQDG<br>RRLLDLLEGLTGQKLPKEKGSTRVHALNNVNKALRVLQNNNVDLVNIG<br>STDIVDGNHKLTLGLIWNIILHWQVKNVMKNIMAGLQQTNSEKILLSWV<br>RQSTRNYPQVNVINFTTSWSDGLALNALIHSHRPDLFDWNSVVCQQSAT<br>QRLEHAFNIARYQLGIEKLLDPEDVDTTYPDKKSILMYITSLFQVLPQQV<br>SIEAIQEVEMLPRPPKVTKEEHFQLHHQMHYSQQITVSLAQGYERTSSPK |

TABLE 7-continued

Amino Acid Sequences of miniaturized dystrophin constructs.

| SEQ ID NO and Description | Sequence |
|---|---|
| | PRFKSYAYTQAAYVTTSDPTRSPFPSQHLEAPEDKSFGSSLMESEVNLDR YQTALEEVLSWLLSAEDTLQAQGEISNDVEVVKDQFHTHEGYMMDLTA HQGRVGNILQLGSKLIGTGKLSEDEETEVQEQMNLLNSRWECLRVASM EKQSNLHRVLMDTYLTEITHVSQALLEVEQLLNAPDLCAKDFEDLFKQ EESLKNIKDSLQQSSGRIDIIHSKKTAALQSATPVERVKLQEALSQLDFQ WEKVNKMYKDRQGRFDRSVEKWRRFHYDIKIFNQWLTEAEQFLRKTQI PENWEHAKYKWYLKELQDGIGQRQTVVRTLNATGEEIIQQSSKTDASIL QEKLGSLNLRWQEVCKQLSDRKKRLEEQAPGLTTIGASPTQTVTLVTQP VVTKETAISKLEMPSSLMLESDQWKRLHLSLQELLVWLQLKDDELSRQ APIGGDFPAVQKQNDVHRAFKRELKTKEPVIMSTLETVRIFLTEQPLEGL EKLYQEPRELPPEERAQNVTRLLRKQAEEVNTEWEKLNLHSADWQRKI DETLERLQELQEATDELDLKLRQAEVIKGSWQPVGDLLIDSLQDHLEKV KALRGEIAPLKENVSHVNDLARQLTTLGIQLSPYNLSTLEDLNTRWKLL QVAVEDRVRQLHEAHRDFGPASQHFLSTSVQGPWERAISPNKVPYYINH ETQTTCWDHPKMTELYQSLADLNNVRFSAYRTAMKLRRLQKALCLDLL SLSAACDALDQHNLKQNDQPMDILQIINCLTTIYDRLEQEHNNLVNVPL CVDMCLNWLLNVYDTGRTGRIRVLSFKTGIISLCKAHLEDKYRYLFKQV ASSTGFCDQRRLGLLLHDSIQIPRQLGEVASFGGSNIEPSVRSCFQFANNK PEIEAALFLDWMRLEPQSMVWLPVLHRVAAAETAKHQAKCNICKECPII GFRYRSLKHFNYDICQSCFFSGRVAKGHKMHYPMVEYCTPTTSGEDVR DFAKVLKNKFRTKRYFAKHPRMGYLPVQTVLEGDNMET |
| SEQ ID NO: 87 - BXA-212372-J4 | MLWWEEVEDCYEREDVQKKTFTKWVNAQFSKFGKQHIENLFSDLQDG RRLLDLLEGLTGQKLPKEKGSTRVHALNNVNKALRVLQNNNVDLVNIG STDIVDGNHKLTLGLIWNIILHWQVKNVMKNIMAGLQQTNSEKILLSWV RQSTRNYPQVNVINFTTSWSDGLALNALIHSHRPDLFDWNSVVCQQSAT QRLEHAFNIARYQLGIEKLLDPEDVDTTYPDKKSILMYITSLFQVLPQQV SIEAIQEVEMLPRPPKVTKEEHFQLHHQMHYSQQITVSLAQGYERTSSPK PRFKSYAYTQAAYVTTSDPTRSPFPSQHLEAPEDKSFGSSLMESEVNLDR YQTALEEVLSWLLSAEDTLQAQGEISNDVEVVKDQFHTHEGYMMDLTA HQGRVGNILQLGSKLIGTGKLSEDEETEVQEQMNLLNSRWECLRVASM EKQSNLHSYVPSTYLTEITHVSQALLEVEQLLNAPDLCAKDFEDLFKQEE SLKNIKDSLQQSSGRIDIIHSKKTAALQSATPVERVKLQEALSQLDFQWE KVNKMYKDRQGRFDRSVEKWRRFHYDIKIFNQWLTEAEQFLRKTQIPE NWEHAKYKWYLKELQDGIGQRQTVVRTLNATGEEIIQQSSKTDASILQE KLGSLNLRWQEVCKQLSDRKKRLEEQAPGLTTIGASPTQTVTLVTQPVV TKETAISKLEMPSSLMLESDQWKRLHLSLQELLVWLQLKDDELSRQAPI GGDFPAVQKQNDVHRAFKRELKTKEPVIMSTLETVRIFLTEQPLEGLEKL YQEPRELPPEERAQNVTRLLRKQAEEVNTEWEKLNLHSADWQRKIDET LERLQELQEATDELDLKLRQAEVIKGSWQPVGDLLIDSLQDHLEKVKAL RGEIAPLKENVSHVNDLARQLTTLGIQLSPYNLSTLEDLNTRWKLLQVA VEDRVRQLHEAHRDFGPASQHFLSTSVQGPWERAISPNKVPYYINHETQ TTCWDHPKMTELYQSLADLNNVRFSAYRTAMKLRRLQKALCLDLLSLS AACDALDQHNLKQNDQPMDILQIINCLTTIYDRLEQEHNNLVNVPLCVD MCLNVVLLNVYDTGRTGRIRVLSFKTGIISLCKAHLEDKYRYLFKQVASS TGFCDQRRLGLLLHDSIQIPRQLGEVASFGGSNIEPSVRSCFQFANNKPEI EAALFLDWMRLEPQSMVWLPVLHRVAAAETAKHQAKCNICKECPIIGF RYRSLKHFNYDICQSCFFSGRVAKGHKMHYPMVEYCTPTTSGEDVRDF AKVLKNKFRTKRYFAKHPRMGYLPVQTVLEGDNMET |
| SEQ ID NO: 88 - BXA-212372 | MLWWEEVEDCYEREDVQKKTFTKWVNAQFSKFGKQHIENLFSDLQDG RRLLDLLEGLTGQKLPKEKGSTRVHALNNVNKALRVLQNNNVDLVNIG STDIVDGNHKLTLGLIWNIILHWQVKNVMKNIMAGLQQTNSEKILLSWV RQSTRNYPQVNVINFTTSWSDGLALNALIHSHRPDLFDWNSVVCQQSAT QRLEHAFNIARYQLGIEKLLDPEDVDTTYPDKKSILMYITSLFQVLPQQV SIEAIQEVEMLPRPPKVTKEEHFQLHHQMHYSQQITVSLAQGYERTSSPK PRFKSYAYTQAAYVTTSDPTRSPFPSQHLEAPEDKSFGSSLMESEVNLDR YQTALEEVLSWLLSAEDTLQAQGEISNDVEVVKDQFHTHEGYMMDLTA HQGRVGNILQLGSKLIGTGKLSEDEETEVQEQMNLLNSRWECLRVASM EKQSNLHIHTVREETMMVMTEDMPLEISYVPSTYLTEITHVSQALLEVEQ LLNAPDLCAKDFEDLFKQEESLKNIKDSLQQSSGRIDIIHSKKTAALQSAT PVERVKLQEALSQLDFQWEKVNKMYKDRQGRFDRSVEKWRRFHYDIKI FNQWLTEAEQFLRKTQIPENVVEHAKYKWYLKELQDGIGQRQTVVRTLN ATGEEIIQQSSKTDASILQEKLGSLNLRWQEVCKQLSDRKKRLEEQAPGL TTIGASPTQTVTLVTQPVVTKETAISKLEMPSSLMLESDQWKRLHLSLQE LLVWLQLKDDELSRQAPIGGDFPAVQKQNDVHRAFKRELKTKEPVIMST LETVRIFLTEQPLEGLEKLYQEPRELPPEERAQNVTRLLRKQAEEVNTEW EKLNLHSADWQRKIDETLERLQELQEATDELDLKLRQAEVIKGSWQPV GDLLIDSLQDHLEKVKALRGEIAPLKENVSHVNDLARQLTTLGIQLSPYN LSTLEDLNTRWKLLQVAVEDRVRQLHEAHRDFGPASQHFLSTSVQGPW ERAISPNKVPYYINHETQTTCWDHPKMTELYQSLADLNNVRFSAYRTA MKLRRLQKALCLDLLSLSAACDALDQHNLKQNDQPMDILQIINCLTTIY DRLEQEHNNLVNVPLCVDMCLNWLLNVYDTGRTGRIRVLSFKTGIISLC KAHLEDKYRYLFKQVASSTGFCDQRRLGLLLHDSIQIPRQLGEVASFGGS |

TABLE 7-continued

Amino Acid Sequences of miniaturized dystrophin constructs.

| SEQ ID NO and Description | Sequence |
|---|---|
| | NIEPSVRSCFQFANNKPEIEAALFLDWMRLEPQSMVWLPVLHRVAAAET AKHQAKCNICKECPIIGFRYRSLKHFNYDICQSCFFSGRVAKGHKMHYP MVEYCTPTTSGEDVRDFAKVLKNKFRTKRYFAKHPRMGYLPVQTVLEG DNMET |

In some embodiments, the miniaturized dystrophin polypeptide comprises an amino acid sequence at least about 80%, at least about 85%, at least about 90%, at least about 95%, at least about 96%, at least about 97%, at least about 98%, at least about 99%, or about 10000 identical to SEQ ID NO: 83. In some embodiments, the miniaturized dystrophin polypeptide comprises an amino acid sequence identical to SEQ ID NO: 83. In some embodiments, the miniaturized dystrophin polypeptide comprises an amino acid sequence at least about 80%, at least about 85%, at least about 90%, at least about 95%, at least about 96%, at least about 97%, at least about 98%, at least about 99%, or about 100% identical to SEQ ID NO: 84. In some embodiments, the miniaturized dystrophin polypeptide comprises an amino acid sequence at least about 80%, at least about 85%, at least about 90%, at least about 95%, at least about 96%, at least about 97%, at least about 98%, at least about 99%, or about 100% identical to SEQ ID NO: 85. In some embodiments, the miniaturized dystrophin polypeptide comprises an amino acid sequence at least about 80%, at least about 85%, at least about 90%, at least about 95%, at least about 96%, at least about 97%, at least about 98%, at least about 99%, or about 100% identical to SEQ ID NO: 86. In some embodiments, the miniaturized dystrophin polypeptide comprises an amino acid sequence at least about 80%, at least about 85%, at least about 90%, at least about 95%, at least about 96%, at least about 97%, at least about 98%, at least about 99%, or about 100% identical to SEQ ID NO: 87.

In some embodiments, the amino acid sequence of the miniaturized dystrophin disclosed herein when expressed has at least one dystrophin activity.

In some embodiments, a nucleic acid sequence encoding each domain can be the following:

TABLE 8

Nucleotide sequence (and domain structure) encoding miniaturized dystrophin polypeptide BXA-220931.

| SEQ ID NO: | Description | Nucleotide Sequence |
|---|---|---|
| 89 | 5' UTR | CCGCCTTCGGCACCATTCCTCACGACACCCAAATATGGCGAC GGGTGAGGAATGGTGGGGAGTTATTTTTAGAGCGGTGAGGAA GGTGGGCAGGCAGCAGGTGTTGGCGCTCTAAAAATAACTCCC GGGAGTTATTTTTAGAGCGGAGGAATGGTGGACACCCAAATA TGGCGACGGTTCCTCACCCGTCGCCATATTTGGGTGTCCGCCC TCGGCCGGGGCCGCATTCCTGGGGGCCGGGCGGTGCTCCCGC CCGCCTCGATAAAAGGCTCCGGGGCCGGCGGCGGCCCACGA GCTACCCGGAGGAGCGGGAGGCACGCGTCTCTAAGGTAAAT ATAAAATTTTTAAGTGTATAATGTGTTAAACTACTGATTCTAA TTGTTTCTCTCTTTTAGATTCCAACCTTTGGAACTGATCTAGA CCACC |
| 90 | ABD1 | ATGCTTTGGTGGGAAGAAGTCGAGGACTGCTACGAGCGCGAG GACGTGCAGAAGAAAACCTTCACCAAATGGGTCAACGCCCA GTTCAGCAAGTTCGGCAAGCAGCACATCGAGAACCTGTTCAG CGACCTGCAGGATGCCAGAAGGCTGCTGGATCTGCTGGAAGG CCTGACAGGCCAGAAGCTGCCTAAAGAGAAGGGCAGCACAA GAGTGCACGCCCTGAACAACGTGAACAAGGCCCTGAGAGTG CTGCAGAACAACAACGTGGACCTGGTCAACATCGGCAGCACC GACATCGTGGACGGCAATCACAAACTGACCCTGGGCCTGATC TGGAACATCATCCTGCACTGGCAAGTGAAGAACGTGATGAAG AACATCATGGCCGGCCTGCAGCAGACCAACAGCGAGAAGAT TCTGCTGAGCTGGGTCCGACAGAGCACCCGGAACTACCCTCA AGTGAACGTGATCAACTTCACCACCTCTTGGAGCGACGGACT GGCCCTGAATGCCCTGATTCACAGCCACAGACCTGACCTGTT CGACTGGAATAGCGTCGTGTGTCAGCAGAGCGCCACACAGAG ACTGGAACACGCCTTCAATATCGCCAGATACCAGCTGGGCAT CGAGAAACTGCTGGACCCCGAGGATGTGGACACCACCTATCC TGACAAGAAATCCATCCTCATGTACATCACCAGCCTGTTCCA GGTGCTGCCCCAGCAAGTGTCTATCGAGGCCATTCAAGAGGT CGAG |
| 91 | Hinge 1 | ATGCTGCCCAGACCTCCTAAAGTGACCAAAGAGGAACACTTC CAGCTGCACCACCAGATGCACTACTCTCAGCAGATCACCGTG TCTCTGGCCCAGGGCTACGAGAGAACAAGCAGCCCCAAGCCT CGGTTCAAGAGCTACGCCTATACACAGGCCGCCTACGTGACC |

TABLE 8-continued

Nucleotide sequence (and domain structure) encoding miniaturized dystrophin polypeptide BXA-220931.

| SEQ ID NO: | Description | Nucleotide Sequence |
|---|---|---|
| | | ACCAGCGATCCCACAAGAAGCCCATTTCCAAGCCAGCATCTG GAAGCCCCTGAGGACAAGAGCTTTGGCAGCAGCCTGATGGA AAGC |
| 92 | Spectrin-1 | GAAGTGAACCTGGATAGATACCAGACAGCCCTGGAAGAGGT GCTGTCTTGGCTGCTGTCTGCCGAAGATACACTGCAGGCTCA GGGCGAGATCAGCAACGACGTGAAGTGGTCAAGGACCAGT TTCACACCCACGAGGGCTACATGATGGACCTGACAGCCCATC AGGGCAGAGTGGGCAATATCCTGCAGCTGGGCTCTAAGCTGA TCGGCACAGGCAAGCTGAGCGAGGACGAAGAGACAGAGGTG CAAGAGCAGATGAACCTGCTGAACAGCAGATGGGAGTGTCT GAGAGTGGCCAGCATGGAAAAGCAGAGCAACCTGCAC |
| 93 | Modified Spectrin-16 | CGGGTCCTGATGGATCTGCAGAATCAGAAGCTGACCGAGATC ACCCACGTGTCACAGGCCCTGCTTGAAGTGGAACAGCTGCTG AACGCCCCTGATCTGTGCGCCAAGGACTTCGAGGATCTGTTC AAGCAAGAGGAAAGCCTGAAGAATATCAAGGACTCTCTGCA GCAGTCCAGCGGCCGGATCGACATCATCCACAGCAAGAAA CAGCTGCCCTGCAGTCCGCCACACCTGTGGAAAGAGTGAAAC TGCAAGAGGCCCTGTCTCAGCTGGACTTCCAGTGGGAGAAAG TGAACAAGATGTACAAGGACCGGCAGGGCAGATTCGACCGC TCT |
| 94 | Spectrin-17 | GTGGAAAAATGGCGGAGATTCCACTACGACATCAAGATCTTC AACCAGTGGCTGACAGAGGCCGAGCAGTTCCTGAGAAAGAC ACAGATCCCCGAGAACTGGGAGCACGCCAAGTACAAGTGGT ATCTGAAAGAACTGCAGGACGGCATCGGCCAAGAGGCAGACA GTCGTTAGAACACTGAATGCCACCGGCGAGGAAATCATCCAG CAGAGCAGCAAGACCGACGCCAGCATCCTGCAAGAGAAGCT GGGCAGCCTGAACCTGAGATGGCAAGAAGTGTGCAAGCAGC TGTCCGACCGGAAGAAGAGGCTGGAAGAACAG |
| 95 | Hinge 3 | GCCCCTGGCCTGACAACAATCGGAGCCTCTCCTACACAGACC GTGACACTGGTCACACAGCCCGTGGTCACCAAAGAGACAGCC ATCAGCAAGCTGGAAATGCCCTCTAGCCTGATGCTCGAG |
| 96 | Spectrin-23 | AGCGACCAGTGGAAGAGACTGCACCTGTCTCTGCAAGAGCTG CTCGTGTGGCTGCAGCTGAAGGACGATGAACTGAGCAGACAG GCCCCCAATCGGAGGCGATTTTCCTGCCGTGCAGAAACAGAAC GACGTGCACAGAGCCTTCAAGCGGGAACTGAAAACAAAGA ACCCGTGATCATGAGCACCCTGGAAACCGTGCGGATCTTCCT GACAGAGCAGCCTCTCGAAGGCCTGGAAAAGCTGTACCAAG AGCCTAGAGAGCTGCCTCCTGAGGAACGGGCCCAGAATGTGA CCAGACTGCTGAGAAAGCAGGCCGAAGAGGTCAACACCGAA TGGGAGAAGCTGAACCTGCACAGCGCCGACTGGCAGAGAAA GATCGACGAGACA |
| 97 | Spectrin-24 | CTGGAACGGCTGCAAGAACTCCAAGAAGCCACCGACGAGCT GGACCTGAAACTGAGGCAGGCTGAAGTGATCAAAGGCAGCT GGCAGCCAGTGGGCGACCTGCTGATTGATAGTCTGCAGGACC ACCTGGAAAAAGTGAAGGCCCTGCGGGGAGAGATCGCCCCA CTGAAAGAAAACGTGTCCCACGTGAACGACCTGGCCAGACA GCTGACAACCCTGGGAATCCAGCTGTCCCCTTACAACCTGTC CACACTGGAAGATCTGAACACCCGGTGGAAACTGCTCCAGGT GGCCGTGGAAGATAGAGTGCGACAGCTGCACGAG |
| 98 | Hinge 4 | GCCCACAGAGATTTTGGACCAGCCAGCCAGCACTTCCTGTCT ACATCTGTGCAAGGCCCTTGGGAGAGAGCTATCAGCCCTAAC AAGGTGCCCTACTACATCAACCACGAGACACAGACCACCTGT TGGGATCACCCCAAGATGACCGAGCTGTATCAGAGCCTGGCC GACCTGAACAATGTGCGCTTTAGCGCCTACCGGACCGCCATG AAGCTG |
| 99 | CR | CGGAGACTGCAGAAAGCCCTGTGTCTGGACCTGCTGTCTCTG TCTGCAGCCTGTGATGCCCTGGACCAGCACAACCTGAAGCAG AACGACCAGCCTATGGACATCCTCCAGATCATCAACTGCCTG ACCACCATCTACGACCGGCTGGAACAAGAGCACAACAACCTC GTGAATGTGCCCCTGTGCGTGGACATGTGTCTGAACTGGCTG CTGAATGTGTACGACACCGGCAGAACCGGCAGGATCAGAGT GCTGAGCTTCAAGACCGGCATCATCTCCCTGTGCAAAGCCCA CCTCGAGGACAAGTACAGATACCTGTTCAAACAGGTGGCCAG CTCCACCGGCTTTTGCGATCAAAGAAGGCTGGGCCTGCTGCT GCACGACAGCATCCAGATTCCTAGACAGCTGGGCGAAGTGGC |

TABLE 8-continued

Nucleotide sequence (and domain structure) encoding miniaturized dystrophin polypeptide BXA-220931.

| SEQ ID NO: | Description | Nucleotide Sequence |
|---|---|---|
| | | CTCCTTCGGCGGATCTAATATTGAGCCTAGCGTGCGGAGCTG CTTCCAGTTCGCCAACAACAAGCCTGAGATCGAGGCCGCTCT GTTCCTGGATTGGATGCGCCTGGAACCTCAGAGCATGGTTTG GCTGCCTGTGCTGCATAGAGTGGCCGCTGCCGAAACAGCCAA GCACCAGGCCAAGTGCAACATCTGCAAAGAGTGCCCCATCAT CGGCTTCCGGTACAGATCCCTGAAGCACTTCAACTACGATAT CTGCCAGAGCTGTTTCTTCTCTGGCCGCGTGGCCAAGGGCCA CAAAATGCACTACCCCATGGTGGAATACTGCACCCCTACCAC ATCTGGCGAAGATGTGCGGGATTTCGCCAAGGTGCTGAAAAA CAAGTTCCGGACCAAGCGGTACTTCGCTAAGCACCCCAGAAT GGGCTATCTGCCCGTGCAGACAGTGCTCGAGGGCGATAACAT GGAAACCTGA |

In some embodiments, a nucleic acid sequence encoding the H1 domain in the miniaturized dystrophin polypeptide is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 91. In some embodiments, a nucleic acid sequence encoding the R1 domain is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 92. In some embodiments, a nucleic acid sequence encoding the modified R16 domain is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 93. In some embodiments, a nucleic acid sequence encoding the R17 domain is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 94. In some embodiments, a nucleic acid sequence encoding the H3 domain is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 95. In some embodiments, a nucleic acid sequence encoding the R23 domain is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 96. In some embodiments, a nucleic acid sequence encoding the R24 domain is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 97. In some embodiments, a nucleic acid sequence encoding the H4 domain is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 98. In some embodiments, a nucleic acid sequence encoding the ABD1 domain in the miniaturized dystrophin polypeptide is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 90. In some embodiments, a nucleic acid sequence encoding the CR/C-term. polypeptide is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 99.

In some embodiments, the miniaturized dystrophin polypeptide encoded by the nucleic acid molecule exhibits one or more properties selected from the group consisting of (i) having a lower CD4 proliferation compared to BXA-212372 (SEQ ID NO: 88), (ii) having a lower CD8 proliferation compared to BXA-212372 (SEQ ID NO: 88), and (iv) any combination thereof.

In some embodiments, the miniaturized dystrophin polypeptide encoded by the nucleic acid molecule has formula (I):

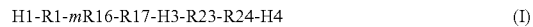

H1-R1-mR16-R17-H3-R23-R24-H4    (I)

wherein: H1 is a hinge 1 domain of dystrophin; R1 is a spectrin repeat 1 domain of dystrophin; mR16 is a modified spectrin repeat 16 of dystrophin; R17 is a spectrin repeat 17 of dystrophin; H3 is a hinge 3 domain of dystrophin; R23 is a spectrin repeat 23 of dystrophin; R24 is a spectrin repeat 24 of dystrophin; H4 is a hinge 4 domain of dystrophin; and (-) is a peptide bond.

In some embodiments, the miniaturized dystrophin polypeptide encoded by the nucleic acid molecule comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 83.

In some embodiments, the miniaturized dystrophin polypeptide exhibits a higher expression of the miniaturized dystrophin polypeptide than BXA-212372 (SEQ ID NO: 88). In some other embodiments, the miniaturized dystrophin polypeptide expression is at least about 1.5 fold, at least about 1.6 fold, at least about 1.7 fold. at least about 1.8 fold, at least about 1.9 fold, at least about 2 fold, at least about 2.1 fold, at least about 2.2 fold, at least about 2.3 fold, at least about 2.4 fold, at least about 2.5 fold, at least about 2.6 fold, at least about 2.7 fold, at least about 2.8 fold, at least about 2.9 fold or at least about 3 fold higher than the BXA-212372 (SEQ ID NO: 88) polypeptide expression.

In some embodiments, the miniaturized dystrophin polypeptides can be encoded by nucleotide sequences. Some examples of the nucleotide sequences are shown in Table 9.

TABLE 9

Nucleotide Sequences of Dystrophin constructs.

| SEQ ID NO and Description | Sequence |
|---|---|
| SEQ ID NO: 100 - BXA-220931 | ATGCTTTGGTGGGAAGAAGTCGAGGACTGCTACGAGCGCGAGGACG<br>TGCAGAAGAAAACCTTCACCAAATGGGTCAACGCCCAGTTCAGCAAG<br>TTCGGCAAGCAGCACATCGAGAACCTGTTCAGCGACCTGCAGGATGG<br>CAGAAGGCTGCTGGATCTGCTGGAAGGCCTGACAGGCCAGAAGCTG<br>CCTAAAGAGAAGGGCAGCACAAGAGTGCACGCCCTGAACAACGTGA<br>ACAAGGCCCTGAGAGTGCTGCAGAACAACAACGTGGACCTGGTCAA<br>CATCGGCAGCACCGACATCGTGGACGGCAATCACAAACTGACCCTGG<br>GCCTGATCTGGAACATCATCCTGCACTGGCAAGTGAAGAACGTGATG<br>AAGAACATCATGGCCGGCCTGCAGCAGACCAACAGCGAGAAGATTC<br>TGCTGAGCTGGGTCCGACAGAGCACCCGGAACTACCCTCAAGTGAAC<br>GTGATCAACTTCACCACCTCTTGGAGCGACGGACTGGCCCTGAATGC<br>CCTGATTCACAGCCACAGACCTGACCTGTTCGACTGGAATAGCGTCG<br>TGTGTCAGCAGAGCGCCACACAGAGACTGGAACACGCCTTCAATATC<br>GCCAGATACCAGCTGGGCATCGAGAAACTGCTGGACCCCGAGGATGT<br>GGACACCACCTATCCTGACAAGAAATCCATCCTCATGTACATCACCA<br>GCCTGTTCCAGGTGCTGCCCCAGCAAGTGTCTATCGAGGCCATTCAA<br>GAGGTCGAGATGCTGCCCAGACCTCCTAAAGTGACCAAAGAGGAAC<br>ACTTCCAGCTGCACCACCAGATGCACTACTCTCAGCAGATCACCGTG<br>TCTCTGGCCCAGGGCTACGAGAGAACAAGCAGCCCCAAGCCTCGGTT<br>CAAGAGCTACGCCTATACACAGGCCGCCTACGTGACCACCAGCGATC<br>CCACAAGAAGCCCATTTCCAAGCCAGCATCTGGAAGCCCCTGAGGAC<br>AAGAGCTTTGGCAGCAGCCTGATGGAAAGCGAAGTGAACCTGGATA<br>GATACCAGACAGCCCTGGAAGAGGTGCTGTCTTGGCTGCTGTCTGCC<br>GAAGATACACTGCAGGCTCAGGGCGAGATCAGCAACGACGTGGAAG<br>TGGTCAAGGACCAGTTTCACACCCACGAGGGCTACATGATGGACCTG<br>ACAGCCCATCAGGGCAGAGTGGGCAATATCCTGCAGCTGGGCTCTAA<br>GCTGATCGGCACAGGCAAGCTGAGCGAGGACGAAGAGACAGAGGTG<br>CAAGAGCAGATGAACCTGCTGAACAGCAGATGGGAGTGTCTGAGAG<br>TGGCCAGCATGGAAAAGCAGAGCAACCTGCACCGGGTCCTGATGGA<br>TCTGCAGAATCAGAAGCTGACCGAGATCACCCACGTGTCACAGGCCC<br>TGCTTGAAGTGGAACAGCTGCTGAACGCCCCTGATCTGTGCGCCAAG<br>GACTTCGAGGATCTGTTCAAGCAAGAGGAAAGCCTGAAGAATATCA<br>AGGACTCTCTGCAGCAGTCCAGCGGCCGGATCGACATCATCCACAGC<br>AAGAAAACAGCTGCCCTGCAGTCCGCCACACCTGTGGAAAGAGTGA<br>AACTGCAAGAGGCCCTGTCTCAGCTGGACTTCCAGTGGGAGAAAGTG<br>AACAAGATGTACAAGGACCGGCAGGGCAGATTCGACCGCTCTGTGG<br>AAAAATGGCGGAGATTCCACTACGACATCAAGATCTTCAACCAGTGG<br>CTGACAGAGGCCGAGCAGTTCCTGAGAAAGACACAGATCCCCGAGA<br>ACTGGGAGCACGCCAAGTACAAGTGGTATCTGAAAGAACTGCAGGA<br>CGGCATCGGCCAGAGGCAGACAGTCGTTAGAACACTGAATGCCACC<br>GGCGAGGAAATCATCCAGCAGAGCAGCAAGACCGACGCCAGCATCC<br>TGCAAGAGAAGCTGGGCAGCCTGAACCTGAGATGGCAAGAAGTGTG<br>CAAGCAGCTGTCCGACCGGAAGAAGAGGCTGGAAGAACAGGCCCCT<br>GGCCTGACAACAATCGGAGCCTCTCCTACACAGACCGTGACACTGGT<br>CACACAGCCCGTGGTCACCAAAGAGACAGCCATCAGCAAGCTGGAA<br>ATGCCCTCTAGCCTGATGCTCGAGAGCGACCAGTGGAAGAGACTGCA<br>CCTGTCTCTGCAAGAGCTGCTCGTGTGGCTGCAGCTGAAGGACGATG<br>AACTGAGCAGACAGGCCCCAATCGGAGGCGATTTTCCTGCCGTGCAG<br>AAACAGAACGACGTGCACAGAGCCTTCAAGCGGGAACTGAAAACAA<br>AAGAACCCGTGATCATGAGCACCCTGGAAACCGTGCGGATCTTCCTG<br>ACAGAGCAGCCTCTCGAAGGCCTGGAAAAGCTGTACCAAGAGCCTA<br>GAGAGCTGCCTCCTGAGGAACGGGCCCAGAATGTGACCAGACTGCTG<br>AGAAAGCAGGCCGAAGAGGTCAACACCGAATGGGAGAAGCTGAACC<br>TGCACAGCGCCGACTGGCAGAGAAAGATCGACGAGACACTGGAACG<br>GCTGCAAGAACTCCAAGAAGCCACCGACGAGCTGGACCTGAAACTG<br>AGGCAGGCTGAAGTGATCAAAGGCAGCTGGCAGCCAGTGGGCGACC<br>TGCTGATTGATAGTCTGCAGGACCACCTGGAAAAAGTGAAGGCCCTG<br>CGGGGAGAGATCGCCCCACTGAAAGAAAACGTGTCCCACGTGAACG<br>ACCTGGCCAGACAGCTGACAACCCTGGGAATCCAGCTGTCCCCTTAC<br>AACCTGTCCACACTGGAAGATCTGAACACCCGGTGGAAACTGCTCCA<br>GGTGGCCGTGGAAGATAGAGTGCGACAGCTGCACGAGGCCCACAGA<br>GATTTTGGACCAGCCAGCCAGCACTTCCTGTCTACATCTGTGCAAGG<br>CCCTTGGGAGAGAGCTATCAGCCCTAACAAGGTGCCCTACTACATCA<br>ACCACGAGACACAGACCACCTGTTGGGATCACCCCAAGATGACCGA<br>GCTGTATCAGAGCCTGGCCGACCTGAACAATGTGCGCTTTAGCGCCT<br>ACCGGACCGCCATGAAGCTGCGGAGACTGCAGAAAGCCCTGTGTCTG<br>GACCTGCTGTCTCTGTCTGCAGCCTGTGATGCCCTGGACCAGCACAA<br>CCTGAAGCAGAACGACCAGCCTATGGACATCCTCCAGATCATCAACT<br>GCCTGACCACCATCTACGACCGGCTGGAACAAGAGCACAACCTC<br>GTGAATGTGCCCCTGTGCGTGGACATGTGTCTGAACTGGCTGCTGAA<br>TGTGTACGACACCGGCAGAACCGGCAGGATCAGAGTGCTGAGCTTCA<br>AGACCGGCATCATCTCCCTGTGCAAAGCCCACCTCGAGGACAAGTAC<br>AGATACCTGTTCAAACAGGTGGCCAGCTCCACCGGCTTTTGCGATCA<br>AAGAAGGCTGGGCCTGCTGCTGCACGACAGCATCCAGATTCCTAGAC |

TABLE 9-continued

Nucleotide Sequences of Dystrophin constructs.

SEQ ID
NO and
Description Sequence

AGCTGGGCGAAGTGGCCTCCTTCGGCGGATCTAATATTGAGCCTAGC
GTGCGGAGCTGCTTCCAGTTCGCCAACAACAAGCCTGAGATCGAGGC
CGCTCTGTTCCTGGATTGGATGCGCCTGGAACCTCAGAGCATGGTTTG
GCTGCCTGTGCTGCATAGAGTGGCCGCTGCCGAAACAGCCAAGCACC
AGGCCAAGTGCAACATCTGCAAAGAGTGCCCCATCATCGGCTTCCGG
TACAGATCCCTGAAGCACTTCAACTACGATATCTGCCAGAGCTGTTTC
TTCTCTGGCCGCGTGGCCAAGGGCCACAAAATGCACTACCCCATGGT
GGAATACTGCACCCCTACCACATCTGGCGAAGATGTGCGGGATTTCG
CCAAGGTGCTGAAAAACAAGTTCCGGACCAAGCGGTACTTCGCTAAG
CACCCCAGAATGGGCTATCTGCCCGTGCAGACAGTGCTCGAGGGCGA
TAACATGGAAACCTGA

SEQ ID
NO: 101 -
BXA-
212372-
J4V13

ATGCTGTGGTGGGAGGAAGTGGAAGATTGCTACGAGCGCGAGGACG
TGCAGAAGAAAACCTTCACCAAATGGGTGAACGCCCAGTTCAGCAA
GTTCGGCAAGCAGCACATCGAGAACCTGTTCAGCGACCTGCAGGACG
GCAGACGGCTGCTGGACCTGCTGGAAGGCCTGACCGGCCAGAAGCT
GCCCAAAGAGAAGGGCAGCACCAGAGTGCACGCCCTGAACAACGTG
AACAAGGCCCTGCGGGTGCTGCAGAACAACAACGTGGACCTGGTGA
ACATCGGCAGCACCGACATCGTGGACGGCAACCACAAGCTGACCCTG
GGCCTGATCTGGAACATCATCCTGCACTGGCAGGTCAAAAACGTGAT
GAAGAACATCATGGCCGGCCTGCAGCAGACCAACAGCGAGAAGATC
CTGCTGAGCTGGGTGCGCCAGAGCACCCGGAACTACCCCCAGGTCAA
CGTGATCAACTTCACCACCTCTTGGAGCGACGGCCTGGCCCTGAACG
CCCTGATCCACAGCCACCGGCCCGACCTGTTCGACTGGAACAGCGTG
GTCTGCCAGCAGAGCGCCACCCAGCGGCTGGAACACGCCTTCAATAT
CGCCAGATACCAGCTGGGCATCGAGAAGCTGCTGGATCCCGAGGAC
GTGGACACCACCTACCCCGACAAGAAATCCATCCTGATGTATATCAC
CAGCCTGTTCCAGGTGCTGCCCCAGCAGGTGTCCATCGAGGCCATCC
AGGAAGTGGAAATGCTGCCCAGACCCCCCAAAGTGACCAAAGAGGA
ACACTTCCAGCTGCACCACCAGATGCACTACAGCCAGCAGATCACCG
TGTCCCTGGCTCAGGGCTACGAGCGGACCAGCAGCCCCAAGCCCCGG
TTCAAGAGCTACGCCTACACCCAGGCCGCCTACGTGACCACCAGCGA
CCCCACCAGAAGCCCATTCCCCAGCCAGCATCTGGAAGCCCCCGAGG
ACAAGAGCTTCGGCAGCAGCCTGATGGAAAGCGAAGTGAACCTGGA
CAGATACCAGACCGCCCTGGAAGAGGTGCTGTCCTGGCTGCTGAGCG
CCGAGGATACACTGCAGGCCCAGGGCGAGATCAGCAACGACGTGGA
AGTGGTGAAAGACCAGTTCCACACCCACGAGGGCTACATGATGGACC
TGACCGCCCACCAGGGCAGAGTGGGCAACATCCTGCAGCTGGGCAG
CAAGCTGATCGGCACCGGCAAGCTGAGCGAGGACGAAGAGACAGAG
GTGCAGGAACAGATGAACCTGCTGAACAGCAGATGGGAGTGCCTGC
GGGTGGCCAGCATGGAAAAGCAGAGCAACCTGCACCGGGTCCTGAT
GGATCTGCAGAATCAGAAGCTGACCGAGATCACCCACGTGTCCCAGG
CTCTGCTGGAAGTGGAACAGCTGCTGAACGCCCCCGACCTGTGCGCC
AAGGACTTCGAGGATCTGTTCAAGCAGGAAGAGAGCCTGAAGAATA
TCAAGGACTCCCTGCAGCAGTCCAGCGGCCGGATCGACATCATCCAC
AGCAAGAAAACAGCCGCCCTGCAGTCCGCCACCCCCGTGGAAAGAG
TGAAGCTGCAGGAAGCCCTGAGCCAGCTGGACTTCCAGTGGGAGAA
AGTGAACAAGATGTACAAGGACCGGCAGGGCAGATTCGACCGCAGC
GTGGAAAAGTGGCGGCGGTTCCACTACGACATCAAGATCTTCAACCA
GTGGCTGACCGAGGCCGAGCAGTTCCTGAGAAAGACCCAGATCCCCG
AGAACTGGGAGCACGCCAAGTACAAGTGGTATCTGAAAGAGCTGCA
GGACGGCATCGGCCAGCGGCAGACAGTGGTCCGCACCCTGAATGCC
ACCGGCGAGGAAATCATCCAGCAGAGCAGCAAGACCGACGCCAGCA
TCCTGCAGGAAAAGCTGGGCAGCCTGAACCTGCGGTGGCAGGAAGT
GTGCAAGCAGCTGAGCGACCGGAAGAAGCGGCTGGAAGAACAGGCC
CCTGGCCTGACCACAATCGGCGCCAGCCCTACCCAGACCGTGACCCT
GGTGACACAGCCCGTGGTGACAAAAGAGACAGCCATCAGCAAGCTG
GAAATGCCCAGCAGCCTGATGCTGGAAAGCGACCAGTGGAAGCGGC
TGCACCTGAGCCTGCAGGAACTGCTGGTCTGGCTGCAGCTGAAGGAC
GACGAGCTGAGCAGACAGGCCCCCATCGGCGGCGATTTCCCCGCCGT
GCAGAAACAGAACGACGTGCACCGGGCCTTCAAGCGCGAGCTGAAA
ACAAAAGAACCCGTGATCATGAGCACCCTGGAAACCGTGCGGATCTT
CCTGACCGAGCAGCCCCTGGAAGGCCTGGAAAAGCTGTACCAGGAA
CCCAGAGAGCTGCCCCCCGAGGAACGGGCCCAGAACGTGACCAGAC
TGCTGCGGAAGCAGGCCGAAGAGGTCAACACCGAGTGGGAGAAGCT
GAACCTGCACAGCGCCGACTGGCAGCGCAAGATCGACGAGACACTG
GAACGGCTGCAGGAACTGCAGGAGGCCACCGACGAGCTGGACCTGA
AGCTGAGACAGGCCGAAGTGATCAAGGGCAGCTGGCAGCCCGTGGG
CGACCTGCTGATCGACTCCCTGCAGGACCACCTGGAAAAAGTGAAGG
CCCTGCGGGGCGAGATCGCCCCCCTGAAAGAAAACGTGTCCCACGTG
AACGACCTGGCCCGGCAGCTGACCACCCTGGGCATCCAGCTGAGCCC
CTACAACCTGTCCACCCTGGAAGATCTGAACACCCGGTGGAAGCTGC
TGCAGGTGGCCGTGGAAGATAGAGTGCGGCAGCTGCACGAGGCCCA
CAGAGACTTTGGCCCTGCCAGCCAGCACTTCCTGAGCACCTCTGTGC

TABLE 9-continued

Nucleotide Sequences of Dystrophin constructs.

| SEQ ID NO and Description | Sequence |
|---|---|
| | AGGGACCCTGGGAGAGAGCCATCAGCCCCAACAAGGTGCCCTACTA
CATCAACCACGAGACACAGACCACCTGTTGGGACCACCCCAAGATGA
CCGAGCTGTACCAGAGCCTGGCCGACCTGAACAATGTGCGGTTCAGC
GCCTACCGGACCGCCATGAAGCTGAGGCGGCTGCAGAAAGCTCTGTG
CCTGGATCTGCTGAGCCTGAGCGCCGCCTGCGACGCCCTGGACCAGC
ACAACCTGAAGCAGAACGACCAGCCCATGGATATCCTGCAGATCATC
AACTGCCTGACCACAATCTACGACAGGCTGGAACAGGAACACAACA
ATCTGGTCAACGTGCCCCTGTGCGTGGACATGTGCCTGAATTGGCTG
CTGAATGTGTACGACACCGGCCGGACCGGCAGAATCCGGGTGCTGAG
CTTCAAGACCGGCATCATCAGCCTGTGCAAGGCCCACCTGGAAGATA
AGTACCGCTACCTGTTCAAACAGGTGGCCAGCTCCACCGGCTTTTGC
GACCAGCGGAGACTGGGCCTGCTGCTGCACGACAGCATCCAGATCCC
CAGACAGCTGGGCGAGGTGGCCTCCTTCGGCGGCAGCAACATTGAGC
CCAGCGTGCGGAGCTGCTTCCAGTTCGCCAACAACAAGCCCGAGATC
GAGGCCGCCCTGTTCCTGGACTGGATGAGACTGGAACCCCAGAGCAT
GGTGTGGCTGCCCGTGCTGCATCGGGTGGCCGCTGCCGAGACAGCCA
AGCACCAGGCCAAGTGCAACATCTGCAAAGAGTGCCCCATCATCGGC
TTCCGGTACAGAAGCCTGAAGCACTTCAACTACGATATCTGCCAGAG
CTGCTTCTTCAGCGGCAGAGTGGCCAAGGGCCACAAAATGCACTACC
CCATGGTGGAATACTGCACCCCCACCACCAGCGGCGAGGATGTGCGG
GACTTCGCCAAGGTGCTGAAAAACAAGTTCCGGACCAAGCGGTACTT
TGCCAAGCACCCCCGGATGGGCTACCTGCCCGTGCAGACAGTGCTGG
AAGGCGACAACATGGAAACCTGA |
| SEQ ID NO: 102 - BXA-212372-J4V12 | ATGCTGTGGTGGGAGGAAGTGGAAGATTGCTACGAGCGCGAGGACG
TGCAGAAGAAAACCTTCACCAAATGGGTGAACGCCCAGTTCAGCAA
GTTCGGCAAGCAGCACATCGAGAACCTGTTCAGCGACCTGCAGGACG
GCAGACGGCTGCTGGACCTGCTGGAAGGCCTGACCGGCCAGAAGCT
GCCCAAAGAGAAGGGCAGCACCAGAGTGCACGCCCTGAACAACGTG
AACAAGGCCCTGCGGGTGCTGCAGAACAACAACGTGGACCTGGTGA
ACATCGGCAGCACCGACATCGTGGACGGCAACCACAAGCTGACCCTG
GGCCTGATCTGGAACATCATCCTGCACTGGCAGGTCAAAAACGTGAT
GAAGAACATCATGGCCGGCCTGCAGACAGCAACAGCGAGAAGATC
CTGCTGAGCTGGGTGCGCCAGAGCACCCGGAACTACCCCCAGGTCAA
CGTGATCAACTTCACCACCTCTTGGAGCGACGGCCTGGCCCTGAACG
CCCTGATCCACAGCCACCGGCCCGACCTGTTCGACTGGAACAGCGTG
GTCTGCCAGCAGAGCGCCACCCAGCGGCTGGAACACGCCTTCAATAT
CGCCAGATACCAGCTGGGCATCGAGAAGCTGCTGGATCCCGAGGAC
GTGGACACCACCTACCCCGACAAGAAATCCATCCTGATGTATATCAC
CAGCCTGTTCCAGGTGCTGCCCCAGCAGGTGTCCATCGAGGCCATCC
AGGAAGTGGAAATGCTGCCCAGACCCCCCAAAGTGACCAAAGAGGA
ACACTTCCAGCTGCACCACCAGATGCACTACAGCCAGCAGATCACCG
TGTCCCTGGCTCAGGGCTACGAGCGGACCAGCAGCCCCAAGCCCCGG
TTCAAGAGCTACGCCTACACCCAGGCCGCCTACGTGACCACCAGCGA
CCCCACCAGAAGCCCATTCCCCAGCCAGCATCTGGAAGCCCCGAGG
ACAAGAGCTTCGGCAGCAGCCTGATGGAAAGCGAAGTGAACCTGGA
CAGATACCAGACCGCCCTGGAAGAGGTGCTGTCCTGGCTGCTGAGCG
CCGAGGATACACTGCAGGCCCAGGGCGAGATCAGCAACGACGTGGA
AGTGGTGAAAGACCAGTTCCACACCCACGAGGGCTACATGATGGACC
TGACCGCCCACCAGGGCAGAGTGGGCAACATCCTGCAGCTGGGCAG
CAAGCTGATCGGCACCGGCAAGCTGAGCGAGGACGAAGAGACAGAG
GTGCAGGAACAGATGAACCTGCTGAACAGCAGATGGGAGTGCCTGC
GGGTGGCCAGCATGGAAAAGCAGAGCAACCTGCACAGAGTTTTAAT
GGATCTCCAGAATCAGAAAACCGAGATCACCCACGTGTCCCAGGCTC
TGCTGGAAGTGGAACAGCTGCTGAACGCCCCCGACCTGTGCGCCAAG
GACTTCGAGGATCTGTTCAAGCAGGAAGAGAGCCTGAAGAATATCA
AGGACTCCCTGCAGCAGTCCAGCGGCCGGATCGACATCATCCACAGC
AAGAAAACAGCCGCCCTGCAGTCCGCCACCCCCGTGGAAAGAGTGA
AGCTGCAGGAAGCCCTGAGCCAGCTGGACTTCCAGTGGGAGAAAGT
GAACAAGATGTACAAGGACCGGCAGGGCAGATTCGACCGCAGCGTG
GAAAAGTGGCGGCGGTTCCACTACGACATCAAGATCTTCAACCAGTG
GCTGACCGAGGCCGAGCAGTTCCTGAGAAAGACCCAGATCCCCGAG
AACTGGGAGCACGCCAAGTACAAGTGGTATCTGAAAGAGCTGCAGG
ACGGCATCGGCCAGCGGCAGACAGTGGTCCGCACCCTGAATGCCACC
GGCGAGGAAATCATCCAGCAGAGCAGCAAGACCGACGCCAGCATCC
TGCAGGAAAAGCTGGGCAGCCTGAACCTGCGGTGGCAGGAAGTGTG
CAAGCAGCTGAGCGACCGGAAGAAGCGGCTGGAAGAACAGGCCCCT
GGCCTGACCACAATCGGCGCCAGCCCTACCCAGACCGTGACCCTGGT
GACACAGCCCGTGGTGACAAAAGAGACAGCCATCAGCAAGCTGGAA
ATGCCCAGCAGCCTGATGCTGGAAAGCGACCAGTGGAAGCGGCTGC
ACCTGAGCCTGCAGGAACTGCTGGTCTGGCTGCAGCTGAAGGACGAC
GAGCTGAGCAGACAGGCCCCCATCGGCGGCGATTTCCCCGCCGTGCA
GAAACAGAACGACGTGCACCGGGCCTTCAAGCGCGAGCTGAAAACA
AAAGAACCCGTGATCATGAGCACCCTGGAAACCGTGCGGATCTTCCT |

TABLE 9-continued

Nucleotide Sequences of Dystrophin constructs.

| SEQ ID NO and Description | Sequence |
|---|---|
| | GACCGAGCAGCCCCTGGAAGGCCTGGAAAAGCTGTACCAGGAACCC<br>AGAGAGCTGCCCCCCGAGGAACGGGCCCAGAACGTGACCAGACTGC<br>TGCGGAAGCAGGCCGAAGAGGTCAACACCGAGTGGGAGAAGCTGAA<br>CCTGCACAGCGCCGACTGGCAGCGGAAGATCGACGAGACACTGGAA<br>CGGCTGCAGGAACTGCAGGAGGCCACCGACGAGCTGGACCTGAAGC<br>TGAGACAGGCCGAAGTGATCAAGGGCAGCTGGCAGCCCGTGGGCGA<br>CCTGCTGATCGACTCCCTGCAGGACCACCTGGAAAAAGTGAAGGCCC<br>TGCGGGGCGAGATCGCCCCCCTGAAAGAAAACGTGTCCCACGTGAAC<br>GACCTGGCCCGGCAGCTGACCACCCTGGGCATCCAGCTGAGCCCCTA<br>CAACCTGTCCACCCTGGAAGATCTGAACACCCGGTGGAAGCTGCTGC<br>AGGTGGCCGTGGAAGATAGAGTGCGGCAGCTGCACGAGGCCCACAG<br>AGACTTTGGCCCTGCCAGCCAGCACTTCCTGAGCACCTCTGTGCAGG<br>GACCCTGGGAGAGAGCCATCAGCCCCAACAAGGTGCCCTACTACATC<br>AACCACGAGACACAGACCACCTGTTGGGACCACCCCAAGATGACCG<br>AGCTGTACCAGAGCCTGGCCGACCTGAACAATGTGCGGTTCAGCGCC<br>TACCGGACCGCCATGAAGCTGAGGCGGCTGCAGAAAGCTCTGTGCCT<br>GGATCTGCTGAGCCTGAGCGCCGCCTGCGACGCCCTGGACCAGCACA<br>ACCTGAAGCAGAACGACCAGCCCATGGATATCCTGCAGATCATCAAC<br>TGCCTGACCACCAATCTACGACAGGCTGGAACAGGAACACAACAATCT<br>GGTCAACGTGCCCCTGTGCGTGGACATGTGCCTGAATTGGCTGCTGA<br>ATGTGTACGACACCGGCCGGACCGGCAGAATCCGGGTGCTGAGCTTC<br>AAGACCGGCATCATCAGCCTGTGCAAGGCCCACCTGGAAGATAAGTA<br>CCGCTACCTGTTCAAACAGGTGGCCAGCTCCACCGGCTTTTGCGACC<br>AGCGGAGACTGGGCCTGCTGCTGCACGACAGCATCCAGATCCCCAGA<br>CAGCTGGGCGAGGTGGCCTCCTTCGGCGGCAGCAACATTGAGCCCAG<br>CGTGCGGAGCTGCTTCCAGTTCGCCAACAACAAGCCCGAGATCGAGG<br>CCGCCCTGTTCCTGGACTGGATGAGACTGGAACCCCAGAGCATGGTG<br>TGGCTGCCCGTGCTGCATCGGGTGGCCGCTGCCGAGACAGCCAAGCA<br>CCAGGCCAAGTGCAACATCTGCAAAGAGTGCCCCATCATCGGCTTCC<br>GGTACAGAAGCCTGAAGCACTTCAACTACGATATCTGCCAGAGCTGC<br>TTCTTCAGCGGCAGAGTGGCCAAGGGCCACAAAATGCACTACCCCAT<br>GGTGGAATACTGCACCCCCACCACCAGCGGCGAGGATGTGCGGGACT<br>TCGCCAAGGTGCTGAAAAACAAGTTCCGGACCAAGCGGTACTTTGCC<br>AAGCACCCCGGATGGGCTACCTGCCCGTGCAGACAGTGCTGGAAGG<br>CGACAACATGGAAACCTGA |
| SEQ ID NO: 103 - BXA-212372-J4V11 | ATGCTGTGGTGGGAGGAAGTGGAAGATTGCTACGAGCGCGAGGACG<br>TGCAGAAGAAAACCTTCACCCAAATGGGTGAACGCCCAGTTCAGCAA<br>GTTCGGCAAGCAGCACATCGAGAACCTGTTCAGCGACCTGCAGGACG<br>GCAGACGGCTGCTGGACCTGCTGGAAGGCCTGACCGGCCAGAAGCT<br>GCCCAAAGAGAAGGGCAGCACCAGAGTGCACGCCCTGAACAACGTG<br>AACAAGGCCCTGCGGGTGCTGCAGAACAACAACGTGGACCTGGTGA<br>ACATCGGCAGCACCGACATCGTGGACGGCAACCACAAGCTGACCCTG<br>GGCCTGATCTGGAACATCATCCTGCACTGGCAGGTCAAAAACGTGAT<br>GAAGAACATCATGGCCGGCCTGCAGCAGACCAACAGCGAGAAGATC<br>CTGCTGAGCTGGGTGCGCCAGAGCACCCGGAACTACCCCCAGGTCAA<br>CGTGATCAACTTCACCACCTCTTGGAGCGACGGCCTGGCCCTGAACG<br>CCCTGATCCACAGCCACCGGCCCGACCTGTTCGACTGGAACAGCGTG<br>GTCTGCCAGCAGAGCGCCACCCAGCGGCTGGAACACGCCTTCAATAT<br>CGCCAGATACCAGCTGGGCATCGAGAAGCTGCTGGATCCCGAGGAC<br>GTGGACACCACCTACCCCGACAAGAAATCCATCCTGATGTATATCAC<br>CAGCCTGTTCCAGGTGCTGCCCCAGCAGGTGTCCATCGAGGCCATCC<br>AGGAAGTGGAAATGCTGCCCAGACCCCCCAAAGTGACCAAAGAGGA<br>ACACTTCCAGCTGCACCACCAGATGCACTACAGCCAGCAGATCACCG<br>TGTCCCTGGCTCAGGGCTACGAGCGGACCAGCAGCCCAAGCCCCGG<br>TTCAAGAGCTACGCCTACACCCAGGCCGCCTACGTGACCACCAGCGA<br>CCCCACCAGAAGCCCATTCCCCAGCCAGCATCTGGAAGCCCCCGAGG<br>ACAAGAGCTTCGGCAGCAGCCTGATGGAAAGCGAAGTGAACCTGGA<br>CAGATACCAGACCGCCCTGGAAGAGGTGCTGTCCTGGCTGCTGAGCG<br>CCGAGGATACACTGCAGGCCCAGGGCGAGATCAGCAACGACGTGGA<br>AGTGGTGAAAGACCAGTTCCACACCCACGAGGGCTACATGATGGACC<br>TGACCGCCCACCAGGGCAGAGTGGGCAACATCCTGCAGCTGGGCAG<br>CAAGCTGATCGGCACCGGCAAGCTGAGCGAGGACGAAGAGACAGAG<br>GTGCAGGAACAGATGAACCTGCTGAACAGCAGATGGGAGTGCCTGC<br>GGGTGGCCAGCATGGAAAAGCAGAGCAACCTGCACAGAGTTTTAAT<br>GGATCTCCAGAATCAGAAAGAGATCACCCACGTGTCCCAGGCTCTGC<br>TGGAAGTGGAACAGCTGCTGAACGCCCCCGACCTGTGCGCCAAGGAC<br>TTCGAGGATCTGTTCAAGCAGGAAGAGAGCCTGAAGAATATCAAGG<br>ACTCCCTGCAGCAGTCCAGCGGCCGGATCGACATCATCCACAGCAAG<br>AAAACAGCCGCCCTGCAGTCCGCCACCCCCGTGGAAAGAGTGAAGCT<br>GCAGGAAGCCCTGAGCCAGCTGGACTTCCAGTGGGAGAAAGTGAAC<br>AAGATGTACAAGGACCGGCAGGGCAGATTCGACCGCAGCGTGGAAA<br>AGTGGCGGCGGTTCCACTACGACATCAAGATCTTCAACCAGTGGCTG<br>ACCGAGGCCGAGCAGTTCCTGAGAAAGACCCAGATCCCCGAGAACT |

TABLE 9-continued

Nucleotide Sequences of Dystrophin constructs.

| SEQ ID NO and Description | Sequence |
|---|---|
| | GGGAGCACGCCAAGTACAAGTGGTATCTGAAAGAGCTGCAGGACGG
CATCGGCCAGCGGCAGACAGTGGTCCGCACCCTGAATGCCACCGGCG
AGGAAATCATCCAGCAGAGCAGCAAGACCGACGCCAGCATCCTGCA
GGAAAAGCTGGGCAGCCTGAACCTGCGGTGGCAGGAAGTGTGCAAG
CAGCTGAGCGACCGGAAGAAGCGGCTGGAAGAACAGGCCCCTGGCC
TGACCACAATCGGCGCCAGCCCTACCCAGACCGTGACCCTGGTGACA
CAGCCCGTGGTGACAAAAGAGACAGCCATCAGCAAGCTGGAAATGC
CCAGCAGCCTGATGCTGGAAAGCGACCAGTGGAAGCGGCTGCACCT
GAGCCTGCAGGAACTGCTGGTCTGGCTGCAGCTGAAGGACGACGAG
CTGAGCAGACAGGCCCCCATCGGCGGCGATTTCCCCGCCGTGCAGAA
ACAGAACGACGTGCACCGGGCCTTCAAGCGCGAGCTGAAAACAAAA
GAACCCGTGATCATGAGCACCCTGGAAACCGTGCGGATCTTCCTGAC
CGAGCAGCCCCTGGAAGGCCTGGAAAAGCTGTACCAGGAACCCAGA
GAGCTGCCCCCCGAGGAACGGGCCCAGAACGTGACCAGACTGCTGC
GGAAGCAGGCCGAAGAGGTCAACACCGAGTGGGAGAAGCTGAACCT
GCACAGCGCCGACTGGCAGCGGAAGATCGACGAGACACTGGAACGG
CTGCAGGAACTGCAGGAGGCCACCGACGAGCTGGACCTGAAGCTGA
GACAGGCCGAAGTGATCAAGGGCAGCTGGCAGCCCGTGGGCGACCT
GCTGATCGACTCCCTGCAGGACCACCTGGAAAAAGTGAAGGCCCTGC
GGGGCGAGATCGCCCCCCTGAAAGAAAACGTGTCCCACGTGAACGA
CCTGGCCCGGCAGCTGACCACCCTGGGCATCCAGCTGAGCCCCTACA
ACCTGTCCACCCTGGAAGATCTGAACACCCGGTGGAAGCTGCTGCAG
GTGGCCGTGGAAGATAGAGTGCGGCAGCTGCACGAGGCCCACAGAG
ACTTTGGCCCTGCCAGCCAGCACTTCCTGAGCACCTCTGTGCAGGGA
CCCTGGGAGAGAGCCATCAGCCCCAACAAGGTGCCCTACTACATCAA
CCACGAGACACAGACCACCTGTTGGGACCACCCCAAGATGACCGAG
CTGTACCAGAGCCTGGCCGACCTGAACAATGTGCGGTTCAGCGCCTA
CCGGACCGCCATGAAGCTGAGGCGGCTGCAGAAAGCTCTGTGCCTGG
ATCTGCTGAGCCTGAGCGCCGCCTGCGACGCCCTGGACCAGCACAAC
CTGAAGCAGAACGACCAGCCCATGGATATCCTGCAGATCATCAACTG
CCTGACCACAATCTACGACAGGCTGGAACAGGAACACAACAATCTG
GTCAACGTGCCCCTGTGCGTGGACATGTGCCTGAATTGGCTGCTGAA
TGTGTACGACACCGGCCGGACCGGCAGAATCCGGGTGCTGAGCTTCA
AGACCGGCATCATCAGCCTGTGCAAGGCCCACCTGGAAGATAAGTAC
CGCTACCTGTTCAAACAGGTGGCCAGCTCCACCGGCTTTTGCGACCA
GCGGAGACTGGGCCTGCTGCTGCACGACAGCATCCAGATCCCCAGAC
AGCTGGGCGAGGTGGCCTCCTTCGGCGGCAGCAACATTGAGCCCAGC
GTGCGGAGCTGCTTCCAGTTCGCCAACAACAAGCCCGAGATCGAGGC
CGCCCTGTTCCTGGACTGGATGAGACTGGAACCCCAGAGCATGGTGT
GGCTGCCCGTGCTGCATCGGGTGGCCGCTGCCGAGACAGCCAAGCAC
CAGGCCAAGTGCAACATCTGCAAAGAGTGCCCCATCATCGGCTTCCG
GTACAGAAGCCTGAAGCACTTCAACTACGATATCTGCCAGAGCTGCT
TCTTCAGCGGCAGAGTGGCCAAGGGCCACAAAATGCACTACCCCATG
GTGGAATACTGCACCCCCACCACCAGCGGCGAGGATGTGCGGGACTT
CGCCAAGGTGCTGAAAAACAAGTTCCGGACCAAGCGGTACTTTGCCA
AGCACCCCCGGATGGGCTACCTGCCCGTGCAGACAGTGCTGGAAGGC
GACAACATGGAAACCTGA |
| SEQ ID NO: 104 - BXA- 212372- J4V4 | ATGCTGTGGTGGGAGGAAGTGGAAGATTGCTACGAGCGCGAGGACG
TGCAGAAGAAAACCTTCACCAAATGGGTGAACGCCCAGTTCAGCAA
GTTCGGCAAGCAGCACATCGAGAACCTGTTCAGCGACCTGCAGGACG
GCAGACGGCTGCTGGACCTGCTGGAAGGCCTGACCGGCCAGAAGCT
GCCCAAAGAGAAGGGCAGCACCAGAGTGCACGCCCTGAACAACGTG
AACAAGGCCCTGCGGGTGCTGCAGAACAACAACGTGGACCTGGTGA
ACATCGGCAGCACCGACATCGTGGACGGCAACCACAAGCTGACCCTG
GGCCTGATCTGGAACATCATCCTGCACTGGCAGGTCAAAAACGTGAT
GAAGAACATCATGGCCGGCCTGCAGCAGACCAACAGCGAGAAGATC
CTGCTGAGCTGGGTGCGCCAGAGCACCCGGAACTACCCCCAGGTCAA
CGTGATCAACTTCACCACCTCTTGGAGCGACGGCCTGGCCCTGAACG
CCCTGATCCACAGCCACCGGCCCGACCTGTTCGACTGGAACAGCGTG
GTCTGCCAGCAGAGCGCCACCCAGCGGCTGGAACACGCCTTCAATAT
CGCCAGATACCAGCTGGGCATCGAGAAGCTGCTGGATCCCGAGGAC
GTGGACACCACCTACCCCGACAAGAAATCCATCCTGATGTATATCAC
CAGCCTGTTCCAGGTGCTGCCCCAGCAGGTGTCCATCGAGGCCATCC
AGGAAGTGGAAATGCTGCCCAGACCCCCCAAAGTGACCAAAGAGGA
ACATTCCAGCTGCACCACCAGATGCACTACAGCCAGCAGATCACCG
TGTCCCTGGCTCAGGGCTACGAGCGGACCAGCAGCCCCAAGCCCCGG
TTCAAGAGCTACGCCTACACCCAGGCCGCCTACGTGACCACCAGCGA
CCCCACCAGAAGCCCATTCCCCAGCCAGCATCTGGAAGCCCCCGAGG
ACAAGAGCTTCGGCAGCAGCCTGATGGAAAGCGAAGTGAACCTGGA
CAGATACCAGACCGCCCTGGAAGAGGTGCTGTCCTGGCTGCTGAGCG
CCGAGGATACACTGCAGGCCCAGGGCGAGATCAGCAACGACGTGGA
AGTGGTGAAAGACCAGTTCCACACCCACGAGGGCTACATGATGGACC
TGACCGCCCACCAGGGCAGAGTGGGCAACATCCTGCAGCTGGGCAG |

TABLE 9-continued

Nucleotide Sequences of Dystrophin constructs.

| SEQ ID NO and Description | Sequence |
|---|---|
| | CAAGCTGATCGGCACCGGCAAGCTGAGCGAGGACGAAGAGACAGAG<br>GTGCAGGAACAGATGAACCTGCTGAACAGCAGATGGGAGTGCCTGC<br>GGGTGGCCAGCATGGAAAAGCAGAGCAACCTGCACAGAGTTTTAAT<br>GGATCTCACCTACCTGACCGAGATCACCCACGTGTCCCAGGCTCTGC<br>TGGAAGTGGAACAGCTGCTGAACGCCCCCGACCTGTGCGCCAAGGAC<br>TTCGAGGATCTGTTCAAGCAGGAAGAGAGCCTGAAGAATATCAAGG<br>ACTCCCTGCAGCAGTCCAGCGGCCGGATCGACATCATCCACAGCAAG<br>AAAACAGCCGCCCTGCAGTCCGCCACCCCCGTGGAAAGAGTGAAGCT<br>GCAGGAAGCCCTGAGCCAGCTGGACTTCCAGTGGGAGAAAGTGAAC<br>AAGATGTACAAGGACCGGCAGGGCAGATTCGACCGCAGCGTGGAAA<br>AGTGGCGGCGGTTCCACTACGACATCAAGATCTTCAACCAGTGGCTG<br>ACCGAGGCCGAGCAGTTCCTGAGAAAGACCCAGATCCCCGAGAACT<br>GGGAGCACGCCAAGTACAAGTGGTATCTGAAAGAGCTGCAGGACGG<br>CATCGGCCAGCGGCAGACAGTGGTCCGCACCCTGAATGCCACCGGCG<br>AGGAAATCATCCAGCAGAGCAGCAAGACCGACGCCAGCATCCTGCA<br>GGAAAAGCTGGGCAGCCTGAACCTGCGGTGGCAGGAAGTGTGCAAG<br>CAGCTGAGCGACCGGAAGAAGCGGCTGGAAGAACAGGCCCCTGGCC<br>TGACCACAATCGGCGCCAGCCCTACCCAGACCGTGACCCTGGTGACA<br>CAGCCCGTGGTGACAAAAGAGACAGCCATCAGCAAGCTGGAAATGC<br>CCAGCAGCCTGATGCTGGAAAGCGACCAGTGGAAGCGGCTGCACCT<br>GAGCCTGCAGGAACTGCTGGTCTGGCTGCAGCTGAAGGACGACGAG<br>CTGAGCAGACAGGCCCCCATCGGCGGCGATTTCCCCGCCGTGCAGAA<br>ACAGAACGACGTGCACCGGGCCTTCAAGCGCGAGCTGAAAACAAAA<br>GAACCCGTGATCATGAGCACCCTGGAAACCGTGCGGATCTTCCTGAC<br>CGAGCAGCCCCTGGAAGGCCTGGAAAAGCTGTACCAGGAACCCAGA<br>GAGCTGCCCCCCGAGGAACGGGCCCAGAACGTGACCAGACTGCTGC<br>GGAAGCAGGCCGAAGAGGTCAACACCGAGTGGGAGAAGCTGAACCT<br>GCACAGCGCCGACTGGCAGCGGAAGATCGACGAGACACTGGAACGG<br>CTGCAGGAACTGCAGGAGGCCACCGACGAGCTGGACCTGAAGCTGA<br>GACAGGCCGAAGTGATCAAGGGCAGCTGGCAGCCCGTGGGCGACCT<br>GCTGATCGACTCCCTGCAGGACCACCTGGAAAAAGTGAAGGCCCTGC<br>GGGGCGAGATCGCCCCCCTGAAAGAAAACGTGTCCCACGTGAACGA<br>CCTGGCCCGGCAGCTGACCACCCTGGGCATCCAGCTGAGCCCCTACA<br>ACCTGTCCACCCTGGAAGATCTGAACACCCGGTGGAAGCTGCTGCAG<br>GTGGCCGTGGAAGATAGAGTGCGGCAGCTGCACGAGGCCCACAGAG<br>ACTTTGGCCCTGCCAGCCAGCACTTCCTGAGCACCTCTGTGCAGGGA<br>CCCTGGGAGAGAGCCATCAGCCCCAACAAGGTGCCCTACTACATCAA<br>CCACGAGACACGACCACCTGTTGGGACCACCCCAAGATGACCGAG<br>CTGTACCAGAGCCTGGCCGACCTGAACAATGTGCGGTTCAGCGCCTA<br>CCGGACCGCCATGAAGCTGAGGCGGCTGCAGAAAGCTCTGTGCCTGG<br>ATCTGCTGAGCCTGAGCGCCGCCTGCGACGCCCTGGACCAGCACAAC<br>CTGAAGCAGAACGACCAGCCCATGGATATCCTGCAGATCATCAACTG<br>CCTGACCACAATCTACGACAGGCTGGAACAGGAACACAACAATCTG<br>GTCAACGTGCCCCTGTGCGTGGACATGTGCCTGAATTGGCTGCTGAA<br>TGTGTACGACACCGGCCGGACCGGCAGAATCCGGGTGCTGAGCTTCA<br>AGACCGGCATCATCAGCCTGTGCAAGGCCCACCTGGAAGATAAGTAC<br>CGCTACCTGTTCAAACAGGTGGCCAGCTCCACCGGCTTTTGCGACCA<br>GCGGAGACTGGGCCTGCTGCTGCACGACAGCATCCAGATCCCCCAGAC<br>AGCTGGGCGAGGTGGCCTCCTTCGGCGGCAGCAACATTGAGCCCAGC<br>GTGCGGAGCTGCTTCCAGTTCGCCAACAACAAGCCCGAGATCGAGGC<br>CGCCCTGTTCCTGGACTGGATGAGACTGGAACCCCAGAGCATGGTGT<br>GGCTGCCCGTGCTGCATCGGGTGGCCGCTGCCGAGACAGCCAAGCAC<br>CAGGCCAAGTGCAACATCTGCAAAGAGTGCCCCATCATCGGCTTCCG<br>GTACAGAAGCCTGAAGCACTTCAACTACGATATCGCCAGAGCTGCT<br>TCTTCAGCGGCAGAGTGGCCAAGGGCCACAAAATGCACTACCCCATG<br>GTGGAATACTGCACCCCCACCACCAGCGGCGAGGATGTGCGGGACTT<br>CGCCAAGGTGCTGAAAAACAAGTTCCGGACCAAGCGGTACTTTGCCA<br>AGCACCCCCGGATGGGCTACCTGCCCGTGCAGACAGTGCTGGAAGGC<br>GACAACATGGAAACCTGA |
| SEQ ID NO: 105 - BXA-212372-J4 | ATGCTGTGGTGGGAGGAAGTGGAAGATTGCTACGAGCGCGAGGACG<br>TGCAGAAGAAAACCTTCACCAAATGGGTGAACGCCCAGTTCAGCAA<br>GTTCGGCAAGCAGCACATCGAGAACCTGTTCAGCGACCTGCAGGACG<br>GCAGACGGCTGCTGGACCTGCTGGAAGGCCTGACCGGCCAGAAGCT<br>GCCCAAAGAGAAGGGCAGCACCAGAGTGCACGCCCTGAACAACGTG<br>AACAAGGCCCTGCGGGTGCTGCAGAACAACAACGTGGACCTGGTGA<br>ACATCGGCAGCACCGACATCGTGGACGGCAACCACAAGCTGACCCTG<br>GGCCTGATCTGGAACATCATCCTGCACTGGCAGGTCAAAAACGTGAT<br>GAAGAACATCATGGCCGGCCTGCAGCAGACCAACAGCGAGAAGATC<br>CTGCTGAGCTGGGTGCGCCAGAGCACCCGGAACTACCCCCAGGTCAA<br>CGTGATCAACTTCACCACCTCTTGGAGCGACGGCCTGGCCCTGAACG<br>CCCTGATCCACAGCCACCGGCCCGACCTGTTCGACTGGAACAGCGTG<br>GTCTGCCAGCAGAGCGCCACCCAGCGGCTGGAACACGCCTTCAATAT<br>CGCCAGATACCAGCTGGGCATCGAGAAGCTGCTGGATCCCGAGGAC |

TABLE 9-continued

Nucleotide Sequences of Dystrophin constructs.

SEQ ID
NO and
Description Sequence

GTGGACACCACCTACCCCGACAAGAAATCCATCCTGATGTATATCAC
CAGCCTGTTCCAGGTGCTGCCCCAGCAGGTGTCCATCGAGGCCATCC
AGGAAGTGGAAATGCTGCCCAGACCCCCCAAAGTGACCAAAGAGGA
ACACTTCCAGCTGCACCACCAGATGCACTACAGCCAGCAGATCACCG
TGTCCCTGGCTCAGGGCTACGAGCGGACCAGCAGCCCCAAGCCCCGG
TTCAAGAGCTACGCCTACACCCAGGCCGCCTACGTGACCACCAGCGA
CCCCACCAGAAGCCCATTCCCCAGCCAGCATCTGGAAGCCCCCGAGG
ACAAGAGCTTCGGCAGCAGCCTGATGGAAAGCGAAGTGAACCTGGA
CAGATACCAGACCGCCCTGGAAGAGGTGCTGTCCTGGCTGCTGAGCG
CCGAGGATACACTGCAGGCCCAGGGCGAGATCAGCAACGACGTGGA
AGTGGTGAAAGACCAGTTCCACACCCACGAGGGCTACATGATGGACC
TGACCGCCCACCAGGGCAGAGTGGGCAACATCCTGCAGCTGGGCAG
CAAGCTGATCGGCACCGGCAAGCTGAGCGAGGACGAAGAGACAGAG
GTGCAGGAACAGATGAACCTGCTGAACAGCAGATGGGAGTGCCTGC
GGGTGGCCAGCATGGAAAAGCAGAGCAACCTGCACAGCTACGTGCC
CAGCACCTACCTGACCGAGATCACCCACGTGTCCCAGGCTCTGCTGG
AAGTGGAACAGCTGCTGAACGCCCCCGACCTGTGCGCCAAGGACTTC
GAGGATCTGTTCAAGCAGGAAGAGAGCCTGAAGAATATCAAGGACT
CCCTGCAGCAGTCCAGCGGCCGGATCGACATCATCCACAGCAAGAAA
ACAGCCGCCCTGCAGTCCGCCACCCCCGTGGAAAGAGTGAAGCTGCA
GGAAGCCCTGAGCCAGCTGGACTTCCAGTGGGAGAAAGTGAACAAG
ATGTACAAGGACCGGCAGGGCAGATTCGACCGCAGCGTGGAAAAGT
GGCGGCGGTTCCACTACGACATCAAGATCTTCAACCAGTGGCTGACC
GAGGCCGAGCAGTTCCTGAGAAAGACCCAGATCCCCGAGAACTGGG
AGCACGCCAAGTACAAGTGGTATCTGAAAGAGCTGCAGGACGGCAT
CGGCCAGCGGCAGACAGTGGTCCGCACCCTGAATGCCACCGGCGAG
GAAATCATCCAGCAGAGCAGCAAGACCGACGCCAGCATCCTGCAGG
AAAAGCTGGGCAGCCTGAACCTGCGGTGGCAGGAAGTGTGCAAGCA
GCTGAGCGACCGGAAGAAGCGGCTGGAAGAACAGGCCCCTGGCCTG
ACCACAATCGGCGCCAGCCCTACCCAGACCGTGACCCTGGTGACACA
GCCCGTGGTGACAAAAGAGACAGCCATCAGCAAGCTGGAAATGCCC
AGCAGCCTGATGCTGGAAAGCGACCAGTGGAAGCGGCTGCACCTGA
GCCTGCAGGAACTGCTGGTCTGGCTGCAGCTGAAGGACGACGAGCTG
AGCAGACAGGCCCCCATCGGCGGCGATTTCCCCGCCGTGCAGAAACA
GAACGACGTGCACCGGGCCTTCAAGCGCGAGCTGAAAACAAAAGAA
CCCGTGATCATGAGCACCCTGGAAACCGTGCGGATCTTCCTGACCGA
GCAGCCCCTGGAAGGCCTGGAAAAGCTGTACCAGGAACCCAGAGAG
CTGCCCCCCGAGGAACGGGCCCAGAACGTGACCAGACTGCTGCGGA
AGCAGGCCGAAGAGGTCAACACCGAGTGGGAGAAGCTGAACCTGCA
CAGCGCCGACTGGCAGCGGAAGATCGACGAGACACTGGAACGGCTG
CAGGAACTGCAGGAGGCCACCGACGAGCTGGACCTGAAGCTGAGAC
AGGCCGAAGTGATCAAGGGCAGCTGGCAGCCCGTGGGCGACCTGCT
GATCGACTCCCTGCAGGACCACCTGGAAAAAGTGAAGGCCCTGCGG
GGCGAGATCGCCCCCCTGAAAGAAAACGTGTCCCACGTGAACGACCT
GGCCCGGCAGCTGACCACCCTGGGCATCCAGCTGAGCCCCTACAACC
TGTCCACCCTGGAAGATCTGAACACCCGGTGGAAGCTGCTGCAGGTG
GCCGTGGAAGATAGAGTGCGGCAGCTGCACGAGGCCCACAGAGACT
TTGGCCCTGCCAGCCAGCACTTCCTGAGCACCTCTGTGCAGGGACCC
TGGGAGAGAGCCATCAGCCCCAACAAGGTGCCCTACTACATCAACCA
CGAGACACAGACCACCTGTTGGGACCACCCCAAGATGACCGAGCTGT
ACCAGAGCCTGGCCGACCTGAACAATGTGCGGTTCAGCGCCTACCGG
ACCGCCATGAAGCTGAGGCGGCTGCAGAAAGCTCTGTGCCTGGATCT
GCTGAGCCTGAGCGCCGCCTGCGACGCCCTGGACCAGCACAACCTGA
AGCAGAACGACCAGCCCATGGATATCCTGCAGATCATCAACTGCCTG
ACCACAATCTACGACAGGCTGGAACAGGAACACAACAATCTGGTCA
ACGTGCCCCTGTGCGTGGACATGTGCCTGAATTGGCTGCTGAATGTG
TACGACACCGGCCGGACCGGCAGAATCCGGGTGCTGAGCTTCAAGAC
CGGCATCATCAGCCTGTGCAAGGCCCACCTGGAAGATAAGTACCGCT
ACCTGTTCAAACAGGTGGCCAGCTCCACCGGCTTTTGCGACCAGCGG
AGACTGGGCCTGCTGCTGCACGACAGCATCCAGATCCCCAGACAGCT
GGGCGAGGTGGCCTCCTTCGGCGGCAGCAACATTGAGCCCAGCGTGC
GGAGCTGCTTCCAGTTCGCCAACAACAAGCCCGAGATCGAGGCCGCC
CTGTTCCTGGACTGGATGAGACTGGAACCCCAGAGCATGGTGTGGCT
GCCCGTGCTGCATCGGGTGGCCGCTGCCGAGACAGCCAAGCACCAGG
CCAAGTGCAACATCTGCAAAGAGTGCCCCATCATCGGCTTCCGGTAC
AGAAGCCTGAAGCACTTCAACTACGATATCTGCCAGAGCTGCTTCTT
CAGCGGCAGAGTGGCCAAGGGCCACAAAATGCACTACCCCATGGTG
GAATACTGCACCCCCACCACCAGCGGCGAGGATGTGCGGGACTTCGC
CAAGGTGCTGAAAAACAAGTTCCGGACCAAGCGGTACTTTGCCAAGC
ACCCCCGGATGGGCTACCTGCCCGTGCAGACAGTGCTGGAAGGCGAC
AACATGGAAACCTGA

TABLE 9-continued

Nucleotide Sequences of Dystrophin constructs.

| SEQ ID NO and Description | Sequence |
|---|---|
| SEQ ID NO: 106 - BXA-212372 | ATGCTGTGGTGGGAGGAAGTGGAAGATTGCTACGAGCGCGAGGACG<br>TGCAGAAGAAAACCTTCACCAAATGGGTGAACGCCCAGTTCAGCAA<br>GTTCGGCAAGCAGCACATCGAGAACCTGTTCAGCGACCTGCAGGACG<br>GCAGACGGCTGCTGGACCTGCTGGAAGGCCTGACCGGCCAGAAGCT<br>GCCCAAAGAGAAGGGCAGCACCAGAGTGCACGCCCTGAACAACGTG<br>AACAAGGCCCTGCGGGTGCTGCAGAACAACAACGTGGACCTGGTGA<br>ACATCGGCAGCACCGACATCGTGGACGGCAACCACAAGCTGACCCTG<br>GGCCTGATCTGGAACATCATCCTGCACTGGCAGGTCAAAAACGTGAT<br>GAAGAACATCATGGCCGGCCTGCAGCAGACCAACAGCGAGAAGATC<br>CTGCTGAGCTGGGTGCGCCAGAGCACCCGGAACTACCCCCAGGTCAA<br>CGTGATCAACTTCACCACCTCTTGGAGCGACGGCCTGGCCCTGAACG<br>CCCTGATCCACAGCCACCGGCCCGACCTGTTCGACTGGAACAGCGTG<br>GTCTGCCAGCAGAGCGCCACCCAGCGGCTGGAACACGCCTTCAATAT<br>CGCCAGATACCAGCTGGGCATCGAGAAGCTGCTGGATCCCGAGGAC<br>GTGGACACCACCTACCCCGACAAGAAATCCATCCTGATGTATATCAC<br>CAGCCTGTTCCAGGTGCTGCCCCAGCAGGTGTCCATCGAGGCCATCC<br>AGGAAGTGGAAATGCTGCCCAGACCCCCCAAAGTGACCAAAGAGGA<br>ACACTTCCAGCTGCACCACCAGATGCACTACAGCCAGCAGATCACCG<br>TGTCCCTGGCTCAGGGCTACGAGCGGACCAGCAGCCCCAAGCCCCGG<br>TTCAAGAGCTACGCCTACACCCAGGCCGCCTACGTGACCACCAGCGA<br>CCCCACCAGAAGCCCATTCCCCAGCCAGCATCTGGAAGCCCCGAGG<br>ACAAGAGCTTCGGCAGCAGCCTGATGGAAAGCGAAGTGAACCTGGA<br>CAGATACCAGACCGCCCTGGAAGAGGTGCTGTCCTGGCTGCTGAGCG<br>CCGAGGATACACTGCAGGCCCAGGGCGAGATCAGCAACGACGTGGA<br>AGTGGTGAAAGACCAGTTCCACACCCACGAGGGCTACATGATGGACC<br>TGACCGCCCACCAGGGCAGAGTGGGCAACATCCTGCAGCTGGGCAG<br>CAAGCTGATCGGCACCGGCAAGCTGAGCGAGGACGAAGAGACAGAG<br>GTGCAGGAACAGATGAACCTGCTGAACAGCAGATGGGAGTGCCTGC<br>GGGTGGCCAGCATGGAAAAGCAGAGCAACCTGCACATCCACACCGT<br>GCGGGAAGAGACAATGATGGTGATGACCGAGGACATGCCCCTGGAA<br>ATCAGCTACGTGCCCAGCACCTACCTGACCGAGATCACCCACGTGTC<br>CCAGGCTCTGCTGGAAGTGGAACAGCTGCTGAACGCCCCCGAGCCTGT<br>GCGCCAAGGACTTCGAGGATCTGTTCAAGCAGGAAGAGAGCCTGAA<br>GAATATCAAGGACTCCCTGCAGCAGTCCAGCGGCCGGATCGACATCA<br>TCCACAGCAAGAAAACAGCCGCCCTGCAGTCCGCCACCCCCGTGGAA<br>AGAGTGAAGCTGCAGGAAGCCCTGAGCCAGCTGGACTTCCAGTGGG<br>AGAAAGTGAACAAGATGTACAAGGACCGGCAGGGCAGATTCGACCG<br>CAGCGTGGAAAAGTGGCGGCGGTTCCACTACGACATCAAGATCTTCA<br>ACCAGTGGCTGACCGAGGCCGAGCAGTTCCTGAGAAAGACCCAGAT<br>CCCCGAGAACTGGGAGCACGCCAAGTACAAGTGGTATCTGAAAGAG<br>CTGCAGGACGGCATCGGCCAGCGGCAGACAGTGGTCCGCACCCTGA<br>ATGCCACCGGCGAGGAAATCATCCAGCAGAGCAGCAAGACCGACGC<br>CAGCATCCTGCAGGAAAAGCTGGGCAGCCTGAACCTGCGGTGGCAG<br>GAAGTGTGCAAGCAGCTGAGCGACCGGAAGAAGCGGCTGGAAGAAC<br>AGGCCCCTGGCCTGACCACAATCGGCGCCAGCCCTACCCAGACCGTG<br>ACCCTGGTGACACAGCCCGTGGTGACAAAAGAGACAGCCATCAGCA<br>AGCTGGAAATGCCCAGCAGCCTGATGCTGGAAAGCGACCAGTGGAA<br>GCGGCTGCACCTGAGCCTGCAGGAACTGCTGGTCTGGCTGCAGCTGA<br>AGGACGACGAGCTGAGCAGACAGGCCCCCATCGGCGGCGATTTCCCC<br>GCCGTGCAGAAACAGAACGACGTGCACCGGGCCTTCAAGCGCGAGC<br>TGAAAACAAAAGAACCCGTGATCATGAGCACCCTGGAAACCGTGCG<br>GATCTTCCTGACCGAGCAGCCCCTGGAAGGCCTGGAAAAGCTGTACC<br>AGGAACCCAGAGAGCTGCCCCCCGAGGAACGGGCCCAGAACGTGAC<br>CAGACTGCTGCGGAAGCAGGCCGAAGAGGTCAACACCGAGTGGGAG<br>AAGCTGAACCTGCACAGCGCCGACTGGCAGCGGAAGATCGACGAGA<br>CACTGGAACGGCTGCAGGAACTGCAGGAGGCCACCGACGAGCTGGA<br>CCTGAAGCTGAGACAGGCCGAAGTGATCAAGGGCAGCTGGCAGCCC<br>GTGGGCGACCTGCTGATCGACTCCCTGCAGGACCACCTGGAAAAAGT<br>GAAGGCCCTGCGGGGCGAGATCGCCCCCCTGAAAGAAAACGTGTCC<br>CACGTGAACGACCTGGCCCGGCAGCTGACCACCCTGGGCATCCAGCT<br>GAGCCCCTACAACCTGTCCACCCTGGAAGATCTGAACACCCGGTGGA<br>AGCTGCTGCAGGTGGCCGTGGAAGATAGAGTGCGGCAGCTGCACGA<br>GGCCCACAGAGACTTTGGCCCTGCCAGCCAGCACTTCCTGAGCACCT<br>CTGTGCAGGGACCCTGGGAGAGAGCCATCAGCCCCAACAAGGTGCC<br>CTACTACATCAACCACGAGACACAGACCACCTGTTGGGACCACCCCA<br>AGATGACCGAGCTGTACCAGAGCCTGGCCGACCTGAACAATGTGCGG<br>TTCAGCGCCTACCGGACCGCCATGAAGCTGAGGCGGCTGCAGAAAGC<br>TCTGTGCCTGGATCTGCTGAGCCTGAGCGCCGCCTGCGACGCCCTGG<br>ACCAGCACAACCTGAAGCAGAACGACCAGCCCATGGATATCCTGCA<br>GATCATCAACTGCCTGACCACAATCTACGACAGGCTGGAACAGGAAC<br>ACAACAATCTGGTCAACGTGCCCCTGTGCGTGGACATGTGCCTGAAT<br>TGGCTGCTGAATGTGTACGACACCGGCCGGACCGGCAGAATCCGGGT<br>GCTGAGCTTCAAGACCGGCATCATCAGCCTGTGCAAGGCCCACCTGG<br>AAGATAAGTACCGCTACCTGTTCAAACAGGTGGCCAGCTCCACCGGC |

TABLE 9-continued

Nucleotide Sequences of Dystrophin constructs.

SEQ ID
NO and
Description Sequence

TTTTGCGACCAGCGGAGACTGGGCCTGCTGCTGCACGACAGCATCCA
GATCCCCAGACAGCTGGGCGAGGTGGCCTCCTTCGGCGGCAGCAACA
TTGAGCCCAGCGTGCGGAGCTGCTTCCAGTTCGCCAACAACAAGCCC
GAGATCGAGGCCGCCCTGTTCCTGGACTGGATGAGACTGGAACCCCA
GAGCATGGTGTGGCTGCCCGTGCTGCATCGGGTGGCCGCTGCCGAGA
CAGCCAAGCACCAGGCCAAGTGCAACATCTGCAAAGAGTGCCCCATC
ATCGGCTTCCGGTACAGAAGCCTGAAGCACTTCAACTACGATATCTG
CCAGAGCTGCTTCTTCAGCGGCAGAGTGGCCAAGGGCCACAAAATGC
ACTACCCCATGGTGGAATACTGCACCCCCACCACCAGCGGCGAGGAT
GTGCGGGACTTCGCCAAGGTGCTGAAAAACAAGTTCCGGACCAAGC
GGTACTTTGCCAAGCACCCCCGGATGGGCTACCTGCCCGTGCAGACA
GTGCTGGAAGGCGACAACATGGAAACCTGA

SEQ ID NO:100 and SEQ ID NO: 101 encode the same miniaturized dystrophin, except that the SEQ ID NO: 100 is codon optimized vis-à-vis SEQ ID NO: 101.

In some embodiments, a nucleotide sequence encoding the miniaturized dystrophin polypeptide comprises a nucleic acid sequence at least about 60%, 15 at least about 70%, at least about 80%, at least about 85%, at least about 90%, at least about 95%, at least about 96%, at least about 97%, at least about 98%, at least about 99%, or about 100% identical to SEQ ID NO: 100, wherein the miniaturized dystrophin polypeptide when expressed from the nucleotide sequence has at least one dystrophin activity. In some embodiments, a nucleotide sequence encoding the miniaturized dystrophin polypeptide comprises a nucleic acid sequence at least about 60%, 15 at least about 70%, at least about 80%, at least about 85%, at least about 90%, at least about 95%, at least about 96%, at least about 97%, at least about 98%, at least about 99%, or about 100% identical to SEQ ID NO: 101, wherein the miniaturized dystrophin polypeptide when expressed from the nucleotide sequence has at least one dystrophin activity. In some embodiments, a nucleotide sequence encoding the miniaturized dystrophin polypeptide comprises a nucleic acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 102, wherein the miniaturized dystrophin polypeptide when expressed from the nucleotide sequence has at least one dystrophin activity. In some embodiments, a nucleotide sequence encoding the miniaturized dystrophin polypeptide comprises a nucleic acid sequence at least about 60%, 15 at least about 70%, at least about 80%, at least about 85%, at least about 90%, at least about 95%, at least about 96%, at least about 97%, at least about 98%, at least about 99%, or about 100% identical to SEQ ID NO: 103, wherein the miniaturized dystrophin polypeptide when expressed from the nucleotide sequence has at least one dystrophin activity. In some embodiments, a nucleotide sequence encoding the miniaturized dystrophin polypeptide comprises a nucleic acid sequence at least about 60%, 15 at least about 70%, at least about 80%, at least about 85%, at least about 90%, at least about 95%, at least about 96%, at least about 97%, at least about 98%, at least about 99%, or about 100% identical to SEQ ID NO: 104, wherein the miniaturized dystrophin polypeptide when expressed from the nucleotide sequence has at least one dystrophin activity. In some embodiments, a nucleotide sequence encoding the miniaturized dystrophin polypeptide comprises a nucleic acid sequence at least about 60%, 15 at least about 70%, at least about 80%, at least about 85%, at least about 90%, at least about 95%, at least about 96%, at least about 97%, at least about 98%, at least about 99%, or about 100% identical to SEQ ID NO: 105, wherein the miniaturized dystrophin polypeptide when expressed from the nucleotide sequence has at least one dystrophin activity.

Non-Coding Polynucleotides

In some aspects, provided herein are nucleic acid molecules, e.g., DNA or RNA, comprising a nucleotide sequence encoding a miniaturized dystrophin polypeptide.

In some embodiments, the nucleic acid molecules disclosed herein comprise non-coding components. In some embodiments, the nucleic acid molecules disclosed herein comprise promoters. Certain exemplary regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources may be used, such as the SRa promoter system, which contains sequences from the SV40 early promoter and the long terminal repeat of human T cell leukemia virus type 1 (Takebe, Y. et al., *Mol. Cell. Biol.* 8:466-472 (1988)). In certain embodiments, the regulatory sequence comprises a tissue specific promoter. In some embodiments, the tissue specific promoter drives expression of the gene of interest in a tissue selected from the group consisting of heart, liver, lungs, eyes, nervous system, lymphatic system, central nervous system, neuronal cells, muscle and stem cells.

In some embodiments, the promoters disclosed herein are tissue-specific promoters. In some embodiments, the promoter drives expression of the therapeutic protein in hepatocytes, muscle cells, endothelial cells, sinusoidal cells, or neuronal cells, or any combination thereof. In some embodiments, the promoter is selected from the group consisting of C5-12(T) promoter, MLC2v-cTNT455 promoter, a synapsin 1 gene promoter, a mouse thyretin promoter (mTTR), an endogenous human factor VIII promoter (F8), a human alpha-1-antitrypsin promoter (hAAT), a human albumin minimal promoter, a mouse albumin promoter, a tristetraprolin (TTP) promoter, a CASI promoter, a CAG promoter, a cytomegalovirus (CMV) promoter, an al-antitrypsin (AAT) promoter, a muscle creatine kinase (MCK) promoter, a myosin heavy chain alpha (αMHC) promoter, a myoglobin (MB) promoter, a desmin (DES) promoter, a SPc5-12 promoter, a 2R5Sc5-12 promoter, a dMCK promoter, a tMCK promoter, an α-synuclein promoter and a phosphoglycerate kinase (PGK) promoter. In some embodiments, the promoter is the C5-12(T) promoter.

In some embodiments, the nucleic acid molecules disclosed herein comprise an intronic sequence. In some embodiments, the intronic sequence is positioned 5' to the nucleotide sequence encoding the miniaturized dystrophin polypeptide. In some embodiments, the intronic sequence is positioned 3' to the promoter. In some embodiments, the intronic sequence comprises a synthetic intronic sequence. In some embodiments, the intronic sequence is an SV40 intronic sequence.

In some embodiments, the nucleic acid molecules disclosed herein comprise a post-transcriptional regulatory element. In some embodiments, the post-transcriptional regulatory element is positioned 3' to the nucleotide sequence encoding the miniaturized dystrophin polypeptide. In some embodiments, the post-transcriptional regulatory element comprises a mutated woodchuck hepatitis virus post-transcriptional regulatory element (WPRE), a microRNA binding site, or a DNA nuclear targeting sequence, or any combination thereof.

In some embodiments, the nucleic acid molecules disclosed herein comprise a 3'UTR poly(A) tail sequence. In some embodiments, the 3'UTR poly(A) tail sequence is selected from the group consisting of bGH poly(A), actin poly(A), hemoglobin poly(A), dystrophin poly(A), and any combination thereof. In some embodiments, the 3'UTR poly(A) tail sequence comprises nucleotides from the N-terminal portion of the endogenous dystrophin 3'UTR. In some embodiments, the 3'UTR poly(A) tail sequence comprises the 25 nucleotides from the N-terminal portion of the endogenous dystrophin 3'UTR.

In some embodiments, the nucleic acid molecules disclosed herein comprise an enhancer sequence. In some embodiments, the nucleic acid molecules disclosed herein comprise a first inverted terminal repeat (ITR) and/or a second ITR. In some embodiments, the first ITR and the second ITR are identical. In some embodiments, the first ITR and/or the second ITR are derived from adeno-associated virus. In some embodiments, the first ITR is derived from adeno-associated virus, and the second ITR is derived from adeno-associated virus.

It is further recognized that the nucleic acid molecule can comprise additional elements that aid in the translation of the polypeptide. Such sequences include, for example, Kozak sequences attached to the 5' end of the polynucleotide encoding polypeptide. The Kozak consensus sequence is a sequence which occurs on eukaryotic mRNA that plays a role in the initiation of the translation process and has the consensus (gee)gccRccAUGG (SEQ ID NO:107); wherein (1) a lower case letter denotes the most common base at a position where the base can nevertheless vary; (2) upper case letters indicate highly-conserved bases, i.e. the 'AUGG' sequence is constant or rarely, if ever, changes, with the exception being the IUPAC ambiguity code 'R' which indicates that a purine (adenine or guanine) is normally observed at this position; and (3) the sequence in brackets ((gee)) is of uncertain significance.

In one non-limiting embodiment, the nucleic acid molecule comprises a functional variant or fragment thereof of a Kozak sequence. A functional variant or fragment thereof of a Kozak sequence will retain the ability to increase translation of the protein when compared to the level of translation from a sequence lacking the leader. Such a functional fragment can comprise at least 5, 6, 7, 8, 9, 10, 11, 12, 13, 14, 15, 16, 17, 18, 19, 20, 30, 40 continuous nucleotides of a Kozak sequence or the sequence set forth in SEQ ID NO:107 or SEQ ID NO:108 (gccaccATGG). Alternatively, a functional variant can comprise at least 80%, 85%, 90%, 91%, 92%, 93%, 94%, 95%, 96%, 97%, 98%, or 99% sequence identity to the Kozak sequence or the sequence set forth in SEQ ID NO:107 or SEQ ID NO:108.

In some embodiments, a nucleotide sequence of the present invention driving expression of a miniaturized dystrophin polypeptide comprises the sequence shown in Table 10.

TABLE 10

Nucleotide sequence (and domain structure thereof) driving expression of and encoding miniaturized dystrophin polypeptide BXA-220931.

| SEQ ID NO: | Description | Nucleotide Sequence |
|---|---|---|
| 109 | C5-12(T) Promoter | CCGCCTTCGGCACCATTCCTCACGACACCCAAATATGGCGAC GGGTGAGGAATGGTGGGGAGTTATTTTTAGAGCGGTGAGGAA GGTGGGCAGGCAGCAGGTGTTGGCGCTCTAAAAATAACTCCC GGGAGTTATTTTTAGAGCGGAGGAATGGTGGACACCCAAATA TGGCGACGGTTCCTCACCCGTCGCCATATTTGGGTGTCCGCCC TCGGCCGGGGCCGCATTCCTGGGGGCCGGGCGGTGCTCCCGC CCGCCTCGATAAAAGGCTCCGGGCCGGCGGCGGCCCACGA GCTACCCGGAGGAGCGGGAGGCACGCGT |
| 110 | SV40 Intron | CTCTAAGGTAAATATAAAATTTTTAAGTGTATAATGTGTTAAA CTACTGATTCTAATTGTTTCTCTCTTTTAGATTCCAACCTTTGG AACTGATCTAGACCACC |
| 111 | Coding Sequence for miniaturized Dystrophin BXA-220931 | ATGCTTTGGTGGGAAGAAGTCGAGGACTGCTACGAGCGCGAG GACGTGCAGAAGAAAACCTTCACCAAATGGGTCAACGCCCA GTTCAGCAAGTTCGGCAAGCAGCACATCGAGAACCTGTTCAG CGACCTGCAGGATGGCAGAAGGCTGCTGGATCTGCTGGAAGG CCTGACAGGCCAGAAGCTGCCTAAAGAGAAGGGCAGCACAA GAGTGCACGCCCTGAACAACGTGAACAAGGCCCTGAGAGTG CTGCAGAACAACAACGTGGACCTGGTCAACATCGGCAGCACC GACATCGTGGACGGCAATCACAAACTGACCCTGGGCCTGATC |

TABLE 10-continued

Nucleotide sequence (and domain structure thereof) driving expression of and encoding miniaturized dystrophin polypeptide BXA-220931.

| SEQ ID NO: | Description | Nucleotide Sequence |
|---|---|---|
| | | TGGAACATCATCCTGCACTGGCAAGTGAAGAACGTGATGAAG |
| | | AACATCATGGCCGGCCTGCAGCAGACCAACAGCGAGAAGAT |
| | | TCTGCTGAGCTGGGTCCGACAGAGCACCCGGAACTACCCTCA |
| | | AGTGAACGTGATCAACTTCACCACCTCTTGGAGCGACGGACT |
| | | GGCCCTGAATGCCCTGATTCACAGCCACAGACCTGACCTGTT |
| | | CGACTGGAATAGCGTCGTGTGTCAGCAGAGCGCCACACAGAG |
| | | ACTGGAACACGCCTTCAATATCGCCAGATACCAGCTGGGCAT |
| | | CGAGAAACTGCTGGACCCCGAGGATGTGGACACCACCTATCC |
| | | TGACAAGAAATCCATCCTCATGTACATCACCAGCCTGTTCCA |
| | | GGTGCTGCCCCAGCAAGTGTCTATCGAGGCCATTCAAGAGGT |
| | | CGAGATGCTGCCCAGACCTCCTAAAGTGACCAAAGAGGAAC |
| | | ACTTCCAGCTGCACCACCAGATGCACTACTCTCAGCAGATCA |
| | | CCGTGTCTCTGGCCCAGGGCTACGAGAGAACAAGCAGCCCCA |
| | | AGCCTCGGTTCAAGAGCTACGCCTATACACAGGCCGCCTACG |
| | | TGACCACCAGCGATCCCACAAGAAGCCCATTTCCAAGCCAGC |
| | | ATCTGGAAGCCCCTGAGGACAAGAGCTTTGGCAGCAGCCTGA |
| | | TGGAAAGCGAAGTGAACCTGGATAGATACCAGACAGCCCTG |
| | | GAAGAGGTGCTGTCTTGGCTGCTGTCTGCCGAAGATACACTG |
| | | CAGGCTCAGGGCGAGATCAGCAACGACGTGGAAGTGGTCAA |
| | | GGACCAGTTTCACACCCACGAGGGCTACATGATGGACCTGAC |
| | | AGCCCATCAGGGCAGAGTGGGCAATATCCTGCAGCTGGGCTC |
| | | TAAGCTGATCGGCACAGGCAAGCTGAGCGAGGACGAAGAGA |
| | | CAGAGGTGCAAGAGCAGATGAACCTGCTGAACAGCAGATGG |
| | | GAGTGTCTGAGAGTGGCCAGCATGGAAAAGCAGAGCAACCT |
| | | GCACCGGGTCCTGATGGATCTGCAGAATCAGAAGCTGACCGA |
| | | GATCACCCACGTGTCACAGGCCCTGCTTGAAGTGGAACAGCT |
| | | GCTGAACGCCCCTGATCTGTGCGCCAAGGACTTCGAGGATCT |
| | | GTTCAAGCAAGAGGAAAGCCTGAAGAATATCAAGGACTCTCT |
| | | GCAGCAGTCCAGCGGCCGGATCGACATCATCCACAGCAAGA |
| | | AAACAGCTGCCCTGCAGTCCGCCACACCTGTGGAAAGAGTGA |
| | | AACTGCAAGAGGCCCTGTCTCAGCTGGACTTCCAGTGGGAGA |
| | | AAGTGAACAAGATGTACAAGGACCGGCAGGGCAGATTCGAC |
| | | CGCTCTGTGGAAAAATGGCGGAGATTCCACTACGACATCAAG |
| | | ATCTTCAACCAGTGGCTGACAGAGGCCGAGCAGTTCCTGAGA |
| | | AAGACACAGATCCCCGAGAACTGGGAGCACGCCAAGTACAA |
| | | GTGGTATCTGAAAGAACTGCAGGACGGCATCGGCCAGAGGC |
| | | AGACAGTCGTTAGAACACTGAATGCCACCGGCGAGGAAATC |
| | | ATCCAGCAGAGCAGCAAGACCGACGCCAGCATCCTGCAAGA |
| | | GAAGCTGGGCAGCCTGAACCTGAGATGGCAAGAAGTGTGCA |
| | | AGCAGCTGTCCGACCGGAAGAAGAGGCTGGAAGAACAGGCC |
| | | CCTGGCCTGACAACAATCGGAGCCTCTCCTACACAGACCGTG |
| | | ACACTGGTCACACAGCCCGTGGTCACCAAAGAGACAGCCATC |
| | | AGCAAGCTGGAAATGCCCTCTAGCCTGATGCTCGAGAGCGAC |
| | | CAGTGGAAGAGACTGCACCTGTCTCTGCAAGAGCTGCTCGTG |
| | | TGGCTGCAGCTGAAGGACGATGAACTGAGCAGACAGGCCCC |
| | | AATCGGAGGCGATTTTCCTGCCGTGCAGAAACAGAACGACGT |
| | | GCACAGAGCCTTCAAGCGGGAACTGAAAACAAAAGAACCCG |
| | | TGATCATGAGCACCCTGGAAACCGTGCGGATCTTCCTGACAG |
| | | AGCAGCCTCTCGAAGGCCTGGAAAAGCTGTACCAAGAGCCTA |
| | | GAGAGCTGCCTCCTGAGGAACGGGCCCAGAATGTGACCAGA |
| | | CTGCTGAGAAAGCAGGCCGAAGAGGTCAACACCGAATGGGA |
| | | GAAGCTGAACCTGCACAGCGCCGACTGGCAGAGAAAGATCG |
| | | ACGAGACACTGGAACGGCTGCAAGAACTCCAAGAAGCCACC |
| | | GACGAGCTGGACCTGAAACTGAGGCAGGCTGAAGTGATCAA |
| | | AGGCAGCTGGCAGCCAGTGGGCGACCTGCTGATTGATAGTCT |
| | | GCAGGACCACCTGGAAAAAGTGAAGGCCCTGCGGGGAGAGA |
| | | TCGCCCCACTGAAAGAAAACGTGTCCCACGTGAACGACCTGG |
| | | CCAGACAGCTGACAACCCTGGGAATCCAGCTGTCCCCTTACA |
| | | ACCTGTCCACACTGGAAGATCTGAACACCCGGTGGAAACTGC |
| | | TCCAGGTGGCCGTGGAAGATAGAGTGCGACAGCTGCACGAG |
| | | GCCCACAGAGATTTTGGACCAGCCAGCCAGCACTTCCTGTCT |
| | | ACATCTGTGCAAGGCCCTTGGGAGAGAGCTATCAGCCCTAAC |
| | | AAGGTGCCCTACTACATCAACCACGAGACACAGACCACCTGT |
| | | TGGGATCACCCCAAGATGACCGAGCTGTATCAGAGCCTGGCC |
| | | GACCTGAACAATGTGCGCTTTAGCGCCTACCGGACCGCCATG |
| | | AAGCTGCGGAGACTGCAGAAAGCCCTGTGTCTGGACCTGCTG |
| | | TCTCTGTCTGCAGCCTGTGATGCCCTGGACCAGCACAACCTG |
| | | AAGCAGAACGACCAGCCTATGGACATCCTCCAGATCATCAAC |
| | | TGCCTGACCACCATCTACGACCGGCTGGAACAAGAGCACAAC |
| | | AACCTCGTGAATGTGCCCCTGTGCGTGGACATGTGTCTGAAC |
| | | TGGCTGCTGAATGTGTACGACACCGGCAGAACCGGCAGGATC |
| | | AGAGTGCTGAGCTTCAAGACCGGCATCATCTCCCTGTGCAAA |

TABLE 10-continued

Nucleotide sequence (and domain structure thereof) driving expression of and encoding miniaturized dystrophin polypeptide BXA-220931.

| SEQ ID NO: | Description | Nucleotide Sequence |
|---|---|---|
| | | GCCCACCTCGAGGACAAGTACAGATACCTGTTCAAACAGGTG GCCAGCTCCACCGGCTTTTGCGATCAAAGAAGGCTGGGCCTG CTGCTGCACGACAGCATCCAGATTCCTAGACAGCTGGGCGAA GTGGCCTCCTTCGGCGGATCTAATATTGAGCCTAGCGTGCGG AGCTGCTTCCAGTTCGCCAACAACAAGCCTGAGATCGAGGCC GCTCTGTTCCTGGATTGGATGCGCCTGGAACCTCAGAGCATG GTTTGGCTGCCTGTGCTGCATAGAGTGGCCGCTGCCGAAACA GCCAAGCACCAGGCCAAGTGCAACATCTGCAAAGAGTGCCCC ATCATCGGCTTCCGGTACAGATCCCTGAAGCACTTCAACTAC GATATCTGCCAGAGCTGTTTCTTCTCTGGCCGCGTGGCCAAGG GCCACAAAATGCACTACCCCATGGTGGAATACTGCACCCCTA CCACATCTGGCGAAGATGTGCGGGATTTCGCCAAGGTGCTGA AAAACAAGTTCCGGACCAAGCGGTACTTCGCTAAGCACCCCA GAATGGGCTATCTGCCCGTGCAGACAGTGCTCGAGGGCGATA ACATGGAAACCTGA |
| 112 | 3' UTR | GAAGTCTTTTCCACATGGCAGATGA |
| 113 | PolyA | AATAAAAGATCCTTATTTTCATTGGATCTGTGTGTTGGTTTTT TGTGTG |

In some embodiments, a nucleotide sequence encoding the miniaturized dystrophin polypeptide comprises a nucleic acid sequence at least about 60%, 15 at least about 70%, at least about 80%, at least about 85%, at least about 90%, at least about 95%, at least about 96%, at least about 97%, at least about 98%, at least about 99%, or about 100% identical to the combined sequence of SEQ ID NO: 109 to 113.

Heterologous Moieties

In some embodiments, the polypeptides of the present disclosure can further comprise an additional element, e.g., heterologous moiety. Such elements can aid in the expression of the polypeptide, aid in the secretion of the polypeptide, improve the stability of the polypeptide, allow for more efficient purification of the polypeptide, and/or modulate the activity of the polypeptide. In some embodiments, the heterologous moiety is a polypeptide moiety. In other embodiments, the heterologous moiety is a non-polypeptide moiety.

In some embodiments, the polypeptide comprises a heterologous moiety fused to the polypeptide.

In some embodiments, the polypeptide disclosed herein comprises one or more additional heterologous moieties. In some embodiments, the heterologous moieties are half-life extending moieties. In some embodiments, the heterologous moiety comprises albumin or a fragment thereof, an immunoglobulin Fc region, the C-terminal peptide (CTP) of the β subunit of human chorionic gonadotropin, a PAS sequence, a HAP sequence, a transferrin or a fragment thereof, or an albumin-binding moiety or a derivative thereof, or any combination thereof.

In some embodiments, the polypeptides disclosed herein comprise one or more additional heterologous moieties. In some embodiments, the heterologous moieties are half-life extending moieties. In some embodiments, the heterologous moiety comprises albumin, an immunoglobulin constant region or a portion thereof, an immunoglobulin-binding polypeptide, an immunoglobulin G (IgG), albumin-binding polypeptide (ABP), a PASylation moiety, a HESylation moiety, XTEN, a PEGylation moiety, or an Fc region, or any combination thereof.

Cells

In certain aspects, provided herein are cells (e.g., host cells) expressing (e.g., recombinantly) proteins described herein and expression vectors comprising nucleotides that encode proteins described herein.

In some embodiments, the host cell comprises the nucleic acid molecules described herein. In some embodiments, the host cell comprises the vectors described herein.

In some embodiments, the host cell is a eukaryotic cell. In some embodiments, the host cell is selected from the group consisting of a mammalian cell, an insect cell, a yeast cell, a transgenic mammalian cell, and a plant cell. In some embodiments, the host cell is a prokaryotic cell. In some embodiments, the prokaryotic cell is a bacterial cell.

In some embodiments, the host cell is a mammalian cell. Such mammalian host cells include but are not limited to CHO, VERO, BHK, Hela, MDCK, HEK 293, NIH 3T3, W138, BT483, Hs578T, HTB2, BT2O and T47D, NSO (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10, HBK, NSO, HT1080 and HsS78Bst cells.

Vectors

Adeno-Associate Virus (AAV)

Overview

Provided herein are vectors (e.g., expression vectors) comprising nucleic acid molecules comprising nucleotide sequences encoding a miniaturized dystrophin protein for recombinant expression in host cells and cells targeted for therapeutic intervention. The term "vector," as used herein, is intended to refer to a nucleic acid molecule capable of transporting another nucleic acid to which it has been linked; or an entity comprising such a nucleic acid molecule capable of transporting another nucleic acid. One type of vector is a "plasmid," which refers to a circular double stranded DNA loop into which additional DNA segments can be ligated. Another type of vector is a viral vector, wherein additional DNA segments can be ligated into the viral genome. Certain vectors, or polynucleotides that are part of vectors, are capable of autonomous replication in a host cell into which they are introduced (e.g., bacterial vectors having a bacterial origin of replication, and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" can sometimes be used interchangeably, depending on the context, as the plasmid is the most commonly used form of vector. However, also disclosed herein are other forms of expression vectors, such as viral vectors (e.g., replication defective retroviruses, adenoviruses and adeno-associated viruses), which serve equivalent functions.

In some embodiments, the polynucleotides disclosed herein are expressed using an adeno-associated virus (AAV). AAV is a nonenveloped, single-stranded DNA virus of the Parvoviridae family. In contrast to most other members of the Parvoviridae family, AAV is replication defective and is only able to replicate efficiently in the presence of a helper virus such as adenovirus or herpes virus.

AAV was first discovered in the mid 1960's as a contaminant of viral preparations of adenovirus. See Atchison R. W., Casto B. C., Hammon W. M., *Science.* 149(3685), 754-756 (1965). Since then, progressively safer and more effective methods to use AAV as a recombinant DNA vector have been developed. See, e.g., Hermonat P. L. and Muzyczka N., *Proc Natl Acad Sci USA.* 81(20):6466-6470 (1984); Laughlin C. A. et al., *Gene,* 23(1): 65-73 (1983); Matsushita T. et al., *Gene Ther.* 5(7):938-945 (1998); and Xiao X. et al., *Journal of Virology* 72(3):2224-2232 (1998). Low numbers of AAV genomes have been shown to integrate into the host chromosome. See Cheung A. K., Hoggan M. D., Hauswirth W. W. et al., Integration of the adeno-associated virus genome into cellular DNA in latently infected human detroit 6 cells, *J. Virol.* 33:739-748 (1980). AAV is immunologically distinct from any known adenovirus antigen. The AAV capsid contains a single-stranded DNA (ssDNA) genome. See Rose J. A., Berns K. I., Hoggan M. D. et al., *Proc. Natl. Acad. Sci. USA* 64:863-869 (1969).

AAV has a single stranded, 4.7 kb DNA genome encoding a replication (rep) gene and a capsid (cap) genes flanked by two inverted terminal repeats (ITRs). It is predominantly non-integrating, and forms stable episomes in non-dividing tissue. In spite of its high seroprevalence in the adult human population, AAV has not been associated with any human disease. See Gonçalves M., *Virol. J.* 2, 43 (2005). AAV's stable expression in tissues, its lack of pathogenicity, and its ease of high titer production have made it a very attractive vector and popular gene transfer platform.

A recombinant AAV (rAAV) is a genetically manipulated AAV in which typically part or all of the rep and cap genes have been replaced with heterologous transgene sequences. Recombinant AAVs too can trigger long-term transgene expression in postmitotic cells, most likely because the recombinant AAV genome persist as largely circular episomes within the nucleus. rAAVs' only DNA cis-element required for the production of rAAVs is the AAV inverted terminal repeats (ITRs), whereas rep, cap, and adenoviral helper genes can be provided in trans. Thus, in some embodiments disclosed herein, rAAVs contain only heterologous transgene DNA flanked by the ITRs, and this genome is encapsidated within a serotype-specific AAV capsid.

AAV possesses unique features that make it attractive as a vector system for delivering foreign DNA into cells. AAV infection of cells in culture has generally been noncytopathic, and natural infection of humans and other animals is silent and asymptomatic. Moreover, AAV infects many different types of mammalian cells allowing the possibility of targeting many different tissues in vivo. AAV also possesses additional advantages that make it a particularly attractive viral system for gene delivery, including the promotion of an immune response that is relatively mild compared to other forms of gene delivery, and persistent expression in both dividing and quiescent cells based on non-integrating, episomal vector DNA. Also, AAV withstands the conditions used to inactivate adenovirus (56° to 65° C. for several hours), making cold preservation of rAAV-based vaccines less critical.

Replication of the viral DNA is not required for integration into the host-cell genome, and thus helper virus is not required for this process. The AAV proviral genome is infectious as cloned DNA in plasmids which makes construction of recombinant genomes feasible. Furthermore, because the signals directing AAV replication, genome encapsidation and integration are contained within the ITRs of the AAV genome, the internal approximately 4.7 kb of the genome (encoding the replication and structural capsid proteins, rep-cap) can thus be replaced with foreign DNA such as a gene cassette containing a promoter, a DNA of interest and a polyadenylation signal.

AAV vectors can include additional elements that function in cis or in trans. In particular embodiments, an AAV vector that includes a vector genome also has one or more inverted terminal repeat (ITR) sequences that flank the 5' or 3' terminus of the donor sequence; an expression control element that drives transcription (e.g., a promoter or enhancer) of the donor sequence, such as a constitutive or regulatable control element, or tissue-specific expression control element; an intron sequence, a stuffer or filler polynucleotide sequence; and/or a poly-Adenine sequence located 3' of the donor sequence.

In some embodiments, AAV replicates using a helper virus. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

Exemplary AAV vectors include capsid sequences of any of AAV1, AAV2, AAV3, AAV4, AAV5, AAV6, AAV7, AAV8, AAV9, AAV10, AAV11, Rh10, Rh74 or AAV-2i8, or a capsid variant of AAV1, AAV2, AAV3, AAV4, AAV5, AAV6, AAV7, AAV8, AAV9, AAV10, AAV11, Rh10, Rh74 or AAV-2i8. Recombinant AAV vectors of the invention also include AAV1, AAV2, AAV3, AAV4, AAV5, AAV6, AAV7, AAV8, AAV9, AAV10, AAV11, Rh10, Rh74 or AAV-2i8, and variants thereof. Particular capsid variants include capsid variants of AAV1, AAV2, AAV3, AAV4, AAV5, AAV6, AAV7, AAV8, AAV9, AAV10, AAV11, Rh10, Rh74 or AAV-2i8, such as a capsid sequence with an amino acid substitution, deletion or insertion/addition. In one embodiment, the AAV vector is AAV9. In one embodiment, the AAV vector is AAV5. In one embodiment, the AAV vector is AAV8.

In some aspects the disclosure relates to AAVs having distinct tissue targeting capabilities (e.g., tissue tropisms). In some embodiments, the variant AAV capsid polypeptides further exhibit increased transduction or tropism in one or more human stem cell types as compared to non-variant parent capsid polypeptides. In some embodiments, the human stem cell types include but are not limited to embryonic stem cells, adult tissue stem cells (i.e., somatic stem cells), bone marrow stem cells, progenitor cells, induced pluripotent stem cells, and reprogrammed stem cells. In some embodiments, adult stem cells can include organoid stem cells (i.e., stem cells derived from any organ or organ system of interest within the body). In some embodiments, the target tissue of an AAV is gonad, diaphragm, heart, stomach, liver, spleen, pancreas, muscle or kidney. In some embodiments, the AAV targets organs of the body that include, but are not limited to, skin, hair, nails, sense receptors, sweat gland, oil glands, bones, muscles, brain, spinal cord, nerve, pituitary gland, pineal gland, hypothalamus, thyroid gland, parathyroid, thymus, adrenals, pancreas (islet tissue), heart, blood vessels, lymph nodes, lymph vessels, thymus, spleen, tonsils, nose, pharynx, larynx, trachea, bronchi, lungs, mouth, pharynx, esophagus, stomach, small intestine, large intestine, rectum, anal canal, teeth, salivary glands, tongue, liver, gallbladder, pancreas, appendix, kidneys, ureters, urinary bladder, urethra, testes, ductus (vas) deferens, urethra, prostate, penis, scrotum, ovaries, uterus, uterine (fallopian) tubes, vagina, vulva, and mammary glands (breasts). Organ systems of the body include but are not limited to the integumentary system, skeletal system, muscular system, nervous system, endocrine system, cardiovascular system, lymphatic system, respiratory system, digestive system, urinary system, and reproductive system. In some embodiments, transduction and/or tropism of an AAV with variant capsid polypeptides is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%, by comparison to an AAV having non-variant capsid polypeptides. In some embodiments, transduction and/or tropism is increased by about 5% to about 80%, about 10% to about 70%, about 20% to about 60% or about 30% to about 60%.

Replication, Capsid, and Assembly AAV Genes

The single-stranded genome of AAV comprises three genes, rep (Replication), cap (Capsid), and aap (Assembly). These three genes give rise to at least nine gene products through the use of three promoters, alternative translation start sites, and differential splicing.

The rep gene encodes four proteins (Rep78, Rep68, Rep52, and Rep40), which are required for viral genome replication and packaging.

Cap gene expression gives rise to the viral capsid proteins (VP1; VP2; VP3), which form the outer capsid shell that protects the viral genome, as well as being actively involved in cell binding and internalization. It is estimated that the viral coat is comprised of 60 proteins arranged into an icosahedral structure.

The aap gene encodes the assembly-activating protein (AAP) in an alternate reading frame overlapping the cap gene. This nuclear protein is thought to provide a scaffolding function for capsid assembly and plays a role in nucleolar localization of VP proteins in some AAV serotypes.

In some embodiments, one or more of the rep, cap, or aap genes are naturally occurring, e.g. the rep, cap, or app genes comprise all or a portion of parvovirus rep, cap, or aap genes. In some embodiments, the one or more of the rep, cap, or aap genes comprise a synthetic sequence.

In one embodiment, the rep gene comprises a synthetic sequence. In one embodiment, the cap gene comprises a synthetic sequence. In one embodiment, the aap gene comprises a synthetic sequence. In one embodiment, the rep and cap genes comprise a synthetic sequence. In one embodiment, the rep and aap genes comprise a synthetic sequence. In one embodiment, the cap and aap genes comprise a synthetic sequence. In one embodiment, the rep, cap, and aap genes comprise a synthetic sequence.

In some embodiments, rep is from an AAV genome selected from AAV1, AAV2, AAV3, AAV4, AAV5, AAV6, AAV7, AAV8, AAV9, AAV10, AAV11, and any combination thereof. In a particular embodiment, rep is from the AAV1 genome. In a particular embodiment, rep is from the AAV2 genome. In a particular embodiment, rep is from the AAV3 genome. In a particular embodiment, rep is from the AAV4 genome. In a particular embodiment, rep is from the AAV5 genome. In a particular embodiment, rep is from the AAV6 genome. In a particular embodiment, rep is from the AAV7 genome. In a particular embodiment, rep is from the AAV8 genome. In a particular embodiment, rep is from the AAV9 genome. In a particular embodiment, rep is from the AAV10 genome. In a particular embodiment, rep is from the AAV11 genome.

In some embodiments, cap is from an AAV genome selected from AAV1, AAV2, AAV3, AAV4, AAV5, AAV6, AAV7, AAV8, AAV9, AAV10, AAV11, and any combination thereof. In a particular embodiment, cap is from the AAV1 genome. In a particular embodiment, cap is from the AAV2 genome. In a particular embodiment, cap is from the AAV3 genome. In a particular embodiment, cap is from the AAV4 genome. In a particular embodiment, cap is from the AAV5 genome. In a particular embodiment, cap is from the AAV6 genome. In a particular embodiment, cap is from the AAV7 genome. In a particular embodiment, cap is from the AAV8 genome. In a particular embodiment, cap is from the AAV9 genome. In a particular embodiment, cap is from the AAV10 genome. In a particular embodiment, cap is from the AAV11 genome.

In some embodiments, aap is from an AAV genome selected from AAV1, AAV2, AAV3, AAV4, AAV5, AAV6, AAV7, AAV8, AAV9, AAV10, AAV11, and any combination thereof. In a particular embodiment, aap is from the AAV1 genome. In a particular embodiment, aap is from the AAV2 genome. In a particular embodiment, aap is from the AAV3 genome. In a particular embodiment, aap is from the AAV4 genome. In a particular embodiment, aap is from the AAV5 genome. In a particular embodiment, aap is from the AAV6 genome. In a particular embodiment, aap is from the AAV7 genome. In a particular embodiment, aap is from the AAV8 genome. In a particular embodiment, aap is from the AAV9 genome. In a particular embodiment, aap is from the AAV10 genome. In a particular embodiment, aap is from the AAV11 genome.

It is to be understood that a particular AAV genome described herein could have genes derived from different AAV genomes (e.g., genomes from AAV1, AAV2, AAV3, AAV4, AAV5, AAV6, AAV7, AAV8, AAV9, AAV10, and AAV11). Thus, disclosed herein are AAVs that comprise any possible permutation/combination of rep, cap, or aap.

In some embodiments disclosed herein, the AAV is recombinant AAV (rAAV). In some embodiments, the rAAV lacks one or more of the rep gene, the cap gene, and the aap gene. In some embodiments, the rAAV lacks a rep gene. In some embodiments, the rAAV lacks a cap gene. In some embodiments, the rAAV lacks an aap gene. In some embodiments, the rAAV lacks a rep gene and lacks a cap gene. In some embodiments, the rAAV lacks a rep gene and lacks an aap gene. In some embodiments, the rAAV lacks a cap gene and lacks an aap gene. In some embodiments, the rAAV lacks a rep gene, a cap gene, and an aap gene.

In some embodiments disclosed herein, the rAAV is modified so that one or more of the rep gene, the cap gene, and the aap gene is mutated so that expression of one or more of the AAV genes is modified. In some embodiments, the rep gene is mutated. In some embodiments, the cap gene is mutated. In some embodiments, the aap gene is mutated. In some embodiments, the rep gene and the cap gene are mutated. In some embodiments, the rep gene and the aap gene are mutated. In some embodiments, the cap gene and the aap gene are mutated. In some embodiments, the cap gene, the rep gene, and the aap gene are mutated.

Inverted Terminal Repeats

In certain embodiments, the AAV comprises a first ITR, e.g., a 5' ITR, and second ITR, e.g., a 3' ITR. Typically, ITRs are involved in parvovirus (e.g., AAV) DNA replication and rescue, or excision, from prokaryotic plasmids (Samulski R. J. et al., *Cell* 33(1):135-143 (1983), *Journal of Virology* 61:3096-3101 (1987); Senapathy P. et al., *Journal of Molecular Biology* 179(1):1-20 (1984); Gottlieb J. and Muzyczka N., *Molecular and Cellular Biology* 6(8): 2513-2522 (1988)). In addition, ITRs have been reported to be the minimum sequences required for AAV proviral integration and for packaging of AAV DNA into virions (McLaughlin et al., 1988; Samulski et al., 1989). These elements are essential for efficient multiplication of a parvovirus genome.

In some embodiments, the ITR comprises a naturally occurring ITR, e.g., the ITR comprises all or a portion of a parvovirus ITR. In some embodiments, the ITR comprises a synthetic sequence. In one embodiment, the first ITR or the second ITR comprises a synthetic sequence. In another embodiment, each of the first ITR and the second ITR comprises a synthetic sequence. In some embodiments, the first ITR or the second ITR comprises a naturally occurring sequence. In another embodiment, each of the first ITR and the second ITR comprises a naturally occurring sequence.

In some embodiments, the ITR comprises an ITR from an AAV genome. In some embodiments, the ITR is an ITR of an AAV genome selected from AAV1, AAV2, AAV3, AAV4, AAV5, AAV6, AAV7, AAV8, AAV9, AAV10, AAV11, and any combination thereof. In a particular embodiment, the ITR is an ITR of the AAV2 genome. In another embodiment, the ITR is a synthetic sequence genetically engineered to include at its 5' and 3' ends ITRs derived from one or more of AAV genomes. In some embodiments, the ITRs are derived from the same genome, e.g., from the genome of the same virus, or from different genomes, e.g., from the genomes of two or more different AAV genomes. In certain embodiments, the ITRs are derived from the same AAV genome. In a specific embodiment, the two ITRs present in the nucleic acid molecule of the invention are the same, and can in particular be AAV2 ITRs. In one particular embodiment, the first ITR and the second ITR are identical.

In some embodiments, the ITRs form hairpin loop structures. In one embodiment, the first ITR forms a hairpin structure. In another embodiment, the second ITR forms a hairpin structure. Still in another embodiment, both the first ITR and the second ITR form hairpin structures.

In some embodiments, an ITR in a nucleic acid molecule described herein is a transcriptionally activated ITR. A transcriptionally-activated ITR can comprise all or a portion of a wild-type ITR that has been transcriptionally activated by inclusion of at least one transcriptionally active element. Various types of transcriptionally active elements are suitable for use in this context. In some embodiments, the transcriptionally active element is a constitutive transcriptionally active element. Constitutive transcriptionally active elements provide an ongoing level of gene transcription, and can be used when it is desired that the transgene be expressed on an ongoing basis. In other embodiments, the transcriptionally active element is an inducible transcriptionally active element. Inducible transcriptionally active elements generally exhibit low activity in the absence of an inducer (or inducing condition), and are up-regulated in the presence of the inducer (or switch to an inducing condition). Inducible transcriptionally active elements can be used when expression is desired only at certain times or at certain locations, or when it is desirable to titrate the level of expression using an inducing agent. Transcriptionally active elements can also be tissue-specific; that is, they exhibit activity only in certain tissues or cell types. Transcriptionally active elements, can be incorporated into an ITR in a variety of ways. In some embodiments, a transcriptionally active element is incorporated 5' to any portion of an ITR or 3' to any portion of an ITR. In other embodiments, a transcriptionally active element of a transcriptionally-activated ITR lies between two ITR sequences. If the transcriptionally active element comprises two or more elements which must be spaced apart, those elements can alternate with portions of the ITR. In some embodiments, a hairpin structure of an ITR is deleted and replaced with inverted repeats of a transcriptional element. This latter arrangement would create a hairpin mimicking the deleted portion in structure. Multiple tandem transcriptionally active elements can also be present in a transcriptionally-activated ITR, and these can be adjacent or spaced apart. In addition, protein binding sites (e.g., Rep binding sites) can be introduced into transcriptionally active elements of the transcriptionally-activated ITRs. A transcriptionally active element can comprise any sequence enabling the controlled transcription of DNA by RNA polymerase to form RNA, and can comprise, for example, a transcriptionally active element, as defined below.

Transcriptionally-activated ITRs provide both transcriptional activation and ITR functions to the nucleic acid molecule in a relatively limited nucleotide sequence length which effectively maximizes the length of a transgene which can be carried and expressed from the nucleic acid molecule. Incorporation of a transcriptionally active element into an ITR can be accomplished in a variety of ways. A comparison of the ITR sequence and the sequence requirements of the transcriptionally active element can provide insight into ways to encode the element within an ITR. For example, transcriptional activity can be added to an ITR through the introduction of specific changes in the ITR sequence that replicates the functional elements of the transcriptionally active element. A number of techniques exist in the art to efficiently add, delete, and/or change particular nucleotide sequences at specific sites (see, for example, Deng W. P and Nickoloff J. A., Anal. Biochem. 200:81-88 (1992)). Another way to create transcriptionally-activated ITRs involves the introduction of a restriction site at a desired location in the ITR. In addition, multiple transcriptionally activate elements can be incorporated into a transcriptionally-activated ITR, using methods known in the art.

By way of illustration, transcriptionally-activated ITRs can be generated by inclusion of one or more transcriptionally active elements such as: TATA box, GC box, CCAAT box, Sp1 site, Inr region, CRE (cAMP regulatory element) site, ATF-1/CRE site, APBβ box, APBα box, CArG box, CCAC box, or any other element involved in transcription as known in the art.

Gene of Interest and Other Sequences

Certain aspects of the present disclosure are directed to methods of administering to a subject an AAV therapy. In some embodiments, the AAV comprises a gene of interest (GOI). In some embodiments, the GOI is a nucleic acid molecule comprising a nucleotide sequence as disclosed herein, which encodes a miniaturized dystrophin polypeptide as disclosed herein.

The GOI being expressed can be either a DNA segment encoding a protein, with any necessary control elements (e.g., promoters, operators) desired by the user, or a non-coding DNA segment, the transcription of which produces all or part of some RNA-containing molecule, such as a ribozyme or an anti-sense molecule.

In some embodiments, the AAV comprises more than one GOI. In AAVs with more than one GOI, some embodiments include elements such as IRES or 2A, to co-express them from one promoter. In some embodiments, the AAV comprises two genes of interest separated by an IRES element. In some embodiments, the AAV comprises two genes of interest separated by a 2A element. In some embodiments, the AAV comprises three genes of interest separated by an IRES element between the genes of interest (e.g., GOI-IRES-GOI-IRES-GOI). In some embodiments, the AAV comprises three genes of interest separated by 2A elements between the genes of interest.

In some embodiments, the AAV comprises a regulatory sequence. In some embodiments, the AAV comprises non-coding regulatory DNA. In some embodiments, the AAV genome comprises regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the AAV, including the selection of regulatory sequences, can depend on such factors as the choice of the host cell to be transformed, the level of expression of protein desired, etc. In some embodiments, the AAV genome comprises mRNA splice donor/splice acceptor sites. Certain regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al., *Mol. Cell. Biol.* 8:466-472 (1988)). In certain embodiments, the regulatory sequence comprises a tissue specific promoter. In some embodiments, the tissue specific promoter drives expression of the gene of interest in a tissue selected from the group consisting of heart, liver, lungs, eyes, nervous system, lymphatic system, muscle and stem cells.

AAV Formulations

In some embodiments, the AAV vector is formulated with a delivery agent. In some embodiments, the delivery agent comprises a lipid nanoparticle. In some embodiments, the delivery agent is selected from the group consisting of liposomes, non-lipid polymeric molecules, endosomes, and any combination thereof.

Non-AAV Vectors

A vector which comprises the above-described polynucleotides operably linked to a promoter is also provided herein. A nucleotide sequence is "operably linked" to an expression control sequence (e.g., a promoter) when the expression control sequence controls and regulates the transcription and translation of that sequence. The term "operably linked" when referring to a nucleotide sequence includes having an appropriate start signal (e.g., ATG) in front of the nucleotide sequence to be expressed and maintaining the correct reading frame to permit expression of the sequence under the control of the expression control sequence and production of the desired product encoded by the sequence. If a gene that one desires to insert into a recombinant nucleic acid molecule does not contain an appropriate start signal, such a start signal can be inserted in front of the gene. A "vector" is a replicon, such as plasmid, phage or cosmid, to which another nucleic acid segment can be attached so as to bring about the replication of the attached segment. The promoter can be, or is identical to, a bacterial, yeast, insect or mammalian promoter.

In some embodiments, the vector can be a plasmid, cosmid, yeast artificial chromosome (YAC), bacteriophage or eukaryotic viral DNA. Other numerous vector backbones known in the art as useful for expressing protein can be employed. Such vectors include, but are not limited to: adenoviral vector, a retroviral vector, poxvirus vector, a baculovirus vector, a herpes viral vector, simian virus 40 (SV40), cytomegalovirus (CMV), mouse mammary tumor virus (MMTV), and Moloney murine leukemia virus. Further, one class of vectors comprises DNA elements derived from viruses such as bovine papilloma virus, polyoma virus, baculovirus, retroviruses, or Semliki Forest virus. Such vectors can be obtained commercially or assembled from the sequences described by methods well-known in the art.

In some embodiments, the vector described herein is formulated with a delivery agent. In some embodiments, the delivery agent comprises a lipid nanoparticle. In some embodiments, the delivery agent is selected from the group consisting of liposomes, non-lipid polymeric molecules, endosomes, and any combination thereof.

Pharmaceutical Compositions

The various polypeptides and polynucleotides disclosed herein (also referred to herein as "active compounds") can be incorporated into pharmaceutical compositions suitable for administration. Such compositions typically comprise the polypeptide, or polynucleotides, and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active compounds is well known in the art. Except insofar as any conventional media or agent is incompatible with the active compound, use thereof in the compositions is contemplated. Supplementary active compounds can also be incorporated into the compositions.

In some embodiments, disclosed is a pharmaceutical composition comprising (a) a polypeptide as described herein and (b) a pharmaceutically acceptable excipient. In some embodiments, disclosed is a pharmaceutical composition comprising (a) a composition comprising a polypeptide as described herein and (b) a pharmaceutically acceptable excipient.

In some embodiments, disclosed is a pharmaceutical composition comprising (a) a polynucleotide as described herein and (b) a pharmaceutically acceptable excipient.

In some embodiments, disclosed is a pharmaceutical composition comprising (a) a vector (e.g., rAAV) as described herein and (b) a pharmaceutically acceptable excipient.

In some embodiments, disclosed is a pharmaceutical composition comprising (a) a host cell as described herein and (b) a pharmaceutically acceptable excipient.

A pharmaceutical composition of the disclosure is formulated to be compatible with its intended route of administration. Examples of routes of administration include parenteral, e.g., intravenous, intradermal, subcutaneous, oral, transdermal (topical), and transmucosal, and any combination thereof. Another route of administration includes pulmonary administration. In addition, it can be desirable to administer a therapeutically effective amount of the pharmaceutical composition locally to an area in need of treatment. This can be achieved by, for example, local or regional infusion or perfusion during surgery, topical application, injection, catheter, suppository, or implant (for example, implants formed from porous, non-porous, or gelatinous materials, including membranes, such as sialastic membranes or fibers), and the like. In another embodiment, the therapeutically effective amount of the pharmaceutical composition is delivered in a vesicle, such as liposomes (see, e.g., Langer, Science 249:1527-33, 1990 and Treat et al., in Liposomes in the Therapy of Infectious Disease and Cancer, Lopez Berestein and Fidler (eds.), Liss, N.Y., pp. 353-65, 1989).

In yet another embodiment, the therapeutically effective amount of the pharmaceutical composition can be delivered in a controlled release system. In one example, a pump can be used (see, e.g., Langer, Science 249:1527-33, 1990; Sefton, Crit. Rev. Biomed. Eng. 14:201-40, 1987; Buchwald et al., Surgery 88:507-16, 1980; Saudek et al., N Engl. J Med. 321:574-79, 1989). In another example, polymeric materials can be used (see, e.g., Levy et al., Science 228: 190-92, 1985; During et al., Ann. Neural. 25:351-56, 1989; Howard et al., J Neurosurg. 71:105-12, 1989). Other controlled release systems, such as those discussed by Langer (Science 249:1527-33, 1990), can also be used.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor ELS (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation can be vacuum drying and freeze-drying, which yields a powder of the active ingredient plus any additional desired ingredient from a previously sterile-filtered solution thereof.

For administration by inhalation, the compounds are delivered in the form of an aerosol spray from a pressurized container or dispenser that contains a suitable propellant, e.g., a gas such as carbon dioxide, or a nebulizer. Systemic administration can also be by transmucosal or transdermal means.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such a functional compound for the treatment of individuals. The pharmaceutical compositions can be included in a container, pack, or dispenser together with instructions for administration.

Uses and Methods

Methods of Producing Miniaturized Dystrophins

Also disclosed herein are methods of producing a miniaturized dystrophin polypeptide, comprising: culturing a host cell described herein under suitable conditions and recovering the miniaturized dystrophin polypeptide.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding a polypeptide described herein is isolated or purified.

The polynucleotides can be obtained, and the nucleotide sequence of the polynucleotides determined, by any method known in the art. Nucleotide sequences encoding polypeptides described herein, e.g., the polypeptides described in Tables 3 and 4, and modified versions of these polypeptides can be determined using methods well known in the art, i.e., nucleotide codons known to encode particular amino acids are assembled in such a way to generate a nucleic acid that encodes the polypeptides. Such a polynucleotide encoding the polypeptide can be assembled from chemically synthesized oligonucleotides (e.g., as described in Kutmeier G. et al., (1994), BioTechniques 17: 242-6), which, briefly, involves the synthesis of overlapping oligonucleotides containing portions of the sequence encoding the polypeptide, annealing and ligating of those oligonucleotides, and then amplification of the ligated oligonucleotides by PCR.

Alternatively, a polynucleotide encoding a polypeptide described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the polypeptide of interest. Such PCR amplification methods can be used to obtain nucleic acids comprising the sequence encoding e.g., IL2, a linker sequence, or IL2-Rα. The amplified nucleic acids can be cloned into vectors for expression in host cells and for further cloning, for example, to generate polypeptides.

If a clone containing a nucleic acid encoding a particular polypeptide is not available, but the sequence of the polypeptide molecule is known, a nucleic acid encoding the polypeptide can be chemically synthesized or obtained from a suitable source (e.g., a cDNA library or a cDNA library generated from, or nucleic acid, preferably poly A+RNA, isolated from, any tissue or cells expressing the proteins of interest, such as hybridoma cells selected to express a polypeptide described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the polypeptides. Amplified nucleic acids generated by PCR can then be cloned into replicable cloning vectors using any method well known in the art.

DNA encoding polypeptides described herein can be readily isolated and sequenced using conventional procedures (e.g., by using oligonucleotide probes that are capable of binding specifically to genes encoding the polypeptides disclosed herein). Hybridoma cells can serve as a source of such DNA. Once isolated, the DNA can be placed into expression vectors, which are then transfected into host cells such as E. coli cells, simian COS cells, Chinese hamster ovary (CHO) cells (e.g., CHO cells from the CHO GS SYSTEM™ (Lonza)), or myeloma cells that do not otherwise produce immunoglobulin protein, to obtain the synthesis of polypeptides in the recombinant host cells.

Therapeutic Uses and Methods

The miniaturized dystrophin polypeptides, polynucleotides encoding miniaturized dystrophin polypeptides, vectors (e.g., rAAV) harboring polynucleotides encoding miniaturized dystrophin polypeptides and methods described herein have numerous in vitro and in vivo utilities. For example, the nucleotide sequence encoding a miniaturized dystrophin polypeptide, e.g., a vector, e.g., an AAV vector, or the polypeptides described herein can be administered to cells in culture, in vitro or ex vivo, or to human subjects, e.g., in vivo, to treat diseases.

Accordingly, disclosed herein are therapeutic methods using any of the miniaturized dystrophin nucleic acid molecules as disclosed herein, polypeptides as disclosed herein, host cells as disclosed herein, vectors as disclosed herein, or pharmaceutical compositions as disclosed herein, or any combination thereof.

In some embodiments, disclosed herein is a method of expressing a miniaturized dystrophin polypeptide in a subject in need thereof, comprising administering to the subject a nucleic acid as disclosed herein, a vector as disclosed herein, a host cell as disclosed herein, or a pharmaceutical composition as disclosed herein.

In some embodiments, disclosed herein is a method of treating a subject having a disease or condition comprising administering to the subject a nucleic acid as disclosed herein, a vector as disclosed herein, a polypeptide as disclosed herein, a host cell as disclosed herein, or a pharmaceutical composition as disclosed herein. In some embodiments, the disease or condition is caused by dystrophin deficiency. In some embodiments, the disease is Duchene muscular dystrophy (DMD), Becker muscular dystrophy (BMD), X-linked dilated cardiomyopathy (XLDC), facioscapulohumeral muscular dystrophy, myotonic muscular dystrophy, limb-girdle muscular dystrophy, oculopharyngeal muscular dystrophy, Emery-Dreifuss muscular dystrophy, distal muscular dystrophy, and/or congenital muscular dystrophy. In other embodiments, the disease to be treated is Sarcopenia, heart disease, cachexia.

In some embodiments, a nucleic acid molecule as disclosed herein, a polypeptide as disclosed herein, a vector (e.g., rAAV) as disclosed herein, a host cell as disclosed herein, or a pharmaceutical composition as disclosed herein is administered intravenously, transdermally, intradermally, subcutaneously, orally, or pulmonarily, or any combination thereof. In some embodiments, the nucleic acid molecule as disclosed herein, the polypeptide as disclosed herein, the vector as disclosed herein, the host cell as disclosed herein, or the pharmaceutical composition as disclosed herein is administered via a topical, epidermal mucosal, intranasal, oral, vaginal, rectal, sublingual, topical, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural or intrasternal route. In some embodiments, the nucleic acid molecule, the vector (e.g., rAAV), the host cell as disclosed herein, or the polypeptide is administered intravenously.

In some embodiments, the method of treatment further comprises administering to the subject a second agent.

As used herein, the term "subject" includes any human or non-human animal. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc. In some embodiments, the subject is a human.

In some embodiments, the administration of the nucleic acid molecule, the vector (e.g., rAAV), the polypeptide, the host cell, or the pharmaceutical composition to the subject results in an increased dystrophin protein expression, relative to dystrophin protein expression in the subject prior to the administration, wherein the dystrophin protein expression is increased by at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 20-fold, at least about 25-fold, at least about 30-fold, at least about 35-fold, at least about 40-fold, at least about 50-fold, at least about 60-fold, at least about 70-fold, at least about 80-fold, at least about 90-fold, or at least about 100-fold.

In certain aspects of the disclosure, the method comprises, or further comprises, administering an AAV therapy to the subject. In some embodiments, the AAV therapy comprises administering a recombinant AAV. Any recombinant AAV known in the art and/or disclosed herein can be used in the methods of the present disclosure. In some embodiments, the AAV therapy comprises administering an AAV selected from the group consisting of AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any combination thereof. In certain embodiments, the AAV therapy comprises administering an AAV type 1. In certain embodiments, the AAV therapy comprises administering an AAV type 2. In certain embodiments, the AAV therapy comprises administering an AAV type 3. In certain embodiments, the AAV therapy comprises administering an AAV type 4. In certain embodiments, the AAV therapy comprises administering an AAV type 5. In certain embodiments, the AAV therapy comprises administering an AAV type 6. In certain embodiments, the AAV therapy comprises administering an AAV type 7. In certain embodiments, the AAV therapy comprises administering an AAV type 8. In certain embodiments, the AAV therapy comprises administering an AAV type 9. In certain embodiments, the AAV therapy comprises administering an AAV type 10. In certain embodiments, the AAV therapy comprises administering an AAV type 11. In certain embodiments, the AAV therapy comprises administering an AAV type 12. In certain embodiments, the AAV therapy comprises administering an AAV type 13.

In some embodiments, treatment of a subject with the miniaturized dystrophin nucleic acid molecules as disclosed herein, polypeptides as disclosed herein, host cells as disclosed herein, vectors as disclosed herein, or pharmaceutical compositions as disclosed herein, or any combination thereof, does not cause significant inflammatory reactions, e.g., immune-mediated pneumonitis, immune-mediated colitis, immune mediated hepatitis, immune-mediated nephritis or renal dysfunction, immune-mediated hypophysitis, immune-mediated hypothyroidism and hyperthyroidism, or other immune-mediated adverse reactions. In some embodiments, treatment of a subject with the miniaturized dystrophin nucleic acid molecules as disclosed herein, polypeptides as disclosed herein, host cells as disclosed herein, vectors as disclosed herein, pharmaceutical compositions as disclosed herein, or any combination thereof does not cause significant cardiac disorders, e.g., ventricular arrhythmia; eye disorders, e.g., iridocyclitis; infusion-related reactions; increased amylase, increased lipase; nervous system disorders, e.g., dizziness, peripheral and sensory neuropathy; skin and subcutaneous tissue disorders, e.g., rash, pruritus, exfoliative dermatitis, erythema multiforme, vitiligo or psoriasis; respiratory, thoracic and mediastinal disorders, e.g., cough; fatigue; nausea; decreased appetite; constipation; arthralgia; or diarrhea.

Kits

Also disclosed herein are kits comprising one or more nucleic acid molecules disclosed herein, one or more vectors (e.g., rAAV) as disclosed herein, one or more polypeptides as disclosed herein, or one or more host cells as disclosed herein, or any combination thereof. In some embodiments, the kit also comprises instructions for administering any of the aforesaid, or a combination thereof, to a subject in need thereof.

The terms "kit" and "system," as used herein are intended to refer to at least one or more nucleic acid molecules disclosed herein, one or more vectors (e.g., rAAV) as disclosed herein, one or more polypeptides as disclosed herein, or one or more host cells as disclosed herein, or any combination thereof, which, in specific embodiments, are in combination with one or more other types of elements or components (e.g., other types of biochemical reagents, containers, packages, such as packaging intended for commercial sale, instructions of use, and the like).

In some embodiments, disclosed is a kit comprising (a) one or more of a miniaturized dystrophin polypeptide as described herein, a composition comprising a miniaturized dystrophin polypeptide as described herein, a nucleic acid encoding for a miniaturized dystrophin polypeptide as described herein, a vector (e.g., rAAV), and/or a host cell; and (b) and instructions for administering any of the aforesaid to a subject in need thereof. In some embodiments, disclosed is a kit comprising (a) a miniaturized dystrophin polypeptide as described herein and (b) and instructions for administering the miniaturized dystrophin polypeptide to a subject in need thereof. In some embodiments, disclosed is a kit comprising (a) a composition comprising a miniaturized dystrophin polypeptide as described herein and (b) and instructions for administering the composition to a subject in need thereof. In some embodiments, disclosed is a kit comprising (a) a nucleic acid encoding for a miniaturized dystrophin polypeptide as described herein and (b) and instructions for administering the nucleic to a subject in need thereof. In some embodiments, disclosed is a kit comprising (a) a vector as described herein and (b) and instructions for administering the vector to a subject in need thereof. In some embodiments, disclosed is a kit comprising (a) an AAV vector as described herein and (b) and instructions for administering the vector to a subject in need thereof. In some embodiments, disclosed is a kit comprising (a) a host cell as described herein and (b) and instructions for administering the host cell to a subject in need thereof.

In a specific embodiment, provided herein is a pharmaceutical pack or kit comprising one or more containers filled with one or more of the ingredients of the pharmaceutical compositions described herein, such as one or more miniaturized dystrophin peptides provided herein. In some embodiments, the kits contain a pharmaceutical composition described herein and any prophylactic or therapeutic agent, such as those described herein. In certain embodiments, the kits can contain a T cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided herein are kits that can be used in the above methods. In one embodiment, a kit comprises a miniaturized dystrophin polypeptide described herein, preferably a purified miniaturized dystrophin polypeptide, in one or more containers. In a specific embodiment, kits described herein contain a substantially isolated miniaturized dystrophin polypeptide as a control. In another specific embodiment, the kits described herein further comprise a control protein which does not react with a miniaturized dystrophin polypeptide antigen. In another specific embodiment, kits described herein contain one or more elements for detecting the binding of the miniaturized dystrophin polypeptide to a dystrophin antigen (e.g., the miniaturized dystrophin polypeptide can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized miniaturized dystrophin polypeptide. The antigen to a miniaturized dystrophin polypeptide disclosed herein as provided in the kit can also be attached to a solid support. In a more specific embodiment, the detecting means of the above described kit includes a solid support to which an antigen of the miniaturized dystrophin polypeptide is attached. Such a kit can also include a non-attached reporter-labeled anti-human antibody or anti-mouse/rat antibody. In this embodiment, binding of the miniaturized dystrophin polypeptide to an antigen can be detected by binding of the said reporter-labeled antibody.

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986);); Crooks, Antisense drug Technology: Principles, strategies and applications, $2^{nd}$ Ed. CRC Press (2007) and in Ausubel et al. (1989) Current Protocols in Molecular Biology (John Wiley and Sons, Baltimore, Md.).

All of the references cited above, as well as all references cited herein and the amino acid or nucleotide sequences (e.g., GenBank numbers and/or Uniprot numbers), are incorporated herein by reference in their entireties.

The following examples are offered by way of illustration and not by way of limitation.

EXAMPLES

Example 1: Design of Novel Miniaturized Dystrophins

Figure 2:
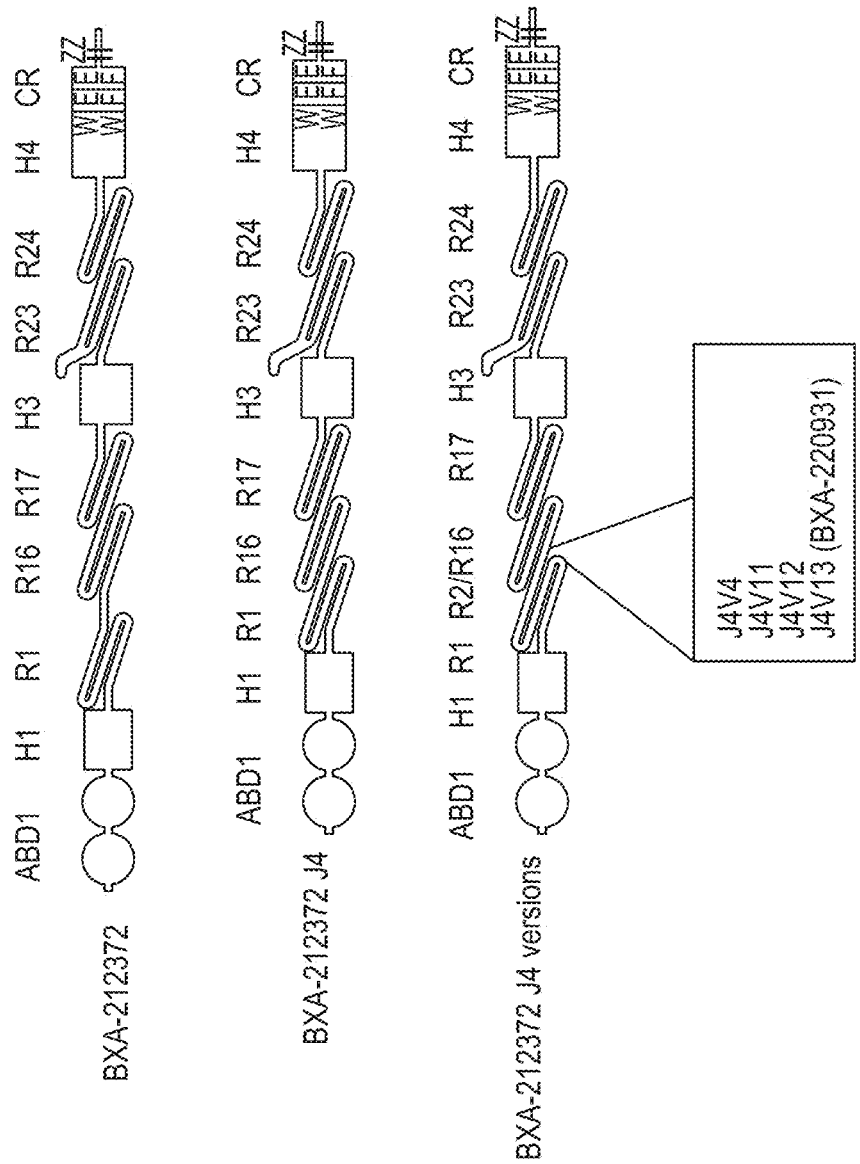
FIG. 2 shows schematic diagrams of miniaturized dystrophin polypeptides BXA-212372, BXA-212372-J4, BXA-212372-J4V4, BXA-212372-J4V11, BXA-212372-J4V12, and BXA-212372-J4V13 (BXA-220931).

Mutations in the dystrophin gene often result in an impairment of the stability of the corresponding dystrophin protein, which in turn leads to proteosomal degradation of the unstable dystrophin protein, and dystrophic pathophysiology. Similarly, miniaturizing dystrophin-encoding DNA to accommodate the limited packaging capacity of AAV can impair the stability of the corresponding miniaturized dystrophin protein. Novel miniaturized dystrophins with novel junctions as depicted in FIG. 2 were designed for further testing.

Figure 3:
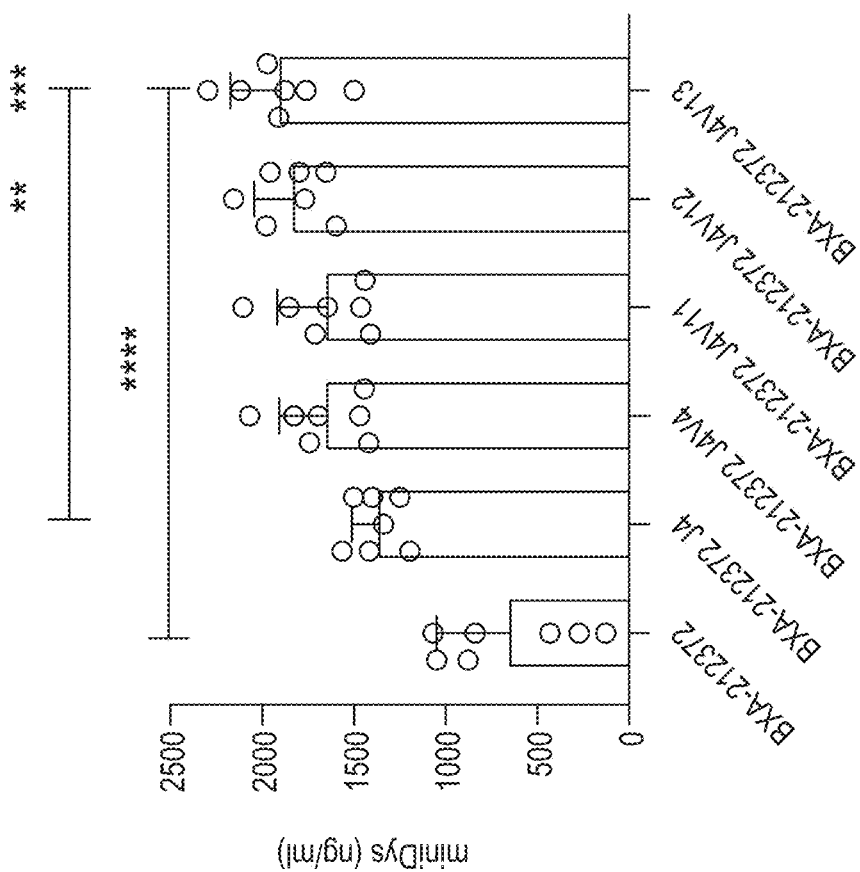
FIG. 3 shows miniaturized dystrophin polypeptide expression in human isogenic induced-pluripotent stem cell (iPSC)-derived cardiac myocytes (iCMs) (carrying an E2035X premature stop codon in the dystrophin gene that prevented endogenous dystrophin expression) after transfection of plasmids expressing the indicated miniaturized dystrophin polypeptides. Polypeptide expression was quantitated by ELISA. Significance: P<0.01, *P<0.001, ****P<0.0001 (one-way ANOVA with post-hoc Tukey test). Bar graphs reflect the means+/−standard deviations.

Example 2: Assessment of Stability of Miniaturized Dystrophin Proteins Expressed in Tissue Culture Cells The stability of the various miniaturized dystrophin proteins depicted in FIG. 2 was examined by comparing the presence of miniaturized dystrophin protein in cells transfected with the corresponding miniaturized dystrophin expression vectors. Male human isogenic induced-pluripotent stem cell (iPSC)-derived induced cardiomyocytes (iCMs) that carry an E2035X premature stop codon in the dystrophin gene that prevented endogenous dystrophin expression were used for these protein stability studies (Fujifilm Cellular Dynamics, Inc., Madison, Wis.). These cells were transfected with various plasmids expressing miniaturized dystrophin proteins and the presence of miniaturized dystrophin protein was examined after the transfected cells had been cultured in vitro for 24 days by a Meso Scale Discovery (MSD) ELISA assay (Meso Scale Diagnostics, Rockville, Md.). The miniaturized dystrophins tested and the test results of the aforesaid assay are shown in FIG. 2 and FIG. 3, respectively. The data indicated that miniaturized dystrophin peptide BXA-212372-J4V13 (SEQ ID NO:83) provides the best protein expression among the miniaturized dystrophin expression vectors and peptides tested.

Figure 4B:
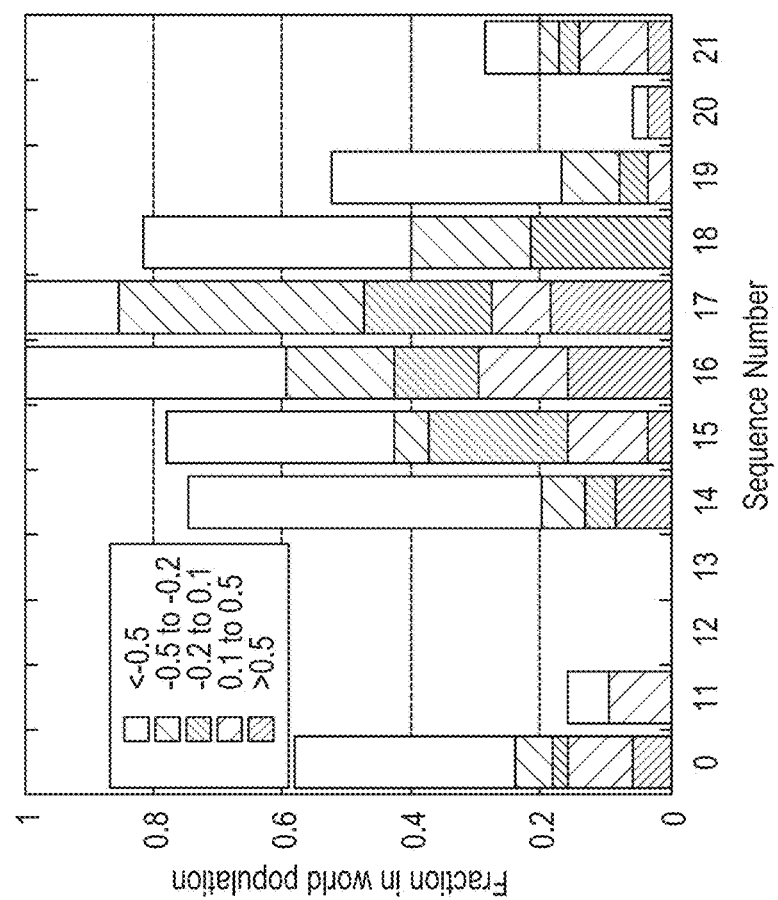
FIG. 4A and FIG. 4B show a stack-plot of the relative binding potential for MHC class I compared to all other peptides in the EIDB database for the miniaturized dystrophin junction BXA-212372 J4 variants. The original non-natural junction 4 (J4) (R1-R16) is labelled as junction 1 in FIG. 4A and junction 0 in FIG. 4B and has a moderate risk for binding MHC class I. The other numbers on the x-axis indicate the J4 variants (e.g., 13=J4V13 etc.). Modifications to the junction sequence (J4V4, J4V11, J4V12, J4V13) showed reduced MHC class I binding potential. Both J4V12 and J4V13 had the lowest predicted binding affinity.
Figure 4A:
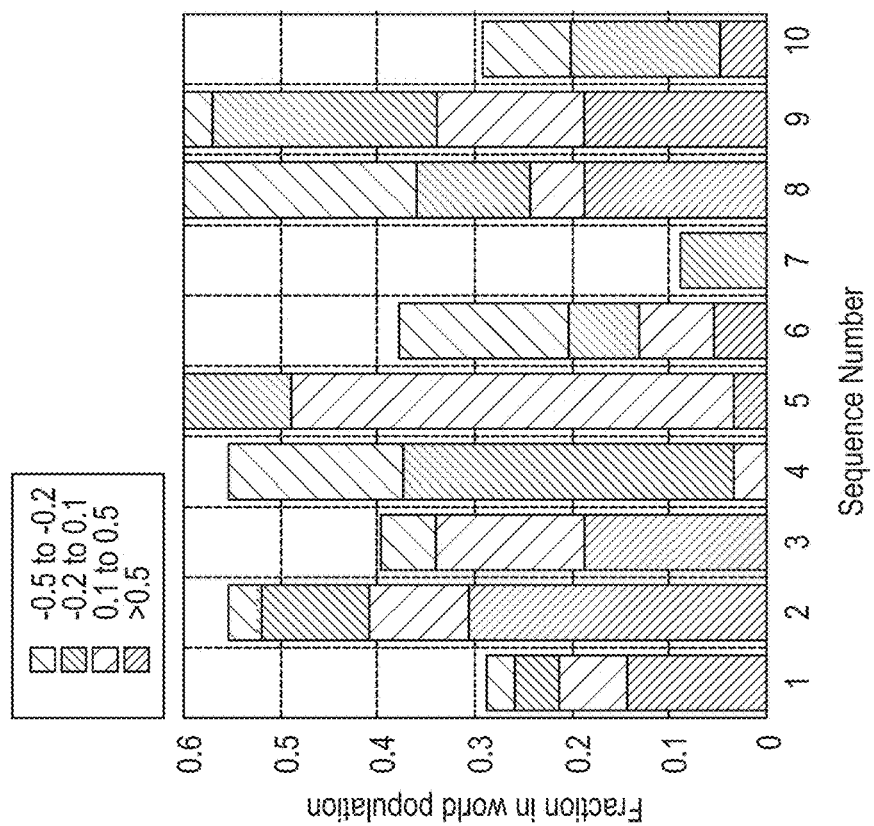

Example 3: Assessment of Immunogenicity of Novel Junctions in Miniaturized Dystrophin Proteins The immunogenicity of each of the peptides listed in Table 5 (SEQ ID NOs: 68 to 72), representing the novel J4 junctions created within the miniaturized dystrophin designs tested for protein stability (see FIG. 3 and Example 2), were tested using an in silico immunogenicity prediction tool. The novel junctions of the BXA-212372-J4V11 and particularly BXA-212372-J4V12 and BXA-212372-J4V13 designs (SEQ ID NO: 70, SEQ ID NO: 69, and SEQ ID NO: 68, respectively) were determined to have minimal immunogenic risk, based on the aforesaid in silico approach (see FIGS. 4A and 4B).

The immunogenic potential of the aforesaid junction peptides (see Table 5) were then tested using an in vitro T cell proliferation assay as described below. Briefly, samples of peripheral blood mononuclear cells (PBMC) were isolated from healthy volunteer human subjects by Ficoll (GE Healthcare Chicago, Ill.) gradient centrifugation and characterized, regarding human lymphocyte antigen (HLA) Class I and II expression, using a combination of polymerase chain reaction (PCR) amplification and hybridization with oligonucleotide probes (ProImmune, Sarasota, Fla.).

Figure 5A:
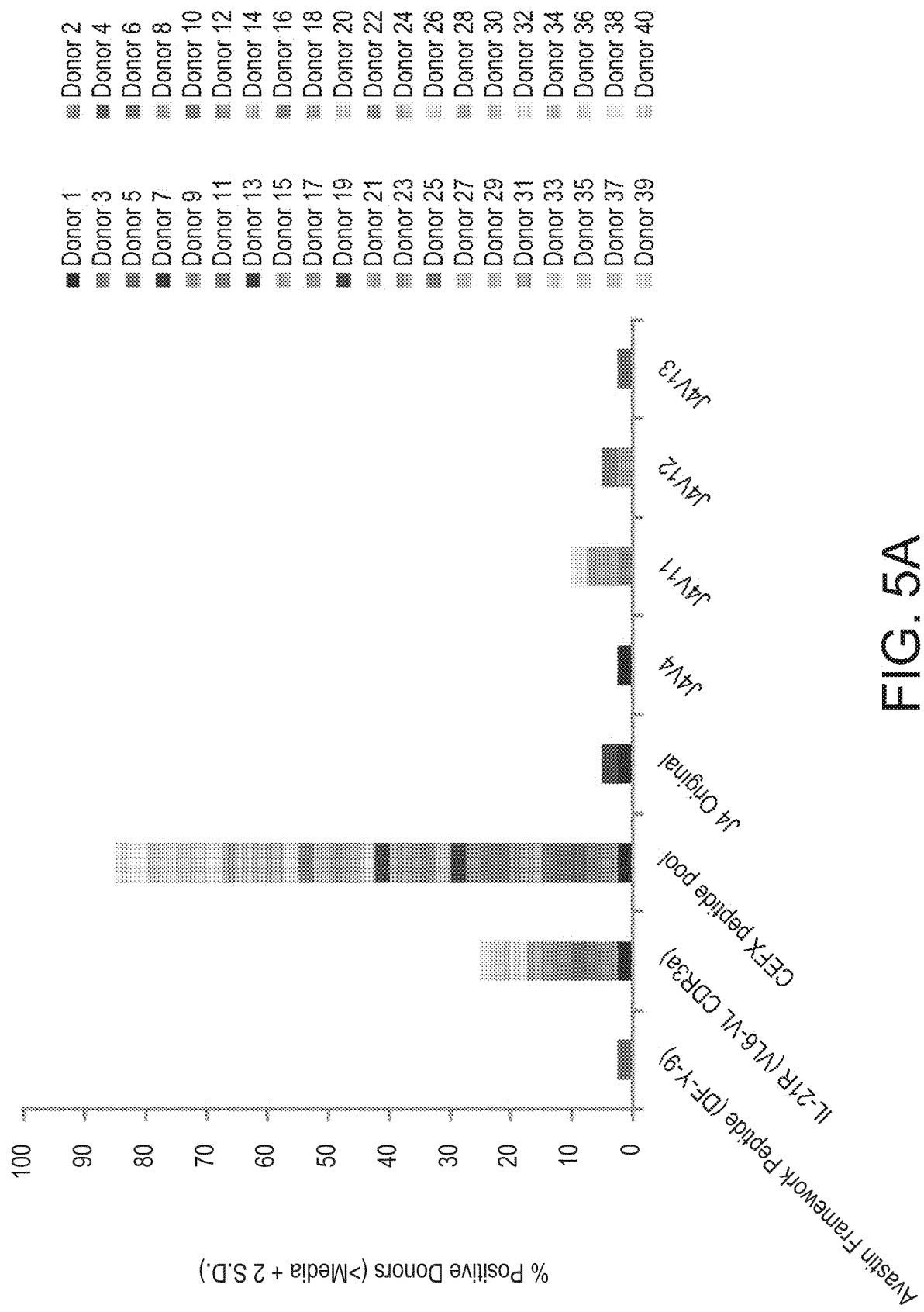
FIG. 5A and FIG. 5B show the immunogenic risk profile of miniaturized dystrophin polypeptide junctions.
Figure 5B:
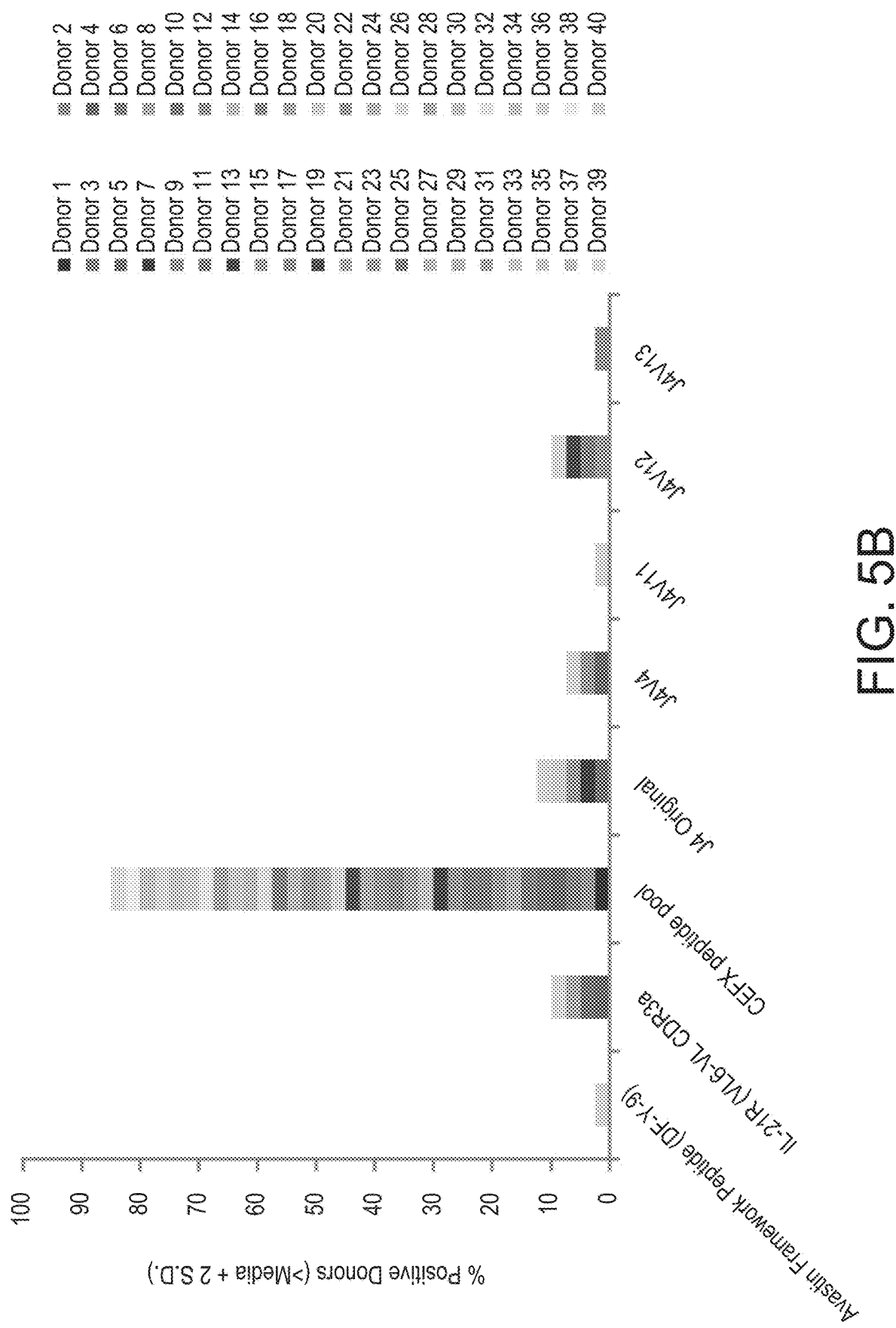

A panel of PBMC samples from 40 donors, having an HLA expression profile closely matching world population frequencies, was used for further analysis. PBMC samples were labeled with CFSE (Invitrogen, Carlsbad, Calif.) to monitor proliferation and plated in 96 well plates in six replicates at 200,000 cells per well in RPMI (Lonza, Basel, Switzerland) containing 10% human AB serum (Bioreclamation, Westbury, N.Y.), non-essential amino acids and pen-strep (both Gibco/Fisher Scientific). The BXA-212372 junction peptides listed in Table 5 and control peptides were each cultured with the panel of 40 PBMC samples at 1 µM for 7 days, after which the media was washed away and cells were labeled with an anti-CD4 and an anti CD8 APC monoclonal antibody (BD Biosciences, Franklin Lake, N.J.). After removal of the unbound antibodies through washing, cells were fixed with 3.7% formalin (Sigma, St. Louis, Mo.) in PBS and analyzed by flow cytometry to determine the percentage of proliferating $CD4^+$ cells or $CD8^+$ cells. The percentage of samples (among the 40 donor samples) that showed a positive response after seven days in culture with the different BXA-212372 junction peptides—defined as a significant increase in the number of $CD4^+$ or $CD8^+$ T proliferating cells compared to PBMC incubated in media without junction peptides or control peptides—is shown in FIG. 5A ($CD4^+$) and FIG. 5B ($CD8^+$). Control peptides used were: (1) Avastin Framework Peptide; (2) IL-21R Peptide; and (3) CEFX Peptide Pool. It was found that the junction peptide of design BXA-212372-J4V13 (see FIG. 2 and Table 5) was among the best in terms of immunogenic risk (see FIG. 4A, FIG. 4B, FIG. 5A and FIG. 5B).

Example 4: Codon Optimization

Figure 6:
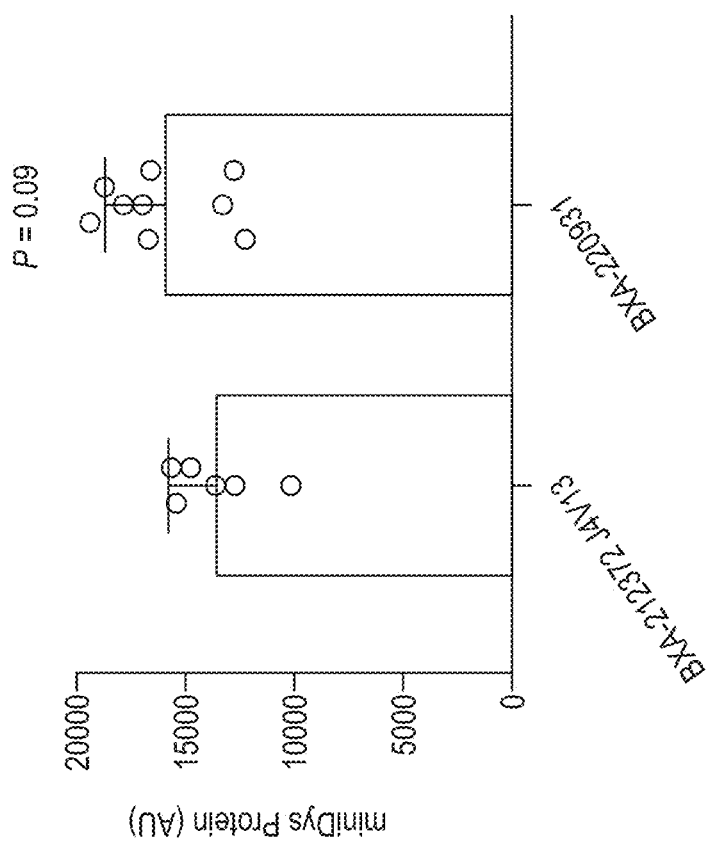
FIG. 6 shows a histogram indicating increased protein expression of miniaturized dystrophin in tissue culture cells transfected with an expression construct with an SV40 intron and a newly codon-optimized BXA-220931 (SEQ ID NO: 100) by comparison to protein expression in tissue culture cells transfected with comparable amounts of the corresponding expression construct without the SV40 intron and an older codon-optimized coding sequence BXA-212372-J4V13 (SEQ ID NO: 101), as determined by ELISA (AU, arbitrary units). Significance was determined by one-way ANOVA with post-hoc Tukey test. Bar graphs reflect the means+/−standard deviations.

The nucleotide sequence encoding miniaturized dystrophin design BXA-212372-J4V13 (SEQ ID NO: 101) was then codon optimized to optimize protein expression, resulting in construct BXA-220931 (SEQ ID NO: 100) (see Table 9 and FIG. 6).

Figure 7B:
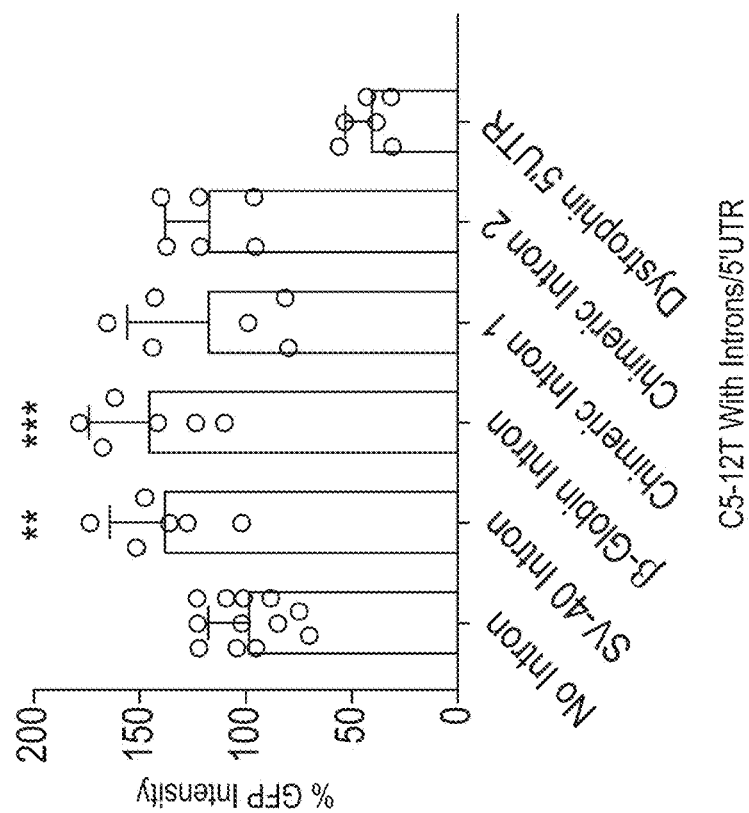
FIG. 7A and FIG. 7B show histograms indicating the effect a variety of promoters and introns/5'UTR coupled to a GFP reporter construct have on expression of GFP in tissue culture.
Figure 7A:
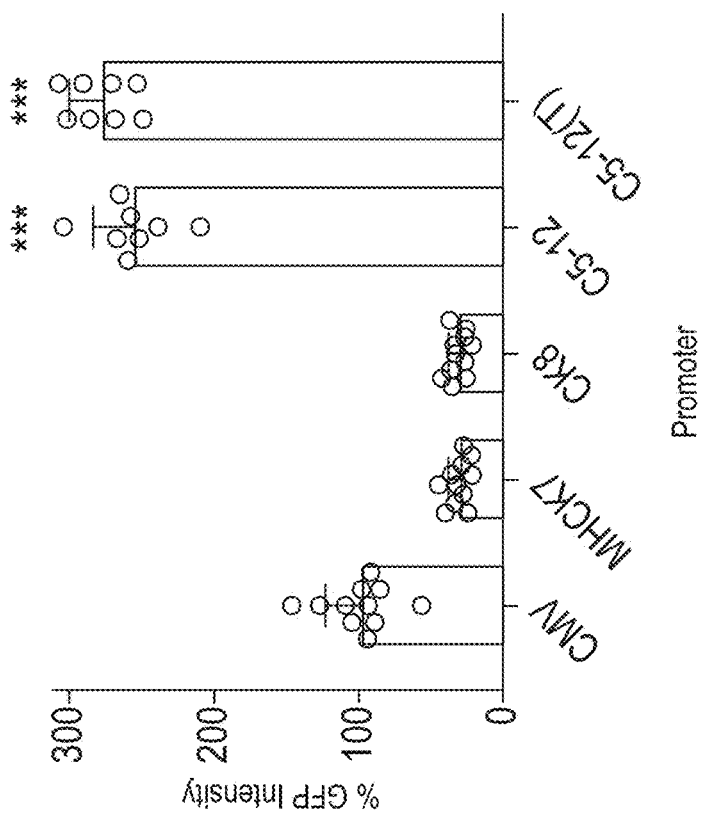

Example 5: Promoter/Intron Screening for Expression of Miniaturized Dystrophin A series of promoters and introns were evaluated for their suitability for driving the expression of miniaturized dystrophin. To that end, promoters and introns were cloned in a GFP reporter plasmid the expression of which was then evaluated by transfection into human iCMs (see Example 2). The results indicated that the C5-12T promoter (see FIG. 7A) (US 2004/0175727) and SV40 intron (see FIG. 7B) were superior to other tested designs in driving the expression of GFP protein. Both elements were therefore included in the miniaturized dystrophin expression constructs used, as described below.

Figure 8A:
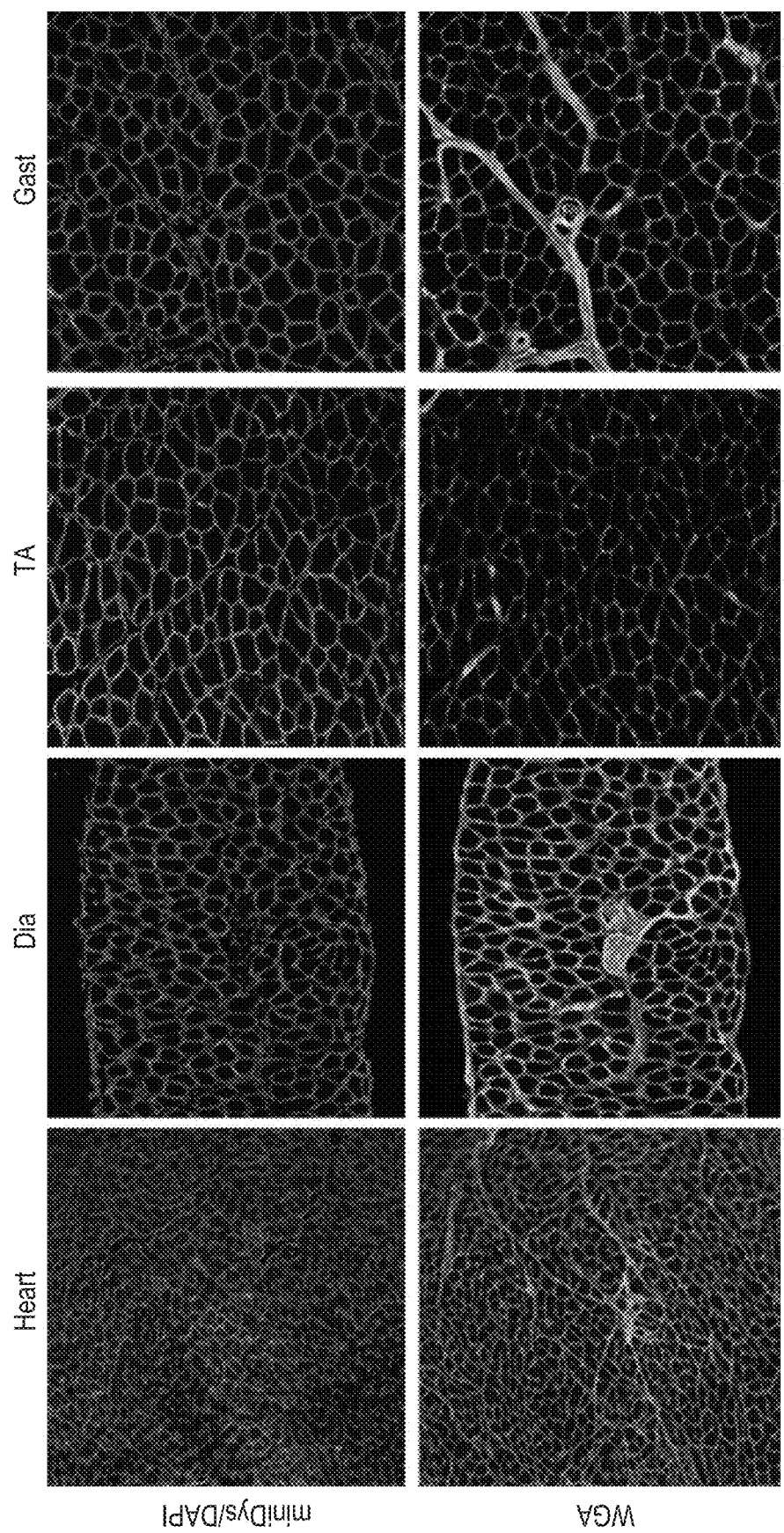
FIG. 8A-FIG. 8D show expression of miniaturized dystrophin polypeptides in mice and lack of dystrophin protein aggregates.
Figure 8B:
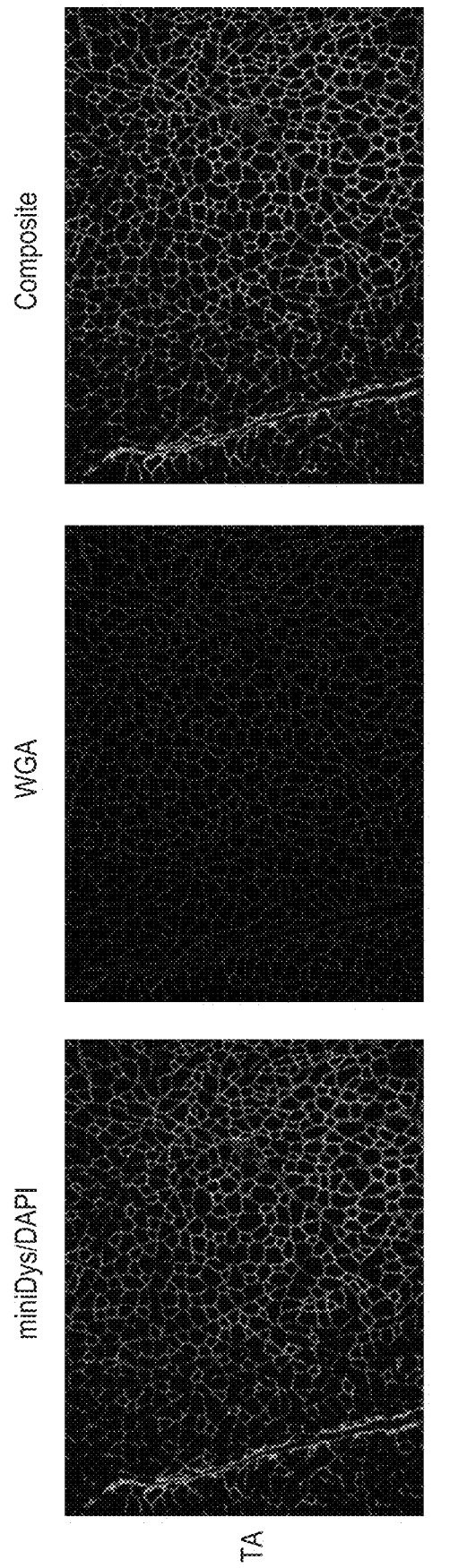
Figure 8C:
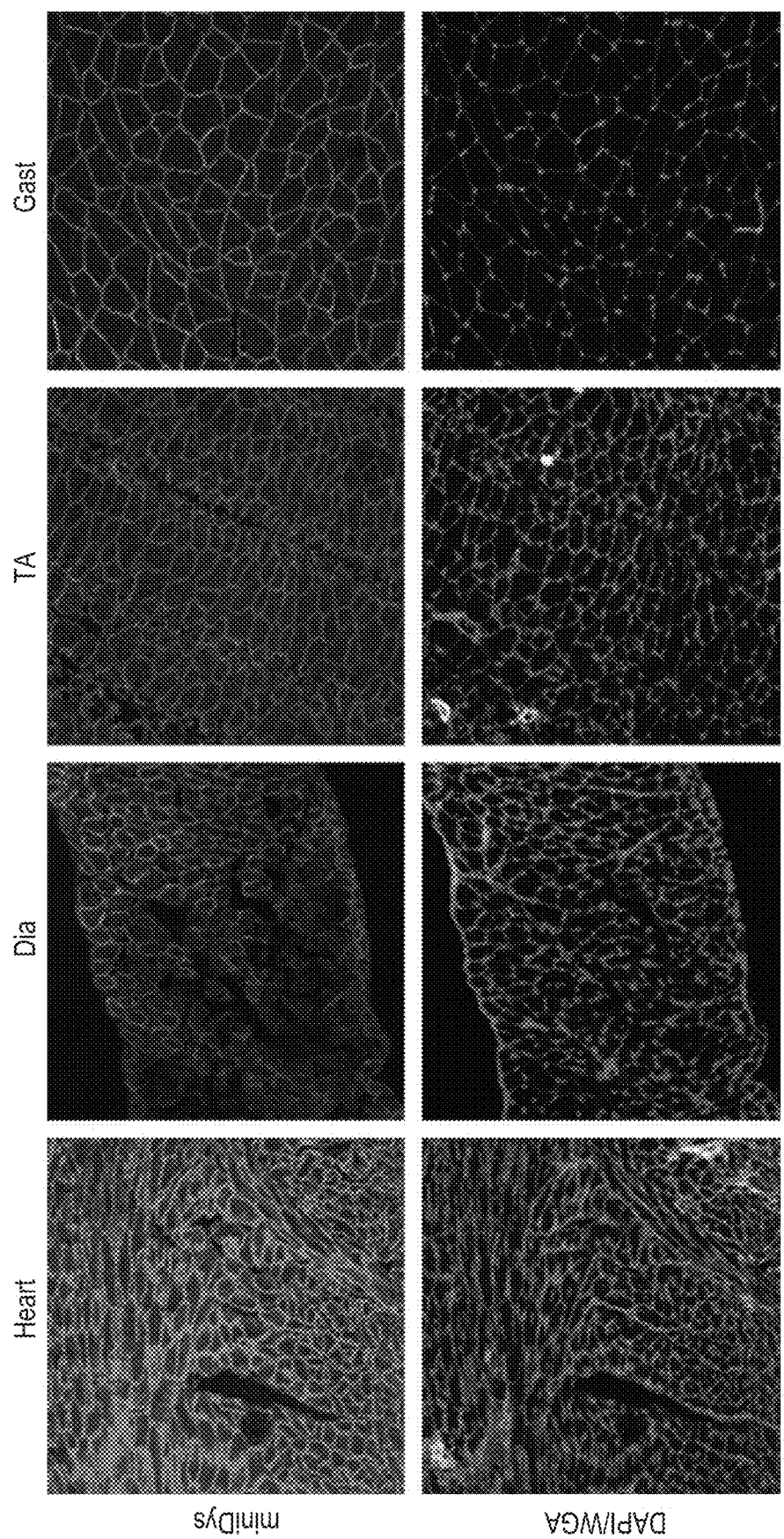
Figure 8D:
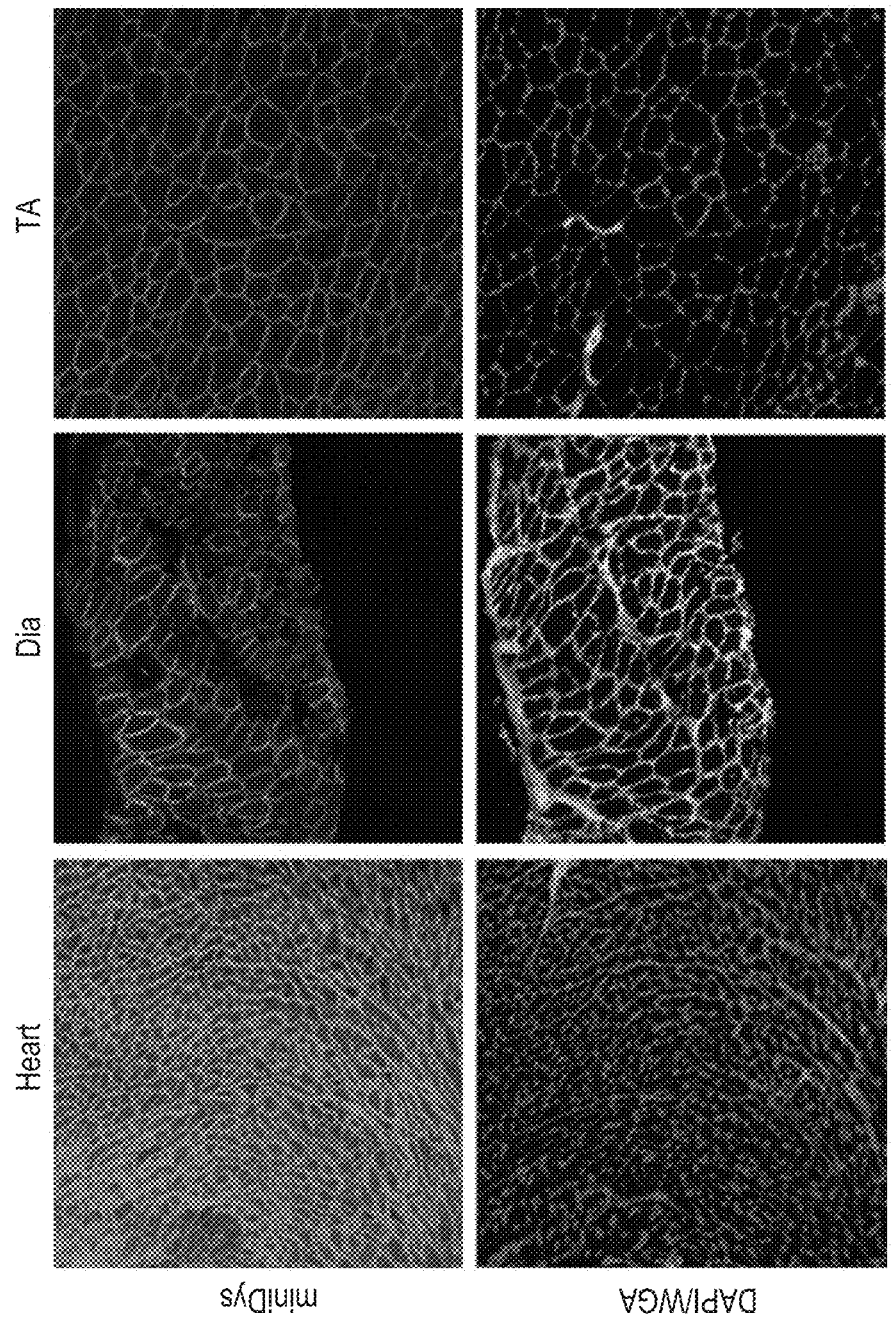
Figure 9:
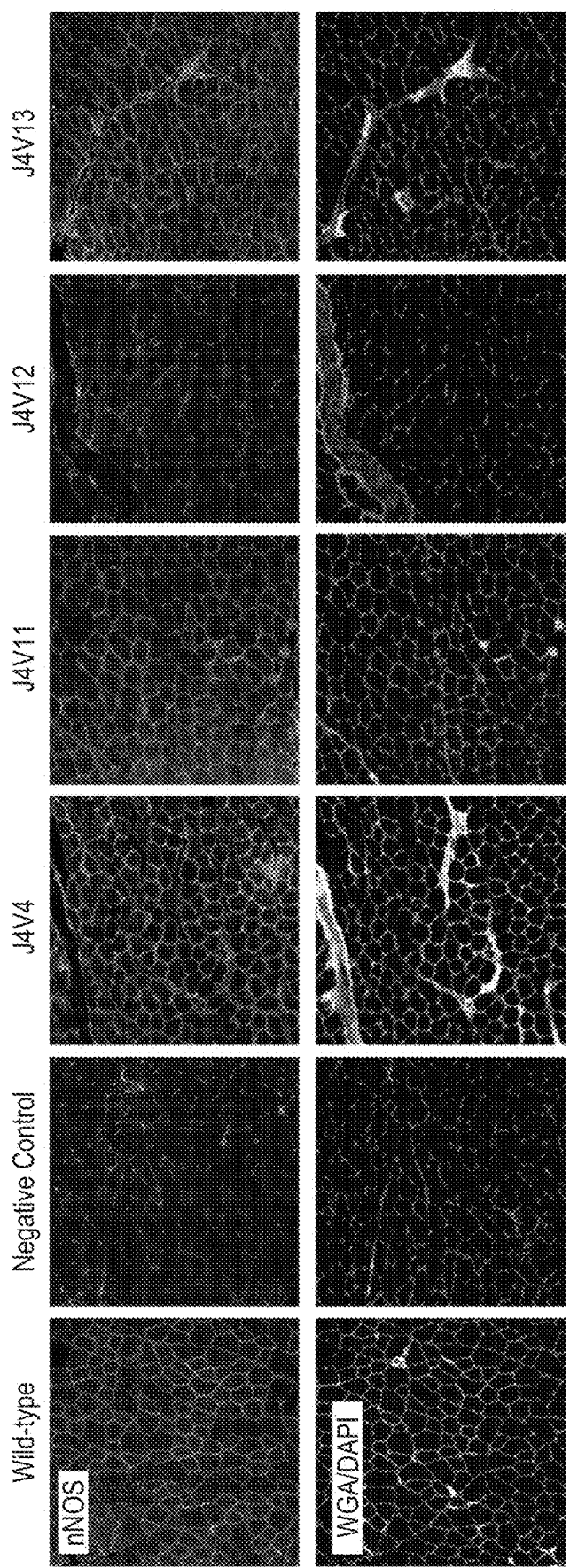
FIG. 9 shows nNOS restoration on the muscle sarcolemma of mdx$^{scsn}$ mice treated with the indicated AAV9 constructs. Samples were stained with an anti-nNOS antibody or WGA/DAPI as indicated.

Example 6: In Vivo Expression of Miniaturized Dystrophin Constructs and nNOS Restoration Mdx mice (dystrophin deficient mdx$^{scsn}$) were treated systemically with 2e14vg/kg AAV9 virus containing miniaturized dystrophin expression constructs (BXA-212372-J4V4, BXA-212372-J4V11, BXA-212372-J4V12, and BXA-212372-J4V13) via retroorbital injection at 2 weeks of age and examined at either 4 weeks of age or 12 weeks of age. Miniaturized dystrophin expression was driven by the C5-12(T) promoter. The heart and skeletal muscles of treated animals were dissected, frozen in OCT 2-methylbutane in liquid $N_2$. 10 μm frozen sections were immunostained for human dystrophin with monoclonal antibody Manex1011B directly conjugated to Alex488 (DSHB, Iowa City, Iowa) (see FIG. 8A-FIG. 8D) or with a polyclonal antibody against nNOS (ThermoFisher, Waltham, Mass.) detected with a secondary fluorescent antibody (see FIG. 9). WGA-conjugated with Alexa-694 was used as control to label muscle cells. Sections were coverslipped in medium containing DAPI to label nuclei. Slides were imaged using a Leica SP8 confocal microscope (Leica Microsystems; see FIGS. 8 and 9). It was found that all AAV9 constructs tested expressed well in the examined muscle tissue, i.e., the heart, diaphragm (Dia), tibialis anterior (TA), and the gastrocnemius muscle (Gast) (FIG. 8A, BXA-212372-J4V4; FIG. 8B, BXA-212372-J4V11; FIG. 8C, BXA-212372-J4V12; and FIG. 8D, BXA-212372-J4V13 (BXA-220931)). No dystrophin protein aggregates were detectable (FIGS. 8A-D). FIG. 9 shows nNOS restoration at the tibialis anterior (TA) muscle sarcolemma of mdx mice treated with the indicated AAV9 constructs. Untreated wild-type mice served as positive controls, and mdx mice treated with an unrelated miniaturized dystrophin construct served as the negative control. Note that all J4 variants, except J4V12, restored nNOS to the sarcolemma.

Example 7: Effect of Miniaturized Dystrophin on In Vitro Physiology of Human iPSC-Derived iCMs Human iPSC-derived iCMs have been reported to have electrophysiological properties close to primary adult cardiomyocytes and to respond similarly to a range of cardiac ion channel inhibitors as well as adrenergic and muscarinic receptor agonists and antagonists. By comparison to isogenic wild-type iCMs, DMD iCMs carrying the E2035X mutation (see above) have a lower $Na^+$ channel amplitude, a prolonged cFPD (Q-T interval), and a greater beat rate variability, as determined using multi-electrode arrays. It was examined whether the expression of miniaturized dystrophin (e.g., BXA-220931) in DMD (E2035X) iCMs can mitigate the cells' DMD phenotype and improve their physiological traits. Multi-electrode arrays, impedance contraction assay, and $Ca^{2+}$ transients can be used to measure the effect of miniaturized dystrophin expression. Human iPSC-derived DMD (E2035X) iCMs were purchased from Fujifilm Cellular Dynamics, Inc. (Madison, Wis.). Our own work has shown that co-culturing hiPSC-derived iCMs with fibroblasts provides a more stable preparation for electrophysiological studies on multi-electrode arrays (MEAs). Human ventricular fibroblasts were purchased from Lonza (Walkersville, Md.).

Microelectrode array (MEA) technology enables high content spatiotemporal analysis of excitable cells or tissues from an array of embedded substrate-integrated extracellular electrodes onto which cells can be cultured or tissues placed. Extracellular field potentials (FPs) are recorded by each electrode and correspond to cellular action potentials. Assessment of FP morphology, duration and conduction velocity provides a picture of ion channel activities of a treatment as well as effects on repolarization and conduction.

Human iPSC-derived DMD (E2035X) iCMs were cultured with 7% $CO_2$ on 0.1% gelatin treated 6-well culture plates for 7 days, then trypsinized and diluted with human adult cardiac fibroblasts at an approximately 5:1 ratio (iCMs vs. fibroblasts). DMD (E2035X) iCMs and fibroblasts were then co-cultured on laminin-coated 9-well multi-electrode array (MEA) plates (256-9 well MEA300/30iR-ITO-mq; Multichannel Systems GmbH, Reutlingen, Germany). After 5 days of culture, the cells formed a spontaneously beating monolayer over recording electrodes imbedded in each well. Spontaneous extracellular field potentials (FPs) were recorded from 28 electrodes/well (30 μm diameter, 300 μm center to center spacing) at a sampling frequency of 10 kHz using an USB-MEA256-System and MC Rack acquisition software (Multichannel Systems GmbH, Reutlingen, Germany). Following a 20-minute equilibration period in a humidified environment at 37° C. with constant 5% $CO_2$ and 95% $O_2$ supply, wells were either infected with AAV8-BXA-220931 (AAV8 virus including as cargo a transgene including the coding sequence for BXA-220931 and the C5-12(T) Promoter, SV40 Intron, 3' UTR and polyA as set forth in Table 10 herein) at MOI of $1 \times 10^6$ in 300 μl maintenance medium for 48 hrs, or were left untreated as negative control.

The DMD (E2035X) iCMs were then evaluated for effects of the expression of the miniaturized dystrophin BXA-220931 on electrophysiological parameters 5 days, 7 days, and 9 days after infection. Electrophysiological parameters measured were field potential (FP) duration, a surrogate for repolarization, field potential conduction velocity, and inter-pulse intervals (IPIs). Field potential duration was corrected for beat rate changes (FPDc). Conduction velocity was quantified by measuring field potential activation times for each electrode imbedded in an MEA well during a synchronized single propagated beat. The digitized recordings of field potentials from each electrode were smoothed using a 21-point least squares smoothing polynomial (Savitsky & Golay, Analytical Chemistry, 1964) with a window of 2.1 ms. The activation time was the value for the peak in the negative derivative of each field potential waveform. The time between two of the earliest and latest activation times was the conduction time for field potential propagation across a monolayer of DMD (E2035X) iCMs and the distance between these two electrodes was the conduction distance. The conduction time divided by the conduction distance of each propagation was the conduction velocity of each beat of the monolayer DMD (E2035X) iCMs in an MEA well. Data were analyzed with custom software written in MatLab (Mathworks, Natick, Mass.). Beat rate (beats/minute), a surrogate for heart rate, was calculated by using BR=60000/IPI, where the IPI is the averaged IPIs (msec) of 100 second recording at steady-state under each condition. All treatments had at least 7 replicates and the study was repeated twice.

Figure 10B:
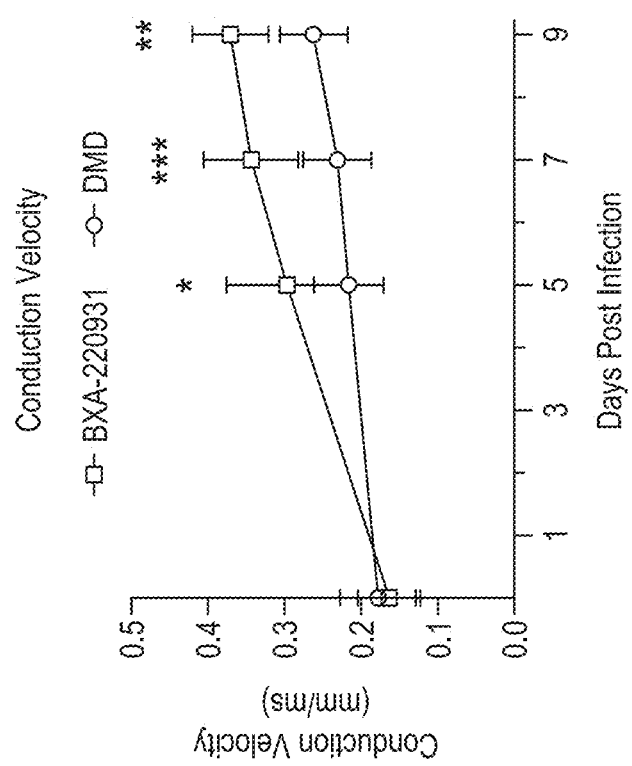
FIG. 10A-FIG. 10C illustrate the effect of miniaturized dystrophin BXA-220931 on the physiology of human isogenic induced-pluripotent stem cell (iPSC)-derived induced cardiomyocytes (iCMs) that carry an E2035X premature stop codon in the dystrophin gene that prevents endogenous dystrophin expression. iCMs were infected with AAV8-BXA-220931 virus to achieve expression.
Figure 10A:
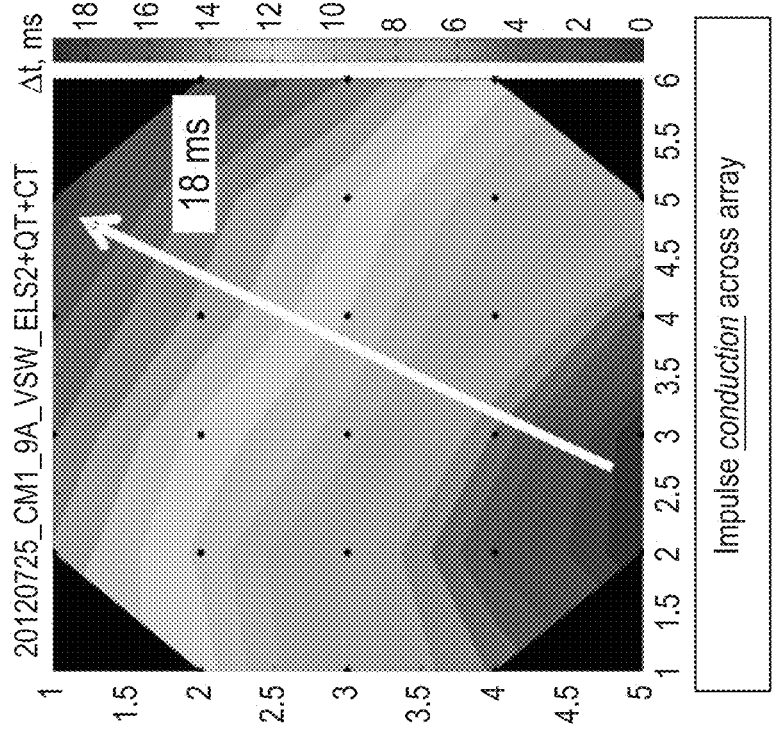
Figure 10C:
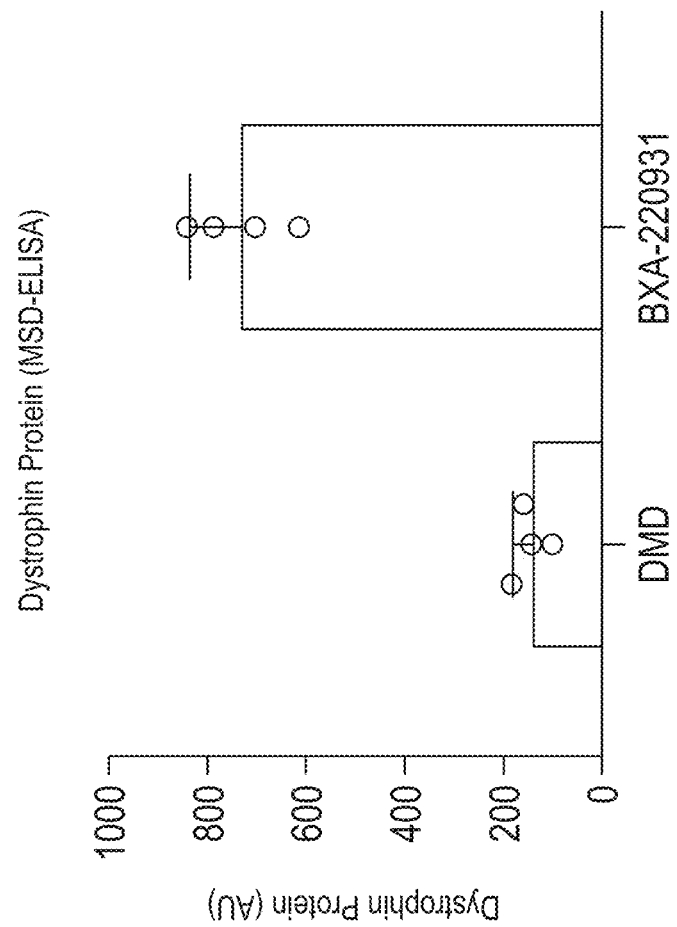

The data showed that miniaturized dystrophin BXA-220931 significantly improved conduction velocity by ~49% compared to untreated DMD (E2035X) iCMs (two-way ANOVA ***P<0.001 with Sidak's post-test n=6) (see FIG. 10B). Expression of miniaturized dystrophin in the DMD (E2035X) iCMs was confirmed by ELISA (see FIG. 10C).

Figures 11A, 11B, 11C:
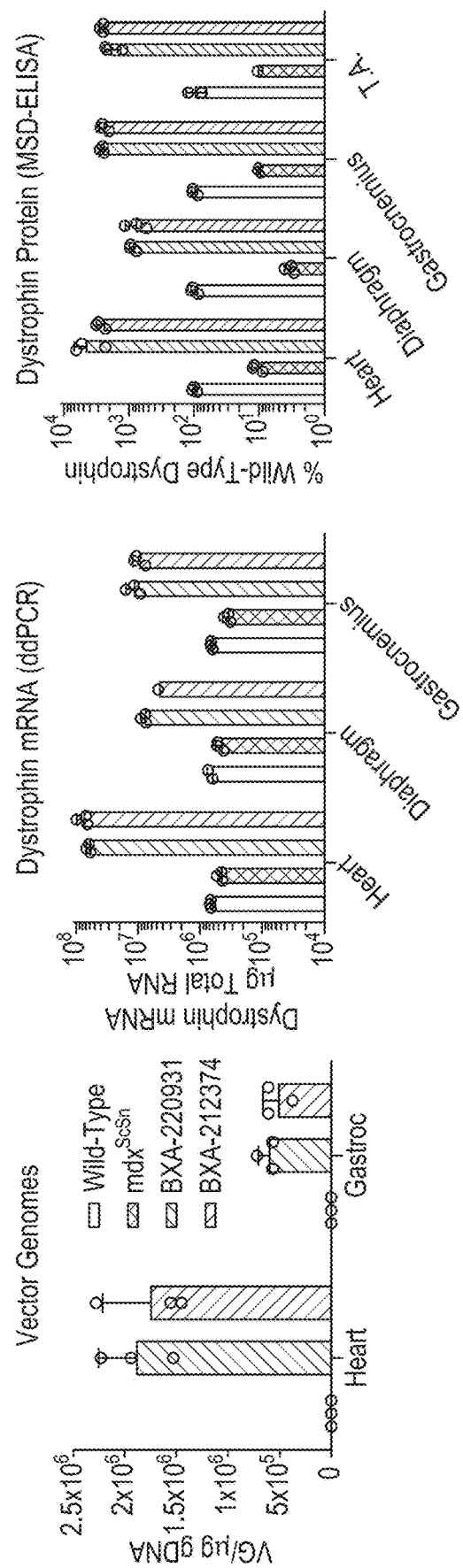
FIG. 11A-FIG. 11C show target engagement and expression of AAV9-BXA-220931 and AAV9-BXA-212374 determined in mdx$^{scsn}$ mice at 4 weeks of age.
Figures 12A, 12B:
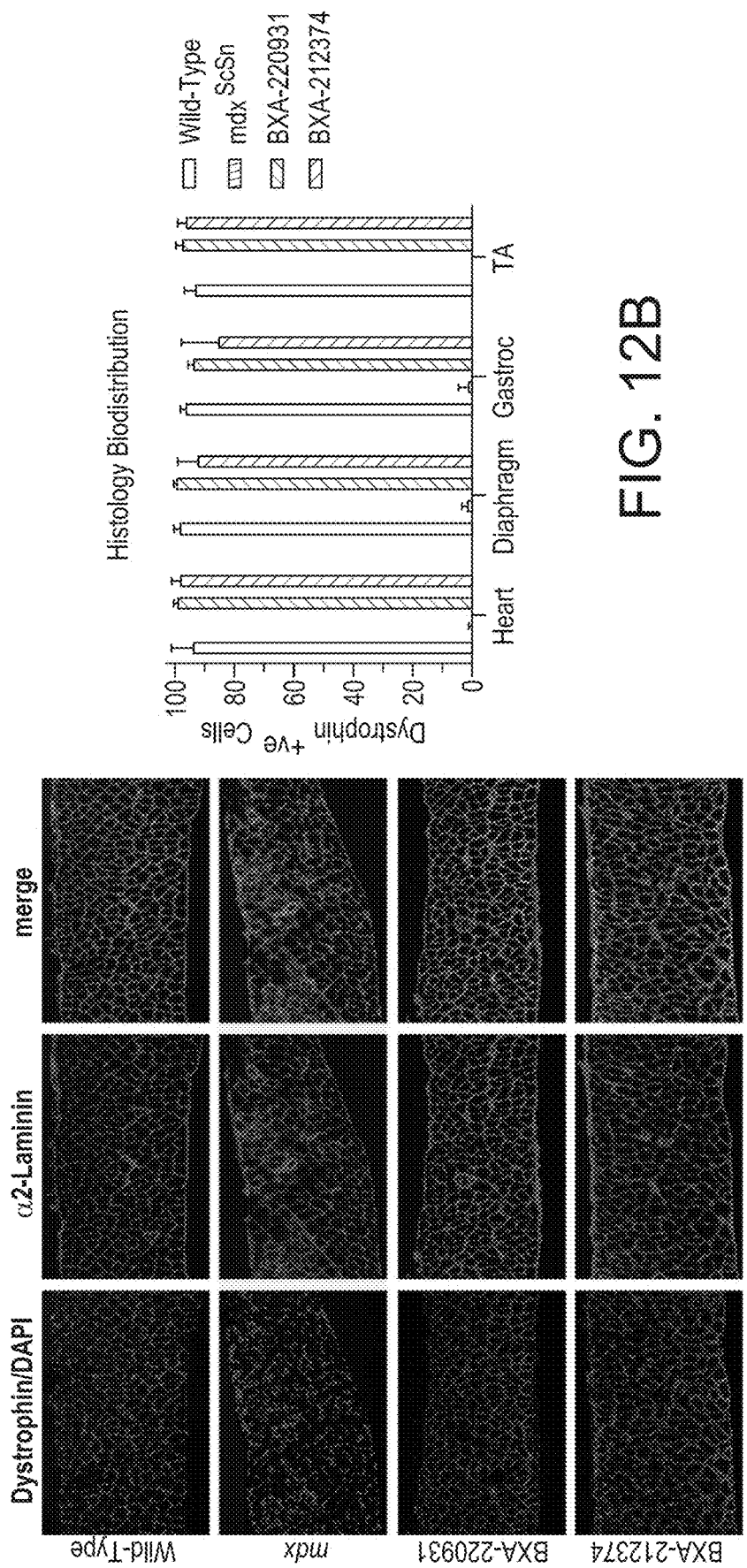
FIG. 12A and FIG. 12B show target engagement of AAV9-BXA-220931 and AAV9-BXA-212374 and biodistribution of the corresponding miniaturized dystrophins determined in mdx$^{scsn}$ mice at 4 weeks of age.
Figure 13:
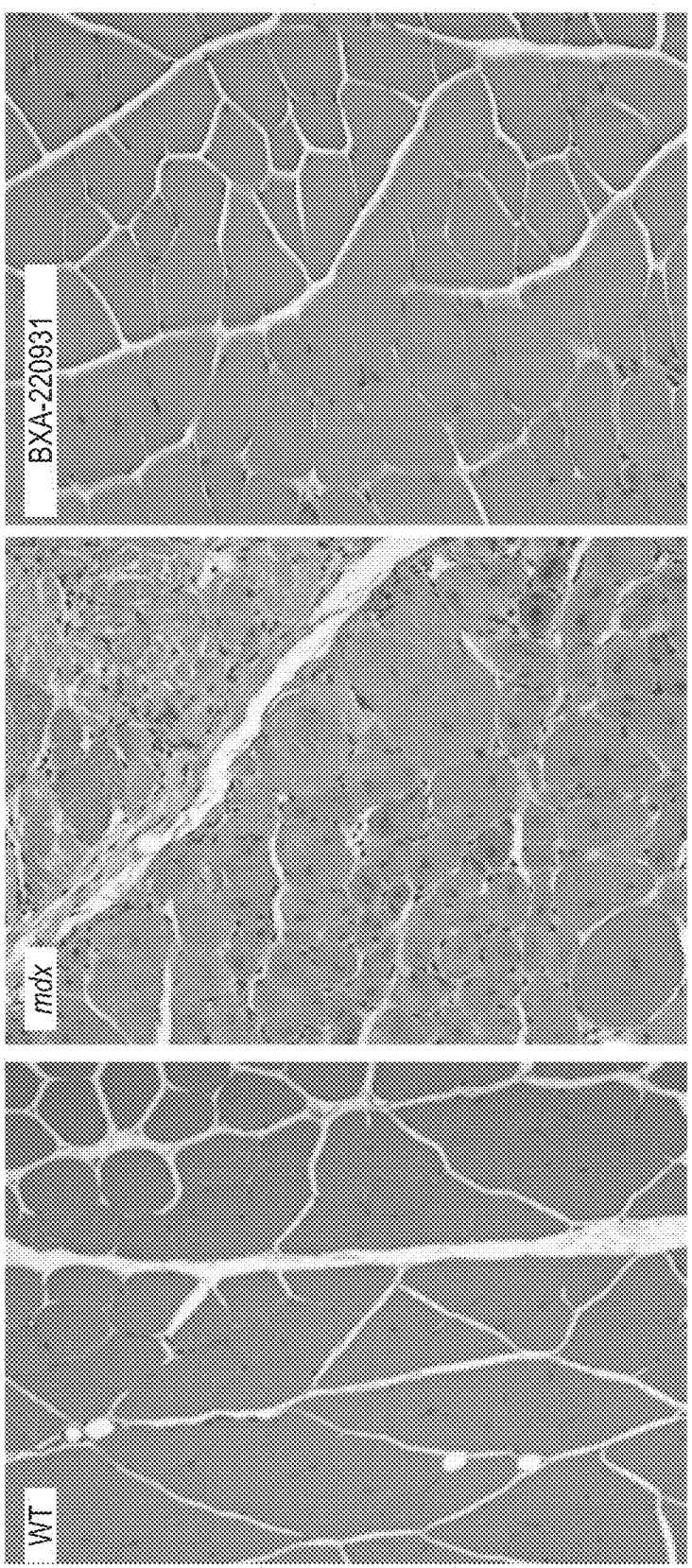
FIG. 13 shows an H&E histological analysis of striated muscle from wild-type mice, mdx$^{scsn}$ mice and mdx$^{scsn}$ mice treated with AAV9-BXA-220931 at 12 weeks of age. Treatment with AAV9-BXA-220931 prevents the mdx$^{scsn}$ dystrophic phenotype.
Figures 14A, 14B, 14C:
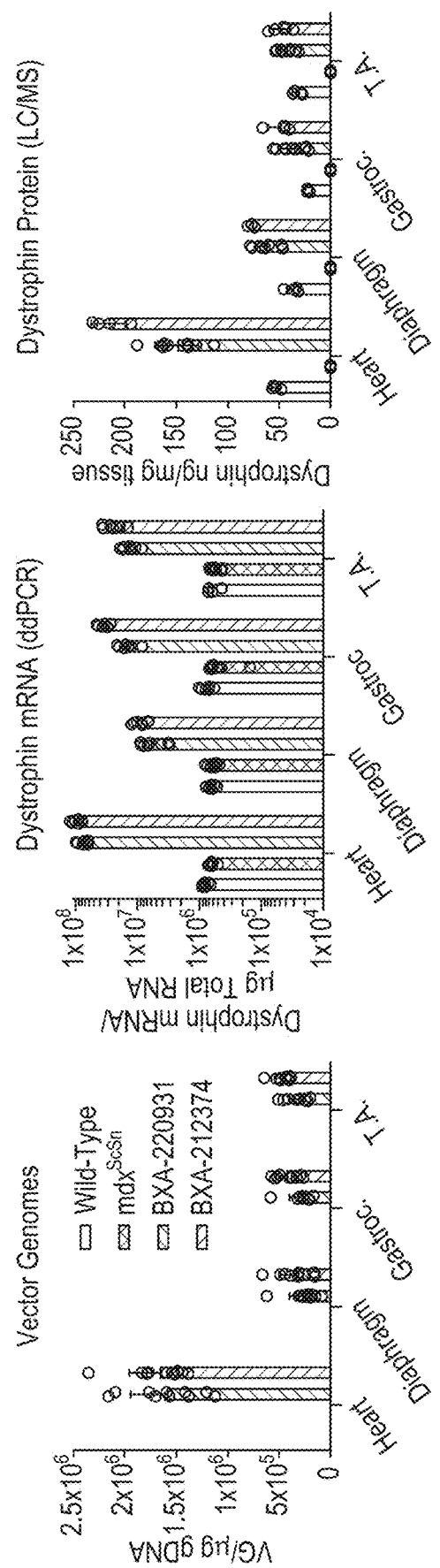
FIG. 14A-FIG. 14C show target engagement and expression of AAV9-BXA-220931 and AAV9-BXA-212374 determined in mdx$^{scsn}$ mice 12 weeks of age.
Figure 15A:
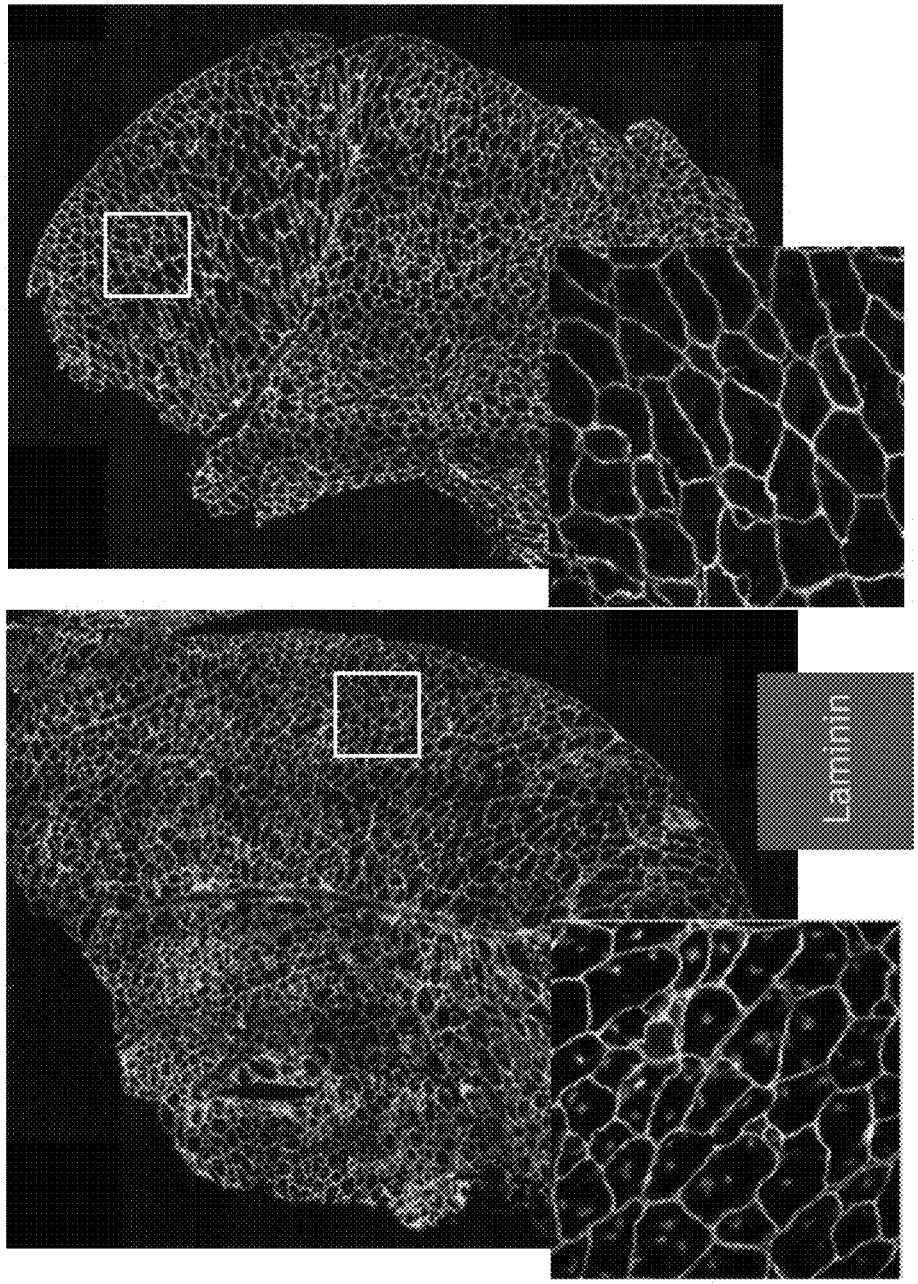
FIG. 15A-FIG. 15C show expression of both miniaturized dystrophin BXA-220931 and BXA-212374 is maintained in nearly every muscle fiber and prevention of central nucleation similar to wild-type muscle in muscles of mdx$^{scsn}$ mice at 12 weeks of age that had been treated with AAV9-BXA-220931 or AAV9-BXA-212374.
Figures 15B, 15C:
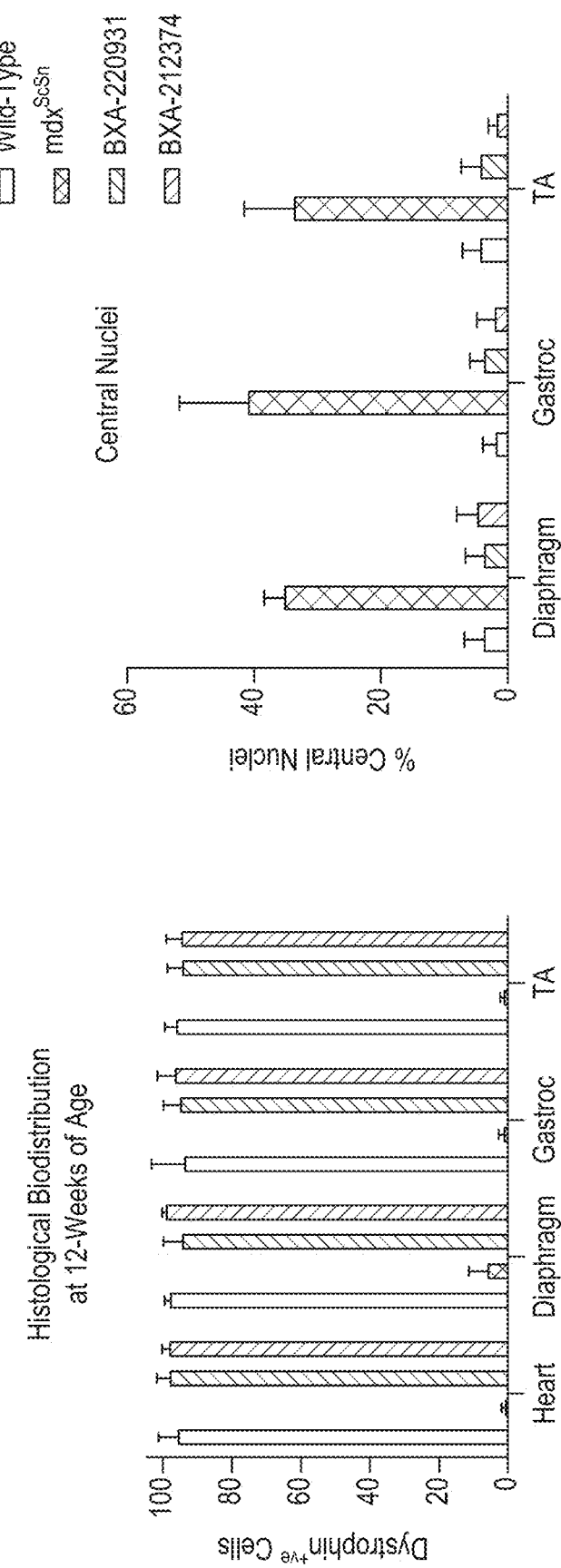
Figure 16:
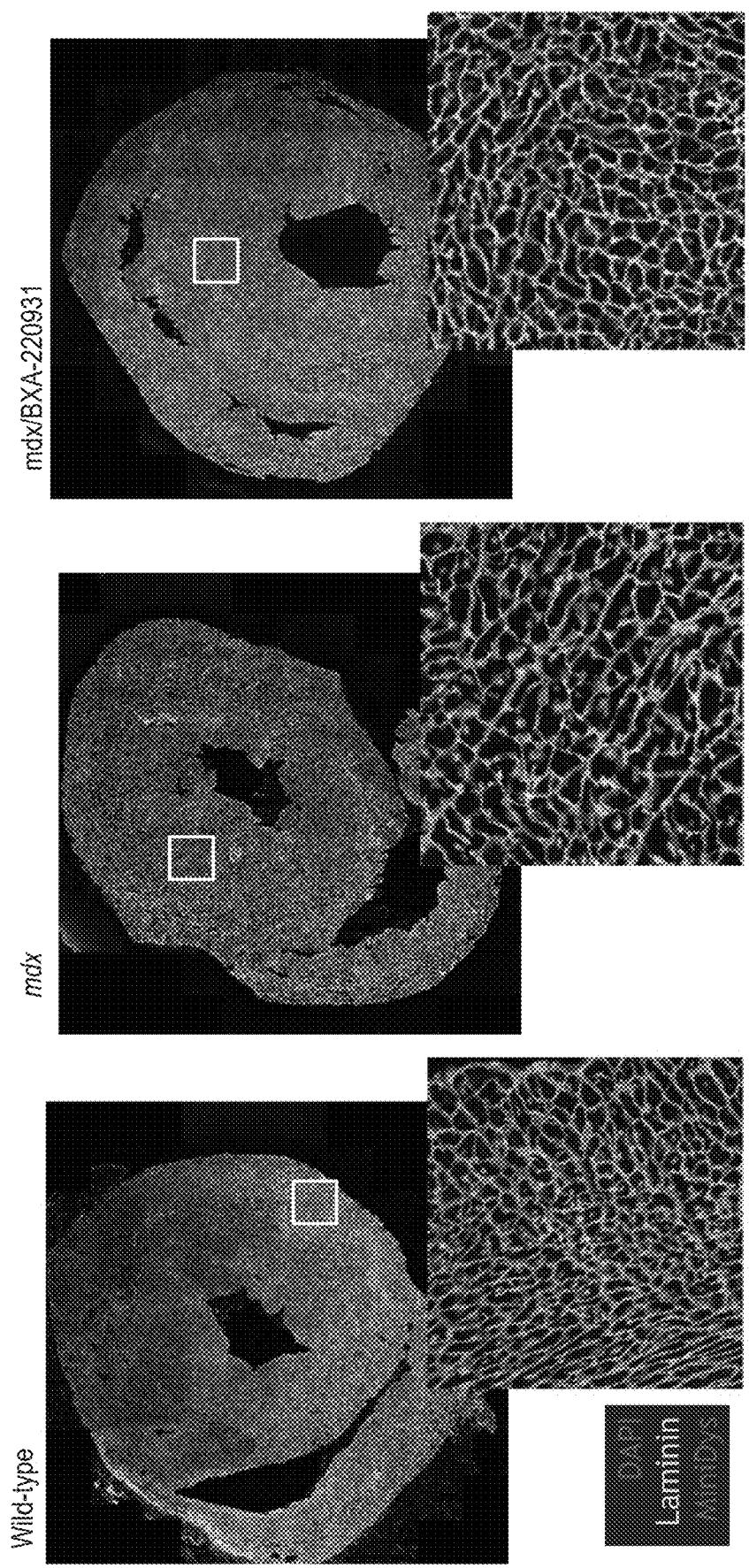
FIG. 16 shows target engagement of AAV9-BXA-220931 and biodistribution of the corresponding miniaturized dystrophin determined in the heart of mdx$^{scsn}$ mice at 12 weeks of age. Miniaturized dystrophin polypeptide and laminin were visualized by immuno-fluorescence in heart muscle tissue of mdx$^{scsn}$ mice treated with AAV9-BXA-220931. Nuclei were visualized with DAPI. Expression of miniaturized dystrophin BXA-220931 is seen in nearly every cardiomyocyte in the heart. Wild-type mice and untreated mdx$^{scsn}$ mice stained for dystrophin and laminin served as controls.
Figure 17:
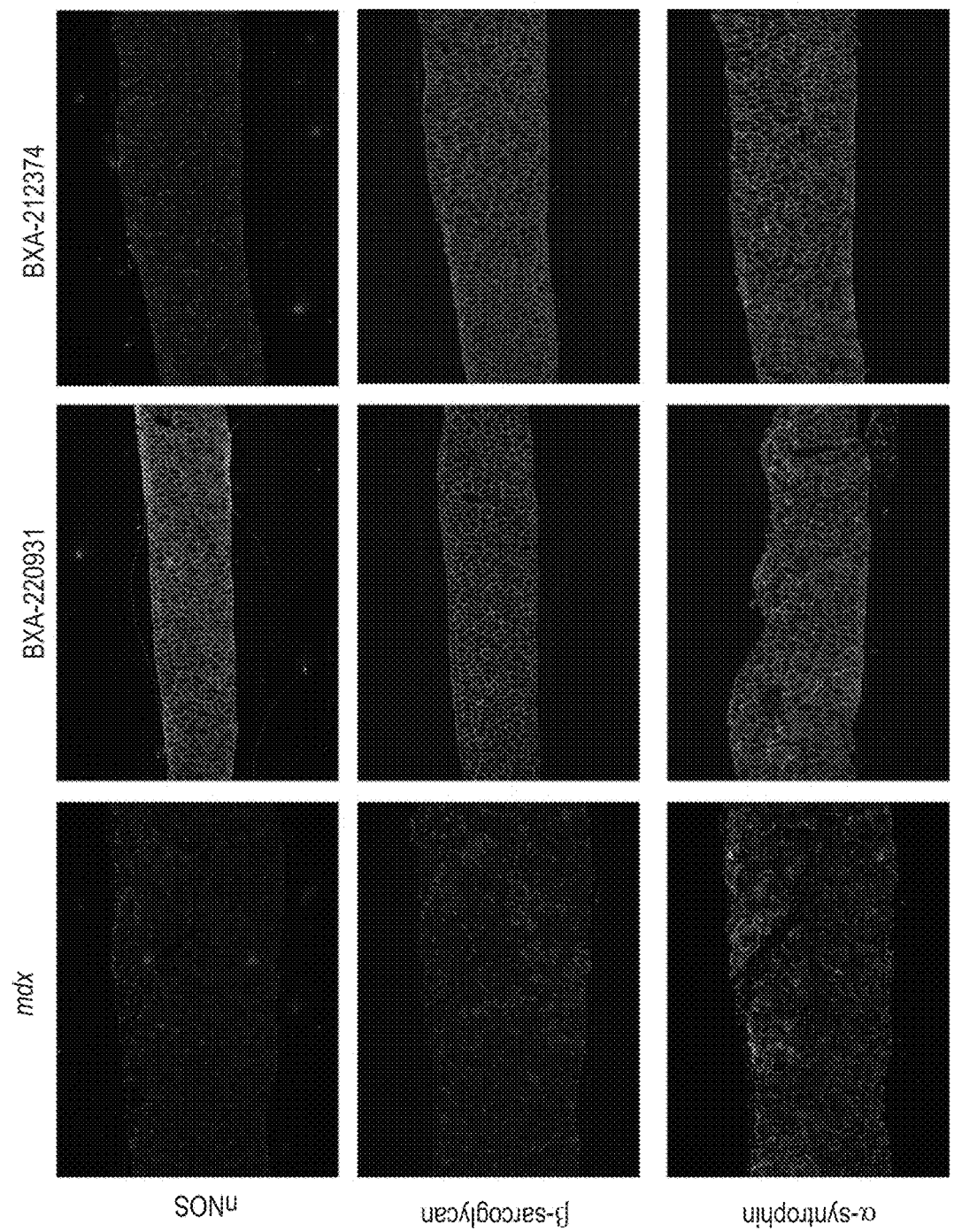
FIG. 17 shows restoration of the dystrophin glycoprotein complex to the sarcolemma of mdx$^{scsn}$ mice treated with AAV9-BXA-220931 at 12 weeks of age. The indicated markers for the muscle sarcolemma, α-syntrophin and β-sarcoglycan, and nNOS were visualized by immuno-fluorescence. Co-localization of nNOS with α-syntrophin and β-sarcoglycan is seen in mdx$^{scsn}$ mice treated with AAV9-BXA-220931, but not in mice treated with AAV9-BXA-212374 or in untreated mice. Untreated mdx$^{scsn}$ mice served as controls.
Figure 18:
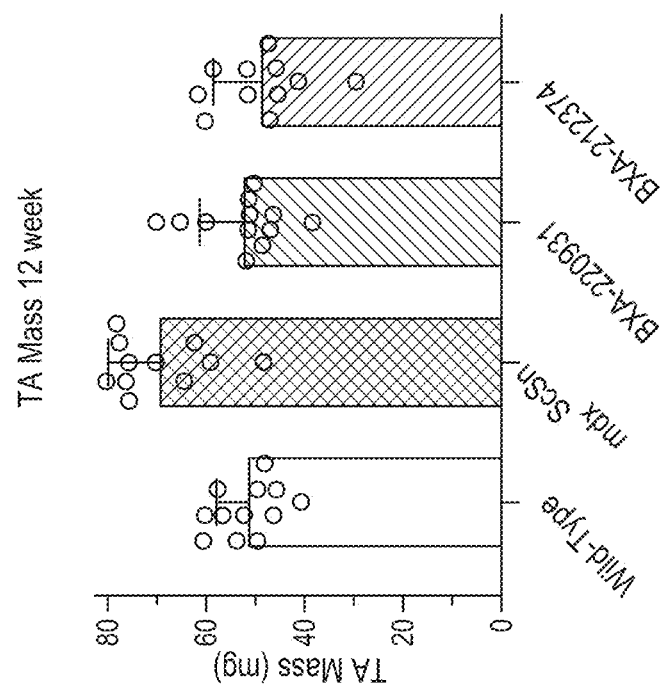
FIG. 18 shows an assessment of muscle mass in treated and untreated mdx$^{scsn}$ mice at 12 weeks of age. Tibialis anterior muscle mass is heavier in untreated mdx$^{scsn}$ mice due to the significant muscle degeneration and regeneration. Treatment with AAV9-BXA-220931 and AAV9-BXA-212374 prevented this phenotype and resulted in normal muscle mass. Wild-type mice and untreated mdx$^{scsn}$ mice served as controls. Bar graphs reflect the means+/−standard deviations.
Figure 19:
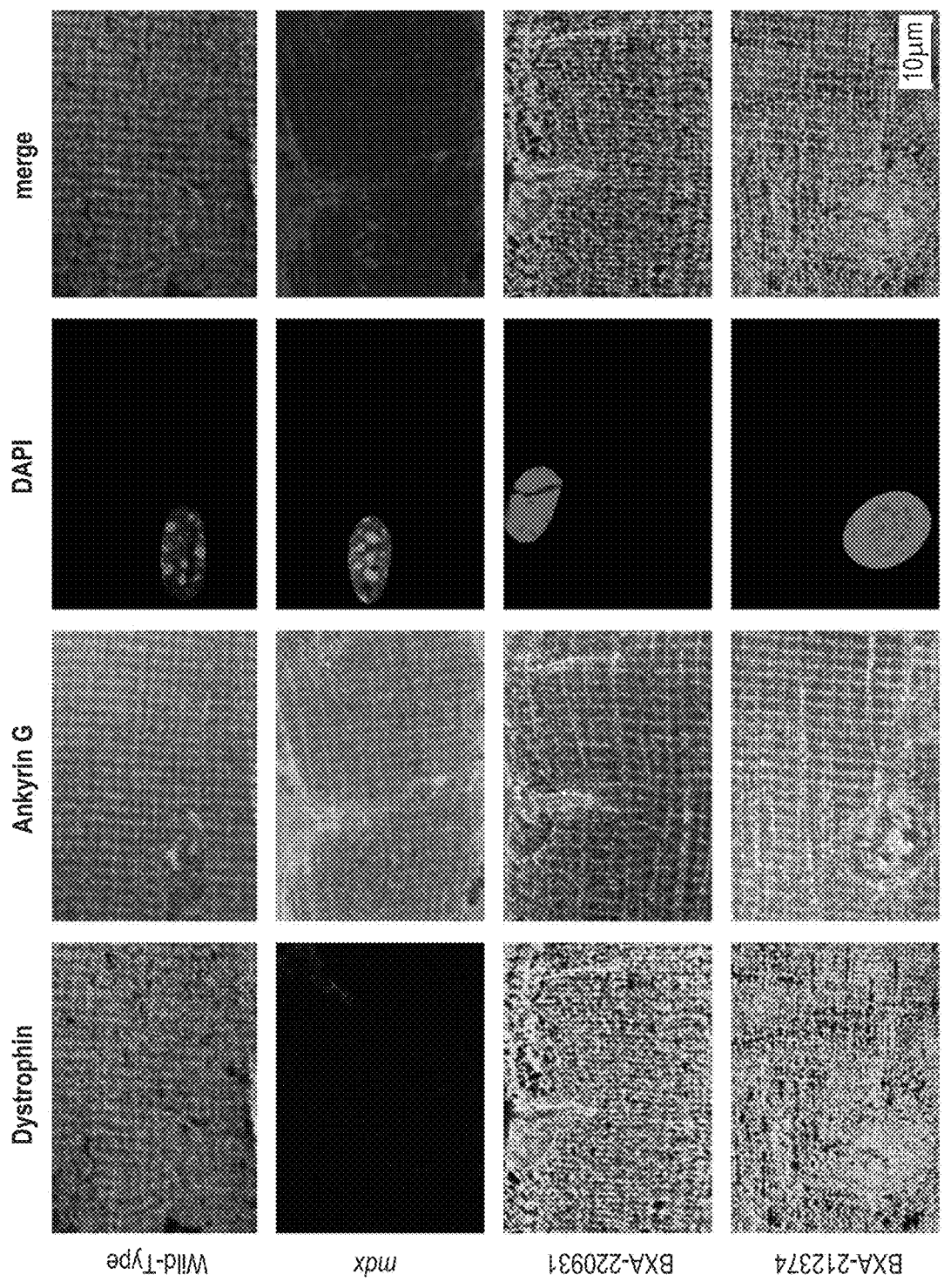
FIG. 19 shows co-localization of miniaturized dystrophins with ankyrin G in costameres within the sarcolemma of mdx$^{scsn}$ mice treated with AAV9-BXA-220931 and AAV9-BXA-212374 at 12 weeks of age. Miniaturized dystrophins and ankyrin G were visualized by immunofluorescence. Both BXA-220931 and BXA-212374 miniaturized dystrophins localize to both the Z-disks and M bands of costameres similar to dystrophin in wild-type muscles. Wild-type mice and untreated mdx$^{scsn}$ mice stained for dystrophin and ankyrin G served as controls.
Figure 20:
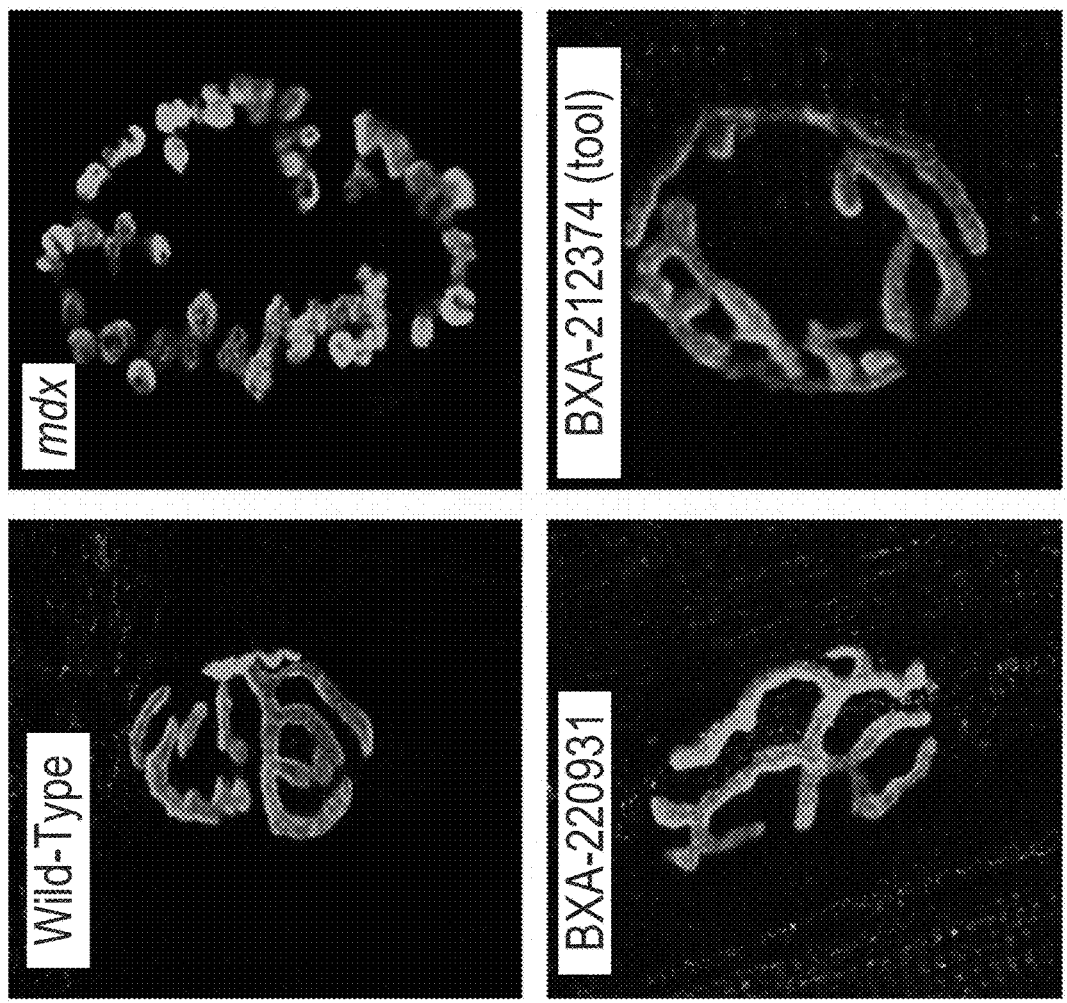
FIG. 20 shows an analysis of the postsynaptic endplate of the 3rd EDL muscle in treated and untreated mdx$^{scsn}$ mice at 12 weeks of age. Neuromuscular junctions were labelled with α-bungarotoxin. The postsynaptic endplate is continuous in wild-type muscles, but fragments upon muscle degeneration in muscles of mdx$^{scsn}$ mice. Treatment with AAV9-BXA-220931 and AAV9-BXA-212374 prevented the fragmentation of neuromuscular junctions in mdx$^{scsn}$ mice.

Example 8: In Vivo Studies—Analysis of Expression, Biodistribution and the Ability to Prevent the Dystrophic Phenotype in mdx$^{scsn}$ Mice of Miniaturized Dystrophins Two miniaturized dystrophin viral constructs were used in these studies. One construct included the coding sequence for BXA-220931 and the C5-12(T) Promoter, SV40 Intron, 3' UTR and polyA as set forth in Table 10 herein. The other included the same non-coding elements but expressed miniaturized dystrophin BXA-212374, which has been described in Banks et. al., (PLOS Genetics, volume 6(5), 2010) and has the following domain structure: ABD1/H1/R1/R2/R3/H3/R24/H4/CR). Dystrophin deficient mdx$^{scsn}$ mice were treated by retro-orbital injection with about 2e14vg/kg AAV9-BXA-220931 virus or AAV9-BXA-212374 virus at 2 weeks of age. Treated and untreated mice were terminated two-weeks after virus administration (n=3) to examine expression levels and biodistribution of human miniaturized dystrophin (see FIGS. 11 and 12). Additional mice (n=10-12) were terminated at 12 weeks of age and examined for expression levels and biodistribution of human miniaturized dystrophin and prevention of dystrophy (see FIGS. 13 to 20 and this and subsequent Examples 9-13). Untreated wild type mice and endogenous mouse dystrophin expression served as controls.

Muscle tissue of treated and untreated mdx$^{scsn}$ mice was analyzed for the amount of virus genomes present as well as dystrophin mRNA and protein expression, as described in more detail below. The data showed that sufficient virus was administered to dystrophin deficient mdx$^{scsn}$ mice to achieve expression levels (mRNA and protein) of miniaturized dystrophin in striated muscle in these animals at 4 weeks of age and at 12 weeks of age that were higher than corresponding expression levels of endogenous dystrophin in wild-type animals (see FIG. 11A-FIG. 11C and FIG. 14A-FIG. 14C, respectively).

The skeletal muscles in dystrophin deficient mdx$^{scsn}$ mice typically undergo necrosis and regeneration from ~3-4 weeks of age. The regenerated muscle fibers are typically more variable in size and contain centrally located nuclei in frozen transverse sections. Also, fibrosis becomes more prevalent in regenerated muscles. The muscle fiber size, proportion of centrally located nuclei, and fibrosis in untreated mdx muscles and mdx muscles treated with miniaturized dystrophin BXA-220931 or BXA-212374 (partly) were measured by histology and immune-fluorescence analysis of tissue sections, as described in more detail below. The proportion of muscle fibers expressing the miniaturized dystrophins was also quantified in a similar fashion, as described in more detail below. The data showed that miniaturized dystrophins BXA-220931 and BXA-212374 were expressed in nearly all analyzed myofibers/myocytes of virus-treated mdx$^{scsn}$ mice, including the heart, and prevented the central nucleation to a degree similar to wild-type muscles at 4 weeks of age and 12 weeks of age (see FIG. 12A and FIG. 12B, FIG. 15A-FIG. 15C and FIG. 16, respectively). Importantly, the expression and biodistribution of miniaturized dystrophin was maintained more than two months post AAV treatment.

Miniaturized dystrophin BXA-220931 also prevented the dystrophic pathology seen in untreated mdx$^{scsn}$ mice, as shown by histological and immuno-fluorescence analysis of muscle tissue sections (FIG. 13 and FIG. 15A-FIG. 15C).

Vector genome quantitation/genomic DNA isolation and qPCR—For genomic DNA isolation, striated muscle tissue was homogenized using Qiagen TissueLyser (Qiagen, Venlo, Netherlands) and genomic DNA was isolated from homogenized tissue using a Qiagen DNeasy 96 Blood & Tissue Kit (Qiagen, Venlo, Netherlands, #69581). Tissue (~10 mg) was placed in 96 well plates (Costar® 96-Well Assay Block 1 ml, #3958) containing 200 µl of proteinase K-buffer ATL and one 5 mm steel bead, homogenized using the Qiagen Tissuelyser at 30 hz for 2 min, which was repeated until the tissue was homogenized. Genomic DNA isolation was performed in accordance with the manufacturer's instructions. For genomic qPCR, each DNA sample was run in duplicates with primer/probe sets (wild-type dystrophin F-5' AAGGCCTGACAGGGCAAAA3' (SEQ ID NO: 114), R-5'CAGGGCATGAACTCTTGTGGAT3' (SEQ ID NO: 115), probe 6FAM-CTGCCAAAAGAAAAA-MGBNFQ (SEQ ID NO: 116); BXA-220931 F-5'CGCGAGGACGTGCAGAA3' (SEQ ID NO: 117), R-5' TTGCTGAACTGGGCGTTGA3' (SEQ ID NO: 118), Probe 6FAM-AAACCTTCACCAAATGG-MGBNFQ (SEQ ID NO: 119); BXA-212374 F-5'TGGAAGATTGC-TACGAGCGC3' (SEQ ID NO: 120), R-5'CAGGTCGCT-GAACAGGTTCT3' (SEQ ID NO: 121), Probe 6FAM-GCAAGTTCGGCAAGCAGCACA-MGBNFQ (SEQ ID NO: 122)) in 384 well clear reaction plates (Applied Biosystems, Waltham, Mass., #4483285). To each qPCR reaction, 20 of genomic DNA (80ng) and 8 µl of master mix (50 of Applied Biosystems™ TaqMan™ Fast Advanced Master Mix (ThermoFisher), 0.5 µl 20×FAM primer probe mix and 2.5 µl water) was added and plates were centrifuged for 1 min at 1000 rpm. Samples were incubated at 95° C. for 2 min followed by 40 cycles at 95° C. for 15 sec and 60° C. for 1 min using the ViiA™ 7 Real-Time PCR System and QuantStudio software for data analysis and vector genome quantitation (Applied Biosystems, Waltham, Mass.). Total genomic DNA was quantitated by absorption spectroscopy.

mRNA isolation—For isolation of total RNA, tissue is was homogenized using Qiagen Tissuelyzer (Qiagen, Venlo, Netherlands) and RNA was isolated from homogenized tissue using a Qiagen RNeasy 96 Universal Tissue Kit (Qiagen, Venlo, Netherlands, #74881). Tissue (~15 mg) was placed in RNeasy kit collection microtubes containing 750 µl of QIAzol Lysis Reagent (Qiagen, Venlo, Netherlands) and one 5 mm steel bead, homogenized using Tissuelyzer at 30 hz for 2 min, which was repeated until the tissue was homogenized. This step was followed by a centrifugation at 6000×g for 1 min at 4° C. To each tube 150 ml of chloroform were added and samples were vortexed vigorously for 15 sec. Following a 3 min incubation step at room temperature, samples were spun at 6000×g for 15 min at 4° C. The aqueous phase was removed (~360 µl) and transferred to a new tube containing 1 volume of RNAse free 70% EtOH. All samples were transferred to a 96 well RNeasy 96 plates, which were then sealed with AirPore tape (Qiagen, Venlo, Netherlands) and centrifuge at 5600×g for 4 min at room temperature. 400 µl of RW1 buffer was added per well and plates resealed and spun for 4 min at 5600×g. During this step, a DNaseI stock solution was prepared by adding 550 µl of RNAse free water per DNase vial (Qiagen, Venlo, Netherlands). 670 µl of the DNase I stock solution was diluted into 7.3 mls RDD buffer, mixed and stored at 4° C. When centrifugation was completed, the flow-through was discarded and 80 µl of DNase I mix was added directly to the center of each well and the plate was incubated at room temperature for 15 min. Following incubation, 400 µl of RW1 was added to each well and the plate was sealed and centrifuged for 4 min at 5600×g. Flow-through was discarded and 800 µl of RPE buffer were added per well and the plate was re-sealed and spun for 4 min at 5600×g. This process was repeated and the plate was centrifuged for 10 min at 5600×g. Each sample was then eluted into a fresh tube by adding 60 µl of RNAse free water to the center of each well and centrifuging the tubes for 4 min at 5600×g. To improve recovery, the eluted 60 µl were re-applied back onto the plate and centrifuged for an additional 4 min at 5600×g. RNA yield was quantitated using a NanoDrop™ 8000 Spectrophotometer (Thermo Fisher Scientific, Waltham, Mass.).

ddPCR Quantification of mRNA—For cDNA synthesis and subsequent quantitative PCR, 1 µg of RNA was added to one well of a 96 well plate in 10 µl $H_2O$ (Axygen™ 96-Well PCR Microplates, EMSCO Scientific Enterprises, Inc., Philadelphia, Pa.). To each well 10 µl of master mix (High Capacity cDNA Reverse Transcription Kit, Applied Biosystems, Waltham, Mass.) was added and the plate was centrifuged at 1000 rpm. cDNA synthesis was carried out at 25° C. for 10 min, 37° C. for 120 min, and 85° C. for 5 min, which was then followed by a hold at 4° C. For ddPCR, each sample was then run in duplicate with the following primer/probe sets: wild-type dystrophin F-5' AAGGCCTGACAGGGCAAAA3' (SEQ ID NO: 114), R-5'CAGGGCATGAACTCTTGTGGAT3' (SEQ ID NO: 115), probe 6FAM-CTGCCAAAAGAAAAA-MGBNFQ (SEQ ID NO: 116); BXA-220931 F-5'CGCGAGGACGTGCAGAA3' SEQ ID NO: 117), R-5' TTGCTGAACTGGGCGTTGA3' (SEQ ID NO: 118), Probe 6FAM-AAACCTTCACCAAATGG-MGBNFQ (SEQ ID NO: 119); BXA-212374 F-5' TGGAAGATTGC-TACGAGCGC3' (SEQ ID NO: 120), R-5'CAGGTCGCT-GAACAGGTTCT3' (SEQ ID NO: 121), Probe 6FAM-GCAAGTTCGGCAAGCAGCACA-MGBNFQ (SEQ ID NO: 122). To each reaction, 7.5 µl of cDNA and 17.5 µl of master mix (12.5 µl ddPCR Supermix (BIO-RAD Laboratories, Hercules, Calif.), 0.5 µl 20×FAM primer probe mix and 4.5 µl water) were added to Eppendorf Twin.tec® semi-skirted 96 well plates (Eppendorf, Germany, #951022055), which were then sealed and centrifuged for 1min at 1000 rpm and processed for droplet generation in DG32 Automated Droplet Generator Cartridges (Bio-Rad Laboratories, Hercules, Calif., #1864108). Samples were PCR-amplified in the Bio-Rad C1000 Touch Thermocycler (95° C. for 10 min followed by 40 cycles at 94° C. for 30 sec/60° C. 1 min; 98° C. 10 min) and immediately analyzed for fluorescence reading in a BioRad Droplet Reader and mRNA levels in target striated muscle tissue were determined. Dystrophin mRNA was quantitated in copy numbers relative to total RNA (µg, quantitated by absorption spectroscopy).

Protein expression determination by MSD-ELISA—Miniaturized dystrophin protein expression in target striated muscle tissue was determined by ELISA assay (Meso Scale Delivery-Enzyme Linked Immunosorbent Assay, Model 1201 MESO™ Sector S 600, Meso Scale Diagnostics, Rockville, Md.). Multi-assay 384-well plates (Meso Scale Diagnostics, Rockville, Md.) were pre-coated with monoclonal mouse anti-human dystrophin antibody Manex 1011b (DSBH, University of Iowa, Developmental Studies Hybridoma Bank) at a concentration of 2 µg/ml in bicarbonate buffer (pH 9.4) overnight. Plates were then washed 3× with PBS and then blocked with blocking buffer (5% BSA in PBS) for 4 hrs with shaking at room temperature. Tissues (~20 mg) were homogenized in RIPA buffer at a concentration of 1 mg tissue/10 µl lysis buffer (Millipore Sigma, Germany, #R0278) with protease inhibitor cocktail tablets (Roche, #04693159 001) using Qiagen Tissuelyzer at 30 hz for 5 min, which was repeated until the tissue was homogenized. The tissue/RIPA lysates were diluted 1:3 in binding buffer (1% BSA, 0.05% Tween-20, 20 mM Tris pH 7.5 in PBS). Tissue lysates and sulfo-conjugated mouse anti-human dystrophin antibody Mandys 106 (DSBH, 0.2 µg/ml) were added to the pre-coated 384 well plates and incubated at 4° C. with shaking overnight. Plates were washed with PBS with 0.05% Tween-20 and additional 40 µl MSD Read Buffer T with surfactant (Meso Scale Diagnostics, Rockville, Md., #R92TC-1). Plates were then read on an MSD Sector® 6000 Imager (Meso Scale Diagnostics, Rockville, Md.). Endogenous dystrophin was assayed using the same protocol but employing antibodies binding murine dystrophin.

Protein expression determination by liquid chromatography-mass spectrometry (LC-MS)—Striated (heart, skeletal) muscle tissues were collected and immediately frozen. Prior to analyses, the tissues were homogenized with RIPA buffer in a 1:20 ratio. The homogenates were digested with trypsin and after fractionation for peptide enrichment, the samples were analyzed by LC-MS/MS by monitoring a previously identified unique peptides common to both mouse and human dystrophin (LLDLLEGLTGQK). Stable isotope labeled analogs (SIL) for human and mouse peptides were spiked into the homogenate and were used to estimate the measured levels. Total protein was also obtained and used for normalization purposes.

Immuno-fluorescence slide preparation—mdx$^{scsn}$ mice were treated with AAV9-BXA-220931 or AAV9-BXA-212374 at 2 weeks of age. Heart and skeletal muscle tissue was collected from these mice at 4 weeks of age or at 12 weeks of age. Muscle tissue was frozen in OCT in liquid $N_2$ and sectioned at 5 µm. Sections were mounted on standard microscope slides and stored at −80° C. Frozen sections were brought to room temperature and blocked with 200 µl of blocking buffer (Dulbeccos Phosphate Buffered Saline (DPBS) (ThermoFisher, Waltham, Mass., #14190144) supplemented with 0.05% TritonX-100 (Sigma-Aldrich, #T8787) and 1% BSA (Sigma-Aldrich #A9576)) for 30 minutes. A murine antibody binding the N-terminus of human and murine dystrophin (not cross-reacting with utrophin) and a rat anti-laminin-2 antibody (Sigma-Aldrich #L0663) were diluted in blocking buffer. Blocking buffer was then removed with a vacuum aspirator and 200 µl of primary antibody solution was added to each slide. Following a one hour incubation at room temperature, slides were washed 3 times in DPBS. A secondary antibody solution was prepared for the detection of the primary antibodies by diluting an Alexafluor 546 goat anti-rat antibody (ThermoFisher, Waltham, Mass., #A11077) and an Alexafluor 647 goat anti-mouse IgG2b antibody (ThermoFisher, Waltham, Mass., #A21242) in blocking buffer (see above). DAPI was also included in the secondary antibody solution to counterstain nuclei in the tissue. 200 µl of secondary antibody solution was added to the tissue and incubated for 30 minutes at room temperature. Following the staining protocol, slides were washed 3 times with DPBS followed by a rinse with diH$_2$O. One drop of ProLong diamond antifade mountant (ThermoFisher, Waltham, Mass., #P36962) was added to each slide and each slide was then sealed with a coverslip. Slides were stored at 4° C. for imaging the next day.

Immuno-fluorescence image acquisition—Fluorescence image acquisition of fluorescently labeled tissue sections was conducted on a Leica SP8 confocal microscope (Leica Microsystems; see FIGS. 12, 17, 19 and 20) or an Opera Phenix™ HCS imager (PerkinElmer, Waltham, Mass.; see FIGS. 15 and 16) equipped with a laser microlens confocal and large 4.7 M pixel CMOS camera. Fluorescent dyes used for labeling tissues were matched with appropriate laser excitation light sources and complementary emission filters (Nuclei (DAPI): ex 375 nm, em 435-480 nm; miniaturized dystrophin (AF647): ex 640 nm, em 650-760 nm; laminin (AF546): ex 561 nm, em 570-630 nm). The software package Harmony 4.9 was used for image acquisition. The software first performed a low magnification scan at 5× to identify the region of interest (ROI). A second round of multi-color image acquisition on the ROI was performed using a water objective lens at 20× magnification. A montage image of the ROI was captured with 20% overlap between fields of view. Images were imported into the Columbus™ Image Data Storage and Analysis System (PerkinElmer, Waltham, Mass.) for analysis and quantitation.

Immuno-fluorescence image analysis—A building block analysis routine was created in the Columbus™ Image Data Storage and Analysis System to identify muscle fibers in both heart and skeletal muscle tissue and quantitate the amount of miniaturized dystrophin staining. A global image of the entire tissue was created. Each field of view was inverted so that the software could identify "cells" that were outlined by laminin staining. Size and intensity filters were applied to identify only true muscle fibers. The outer membrane identified by laminin staining was dilated and the miniaturized dystrophin intensity inside this region was calculated. Intensities were calculated for all tissues for all animal groups. Intensity cutoffs for "cells" or muscle fibers positive for miniaturized dystrophin were determined from the tissue of DMD mice, using a mean intensity plus 3 standard deviations. The proportion of laminin$^+$ muscle fibers also positive for mini-dystrophin protein and the proportion of laminin$^+$ muscle fibers with central nuclei were determined.

Standard histology—Tissue slides prepared as described above were also used for standard histology.

Example 9: Analysis of the Dystrophin-Glycoprotein Complex (DGC) in Muscle Fibers of mdx$^{scsn}$ Mice Untreated and Treated with Miniaturized Dystrophins To test if miniaturized dystrophin restored components of the dystrophin-glycoprotein complex (DGC), the diaphragm muscles from mdx$^{scsn}$ mice and mdx$^{scsn}$ mice treated with either BXA-220931 or with BXA-212374 miniaturized dystrophin as described in Example 8 were analyzed by immune-fluorescence histology, in principle as described in Example 8. Briefly, frozen OCT sections were incubated in blocking buffer (1×PBS, 1% BSA, 0.05% Triton) for 30 min, then incubated with primary antibodies to nNOS (1:200; ThermoFisher, Waltham, Mass., #61-7000), β-sarcoglycan (1:20; Novus Biologicals, Centennial, CO, #NBP1-90300), or β-syntrophin (1:200; Novus Biologicals, Centennial, CO, NB600-1294) for 1 hr, washed three times in 1×PBS, and then incubated with secondary antibodies conjugated to Alexa-488 (1:800 ThermoFisher, Waltham, Mass.) for 30 min, washed three times in 1×PBS, and coverslipped with prolong gold mounting medium with DAPI. The data showed that BXA-220931 restored dystrophin glycoprotein complex (DGC) components including nNOS to the sarcolemma of treated mice, whereas BXA-212374 was unable to restore nNOS to the sarcolemma (see FIG. 17).

Example 10: Analysis of Muscle Mass in mdx$^{scsn}$ Mice Untreated and Treated with Miniaturized Dystrophins Typically, muscle mass is heavier in mdx$^{scsn}$ mice due to the significant muscle degeneration and regeneration. The mass of tibialis anterior muscle in untreated and treated mice (as described in Example 8) was determined. Our analysis showed that mdx$^{scsn}$ mice treated with both BXA-220931 or BXA-212374 miniaturized dystrophins maintained normal muscle mass (see FIG. 18).

Example 11: Analysis of Costameres in Muscles of mdx$^{scsn}$ Mice Untreated and Treated with Miniaturized Dystrophins To immunostain costameres in muscles of mdx$^{scsn}$ mice untreated and treated with miniaturized dystrophins as described in Example 8, a method similar to Williams M. W. and Bloch R. J., *Extensive but coordinated reorganization of the membrane skeleton in myofibers of dystrophic (mdx) mice*, J. Cell. Biol. 144(6):1259-70 (1999), was used. Briefly, the mdx$^{scsn}$ mice were anesthetized and perfusion fixed with 2% paraformaldehyde in 1×PBS. The gastrocnemius muscles were then dissected, placed in 20% sucrose in 1×PBS for 2 hours at 4° C., placed in a cryovial, and finally snap frozen in liquid N$_2$. 40 µm longitudinal sections were cut from the 3rd digit of the extensor digitorum longus muscle similar to a previously described protocol (Banks G. B. et al., *Muscle structure influences utrophin expression in mdx mice*, PLoS Genet. 10(6):e1004431 (2010)) and the tissue was immune-stained with an N-terminal dystrophin antibody (binding both human and murine dystrophin) and an ankyrin G antibody (Santa Cruz Biotechnology, Dallas, Tex.). The samples were then washed 3 times in 1×PBS and secondary antibodies conjugated to Alexa 488 to label dystrophin and Alexa-594 to label ankyrin G were applied. The samples were then washed again 3 times in 1×PBS and then finally mounted with ProLong™ Gold antifade mountant containing DAPI. Images were gathered using a Leica SP8 confocal microscope (Leica Microsystems). The data showed that miniaturized dystrophins localized to both the Z-disks and M bands of costameres similar to dystrophin in wild-type muscles (see FIG. 19).

Example 12: Analysis of Neuromuscular Junctions of mdx$^{scsn}$ Mice Untreated and Treated with Miniaturized Dystrophins The neuromuscular junctions in mdx$^{scsn}$ mice untreated and treated with miniaturized dystrophins as described in Example 8 were labelled with α-bungarotoxin in the third digit of the extensor digitorum longus muscles according to Faber R. M. et al., *Myofiber branching rather than myofiber hyperplasia contributes to muscle hypertrophy in mdx mice*, Skelet. Muscle 4:10 (2014). The analysis of neuromuscular junctions in mdx$^{scsn}$ mice by α-bungarotoxin staining showed that the postsynaptic apparatus fragments upon muscle degeneration in muscles of untreated mdx$^{scsn}$ mice, but that both BXA-220931 and BXA-212374 miniaturized dystrophins prevented synaptic fragmentation in mice treated with the respective AAV (see FIG. 20).

Example 13: Analysis of Serum Creatine Kinase Levels in Mdx$^{scsn}$ Mice Untreated and Treated with Miniaturized Dystrophins Creatine kinase as an indicator of muscle damage was measured in serum using commercially available kits. Creatine kinase was measured at 4 weeks of age (2-weeks post virus delivery) and 12 weeks of age. The data indicated that in mdx$^{scsn}$ mice treated with AAV9-BXA-220931 or AAV9-BXA-212374 as described in Example 8, serum creatine kinase levels and thus muscle damage were significantly reduced (not shown).

The AAV used herein was AAV9 or AAV8, wherein the ITRs were AAV2.

Example 14: Functional In Vivo Studies

Dystrophin-deficient skeletal muscles produce less specific force (force per area) and are highly susceptible to contraction-induced injury. Restoration of dystrophin expression can mitigate these disorders. Dystrophic mdx mice are systemically treated with about 2el4vg/kg AAV9-C5-12(T)-BXA-220931 (SEQ ID NO: 83) at 2 weeks of age by retro-orbital injection. The limb muscle physiology is examined at 8 weeks of age. Briefly, the mouse knee is clamped and the foot is placed in a stirrup, and the stirrup is moved while the muscles are maximally contracted with a needle electrode. This assay measures the peak twitch and tetanic muscle force production and contraction-induced injury.

The tibialis anterior (TA) muscle contractile properties are tested by an in vivo (foot plate) apparatus as per manufacturer's instructions (Aurora Scientific). Briefly, the peak tetanic contraction is achieved at 150 Hz in force frequency curve (force is measured in Torque as Newton Meters). The peak tetanic contraction is the same in wild-type, mdx$^{scsn}$ and mdx$^{scsn}$ mice treated with BXA-220931. However, the TA muscle mass is greater in mdx$^{scsn}$ mice, such that peak tetanic force normalized to TA mass is reduced in mdx$^{scsn}$ mice, whereas it is at wild-type levels in the treated mdx$^{scsn}$ mice.

The right tibialis anterior muscle is examined for strength and resistance to contraction-induced injury similar to previously described protocols (Khairallah et. al., *Science Signaling* 5(236) (2012). The tibialis anterior (TA) muscle injury is measured by an in vivo (foot plate) apparatus as per manufacturers instructions (Aurora Scientific). During peak tetanic contraction at 150 Hz (maximum isometric torque), the foot plate is rotated from 900 to 135° degrees to strain the muscles. This contraction is repeated every minute for 20 contractions as previously described (Khairallah et. al., 2012). The maximum isometric torque immediately prior to strain is significantly reduced with each contraction in mdx$^{scsn}$ mice. In contrast, BXA-220931 prevents the contraction-induced injury similar to wild-type levels. The data are to show that the miniaturized dystrophin design protects the TA muscles from contraction-induced injury.

In vitro and in vivo expression of miniaturized dystrophin constructs is under the control of a C5-12(T) promoter (see, e.g., US 2004/0175727). The AAV used is AAV9 or AAV8, wherein the ITRs are AAV2.

What is claimed is:

1. A nucleic acid molecule comprising a nucleotide sequence, which encodes a miniaturized dystrophin polypeptide comprising a modified spectrin repeat 16 (R16) domain, wherein a part of the R16 domain is replaced by a corresponding part of a spectrin repeat 2 (R2) domain, and wherein the miniaturized dystrophin polypeptide comprises an amino acid sequence at least about 98% identical to the amino acid sequence set forth as SEQ ID NO: 83.

2. The nucleic acid molecule of claim 1, wherein the miniaturized dystrophin polypeptide comprises the amino acid sequence set forth as SEQ ID NO: 83.

3. The nucleic acid molecule of claim 1, comprising a nucleotide sequence comprising in order a C5-12(T) promoter, an SV40 intron, a coding sequence for the miniaturized dystrophin polypeptide comprising the amino acid sequence set forth as SEQ ID NO: 83, a 3' UTR, and a polyA sequence.

4. The nucleic acid molecule of claim 1, comprising a nucleotide sequence comprising in order a C5-12(T) promoter having the nucleotide sequence set forth as SEQ ID NO: 109, an SV40 intron having the nucleotide sequence set forth as SEQ ID NO: 110, a coding sequence for the miniaturized dystrophin polypeptide having the nucleotide sequence set forth as SEQ ID NO: 111, a 3' UTR having the nucleotide sequence set forth as SEQ ID NO: 112, and a polyA sequence having the nucleotide sequence set forth as SEQ ID NO: 113.

5. The nucleic acid molecule of claim 4, which further comprises a first inverted terminal repeat (ITR) and a second ITR both from adeno-associated virus (AAV).

6. A host cell comprising the nucleic acid molecule of claim 5.

7. A vector comprising the nucleic acid molecule of claim 5.

8. A pharmaceutical composition comprising (a) the vector of claim 7; and (b) a pharmaceutically acceptable excipient.

9. A recombinant adeno-associated virus (rAAV) vector particle comprising an AAV capsid and a nucleic acid molecule comprising a nucleotide sequence, which encodes a miniaturized dystrophin polypeptide comprising a modified R16 domain, wherein a part of the R16 domain is replaced by a corresponding part of a R2 domain, and wherein the miniaturized dystrophin polypeptide comprises an amino acid sequence at least about 98% identical to the amino acid sequence set forth as SEQ ID NO: 83.

10. The rAAV vector particle of claim 9, wherein the miniaturized dystrophin polypeptide comprises the amino acid sequence set forth as SEQ ID NO: 83.

11. The rAAV vector particle of claim 9, wherein the nucleotide sequence comprises in order a C5-12(T) promoter, an SV40 intron, a coding sequence for the miniaturized dystrophin polypeptide comprising the amino acid sequence set forth as SEQ ID NO: 83, a 3' UTR, and a polyA sequence.

12. The rAAV vector particle of claim 9, wherein the nucleotide sequence comprises in order a C5-12(T) promoter having the nucleotide sequence set forth as SEQ ID NO: 109, an SV40 intron having the nucleotide sequence set forth as SEQ ID NO: 110, a coding sequence for the miniaturized dystrophin polypeptide having the nucleotide sequence set forth as SEQ ID NO: 111, a 3' UTR having the nucleotide sequence set forth as SEQ ID NO: 112, and a polyA sequence having the nucleotide sequence set forth as SEQ ID NO: 113.

13. The rAAV vector particle of claim 12, wherein the nucleic acid molecule further comprises a first ITR and a second ITR both from AAV.

14. The rAAV vector particle of claim 13, wherein the first ITR and the second ITR are from the genome of AAV2.

15. The rAAV vector particle of claim 14, wherein the AAV capsid is from AAV8.

16. The rAAV vector particle of claim 14, wherein the AAV capsid is from AAV9.

17. The rAAV vector particle of claim 12, wherein the AAV capsid is from AAV8 or AAV9.

18. The rAAV vector particle of claim 12, wherein the AAV capsid is from AAV8.

19. The rAAV vector particle of claim 12, wherein the AAV capsid is from AAV9.

20. A rAAV vector particle comprising an AAV capsid and a nucleic acid molecule comprising a nucleotide sequence comprising in order a C5-12(T) promoter having the nucleotide sequence set forth as SEQ ID NO: 109, an SV40 intron having the nucleotide sequence set forth as SEQ ID NO: 110, a coding sequence for a miniaturized dystrophin polypeptide having the nucleotide sequence set forth as SEQ ID NO: 111, a 3' UTR having the nucleotide sequence set forth as SEQ ID NO: 112, and a polyA sequence having the nucleotide sequence set forth as SEQ ID NO: 113, wherein the nucleic acid molecule further comprises a first ITR and a second ITR both from the genome of AAV2 flanking the nucleotide sequence, and wherein the AAV capsid is from AAV8 or AAV9.

21. The rAAV vector particle of claim 20, wherein the AAV capsid is from AAV8.

22. A pharmaceutical composition comprising (a) the rAAV vector particle of claim 21; and (b) a pharmaceutically acceptable excipient.

23. A kit comprising the pharmaceutical composition of claim 22, and instructions for administering the pharmaceutical composition to a subject in need thereof.

24. The rAAV vector particle of claim 20, wherein the AAV capsid is from AAV9.

25. A pharmaceutical composition comprising (a) the rAAV vector particle of claim 24; and (b) a pharmaceutically acceptable excipient.

26. A kit comprising the pharmaceutical composition of claim 25, and instructions for administering the pharmaceutical composition to a subject in need thereof.

* * * * *

UNITED STATES PATENT AND TRADEMARK OFFICE
CERTIFICATE OF CORRECTION

PATENT NO. : 11,535,868 B2
APPLICATION NO. : 17/242357
DATED : December 27, 2022
INVENTOR(S) : Glen Banks et al.

It is certified that error appears in the above-identified patent and that said Letters Patent is hereby corrected as shown below:

In the Claims

Line 27, In Claim 13, delete "AAV." and insert --adeno-associated virus (AAV).--

Signed and Sealed this
Twenty-eighth Day of March, 2023

Katherine Kelly Vidal
Director of the United States Patent and Trademark Office